US008252916B2

(12) United States Patent
Simard et al.

(10) Patent No.: US 8,252,916 B2
(45) Date of Patent: Aug. 28, 2012

(54) EXPRESSION VECTORS ENCODING EPITOPES OF TARGET-ASSOCIATED ANTIGENS AND METHODS FOR THEIR DESIGN

(75) Inventors: John J. L. Simard, Vancouver (CA); David C. Diamond, West Hills, CA (US); Zhiyong Qiu, Los Angeles, CA (US); Xiang-Dong Lei, West Hills, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

(21) Appl. No.: 10/837,217

(22) Filed: Apr. 30, 2004

(65) Prior Publication Data
US 2004/0203051 A1 Oct. 14, 2004

Related U.S. Application Data

(63) Continuation of application No. 10/292,413, filed on Nov. 7, 2002.

(60) Provisional application No. 60/336,968, filed on Nov. 7, 2001.

(51) Int. Cl.
C07H 21/04 (2006.01)
C07K 1/00 (2006.01)
(52) U.S. Cl. .................... 536/23.5; 536/24.2
(58) Field of Classification Search ............... None
See application file for complete search history.

(56) References Cited

U.S. PATENT DOCUMENTS

| | | | |
|---|---|---|---|
| 4,439,199 A | 3/1984 | Amkraut et al. | |
| 4,683,199 A | 7/1987 | Palladino | |
| 4,937,190 A | 6/1990 | Palmenberg et al. | |
| 5,093,242 A | 3/1992 | Bachmair et al. | |
| 5,132,213 A | 7/1992 | Bachmair et al. | |
| 5,168,062 A | 12/1992 | Stinski | |
| 5,258,294 A | 11/1993 | Boyle et al. | |
| 5,385,839 A | 1/1995 | Stinski | |
| 5,405,940 A | 4/1995 | Boon et al. | |
| 5,478,556 A | 12/1995 | Elliott et al. | |
| 5,487,974 A | 1/1996 | Boon-Falleur et al. | |
| 5,496,721 A | 3/1996 | Bachmair et al. | |
| 5,519,117 A | 5/1996 | Wolfel et al. | |
| 5,530,096 A | 6/1996 | Wolfel et al. | |
| 5,554,506 A | 9/1996 | Van der Bruggen et al. | |
| 5,554,724 A | 9/1996 | Melief et al. | |
| 5,558,995 A | 9/1996 | Van der Bruggen et al. | |
| 5,580,859 A | 12/1996 | Felgner et al. | |
| 5,585,461 A | 12/1996 | Townsend et al. | |
| 5,589,466 A | 12/1996 | Felgner et al. | |
| 5,646,017 A | 7/1997 | Bachmair et al. | |
| 5,648,226 A | 7/1997 | Van den Eynde et al. | |
| 5,679,647 A | 10/1997 | Carson et al. | |
| 5,698,396 A | 12/1997 | Pfreundschuh | |
| 5,733,548 A | 3/1998 | Restifo et al. | |
| 5,744,316 A | 4/1998 | Lethe et al. | |
| 5,747,269 A | 5/1998 | Rammensee et al. | |
| 5,844,075 A | 12/1998 | Kawakami et al. | |
| 5,846,540 A | 12/1998 | Restifo et al. | |
| 5,847,097 A | 12/1998 | Bachmair et al. | |
| 5,856,187 A | 1/1999 | Restifo et al. | |
| 5,925,565 A | 7/1999 | Berlioz et al. | |
| 5,962,428 A | 10/1999 | Carrano et al. | |
| 5,989,565 A | 11/1999 | Storkus et al. | |
| 5,993,828 A | 11/1999 | Morton | |
| 5,994,523 A | 11/1999 | Kawakami et al. | |
| 6,004,777 A | 12/1999 | Tartaglia et al. | |
| 6,037,135 A | 3/2000 | Kubo et al. | |
| 6,060,273 A | 5/2000 | Dirks et al. | |
| 6,074,817 A | 6/2000 | Tartaglia et al. | |
| 6,130,066 A | 10/2000 | Tartaglia et al. | |
| 6,287,569 B1 | 9/2001 | Kipps et al. | |
| 7,084,239 B1 * | 8/2006 | Wang et al. ............... | 530/300 |
| 2003/0186355 A1 | 10/2003 | Ossendorp et al. | |
| 2003/0220239 A1 * | 11/2003 | Simard et al. ............ | 514/12 |
| 2004/0214284 A1 * | 10/2004 | Tureci et al. ............. | 435/69.1 |
| 2005/0130920 A1 * | 6/2005 | Simard et al. ............ | 514/44 |

FOREIGN PATENT DOCUMENTS

| | | |
|---|---|---|
| CA | 2147863 | 5/1994 |
| EP | 93/03175 | 4/1995 |
| EP | 1118860 A1 | 7/2001 |
| IE | 74899 | 8/1997 |
| WO | WO 96/03144 A1 | 2/1996 |
| WO | WO 96/40209 | 12/1996 |
| WO | WO 97/34613 | 9/1997 |
| WO | WO 97/41440 A1 | 11/1997 |
| WO | WO 98/13489 | 4/1998 |

(Continued)

OTHER PUBLICATIONS

Eisenlohr et al. J. Exp. Med. 1992, vol. 175, pp. 481-487.*
Shastri et al. J. Immunol. 1995, vol. 155, pp. 4339-4346.*
Bergmann et al. J. Virol. 1994, pp. 5306-5310.*
Wang et al. Cell. Immunol. 1992, vol. 143 pp. 284-297.*
Perkins et al. J. Immunol. 1991, vol. 146, pp. 2137-2144.*
Theobald et al. J. Exp. Med. 1998, vol. 188, No. 6, pp. 1017-1028.*
Gileadi et al. Eur. J. Immunol. 1999, vol. 29, pp. 2213-2222.*
Celis et al. Mol. Immunol. 1994, vol. 31, No. 18, pp. 1423-1430.*
Ochoa-Garay et al. Mol. Immunol. 1997, vol. 34, No. 3, pp. 273-281.*
Chaux et al. Int. J. Cancer, 1998, vol. 77, pp. 538-542.*
Gnjatic et al. PNAS USA 2003, vol. 100, No. 15, pp. 8862-8867.*
Gnjatic et al. J. Immunol. 2003, vol. 170, pp. 1191-1196.*
N_Geneseq Accession No. AAD14184, Nov. 6, 2001, p. 2.*

(Continued)

Primary Examiner — Gerald R Ewoldt
Assistant Examiner — Marianne Dibrino
(74) Attorney, Agent, or Firm — Davis Wright Tremaine LLP

(57) ABSTRACT

The invention disclosed herein is directed to methods of identifying a polypeptide suitable for epitope liberation including, for example, the steps of identifying an epitope of interest; providing a substrate polypeptide sequence including the epitope, wherein the substrate polypeptide permits processing by a proteasome; contacting the substrate polypeptide with a composition including the proteasome, under conditions that support processing of the substrate polypeptide by the proteasome; and assaying for liberation of the epitope. The invention further relates to vectors including a housekeeping epitope expression cassette. The invention relates to epitope cluster regions and to vectors including epitope cluster regions. The invention also relates to a method of activating a T cell comprising contacting a substrate polypeptide with an APC and contacting the APC with a T cell.

39 Claims, 13 Drawing Sheets

FOREIGN PATENT DOCUMENTS

| WO | WO 98/14464 | | 4/1998 |
|---|---|---|---|
| WO | WO 98/40501 | A1 | 9/1998 |
| WO | WO 99/02183 | | 1/1999 |
| WO | WO 99/24596 | A1 | 5/1999 |
| WO | WO 99/45954 | A1 * | 9/1999 |
| WO | WO 99/55730 | A2 | 11/1999 |
| WO | WO 00/06723 | A1 | 2/2000 |
| WO | WO 00/29008 | A2 | 5/2000 |
| WO | WO 00/40261 | A2 | 7/2000 |
| WO | WO 00/52451 | A1 | 9/2000 |
| WO | WO 00/71158 | A1 | 11/2000 |
| WO | WO 01/18035 | A2 | 3/2001 |
| WO | WO 01/19408 | A1 | 3/2001 |
| WO | WO 01/23577 | A3 | 4/2001 |
| WO | WO 01/52614 | | 7/2001 |
| WO | WO 01/55393 | A2 * | 8/2001 |
| WO | WO 01/58478 | A1 | 8/2001 |
| WO | WO 01/82963 | A | 11/2001 |
| WO | WO 01/90197 | A1 | 11/2001 |
| WO | WO/03/011331 | | 2/2003 |
| WO | WO 2004/018666 | A1 | 3/2004 |
| WO | WO 2004/022709 | A2 | 3/2004 |

OTHER PUBLICATIONS

Qaigen. www.qaigen.com/literature/pqesequences/pqe9.pdf, Apr. 2007, one page.*
Invitrogen. www.invitrogen.com/content/sfs/vectors/pcdna3_1mychis%20_map.pdf, Apr. 2007, one page.*
Eisenlhor et al. J. Exp. Med. 175: 481-487, 1992.*
Shastri et al. J. Immunol. 155: 4339-4346, 1995.*
Bergmann et al. J. Virol. 68(8): 5306-5310, 1994.*
Wang et al. Cell. Immunol. 143: 284-297, 1992.*
Perkins et al. J. Immunol. 146(7): 2137-2144, 1991.*
Theobald et al. J. Exp. Med. 188(6): 1017-1028, 1998.*
Gileadi et al. Eur. J. Immunol. 29: 2213-2222, 1999.*
Jager et al. J. Exp. Med. 1998, 187(2): 265-270.*
Zeng et al (PNAS USA, Mar. 27, 2001, (7): 3964-3969).*
SYFPEITHI search report. Jan. 4, 2010.*
Swiss-Prot P78358, 2011, 7 pages.*
Aki et al., "Interferon-( Induces Different Subunit Organizations and Functional Diversity of Proteasomes," *J. Biochem.*, 115: 257-269 (1994).
Altuvia et al., "A structure-based algorithm to predict potential binding peptides to MHC molecules with hydrophobic binding pockets," *Human Immunology*, 58: 1-11 (1997).
An et al. "A Multivalent Minigene Vaccine, Containing B-Cell, Cytoxic T-Lymphocyte, and $T_h$ Epitopes from Several Microbes, Induces Appropriate Responses in Vivo and Confers Protection against More than One Pathogen", *J Virol*; 71(3):2292-302 (1997).
Aria et al., "Isolation of Highly Purified Lysosomes from Rat Liver: Identification of Electron Carrier Components on Lysosomal Membranes", *J. Biochem.*, 110:541-7 (1991).
Arnold et al., "Proteasome subunits encoded in the MHC are not generally required for the processing of peptides bound by MHC class I molecules," *Nature*, 360: 171-174 (1992).
Ausubel et al., *Short Protocols in Molecular Biology*, Unit 11.2 (3d ed. 1997).
Ayyoub, et al., "Lack of tumor recognition by hTERT peptide 540-548-specific CD8+ T cells from melanoma patients reveals inefficient antigen processing," *Eur. J. Immunol.*, 31:2642-2651 (2001).
Bachmann et al., "In vivo vs. In vitro assays for the assessment of T- and B-cell function," *Curr. Opin. Immunol.*, 6:320-326 (1994).
Bettinotti et al., "Stringent Allele/Epitope Requirements for MART-1/Melan A Immunodominance: Implications for Peptide-Based Immunotherapy," *J. Immunol.*, 161: 877-889 (1998).
Boes et al., "Interferon y Stimulation Modulates the Proteolytic Activity and Cleavage Site Preference of 20S Mouse Proteasomes," *J. Exp. Med.*, 179: 901-909 (1994).
Brown et al., "Structural and serological simularity of MHC-linked LMP and proteasome (multicatalytic proteinase) complexes," *Nature*, 353: 355-357 (1991).

Butterfield et al., "Generation of Melanoma-Specific Cytotoxic T Lymphocytes by Dendritic Cells Tranduced with a MART-1 Adenovirus," *J. Immunol.*, 161: 5607-5613 (1998).
Carulli et al., "High Throughput Analysis of Differential Gene Expression", *J. Cellular Biochem Suppl.*, 30/31:286-96 (1998).
Chattergoon, et al., "Genetic Immunization: a new era in vaccines and immune therapeutics," *FASEB J.*, 11:753-763 (1997).
Chaux et al., "Identification of Five MAGE-A1 Epitopes Recognized by Cytolytic T Lymphocytes Obtained by in Vitro Stimulation with Dendritic Cells Transduced with MAGE-A1," *The Journal of Immunology*, 163: 2928-2936 (1999).
Cleland et al., "Design and developmental strategy", *Formulation and Delivery of Proteins and Peptides*, American Chemical Society Symposium Series, No. 567, (1994).
Davis, H. L., "Plasmid DNA expression systems for the purpose of immunization," *Current Opinion in Immunology*, 8: 635-640 (1997).
Dean et al., "Proteolysis in Mitochondrial Preparations and in Lysosomal Preparations Derived from Rat Liver", *Arch. Biochem. Biophys.*, 227:154-63 (1983).
Dean et al., "Sequence requirements for plasmid nuclear import," *Experimental Cell Research*, 253: 713-722 (1999).
DeGroot et al., "An Interactive Web Site Providing Major Histocompatibility Ligand Predictions: Application to HIV Research," *Aids Res. And Human Retrov*, 13: 529-531 (1997).
Dick et al., "Coordinated Dual Cleavages Induced by the Proteasome Regulator PA28 Lead to Dominant MHC Ligands," *Cell*, 86: 253-262 (1996).
Dick, et al., "Proteolytic Processing of Ovalbumin and ∃-galactosidase by the Proteasome to Yield Antigenic Peptides," *J. of Immunology*, 152:3884-3894 (1994).
Driscoll et al., "MHC-linked LMP gene products specifically alter peptidase activities of the proteasome," *Nature*, 365: 262-264 (1993).
Durrant, L.G., "Cancer vaccines," *Anti-cancer drugs*, 8: 727-733 (1997).
Elliot et al., "Intercellular Trafficking and Protein Delivery by a Herpesvirus Structural Protein", *Cell* 88:223-233 (1997).
Escola et al., "Characterization of a Lysozyme-Major Histocompatibility Complex Class II Molecule-loading Compartment as a Specialized Recycling Endosome in Murine B Lymphocytes", *J. Biol. Chem.* 271:27360-65 (1996).
Falk et al., "Allele-specific Motifs Revealed by Sequencing of Self-peptides Eluted from MHC Molecules", *Nature*, 351:290-296 (1991).
Fang et al., "Expression of Vaccinia E3L and K3L Genes by a Novel Recombinant Canarypox HIV Vaccine Vector Enhances HIV-1 Pseudovirion Production and Inhibits Apoptosis in Human Cells", *Virology* 291(2):272-84 (2001).
Farrar et al., "The molecular cell biology of interferon- ( and its receptor," *Annu. Rev. Immunol.*, 11: 571-611 (1993).
Fayolle et al., "Delivery of Multiple Epitopes by Recombinant Detoxified Adenylate Cyclase of *Bordetella pertussis* Induces Protective Antiviral Immunity",*J Virol* 75(16):7330-8 (2001).
Fiette et al., "Theiler's virus infection of 129Sv mice that lack the interferon α/β or interferon y receptors," *J. Exp. Med.*, 181: 2069-2076 (1995).
Firat et al., "Design of a Polyepitope Construct for the Induction of HLA-A0201-restricted HIV 1-specific CTL Responses Using HLA-A•0201 Transgenic, H-2 Class I KO Mice", *Eur J Immunol* 31(10):3064-74 (2001).
Firat et al., "H-2 Class I Knockout, HLA-A2.1-Transgenic Mice: a Versatile Animal Model for Preclinical Evaluation or Antitumor Immunotherapeutic Strategies", *Eur J Immunol* 29(10):3112-21 (1999).
Firat et al., "Use of a Lentiviral Flap Vector for Induction of CTL Immunity Against Melanoma. Perspectives for Immunotherapy", *J Gene Med*; 4(1):38-45 (2001).
Fomsgaard et al., "Induction of Cytotoxic T-cell Responses by Gene Gun DNA Vaccination with Minigenes Encoding Influenza a Virus HA and NP CTL-Epitopes", *Vaccine* 18(7-8):681-91 (2000).
Ford et al., "Protein Transduction: an Alternative to Genetic Intervention?", *Gene Ther.* 8:1-4, (2001).

Gaczynska et al., "γ-Interferon and expression of MHC genes regulate peptide hydrolysis by proteasomes," *Nature*, 365: 264-267 (1993).
Gale et al., "Evidence that hepatitis C Virus resistance to interferon is mediated through repression of the PKR protein kinase by the onostructural 5A protein," *Virology*, 230: 217-227 (1997).
Gariglio et al., "Therapeutic Uterine-Cervix Cancer Vaccines in Humans", *Arch Med Res* 29(4):279-84 (1998).
Gilbert et al., Nat. Biotech. 15:1280-1284, 1997.
Gileadi et al., "Generation of an Immunodominant CTL Epitope is Affected by Proteasome Subunit Composition and Stability of the Antigenic Protein," *Am. Assoc. of Immunol.*, 163: 6045-6052 (1999).
Glynne et al., "A proteasome-related gene between the two ABC transporter loci in the class II region of the human MHC," *Nature*, 353: 357-360 (1991).
Groettrup et al., "A role for the proteasome regulator PA28a in antigen presentation," *Nature*, 381: 166-168 (1996).
Gulukota et al., "Two complementary methods for predicting peptides binding major histocompatibility complex molecules," *J. Mol. Biol.*, 267: 1258-1267 (1997).
Gurunathan et al., "DNA vaccines: a key for inducing long-term cellular immunity," *Current Opinion in Immunology*, 12: 442-447 (2000).
Hammond et al., "Heavy Endosomes Isolated from the Rat Renal Cortex Show Attributes of Intermicrovillar Clefts", *Am. J. Physiol.* 267:F516-27 (1994).
Hanke et al., "DNA Multi-CTL Epitope Vaccines for HIV and *Plasmodium Falciparum*: Immunogenicity in Mice", *Vaccine* 16(4):426-35 (1998).
Heemskerk et al., "Enrichment of an Antigen-Specific T Cell Response by Retrovirally Transduced Human Dendritic Cells", *Cell Immunol.* 195(1):10-7 (1999).
Heim et al., "Expression of hepatitis C virus proteins inhibits signal transduction through the Jak-STAT pathway," *Journal of Virology*, 73: 8469-8475 (1999).
Hirano et al., "Expression of a Mutant ER-retained Polytope Membrane Protein in Cultured Rat Hepatocytes Results in Mallory Body Formation", *Histochem. Cell Biol.* 117(1):41-53 (2002).
Huang et al., "Immune response in mice that lack the interferon-( receptor," *Science*, 259: 1742-1745 (1993).
Hung et al., "Improving DNA Vaccine Potency by Linking Marek's Disease Virus Type I VP22 to an Antigen", *J. Virol.* 76:2676-2682 (2002).
Hypertext transfer protocol address syfpeithi.bmi-heidelberg.com/Scripts/MHCServer.dil/EpPredict.htm (Apr. 3, 2003).
Inaba et al., "Identification of Proliferating Dendritic Cell Precursors in Mouse Blood," *J. Exp. Med.* 175:1157-67 (1992).
International Search Report from co-pending Application No. PCT/US01/13806.
Jäger et al., "Granulocyte-macrophage-colony-stimulating Factor Enhances Immune Responses to Melanoma-associated Peptides in Vivo", *Int. J Cancer* 67, 54-62 (1996).
Jager et al., "Simultaneous humoral and cellular immune response against cancer-testis antigen NY-ESO-I: definition of human histocompatibility leukocyte antigen (HLA)-A2-binding Peptide Epitopes," *J. Exp. Med.*, 187: 265-270 (1998).
Kang et al., "Induction of Melanoma Reactive T Cells by Stimulator Cells Expressing Melanoma Epitope-Major Histocompatibility Complex Class I Fusion Proteins," *Cancer Res.*, 57: 202-205 (1997).
Kawakami et al., "The Use of Melanosomal Proteins in the Immunotherapy of Melanoma," *J. Immunother.*, 21:237-246 (1998).
Kawashima et al., "A Simple Procedure for the Isolation of Rat Kidney Lysosomes", *Kidney Int.* 54:275-8 (1998).
Kawashima et al., "The Multi-epitope Approach for Immunotherapy for Cancer: Identification of Several CTL Epitopes from Various Tumor-associated Antigens Expressed on Solid Epithelial Tumors", *Human Immunology* 59:1-14 (1998).
Kelly et al., "Second proteasome-related gene in the human MHC class II region," *Nature*, 353:667-668 (1991).
Kittlesen et al., "Human Melanoma Patients Recognize an HLA-AI-Restricted CTL Epitope from Tyrosinase Containing Two Cysteine Residues: Implications for Tumor Vaccine Development," *J. Immunol.*, 160: 2099-2106 (1998).

Kuby, Janis, "Cell-mediated Immunity", *Immunology* Chapter 15 (2d ed., W.H. Freeman and Company 1991).
Kündig et al., "Skin Test to Assess Virus-Specific Cytotoxic T-cell Activity," *Proc. Natl. Acad Sci. USA* 89:7757-7761 (1992).
Kundig et al., "Fibroblasts as efficient antigen-presenting cells in lymphoid organs," *Proc. Natl. Acad. Sci.*, 268:1343-1347 (1995).
Kündig et al., "On the Role of Antigen in Maintaining Cytotoxic T-cell Memory," *Proc. Natl. Acad Sci. USA* 93:9716-23 (1996).
Larregina et al., "Direct Transfection and Activation of Human Cutaneous Dendritic Cells," *Gene Ther.*, 8:608-617 (2001).
Le et al., "Cytotoxic T Cell Polyepitope Vaccines Delivered by ISCOMs", *Vaccine* 19(32):4669-75 (2001).
Lee et al., "Characterization of circulating T cells specific for tumor-associated antigens in melanoma patients," *Nature Medicine*, 5:677-685 (1999).
Leitner, et al., "DNA and RNA-based vaccines: principles, progress and prospects," *Vaccine*, 18:765-777 (2000).
Levy et al., "Using ubiquitin to follow the metabolic fate of a protein," *Proc. Natl. Acad. Sci USA*, 93: 4907-4912 (1996).
Linette et al., "In Vitro Priming with Adenovirus/gp100 Antigen-Transduced Dendritic Cells Reveals the Epitope Specificity of HLA-A*0201-Restricted CD8+ T Cells in Patients with Melanoma," *J. Immunol.*, 164: 3402-3412 (2000).
Lisman et al., "A Separation Method by Means of Alteration of Mitochondrial and Synaptosomal Sedimentation Properties", *Biochem. J.* 178:79-87 (1979).
Liu et al., "Papillomavirus Virus-like Particles for the Delivery of Multiple Cytotoxic T Cell Epitopes",. *Virology* 273(2):374-82 (2000).
Loftus et al., "Peptides Derived from Self-Proteins as Partial Agonists and Antagonists of Human CD8+ T-cell Clones Reactive to Melanoma/Melanocyte Epitope MART1(27-35)," *Cancer Res.*, 11:2433-2439 (1998).
Maksymowych et al., Invasion by *Salmonella typhimurium* Induces Increased Expression of the LMP, MECL, and PA28 Proteasome Genes and Changes in the Peptide Repertoire of HLA-B27, *Infection and Immunity*, 66:4624-4632 (1998).
Marsh, M., "Endosome and Lysosome Purification by Free-flow Electrophoresis", *Methods Cell Biol.* 31:319-34 (1989).
Martinez et al., "Homology of proteasome subunits to a major histocompatibility complex-linked LMP gene," *Nature*, 353:664-667 (1991).
Mateo et al., "An HLA-A2 polyepitope vaccine for melanoma immunotherapy," *The Journal of Immunology*, 163: 4058-4063 (1999).
McCluskie, et al., "Route and Method of Delivery of DNA Vaccine Influence Immune Response in Mice and Non-Human Primates," *Molecular Medicine*, 5:287-300 (1999).
Meister et al., "Two novel T cell epitope prediction algorithms based on MHC-binding motifs; comparison of predicted and published epitopes from Mycobacterium tuberculosis and HIV protein sequences," *Vaccine*, 13: 581-591 (1995).
Melief, C. J., *Cancerlit*, Database Accession No. 1998625858, "Towards T-cell immunotherapy of cancer," Meeting Abstract (1996).
Miconnet et al., "Amino acid identity and/or position determine the proteasomal cleavage of the HLA-A *0201-restricted peptide tumor antigen MAGE-3," *The American Society for Biochemistry and Molecular Biology, Inc.*, p. 20 (2000).
Missale et al., "HLA-A31-and HLA-Aw68-restricted Cytotoxic T cell Responses to a Single Hepatitis B Virus Nucelocapsid Epitope during Acute Viral Hepatitis," *J. Exp. Med.*, 177: 751-762 (1993).
Momburg et al., "Proteasome subunits encoded by the major histocompatilbity complex are not essential for antigen presentation," *Nature*, 360: 174-177 (1992).
Morel et al., Processing of Some Antigens by the Standard Proteasome but not by the Immunoproteasome Results in Poor Presentation by Dendritic Cells, *Immunity* 12:107-117 (2000).
Morris et al., "A Peptide Carrier for the Delivery of Biologically Active Proteins into Mammalian Cells", *Nat. Biotech.* 19:1173-1176 (2001).

Moskophidis et al., "Immunobiology of Cytotoxic T-cell escape mutants of lymphocytic choriomentingitis virus," *Journal of Virology*, 69: 7423-7429 (1995).

Murphy et al., "Higher-Dose and Less Frequent Dendritic Cell Infusions with PSMA Peptides in Hormone-Refractory Metastatic Prostate Cancer Patients," *The Prostate*, 43: 59-62 (2000).

Nakabayshi et al., "Isolation and Characterization of Chicken Liver Lysosomes", *Biochem. Int.* 16:1119-25 (1988).

NCBI Blast Accession No. NP_005502.

Noppen et al., Naturally processed and concealed HLA-A2.1-restricted epitopes from tumor-associated antigen tyrosinase-related protein-2, *Int. J. Cancer*, 87: 241-246 (2000).

Normand et al., "Particle Formation by a Conserved Domain of the Herpes Simplex Virus Protein VP22 Facilitating Protein and Nucleic Acid Delivery", *J. Biol. Chem.* 276:15042-15050 (2001).

Nussbaum et al., "Cleavage motifs of the yeast 20S proteasome β subunits deduced from digest of enolase 1," *Proc. Natl. Acad. Sci USA*, 95: 12504-12509 (1998).

Oehen et al., "Antivirally protective cytotoxic T cell memory to lymphocytic choriomeningitis virus is governed by persisting antigen," *J.Exp.Med*. 176: 1273-1281 (1992).

Oess et al., Novel Cell Permeable Motif Derived from the PreS2-domain of Hepatitis-B Virus Surface Antigens, *Gene Ther*. 7:750-758 (2000).

Ohshita et al., "Simple Preparation of Rat Brain Lysosomes and Their Proteolytic Properties", *Anal. Biochem*. 230:41-47 (1995).

Oldstone et al., "Discriminated selection among viral peptides with the appropriate anchor residues: Implications for the size of the cytotoxic T-lymphocyte repertoire and control of viral infection," *Journal of Virology*, 69: 7423-7429 (1995).

Oliveira et al., "A Genetic Immunization Adjuvant System based on BVP22-Antigen Fusion", *Hum. Gene Ther*. 12:1353-1359 (2001).

Ortiz-Navarrete et al., "Subunit of the 20S proteasome (multicatalytic proteinase) encoded by the major histocompatibility complex," *Nature*, 353: 662-664 (1991).

Overdijk et al., "Isolation of Lysosomes from Bovine Brain Tissue a New Zonal Centrifugation Technique", *Adv. Exp. Med. Biol./Enzymes of Lipid Metabolism* 101:601-10 (1978).

Palmowski et al., "Competition Between CTL Narrows the Immune Response Induced by Prime-Boost Vaccination Protocols", *J Immunol* 168(9):4391-8 (2002).

Pantaleo et al., "Evidence for rapid disappearance of initially expanded HIV-specific CD8+ T cell clones during primary HIV infection," *Proc. Natl. Acad. Sci.*, 94: 9848-9853 (1997).

Parker et al., "Scheme for Ranking Potential HLA-A2 Binding Peptides Based on Independent Binding of Individual Peptide Sidechains," *J. Immunol*. 152:163-175 (1994).

Pascolo et al., "HLA-A2.1-restricted Education and Cytolytic Activity of CD8 T Lymphocytes from β2 Microglobulin (β2m) HLA-A2.1 Monochain Transgenic H-2D$^b$ β2m Double Knockout Mice" *J. Exp. Med*. 185:2043-2051 (1997).

Perez-Diez et al., "Generation of CD8+ and CD4+ T-cell Response to Dendritic Cells Genetically Engineered to Express the MART-1/Melan-A Gene," *Cancer Res.*, 58: 5305-5309 (1998).

Preckel et al., "Impaired Immunoproteasome Assembly, and Immune Reponses in PA28-I-Mice," *Science*, 286: 2162-2165 (1999).

Puccetti et al., "Use of skin test assay to determine tumor-specific CD8+ T cell reactivity," *Eur. J. Immunol*. 24: 1446-1452 (1994).

Rammensee et al., "MHC ligands and peptide motifs: first listing," *Immunogenetics*, 41: 178-228 (1995).

Rammensee et al., "Peptide motifs: amino acids in peptide-MHC interactions," *Landes Bioscence* Austin Texas, Chapter 4: 217-369 (1997).

Rammensee et al., "SYFPEITHI: Database for MHC ligands and peptide motifs, " *Immunogenetics*, 50: 213-219 (1999).

Raz et al., "Preferential induction of a Th$_1$ immune response and inhibition of specific IgE antibody formation by plasmid DNA immunization," *Proc. Natl. Acad. Sci. USA*, 93: 5141-5145 (1996).

Reeves et al., "Retroviral Transduction of Human Dendritic Cells with a Tumor-Associated Antigen Gene," *Cancer Res.*, 56: 5672-5677(1996).

Rehermann et al., "The Cytotoxic T Lymphocyte Response to Multiple Hepatitis B Virus Polymerase Epitopes During and After Acute Viral Hepatitis," *Journal of Exp. Medicine*, 181: 1047-1058 (1995).

Remington, *The Science and Practice of Pharmacy*, Nineteenth Edition, Chapters 86-88 (1985).

Ripalti et al., "Construction of Polyepitope Fusion Antigens of Human Cytomegalovirus ppUL32: Reactivity with Human Antibodies", *J Clin Microbiol* 32(2):358-63 (1994).

Roberts et al., "Prediction of HIV Peptide Epitopes by a Novel Algorithm," *Aids Research and Human Retroviruses*, 12: 593-610 (1996).

Rock et al., "Degradation of cell proteins and the generation of MHC class I-presented peptides," *Annu. Rev. Immunol.*, 17: 739-779 (1999).

Roman et al., "Immunostimulatory DNA sequences function as T helper-1 -promoting adjuvants," *Nature Medicine*, 3: 849-854 (1997).

Rosmorduc et al., "Inhibition of interferon-inducible MxA protein expression by hepatitis B virus capsid protein," *Journal of General Virology*, 80: 1253-1262 (1999).

Ryan et al., "A model for nonstoichiometric, cotranslational protein scission in eukaryotic ribosomes," *Bioorganic Chemistry*, 27: 55-79 (1999).

Ryser et al., "The Cellular Uptake of Horseradish Peroxidase and its Poly(Lysine) Conjugate by Cultured Fibroblasts Is Qualitively Similar Despite a 900-Fold Difference in Rate", *J. Cell Physiol*. 113:167-178 (1982).

Salmi et al., "Tumor endothelium selectively supports binding of IL-2 propagated tumor-infiltrating lymphocytes," *The Journal of Immunology*, 154: 6002-6012 (1995).

Santus et al., "Osmotic Drug Delivery: A Review of the Patent Literature," *Journal of Controlled Release*, 35:1-21 (1995).

Sato et al., "Immunostimulatory DNA sequences necessary for effective intradermal gene immunization," *Science*, 273: 352-354 (1996).

Schirle et al., "Combining computer algorithms with experimental approaches permits the rapid and accurate identification of T cell epitopes from defined antigens," *Journal of Immunological Methods*, 257: 1-16 (2001).

Schmid et al., "Isolation of Functionally Distinct Endosome Subpopulations by Free-Flow Electrophoresis", *Prog. Clin. Biol. Res./Cell-Free Analysis of Membrane Traffic* 270:35-49 (1988).

Schneider, et al., "Overlapping peptides of melanocyte differentiation antigen Melan-A/MART-1 recognized by autologous cytolytic T lymphocytes in association with HLA-B45.1 and HLA-A2.1," *Int. J. Cancer*, 75(3):451-458 (1998).

Schwartz, J.J. & Zhang, S., "Peptide-mediated cellular delivery", *Curr. Opin. Mol. Ther*. 2:162-167 (2000).

Seipelt et al., "The Structures of Picornaviral Proteinases," *Virus Research* 62:159-68 (1999).

Sewell et al., "IFN-( Exposes a Cryptic Cytotoxic T Lymphocyte Epitope in HIV-1 Reverse Transcriptase," *J. Immunol.*, 162: 7075-7079 (1999).

Sheldon et al., "Loligomers: Design of de novo Peptide-based Intracellular Vehicles", *Proc. Natl. Aced. Sci. USA* 92:2056-2060 (1995).

Shen et al., "Conjugation of Poly-L-lysine to Albumin and Horseradish Peroxidase: A Novel Method of Enhancing the Cellular Uptake of Proteins", *Proc. Natl. Acad. Sci. USA* 75:1872-1876 (1978).

Sijts et al., "Efficient Generation of a Hepatitis B Virus Cytotoxic T Lymphocyte Epitope Requires the Structural Features of Imrnunoproteasomes," *Journal of Exp. Medicine*, 191: 503-513 (2000).

Smith et al., "Human Dendritic Cells Genetically Engineered to Express a Melanoma Polyepitope DNA Vaccine Induce Multiple Cytotoxic T-Cell Responses", *Clin Cancer Res*; 7(12):4253-61 (2001).

Smith, "The polyepitope approach to DNA vaccination", *Curr Opin Mol Ther* 1(1):10-5 (1999).

Speiser et al., "Self antigens expressed by solid tumors do not efficiently stimulate naive or activated T cells: implications for immunotherapy," *Journal Exp. Medicine*, 186: 645-653 (1997).

Stauss et al., "Induction of Cytotoxic T Lymphocytes with Peptides In Vitro: Identification of Candidate T-cell Epitopes in Human Papilloma," *Proc. Natl. Acad. Sci*, 89: 7871-7875 (1992).

Steinmann et al., "The Dendritic Cells System and Its Role in Immunogenicity," *Ann. Rev. Immunol.* 9:271-96 (1991).

Street et al., "Limitations of HLA-transgenic Mice in Presentation of HLA-restricted Cytotoxic T-cell Epitopes from Endogenously Processed Human Papillomavirus type 16 E7 Protein", *Immunology* 106(4):526-36 (2002).

Stromhaug et al., "Purification and Characterization of Autophagosomes from Rat Hepatocytes", *Biochem. J.* 335:217-24 (1998).

Stumiolo et al., "Generation of tissue-specific and promiscuous HLA ligand databases using DNA microarrays and virtual HLA class II matrices," *Nature Biotechnology*, 17: 555-561 (1999).

Suhrbier A, "Multi-epitope DNA Vaccines", *Immunol Cell Biol* 75(4):402-8 (1997).

Taylor et al., "Inhibition of the interferon-inducible protein kinase PKR by HCV E2 protein," *Science*, 285: 107-110 (1999).

Thomson et al., "Delivery of Multiple CD8 Cytotoxic T Cell Epitopes by DNA Vaccination", *J Immunol* 160(4):1717-23 (1998).

Thomson et al., "Minimal Epitopes Expressed in a Recombinant Polyepitope Protein are Processed and Presented to CD8 Cytotoxic T cells: Implications for Vaccine Design", *Proc Natl Acad Sci USA* 92(13):5845-9 (1995).

Thomson et al., "Recombinant Polyepitope Vaccines for the Delivery of Multiple CD8 Cytotoxic T Cell Epitopes", *J Immunol* 157(2):822-6 (1996).

Tjoa et al, "Evaluation of Phase I/II Clinical Trials in Prostate Cancer with Dendritic Cells and PSMA Peptides," *The Prostate*, 36: 39-44 (1998).

Toes et al., "Discrete Cleavage Motifs of Constitutive and Immunoproteasomes Revealed by Quantitative Analysis of Cleavage Products", *J. Exp. Med.* 194:1-12 (2001).

Toes et al., "Protective Anti-tumor Immunity Induced by Vaccination with Recombinant Adenoviruses Encoding Multiple Tumor-associated Cytotoxic T Lymphocyte Epitopes in a String-of-beads Fashion", *Proc Natl Acad Sci USA* 94(26):14660-5 (1997).

Tüeci et al., "Serological Analysis of Human Tumor Antigens: Molecular Definition and Implications," *Molecular Medicine Today* 3:342 (1997).

Twu et al., "Transcription of the human beta interferon gene is inhibited by hepatitis B virus," *Journal of Virology*, 63: 3065-3071 (1989).

Valmori et al., "Induction of Potent Antitumor CTL Responses by Recombinant Vaccinia Encoding a Melan-A Peptide Analogue," *J. Immunol.*, 164: 1125-1131 (2000).

Van den Eynde et al., "Differential Processing of Class-1-Restricted Epitopes by the Standard Proteasome and the Immunoproteasome," *Curr. Opinion in Immunol.*, 13: 147-153 (2001).

Van Kaer et al., "Altered Peptidase and Viral-Specific T Cell Response in LMP2 Mutant Mice," *Immunity* 1: 533-541 (1994).

Vitiello et al., "Comparison of Cytotoxic T lymphocyte responses induced by peptide or DNA immunization: implications on immunogenicity and irnmunodominance," *Euro. Jr. Immunol.*, 27:671-678 (1997).

Vonderheide et al., "Characterization of HLA-A3-restricted Cytotoxic T Lymphocytes Reactive Against the Widely Expressed Tumor Antigen Telomerase", *Clin Cancer Res* 7(11):3343-8 (2001).

Wang et al., "Phase I Trial of a MART-1 Peptide Vaccine with Incomplete Freund's Adjuvant for Resected High-Risk Melanoma," *Clin. Cancer Res.*, 10: 2756-2765 (1999).

Ward et al., "Development and Characterisation of Recombinant Hepatitis Delta Virus-like Particle", *Virus Genes* 23(1):97-104 (2001).

Wattiaux et al., "Isolation of Rat Liver Lysosomes by Isopycnic Centrifugation in a Metrizamide Gradient", *J. Cell Biol.* 78:349-68 (1978).

Whitton et al., "A "String-of-Beads" Vaccine, Comprising Linked Minigenes, Confers Protection from Lethal-Dose Virus Challenge", *J Virol* 67(1):348-52 (1993).

Williams et al., "Isolation of a Membrane-Associated Cathespin D-like Enzyme form the Model Antigen Presenting Cell, A20, and Its Ability to Generate Antigenic Fragments from a Protein Antigen in a Cell-Free System", *Arch. Biochem. Biophys.* 305:298-306 (1993).

Woodberry et al., "Immunogenicity of a Human Immunodeficiency Virus (HIV) Polytope Vaccine Containing Multiple HLA A2 HIV CD8 Cytotoxic T-Cell Epitopes", *J Virol* 73(7):5320-5 (1999).

Yamada et al., "A Simple Procedure for the Isolation of Highly Purified Lysosomes from Normal Rat Liver" *J. Biochem.* 95:1155-60 (1984).

Yang et al., "Proteasomes Are Regulated by Interferon (: Implications for Antigen Processing," *Proc. Natl. Acad. Sci.*, 89: 4928-4932 (1992).

Yewedell, et al., "MHC-Encoded Proteasome Subunits LMP2 and LMP7 Are Not Required for Efficient Antigen Presentation," *J. Immunology* 1994, 152:1163-1170 (1994).

Young et al., "Dendritic Cells as Adjuvants for Class I Major Histocompatibility Complex-restricted Anti-tumor Immunity, " *J Exp Med* 183:7-11 (1996).

Zajac et al., "Enhanced Generation of Cytotoxic T Lymphocytes Using Recombinant Vaccinia Virus Expressing Human Tumor-Associated Antigens and B7 Costimulatory Molecules," *Cancer Res.*, 58: 4567-4571 (1998).

Zajac et al., "Generation of Tumoricidal Cytotoxic T Lymphocytes from Healthy Donors after In Vitro Stimulation with a Replication-Incompetent Vaccinia Virus Encoding MART-1/Melan-A 27-35 Epitope," *Int. J. Cancer*, 71: 491-496 (1997).

Zhai et al., "Antigen-Specific Tumor Vaccines. Development and Characterization of Recombinant Adenoviruses Encoding MART1 or gp100 for Cancer Therapy,"*J. Immunol.*, 156: 700-710 (1996).

Zipkin, I., "Cancer vaccines," *Bio Century*, 6: A1-A6 (1998).

International Search Report re International Application No. PCT/US03/26231 Date of Mailing of International Search Report: Dec. 2, 2003.

International Search Report re International Application No. PCT/US02/35582 Date of Mailing of International Search Report: Nov. 14, 2003.

Borbulevych et al., "Increased immunogenicity of an anchor-modified tumor-associated antigen is due to the enhanced stability of the peptide/MHC complex: Implications for vaccine design," *The Journal of Immunology*, 2005, pp. 4812-4820, The American Association of Immunologists, Inc., vol. 174.

U.S. Appl. No. 10/777,053, filed Feb. 10, 2004, Simard et al.

Lim et al. *Oncogene*. 17:2013-2018 (1998).

Schadendorf et al., "Listeria Expression Vector for Immunotherapy, Particularly of Malignant Melanoma, Comprises a DNA Sequence Encoding Tumor-Associate Antigens," XP002401738, Database Geneseq Derwent; Jul. 16, 2001.

Supplementary European Search Report from European Patent Application No. 02806695.9 dated Oct. 30, 2006.

Ayyoub et al. *J. Immunol.* 168(4):1717-1722 (2002).

Kessler et al., *J Exp Med* 193, 73-88 (2001).

Office Action dated Aug. 11, 2004, from U.S. Appl. No. 10/292,413, filed Nov. 7, 2002, 5 pages.

Response to Office Action filed Sep. 10, 2004, from U.S. Appl. No. 10/292,413, filed Nov. 7, 2002, 4 pages.

Office Action dated Dec. 2, 2004, from U.S. Appl. No. 10/292,413, filed Nov. 7, 2002, 6 pages.

Response to Office Action filed Mar. 24, 2005, from U.S. Appl. No. 10/292,413, filed Nov. 7, 2002, 53 pages.

Office Action dated Oct. 11, 2005, from U.S. Appl. No. 10/292,413, filed Nov. 7, 2002, 4 pages.

Response to Office Action filed Nov. 11, 2005, from U.S. Appl. No. 10/292,413, filed Nov. 7, 2002, 6 pages.

Office Action dated Dec. 13, 2006, from U.S. Appl. No. 10/292,413, filed Nov. 7, 2002, 6 pages.

Response to Office Action dated Mar. 12, 2007, from U.S. Appl. No. 10/292,413, filed Nov. 7, 2002, 9 pages.

Office Action dated Jul. 9, 2007, from U.S. Appl. No. 10/292,413, filed Nov. 7, 2002, 15 pages.

Response to Office Action filed Jan. 9, 2008 , from U.S. Appl. No. 10/292,413, filed Nov. 7, 2002, 12 pages.

Manickan, E et al. 1997. Crit. Rev. Immunol. 17(2): 139-154.

Campbell, A. 1985. "General properties and applications of monoclonal antibodies." *Monoclonal Antibody Technology*. Chapter 1, pp. 1-32.

Clark, et al. 1994. "Identification of novel genes, SYT and SSX, involved in the t(X;18)(p11.2;q11.2) translocation found in humna synovial sarcoma." *Nature Genetics* 7(4): 502-508.

Crew, et al. 1995. "Fusion of SYT to two genes, SSX1 and SSX2, encoding proteins with homology to the Kruppel-associated box in human synovial sarcoma" *The EMBO Journal*. 14(10): 2333-2340.

Gene Therapy Advisory Committee. 2003. "Ninth Annual Report." Health Departments of the UK, 2003, pp. 1-52.

International Search Report re International Application No. PCT/US02/36098, Jan. 2004.

Kessler, et al. 2001. "Efficient Identification of Novel HLA-A*0201-presented Cytotoxic T Lymphocyte Epitopes in the Widely Expressed Tumor Antigen PRAME by Proteasome-mediated Digestion Analysis." *J.Exp. Med.* 193(1):73-78.

Lu, J. et al. 2004. "Multiepitope Trojan Antigen Peptide Vaccines for the Induction of Antitumor CTL and Th Immune Responses." *J. Immunol.* 172:4575-4582.

US 6,008,200, 12/1999, Krieg (withdrawn)

* cited by examiner

FIG. 1

Melan-A Class I HLA-A2 Epitopes

MPREDAHFIYGYPKKGHGHSYTTAEEAAGIGILTVILGVLLLIGCWYCR

RRNGYRALMDKSLHVGTQCALTRRCPQEGFDHRDSKVSLQEKNCEPVVP

NAPPAYEKLSAEQSPPPYSP (SEQ. ID NO. 2)

FIG. 2

(SEQ. ID NO. 40)

MNGDDAFARRPTVGAQIPEKIQKAFDDIAKYFSKEEWEKM

KASEKIFYVYMKRKYEAMTKLGFKATLPPFMCNKRAEDFQ

GNDLDNDPNRGNQVERPQMTFGRLQGISPKIMPKKPAEEG

NDSEEVPEASGPQNDGKELCPPPGKPTTSEKIHERSGPKRG

EHAWTHRLRERKQLVIYEEISDPEEDDE

FIG. 3

(SEQ. ID NO. 11)

MQAEGRGTGG STGDADGPGG PGIPDGPGGN AGGPGEAGAT

GGRGPRGAGA ARASGPGGGA PRGPHGGAAS GLNGCCRCGA

RGPES RLLEFYLAM PFATPMEAELARRSLAQDAPPLPVP

GVLLKEFTVSGN ILTIRLTAA DHR

QLQLSISSCLQ QLSLLMWIT QCFLPV FLAQ PPSGQRR

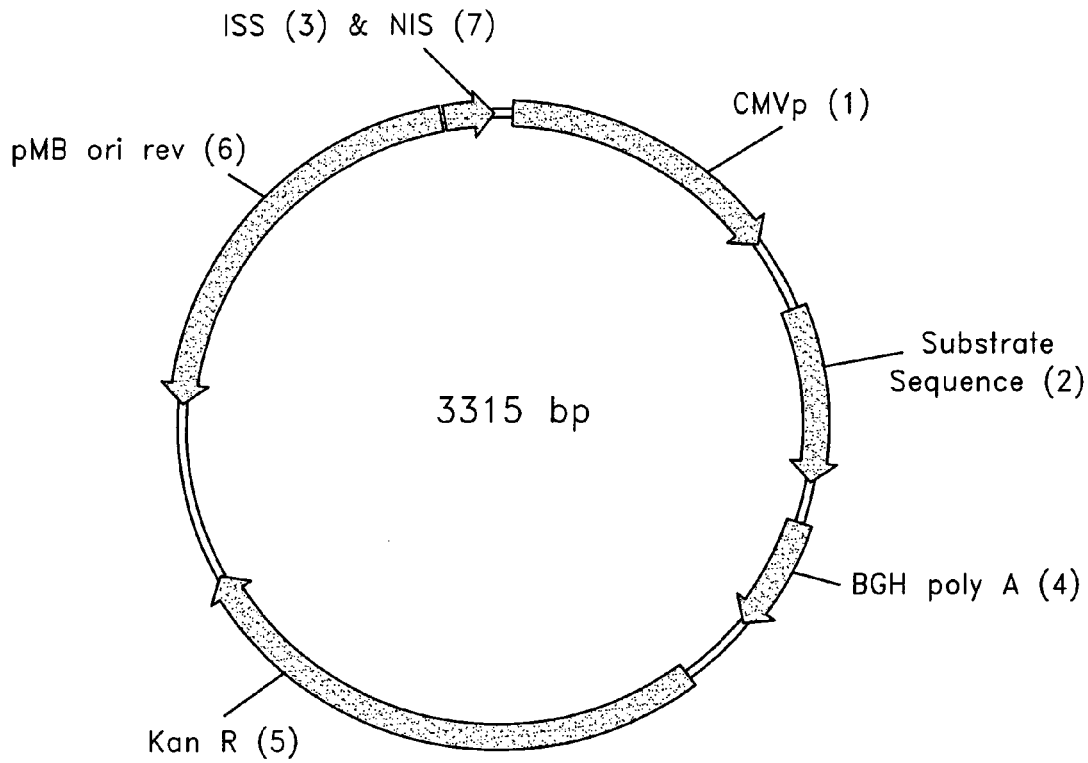

Figure Legend:

| Code in Figure | Genetic Element | Region |
| --- | --- | --- |
| 1. CMVp | Cytomeglovirus Enhancer/Promoter | 63-637 |
| 2. Substrate Sequence | Substrate Sequence Containing Epitope | 696-983 |
| 3. ISS | Immunostimulatory Sequence | 3220-3226 |
| 4. BGH poly A | Bovine Growth Hormone Polyadenylation Signal | 1028-1045 |
| 5. Kan R | Kanamycin Resistance Gene | 1431-2225 |
| 6. pMB ori rev | Bacterial pMB Origin of Replication | 3165-2492 |
| 7. NIS | Nuclear Import Sequence from Simian Virus 40-72bp repeat | 3227-3304 |

FIG. 4

(SEQ. ID NO. 22)

NY-ESO-1 150-177
(SEQ. ID NO. 12)

Cleavage sites in the NY-ESO-1 150-177 substrate upon digestion with 20S housekeeping proteasome (upper arrows) and immunoprteasome (lower arrows). The size of each arrow indicates the efficiency of cleavage as determined by pool sequencing analysis. The epitope NY-ESO-1 157-165 (SEQ ID NO. 12) is underlined.

Human Immunoproteasome Digest of SEQ ID NO. 31

(SEQ. ID NO. 31)

(SEQ. ID NO. 31)

SSX2 31-68

SEQUENCE LISTING

<160> NUMBER OF SEQ ID NOS: 986

<210> SEQ ID NO 1
<211> LENGTH: 10
<212> TYPE: PRT
<213> ORGANISM: Homo Sapien

<400> SEQUENCE: 1

Glu Leu Ala Gly Ile Gly Ile Leu Thr Val
1               5                   10

<210> SEQ ID NO 2
<211> LENGTH: 118
<212> TYPE: PRT
<213> ORGANISM: Homo Sapien

<400> SEQUENCE: 2

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
                20                  25                  30

Leu Thr Val Ile Leu Gly Val Leu Leu Ile Gly Cys Trp Tyr Cys
            35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 3
<211> LENGTH: 529
<212> TYPE: PRT
<213> ORGANISM: Homo Sapien

<400> SEQUENCE: 3

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
                20                  25                  30

Lys Glu Cys Cys Pro Pro Trp Ser Gly Asp Arg Ser Pro Cys Gly Gln
            35                  40                  45

Leu Ser Gly Arg Gly Ser Cys Gln Asn Ile Leu Leu Ser Asn Ala Pro
    50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

```
Gly Phe Asn Cys Gly Asn Cys Lys Phe Gly Phe Trp Gly Pro Asn Cys
                100                 105                 110
Thr Glu Arg Arg Leu Leu Val Arg Arg Asn Ile Phe Asp Leu Ser Ala
            115                 120                 125
Pro Glu Lys Asp Lys Phe Phe Ala Tyr Leu Thr Leu Ala Lys His Thr
        130                 135                 140
Ile Ser Ser Asp Tyr Val Ile Pro Ile Gly Thr Tyr Gly Gln Met Lys
145                 150                 155                 160
Asn Gly Ser Thr Pro Met Phe Asn Asp Ile Asn Ile Tyr Asp Leu Phe
                165                 170                 175
Val Trp Met His Tyr Tyr Val Ser Met Asp Ala Leu Leu Gly Gly Ser
            180                 185                 190
Glu Ile Trp Arg Asp Ile Asp Phe Ala His Glu Ala Pro Ala Phe Leu
        195                 200                 205
Pro Trp His Arg Leu Phe Leu Leu Arg Trp Glu Gln Glu Ile Gln Lys
        210                 215                 220
Leu Thr Gly Asp Glu Asn Phe Thr Ile Pro Tyr Trp Asp Trp Arg Asp
225                 230                 235                 240
Ala Glu Lys Cys Asp Ile Cys Thr Asp Glu Tyr Met Gly Gly Gln His
                245                 250                 255
Pro Thr Asn Pro Asn Leu Leu Ser Pro Ala Ser Phe Phe Ser Ser Trp
            260                 265                 270
Gln Ile Val Cys Ser Arg Leu Glu Glu Tyr Asn Ser His Gln Ser Leu
        275                 280                 285
Cys Asn Gly Thr Pro Glu Gly Pro Leu Arg Arg Asn Pro Gly Asn His
        290                 295                 300
Asp Lys Ser Arg Thr Pro Arg Leu Pro Ser Ser Ala Asp Val Glu Phe
305                 310                 315                 320
Cys Leu Ser Leu Thr Gln Tyr Glu Ser Gly Ser Met Asp Lys Ala Ala
                325                 330                 335
Asn Phe Ser Phe Arg Asn Thr Leu Glu Gly Phe Ala Ser Pro Leu Thr
            340                 345                 350
Gly Ile Ala Asp Ala Ser Gln Ser Ser Met His Asn Ala Leu His Ile
        355                 360                 365
Tyr Met Asn Gly Thr Met Ser Gln Val Gln Gly Ser Ala Asn Asp Pro
        370                 375                 380
Ile Phe Leu Leu His His Ala Phe Val Asp Ser Ile Phe Glu Gln Trp
385                 390                 395                 400
Leu Arg Arg His Arg Pro Leu Gln Glu Val Tyr Pro Glu Ala Asn Ala
                405                 410                 415
Pro Ile Gly His Asn Arg Glu Ser Tyr Met Val Pro Phe Ile Pro Leu
            420                 425                 430
Tyr Arg Asn Gly Asp Phe Phe Ile Ser Ser Lys Asp Leu Gly Tyr Asp
        435                 440                 445
Tyr Ser Tyr Leu Gln Asp Ser Asp Pro Asp Ser Phe Gln Asp Tyr Ile
        450                 455                 460
Lys Ser Tyr Leu Glu Gln Ala Ser Arg Ile Trp Ser Trp Leu Leu Gly
465                 470                 475                 480
Ala Ala Met Val Gly Ala Val Leu Thr Ala Leu Leu Ala Gly Leu Val
                485                 490                 495
Ser Leu Leu Cys Arg His Lys Arg Lys Gln Leu Pro Glu Glu Lys Gln
            500                 505                 510
Pro Leu Leu Met Glu Lys Glu Asp Tyr His Ser Leu Tyr Gln Ser His
        515                 520                 525
```

Leu

<210> SEQ ID NO 4
<211> LENGTH: 94
<212> TYPE: PRT
<213> ORGANISM: Artificial Sequence
<220> FEATURE:
<223> OTHER INFORMATION: expression product of chemically synthesized
      pMA2M

<400> SEQUENCE: 4

```
Met Leu Leu Ala Val Leu Tyr Cys Leu Glu Leu Ala Gly Ile Gly Ile
1               5                   10                  15

Leu Thr Val Tyr Met Asp Gly Thr Met Ser Gln Val Gly Ile Leu Thr
            20                  25                  30

Val Ile Leu Gly Val Leu Leu Leu Ile Gly Cys Trp Tyr Cys Arg Arg
        35                  40                  45

Arg Asn Gly Tyr Arg Ala Leu Met Asp Lys Ser Leu His Val Gly Thr
    50                  55                  60

Gln Cys Ala Leu Thr Arg Arg Cys Pro Gln Glu Gly Phe Asp His Arg
65                  70                  75                  80

Asp Ser Lys Val Ser Leu Gln Glu Lys Asn Cys Glu Pro Val
                85                  90
```

<210> SEQ ID NO 5
<211> LENGTH: 28
<212> TYPE: PRT
<213> ORGANISM: Artificial Sequence
<220> FEATURE:
<223> OTHER INFORMATION: chemically synthesized epitope liberation
      sequence for SEQ ID NO. 1 from pMA2M

<400> SEQUENCE: 5

```
Met Leu Leu Ala Val Leu Tyr Cys Leu Glu Leu Ala Gly Ile Gly Ile
1               5                   10                  15

Leu Thr Val Tyr Met Asp Gly Thr Met Ser Gln Val
            20                  25
```

<210> SEQ ID NO 6
<211> LENGTH: 9
<212> TYPE: PRT
<213> ORGANISM: Homo Sapien

<400> SEQUENCE: 6

```
Met Leu Leu Ala Val Leu Tyr Cys Leu
1               5
```

<210> SEQ ID NO 7
<211> LENGTH: 9
<212> TYPE: PRT
<213> ORGANISM: Homo Sapien

<400> SEQUENCE: 7

```
Tyr Met Asp Gly Thr Met Ser Gln Val
1               5
```

<210> SEQ ID NO 8
<211> LENGTH: 10
<212> TYPE: PRT
<213> ORGANISM: Homo Sapien

<400> SEQUENCE: 8

Glu Ala Ala Gly Ile Gly Ile Leu Thr Val

<210> SEQ ID NO 9
<211> LENGTH: 307
<212> TYPE: DNA
<213> ORGANISM: Artificial Sequence
<220> FEATURE:
<223> OTHER INFORMATION: insert coding region of chemically synthesized pMA2M

<400> SEQUENCE: 9

```
cttaagccac catgttacta gctgttttgt actgcctgga actagcaggg atcggcatat      60
tgacagtgta tatggatgga acaatgtccc aggtaggaat tctgacagtg atcctgggag     120
tcttactgct catcggctgt tggtattgta gaagacgaaa tggatacaga gccttgatgg     180
ataaaagtct tcatgttggc actcaatgtg ccttaacaag aagatgccca caagaagggt     240
ttgatcatcg ggacagcaaa gtgtctcttc aagagaaaaa ctgtgaacct gtgtagtgag     300
cggccgc                                                               307
```

<210> SEQ ID NO 10
<211> LENGTH: 85
<212> TYPE: PRT
<213> ORGANISM: Artificial Sequence
<220> FEATURE:
<223> OTHER INFORMATION: chemically synthesized epitope array from pVAXM2 and pVAXM1

<400> SEQUENCE: 10

Met Val Leu Tyr Cys Leu Glu Leu Ala Gly Ile Gly Ile Leu Thr Val
1               5                   10                  15
Tyr Met Asp Gly Thr Ala Val Leu Tyr Cys Leu Glu Leu Ala Gly Ile
                20                  25                  30
Gly Ile Leu Thr Val Tyr Met Asp Gly Thr Met Leu Ala Val Leu Tyr
            35                  40                  45
Cys Leu Glu Leu Ala Gly Ile Gly Ile Leu Thr Val Tyr Met Asp Gly
        50                  55                  60
Thr Met Ser Leu Leu Ala Val Leu Tyr Cys Leu Glu Leu Ala Gly Ile
65 70 75 80

Gly Ile Leu Thr Val
85

<210> SEQ ID NO 11
<211> LENGTH: 180
<212> TYPE: PRT
<213> ORGANISM: Homo Sapien

<400> SEQUENCE: 11

Met Gln Ala Glu Gly Arg Gly Thr Gly Gly Ser Thr Gly Asp Ala Asp
1 5 10 15

Gly Pro Gly Gly Pro Gly Ile Pro Asp Gly Pro Gly Gly Asn Ala Gly
20 25 30

Gly Pro Gly Glu Ala Gly Ala Thr Gly Gly Arg Gly Pro Arg Gly Ala
35 40 45

Gly Ala Ala Arg Ala Ser Gly Pro Gly Gly Gly Ala Pro Arg Gly Pro
50 55 60

His Gly Gly Ala Ala Ser Gly Leu Asn Gly Cys Cys Arg Cys Gly Ala
65 70 75 80

Arg Gly Pro Glu Ser Arg Leu Leu Glu Phe Tyr Leu Ala Met Pro Phe
85 90 95

```
Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
        180

<210> SEQ ID NO 12
<211> LENGTH: 9
<212> TYPE: PRT
<213> ORGANISM: Homo Sapien

<400> SEQUENCE: 12

Ser Leu Leu Met Trp Ile Thr Gln Cys
1               5

<210> SEQ ID NO 13
<211> LENGTH: 9
<212> TYPE: PRT
<213> ORGANISM: Homo Sapien

<400> SEQUENCE: 13

Lys Ala Ser Glu Lys Ile Phe Tyr Val
1               5

<210> SEQ ID NO 14
<211> LENGTH: 9
<212> TYPE: PRT
<213> ORGANISM: Homo Sapien

<400> SEQUENCE: 14

Thr Gln Cys Phe Leu Pro Val Phe Leu
1               5

<210> SEQ ID NO 15
<211> LENGTH: 10
<212> TYPE: PRT
<213> ORGANISM: Homo Sapien

<400> SEQUENCE: 15

Gly Leu Pro Ser Ile Pro Val His Pro Ile
1               5                   10

<210> SEQ ID NO 16
<211> LENGTH: 6
<212> TYPE: PRT
<213> ORGANISM: Homo Sapien

<400> SEQUENCE: 16

Ala Val Leu Tyr Cys Leu
1               5

<210> SEQ ID NO 17
<211> LENGTH: 123
<212> TYPE: PRT
<213> ORGANISM: Artificial Sequence
<220> FEATURE:
<223> OTHER INFORMATION: expression product of chemically synthesized
``` pN157

<400> SEQUENCE: 17

Met Ser Leu Leu Met Trp Ile Thr Gln Cys Lys Ala Ser Glu Lys Ile
1               5                   10                  15

Phe Tyr Val Arg Cys Gly Ala Arg Gly Pro Glu Ser Arg Leu Leu Glu
            20                  25                  30

Phe Tyr Leu Ala Met Pro Phe Ala Thr Pro Met Glu Ala Glu Leu Ala
        35                  40                  45

Arg Arg Ser Leu Ala Gln Asp Ala Pro Pro Leu Pro Val Pro Gly Val
    50                  55                  60

Leu Leu Lys Glu Phe Thr Val Ser Gly Asn Ile Leu Thr Ile Arg Leu
65                  70                  75                  80

Thr Ala Ala Asp His Arg Gln Leu Gln Leu Ser Ile Ser Ser Cys Leu
                85                  90                  95

Gln Gln Leu Ser Leu Leu Met Trp Ile Thr Gln Cys Phe Leu Pro Val
            100                 105                 110

Phe Leu Ala Gln Pro Pro Ser Gly Gln Arg Arg
        115                 120

<210> SEQ ID NO 18
<211> LENGTH: 19
<212> TYPE: PRT
<213> ORGANISM: Artificial Sequence
<220> FEATURE:
<223> OTHER INFORMATION: chemically synthesized epitope liberation
      sequence for SEQ ID NO. 12 from pN157

<400> SEQUENCE: 18

Met Ser Leu Leu Met Trp Ile Thr Gln Cys Lys Ala Ser Glu Lys Ile
1               5                   10                  15

Phe Tyr Val

<210> SEQ ID NO 19
<211> LENGTH: 392
<212> TYPE: DNA
<213> ORGANISM: Artificial Sequence
<220> FEATURE:
<223> OTHER INFORMATION: insert coding region of chemically synthesized
      pN157

<400> SEQUENCE: 19
cttaagccac catgtccctg ttgatgtgga tcacgcagtg caaagcttcg gagaaaatct     60
tctacgtacg gtgcggtgcc aggggggccgg agagccgcct gcttgagttc tacctcgcca   120
tgcctttcgc gacacccatg gaagcagagc tggcccgcag gagcctggcc caggatgccc   180
caccgcttcc cgtgccaggg gtgcttctga aggagttcac tgtgtccggc aacatactga   240
ctatccgact gactgctgca gaccaccgcc aactgcagct ctccatcagc tcctgtctcc   300
agcagctttc cctgttgatg tggatcacgc agtgcttcct gcccgtgttt ttggctcagc   360
ctccctcagg gcagaggcgc tagtgagaat tc                                  392

<210> SEQ ID NO 20
<211> LENGTH: 179
<212> TYPE: PRT
<213> ORGANISM: Artificial Sequence
<220> FEATURE:
<223> OTHER INFORMATION: expression product of chemically synthesized
      pBPL

<400> SEQUENCE: 20

```
Met Ser Leu Leu Met Trp Ile Thr Gln Cys Lys Ala Ser Glu Lys Ile
1               5                   10                  15

Phe Tyr Val Gly Leu Pro Ser Ile Pro Val His Pro Ile Gly Leu Pro
                20                  25                  30

Ser Ile Pro Val His Pro Ile Lys Ala Ser Glu Lys Ile Phe Tyr Val
            35                  40                  45

Ser Leu Leu Met Trp Ile Thr Gln Cys Lys Ala Ser Glu Lys Ile Phe
50                      55                  60

Tyr Val Lys Ala Ser Glu Lys Ile Phe Tyr Val Arg Cys Gly Ala Arg
65                  70                  75                  80

Gly Pro Glu Ser Arg Leu Leu Gly Phe Tyr Leu Ala Met Pro Phe Ala
                85                  90                  95

Thr Pro Met Glu Ala Glu Leu Ala Arg Arg Ser Leu Ala Gln Asp Ala
            100                 105                 110

Pro Pro Leu Pro Val Pro Gly Val Leu Leu Lys Glu Phe Thr Val Ser
                115                 120                 125

Gly Asn Ile Leu Thr Ile Arg Leu Thr Ala Ala Asp His Arg Gln Leu
    130                 135                 140

Gln Leu Ser Ile Ser Ser Cys Leu Gln Gln Leu Ser Leu Leu Met Trp
145                 150                 155                 160

Ile Thr Gln Cys Phe Leu Pro Val Phe Leu Ala Gln Pro Pro Ser Gly
                165                 170                 175

Gln Arg Arg

<210> SEQ ID NO 21
<211> LENGTH: 543
<212> TYPE: DNA
<213> ORGANISM: Artificial Sequence
<220> FEATURE:
<223> OTHER INFORMATION: insert coding region of chemically synthesized
      pBPL

<400> SEQUENCE: 21
atgtccctgt tgatgtggat cacgcagtgc aaagcttcgg agaaaatctt ctatgtgggt      60
cttccaagta ttcctgttca tccaattggt cttccaagta ttcctgttca tccaattaaa     120
gcttcggaga aaatcttcta tgtgtccctg ttgatgtgga tcacgcagtg caaagcttcg     180
gagaaaatct tctatgtgaa agcttcggag aaaatcttct acgtacggtg cggtgccagg     240
gggccggaga gccgcctgct tgagttctac ctcgccatgc ctttcgcgac acccatggaa     300
gcagagctgg cccgcaggag cctggcccag gatgccccac gcttcccgt gccaggggtg      360 cttctgaagg agttcactgt gtccggcaac atactgacta tccgactgac tgctgcagac     420
caccgccaac tgcagctctc catcagctcc tgtctccagc agctttccct gttgatgtgg     480
atcacgcagt gctttctgcc cgtgtttttg gctcagcctc cctcagggca gaggcgctag     540
tga                                                                    543

<210> SEQ ID NO 22
<211> LENGTH: 29
<212> TYPE: PRT
<213> ORGANISM: Artificial Sequence
<220> FEATURE:
<223> OTHER INFORMATION: chemically synthesized liberation sequence for
      SEQ ID NO. 22

<400> SEQUENCE: 22

Ile Lys Ala Ser Glu Lys Ile Phe Tyr Val Ser Leu Leu Met Trp Ile
1               5                   10                  15
```

```
Thr Gln Cys Lys Ala Ser Glu Lys Ile Phe Tyr Val Lys
        20                  25

<210> SEQ ID NO 23
<211> LENGTH: 9
<212> TYPE: PRT
<213> ORGANISM: Homo Sapien

<400> SEQUENCE: 23

Val Met Thr Lys Leu Gly Phe Lys Val
1               5

<210> SEQ ID NO 24
<211> LENGTH: 10
<212> TYPE: PRT
<213> ORGANISM: Homo Sapien

<400> SEQUENCE: 24

Arg Gln Ile Tyr Val Ala Ala Phe Thr Val
1               5                   10

<210> SEQ ID NO 25
<211> LENGTH: 169
<212> TYPE: PRT
<213> ORGANISM: Homo Sapien

<400> SEQUENCE: 25

Ala Gln Ile Pro Glu Lys Ile Gln Lys Ala Phe Asp Asp Ile Ala Lys
1               5                   10                  15

Tyr Phe Ser Lys Glu Glu Trp Glu Lys Met Lys Ala Ser Glu Lys Ile
            20                  25                  30

Phe Tyr Val Tyr Met Lys Arg Lys Tyr Glu Ala Met Thr Lys Leu Gly
        35                  40                  45

Phe Lys Ala Thr Leu Pro Pro Phe Met Cys Asn Lys Arg Ala Glu Asp
    50                  55                  60

Phe Gln Gly Asn Asp Leu Asp Asn Asp Pro Asn Arg Gly Asn Gln Val
65                  70                  75                  80

Glu Arg Pro Gln Met Thr Phe Gly Arg Leu Gln Gly Ile Ser Pro Lys
                85                  90                  95

Ile Met Pro Lys Lys Pro Ala Glu Glu Gly Asn Asp Ser Glu Glu Val
            100                 105                 110

Pro Glu Ala Ser Gly Pro Gln Asn Asp Gly Lys Glu Leu Cys Pro Pro
        115                 120                 125

Gly Lys Pro Thr Thr Ser Glu Lys Ile His Glu Arg Ser Gly Pro Lys
    130                 135                 140

Arg Gly Glu His Ala Trp Thr His Arg Leu Arg Glu Arg Lys Gln Leu
145                 150                 155                 160

Val Ile Tyr Glu Glu Ile Ser Asp Pro
                165

<210> SEQ ID NO 26
<211> LENGTH: 245
<212> TYPE: PRT
<213> ORGANISM: Artificial Sequence
<220> FEATURE:
<223> OTHER INFORMATION: expression product of chemically synthesized
      CTLS1/pCBP

<400> SEQUENCE: 26

Met Val Met Thr Lys Leu Gly Phe Lys Val Lys Ala Ser Glu Lys Ile
1               5                   10                  15
```

```
Phe Tyr Val Arg Gln Ile Tyr Val Ala Ala Phe Thr Val Gly Leu Pro
             20                  25                  30

Ser Ile Pro Val His Pro Ile Thr Gln Cys Phe Leu Pro Val Phe Leu
         35                  40                  45

Val Met Thr Lys Leu Gly Phe Lys Val Arg Gln Ile Tyr Val Ala Ala
 50                  55                  60

Phe Thr Val Lys Ala Ser Glu Lys Ile Phe Tyr Val Ala Gln Ile Pro
 65                  70                  75                  80

Glu Lys Ile Gln Lys Ala Phe Asp Asp Ile Ala Lys Tyr Phe Ser Lys
                 85                  90                  95

Glu Glu Trp Glu Lys Met Lys Ala Ser Glu Lys Ile Phe Tyr Val Tyr
            100                 105                 110

Met Lys Arg Lys Tyr Glu Ala Met Thr Lys Leu Gly Phe Lys Ala Thr
        115                 120                 125

Leu Pro Pro Phe Met Cys Asn Lys Arg Ala Glu Asp Phe Gln Gly Asn
    130                 135                 140

Asp Leu Asp Asn Asp Pro Asn Arg Gly Asn Gln Val Glu Arg Pro Gln
145                 150                 155                 160

Met Thr Phe Gly Arg Leu Gln Gly Ile Ser Pro Lys Ile Met Pro Lys
                165                 170                 175

Lys Pro Ala Glu Glu Gly Asn Asp Ser Glu Glu Val Pro Glu Ala Ser
            180                 185                 190

Gly Pro Gln Asn Asp Gly Lys Glu Leu Cys Pro Pro Gly Lys Pro Thr
        195                 200                 205

Thr Ser Glu Lys Ile His Glu Arg Ser Gly Pro Lys Arg Gly Glu His
    210                 215                 220

Ala Trp Thr His Arg Leu Arg Glu Arg Lys Gln Leu Val Ile Tyr Glu
225                 230                 235                 240

Glu Ile Ser Asp Pro
                245

<210> SEQ ID NO 27
<211> LENGTH: 245
<212> TYPE: PRT
<213> ORGANISM: Artificial Sequence
<220> FEATURE:
<223> OTHER INFORMATION: expression product of chemically synthesized
      CTLS2

<400> SEQUENCE: 27

Met Ala Gln Ile Pro Glu Lys Ile Gln Lys Ala Phe Asp Asp Ile Ala
 1               5                  10                  15

Lys Tyr Phe Ser Lys Glu Glu Trp Glu Lys Met Lys Ala Ser Glu Lys
             20                  25                  30

Ile Phe Tyr Val Tyr Met Lys Arg Lys Tyr Glu Ala Met Thr Lys Leu
         35                  40                  45

Gly Phe Lys Ala Thr Leu Pro Pro Phe Met Cys Asn Lys Arg Ala Glu
 50                  55                  60

Asp Phe Gln Gly Asn Asp Leu Asp Asn Asp Pro Asn Arg Gly Asn Gln
 65                  70                  75                  80

Val Glu Arg Pro Gln Met Thr Phe Gly Arg Leu Gln Gly Ile Ser Pro
                 85                  90                  95

Lys Ile Met Pro Lys Lys Pro Ala Glu Glu Gly Asn Asp Ser Glu Glu
            100                 105                 110

Val Pro Glu Ala Ser Gly Pro Gln Asn Asp Gly Lys Glu Leu Cys Pro
        115                 120                 125
```

```
Pro Gly Lys Pro Thr Thr Ser Glu Lys Ile His Glu Arg Ser Gly Pro
            130                 135                 140

Lys Arg Gly Glu His Ala Trp Thr His Arg Leu Arg Glu Arg Lys Gln
145                 150                 155                 160

Leu Val Ile Tyr Glu Glu Ile Ser Asp Pro Val Met Thr Lys Leu Gly
                165                 170                 175

Phe Lys Val Lys Ala Ser Glu Lys Ile Phe Tyr Val Arg Gln Ile Tyr
                180                 185                 190

Val Ala Ala Phe Thr Val Gly Leu Pro Ser Ile Pro Val His Pro Ile
            195                 200                 205

Thr Gln Cys Phe Leu Pro Val Phe Leu Val Met Thr Lys Leu Gly Phe
210                 215                 220

Lys Val Arg Gln Ile Tyr Val Ala Ala Phe Thr Val Lys Ala Ser Glu
225                 230                 235                 240

Lys Ile Phe Tyr Val
                245

<210> SEQ ID NO 28
<211> LENGTH: 208
<212> TYPE: PRT
<213> ORGANISM: Artificial Sequence
<220> FEATURE:
<223> OTHER INFORMATION: expression product of chemically synthesized
      CTLS3

<400> SEQUENCE: 28

Met Val Met Thr Lys Leu Gly Phe Lys Val Lys Ala Ser Glu Lys Ile
1               5                   10                  15

Phe Tyr Val Arg Gln Ile Tyr Val Ala Ala Phe Thr Val Gly Leu Pro
                20                  25                  30

Ser Ile Pro Val His Pro Ile Ala Gln Ile Pro Glu Lys Ile Gln Lys
            35                  40                  45

Ala Phe Asp Asp Ile Ala Lys Tyr Phe Ser Lys Glu Glu Trp Glu Lys
50                  55                  60

Met Lys Ala Ser Glu Lys Ile Phe Tyr Val Tyr Met Lys Arg Lys Tyr
65                  70                  75                  80

Glu Ala Met Thr Lys Leu Gly Phe Lys Ala Thr Leu Pro Pro Phe Met
                85                  90                  95

Cys Asn Lys Arg Ala Glu Asp Phe Gln Gly Asn Asp Leu Asp Asn Asp
                100                 105                 110

Pro Asn Arg Gly Asn Gln Val Glu Arg Pro Gln Met Thr Phe Gly Arg
            115                 120                 125

Leu Gln Gly Ile Ser Pro Lys Ile Met Pro Lys Lys Pro Ala Glu Glu
130                 135                 140

Gly Asn Asp Ser Glu Glu Val Pro Glu Ala Ser Gly Pro Gln Asn Asp
145                 150                 155                 160

Gly Lys Glu Leu Cys Pro Pro Gly Lys Pro Thr Thr Ser Glu Lys Ile
                165                 170                 175

His Glu Arg Ser Gly Pro Lys Arg Gly Glu His Ala Trp Thr His Arg
            180                 185                 190

Leu Arg Glu Arg Lys Gln Leu Val Ile Tyr Glu Glu Ile Ser Asp Pro
        195                 200                 205

<210> SEQ ID NO 29
<211> LENGTH: 207
<212> TYPE: PRT
<213> ORGANISM: Artificial Sequence
<220> FEATURE:
```

<223> OTHER INFORMATION: expression product of chemically synthesized
      CTLS4

<400> SEQUENCE: 29

```
Met Ala Gln Ile Pro Glu Lys Ile Gln Lys Ala Phe Asp Asp Ile Ala
1               5                   10                  15

Lys Tyr Phe Ser Lys Glu Glu Trp Glu Lys Met Lys Ala Ser Glu Lys
            20                  25                  30

Ile Phe Tyr Val Tyr Met Lys Arg Lys Tyr Glu Ala Met Thr Lys Leu
        35                  40                  45

Gly Phe Lys Ala Thr Leu Pro Pro Phe Met Cys Asn Lys Arg Ala Glu
    50                  55                  60

Asp Phe Gln Gly Asn Asp Leu Asp Asn Asp Pro Asn Arg Gly Asn Gln
65                  70                  75                  80

Val Glu Arg Pro Gln Met Thr Phe Gly Arg Leu Gln Gly Ile Ser Pro
                85                  90                  95

Lys Ile Met Pro Lys Lys Pro Ala Glu Glu Gly Asn Asp Ser Glu Glu
            100                 105                 110

Val Pro Glu Ala Ser Gly Pro Gln Asn Asp Gly Lys Glu Leu Cys Pro
        115                 120                 125

Pro Gly Lys Pro Thr Thr Ser Glu Lys Ile His Glu Arg Ser Gly Pro
    130                 135                 140

Lys Arg Gly Glu His Ala Trp Thr His Arg Leu Arg Glu Arg Lys Gln
145                 150                 155                 160

Leu Val Ile Tyr Glu Glu Ile Ser Asp Pro Thr Gln Cys Phe Leu Pro
                165                 170                 175

Val Phe Leu Val Met Thr Lys Leu Gly Phe Lys Val Arg Gln Ile Tyr
            180                 185                 190

Val Ala Ala Phe Thr Val Lys Ala Ser Glu Lys Ile Phe Tyr Val
        195                 200                 205
```

<210> SEQ ID NO 30
<211> LENGTH: 741
<212> TYPE: DNA
<213> ORGANISM: Artificial Sequence
<220> FEATURE:
<223> OTHER INFORMATION: insert coding region of chemically synthesized
      pCBP

<400> SEQUENCE: 30

| | | |
|---|---|---|
| atggtcatga ctaaactagg tttcaaggtc aaagcttcgg agaaaatctt ctatgtgaga | 60 |
| cagatttatg ttgcagcctt cacagtgggt cttccaagta ttcctgttca tccaattacg | 120 |
| cagtgctttc tgcccgtgtt tttggtcatg actaaactag gtttcaaggt cagacagatt | 180 |
| tatgttgcag ccttcacagt gaaagcttcg gagaaaatct tctacgtagc tcaaatacca | 240 |
| gagaagatcc aaaaggcctt cgatgatatt gccaaatact ctctaaggaa agagtgggaa | 300 |
| aagatgaaag cctcggagaa aatcttctat gtgtatatga gagaaagta tgaggctatg | 360 |
| actaaactag gtttcaaggc caccctccca cctttcatgt gtaataaacg ggccgaagac | 420 |
| ttccagggga tgatttgga taatgaccct aaccgtggga tcaggttga acgtcctcag | 480 |
| atgactttcg gcaggctcca gggaatctcc ccgaagatca tgcccaagaa gccagcagag | 540 |
| gaaggaaatg attcggagga agtgccagaa gcatctggcc cacaaaatga tgggaaagag | 600 |
| ctgtgccccc cgggaaaacc aactacctct gagaagattc acgagagatc tggacccaaa | 660 |
| agggggaac atgcctggac ccacagactg cgtgagagaa acagctggt gatttatgaa | 720 |
| gagatcagcg acccttagtg a | 741 |

<210> SEQ ID NO 31
<211> LENGTH: 28
<212> TYPE: PRT
<213> ORGANISM: Artificial Sequence
<220> FEATURE:
<223> OTHER INFORMATION: chemically synthesized CTLS11-2
      liberation/substrate sequence

<400> SEQUENCE: 31

Arg Gln Ile Tyr Val Ala Ala Phe Thr Val Lys Ala Ser Glu Lys Ile
1               5                   10                  15

Phe Tyr Val Ala Gln Ile Pro Glu Lys Ile Gln Lys
            20                  25

<210> SEQ ID NO 32
<211> LENGTH: 9
<212> TYPE: PRT
<213> ORGANISM: Homo Sapien

<400> SEQUENCE: 32

Phe Leu Pro Trp His Arg Leu Phe Leu
1               5

<210> SEQ ID NO 33
<211> LENGTH: 104
<212> TYPE: PRT
<213> ORGANISM: Artificial Sequence
<220> FEATURE:
<223> OTHER INFORMATION: expression product of chemically synthesized
      CTLT2/pMEL

<400> SEQUENCE: 33

Met Leu Leu Ala Val Leu Tyr Cys Leu Leu Trp Ser Phe Gln Thr Ser
1               5                   10                  15

Ala Phe Leu Pro Trp His Arg Leu Phe Leu Met Leu Leu Ala Val Leu
            20                  25                  30

Tyr Cys Leu Leu Trp Ser Phe Gln Thr Ser Ala Phe Leu Pro Trp His
        35                  40                  45

Arg Leu Phe Leu Met Leu Leu Ala Val Leu Tyr Cys Leu Leu Trp Ser
    50                  55                  60

Phe Gln Thr Ser Ala Phe Leu Pro Trp His Arg Leu Phe Leu Met Leu
65                  70                  75                  80

Leu Ala Val Leu Tyr Cys Leu Leu Trp Ser Phe Gln Thr Ser Ala Phe
                85                  90                  95

Leu Pro Trp His Arg Leu Phe Leu
            100

<210> SEQ ID NO 34
<211> LENGTH: 318
<212> TYPE: DNA
<213> ORGANISM: Artificial Sequence
<220> FEATURE:
<223> OTHER INFORMATION: chemically synthesized CTLT2/pMEL insert coding
      region

<400> SEQUENCE: 34
atgctcctgg ctgttttgta ctgcctgctg tggagtttcc agacctccgc ttttctgcct      60
tggcatagac tcttcttgat gctcctggct gttttgtact gcctgctgtg gagtttccag     120
acctccgctt ttctgcctyg gcatagactc ttcttgatgc tcctggctgt tttgtactgc     180
ctgctgtgga gtttccagac ctccgctttt ctgccttggc atagactctt cttgatgctc     240

| | |
|---|---|
| ctggctgttt tgtactgcct gctgtggagt ttccagacct ccgcttttct gccttggcat | 300 |
| agactcttct tgtagtga | 318 |

<210> SEQ ID NO 35
<211> LENGTH: 1524
<212> TYPE: DNA
<213> ORGANISM: Homo Sapien

<400> SEQUENCE: 35

| | |
|---|---|
| agcagacaga ggactctcat taaggaaggt gtcctgtgcc ctgaccctac aagatgccaa | 60 |
| gagaagatgc tcacttcatc tatggttacc ccaagaaggg gcacggccac tcttacacca | 120 |
| cggctgaaga ggccgctggg atcggcatcc tgacagtgat cctgggagtc ttactgctca | 180 |
| tcggctgttg gtattgtaga agacgaaatg gatacagagc cttgatggat aaaagtcttc | 240 |
| atgttggcac tcaatgtgcc ttaacaagaa gatgcccaca agaagggttt gatcatcggg | 300 |
| acagcaaagt gtctcttcaa gagaaaaact gtgaacctgt ggttcccaat gctccacctg | 360 |
| cttatgagaa actctctgca gaacagtcac caccaccta ttcaccttaa gagccagcga | 420 |
| gacacctgag acatgctgaa attatttctc tcacactttt gcttgaattt aatacagaca | 480 |
| tctaatgttc tcctttggaa tggtgtagga aaaatgcaag ccatctctaa taataagtca | 540 |
| gtgttaaaat tttagtaggt ccgctagcag tactaatcat gtgaggaaat gatgagaaat | 600 |
| attaaattgg gaaaactcca tcaataaatg ttgcaatgca tgatactatc tgtgccagag | 660 |
| gtaatgttag taaatccatg gtgttatttt ctgagagaca gaattcaagt gggtattctg | 720 |
| gggccatcca atttctcttt acttgaaatt tggctaataa caaactagtc aggttttcga | 780 |
| accttgaccg acatgaactg tacacagaat tgttccagta ctatggagtg ctcacaaagg | 840 |
| atactttttac aggttaagac aaaggggttga ctggcctatt tatctgatca agaacatgtc | 900 |
| agcaatgtct ctttgtgctc taaaattcta ttatactaca ataatatatt gtaaagatcc | 960 |
| tatagctctt ttttttgag atggagtttc gcttttgttg cccaggctgg agtgcaatgg | 1020 |
| cgcgatcttg gctcaccata acctccgcct cccaggttca agcaattctc ctgccttagc | 1080 |
| ctcctgagta gctgggatta caggcgtgcg ccactatgcc tgactaattt tgtagtttta | 1140 |
| gtagagacgg ggtttctcca tgttggtcag gctggtctca aactcctgac ctcaggtgat | 1200 |
| ctgcccgcct cagcctccca agtgctgga attacaggcg tgagccacca cgcctggctg | 1260 |
| gatcctatat cttaggtaag acatataacg cagtctaatt acatttcact tcaaggctca | 1320 |
| atgctattct aactaatgac aagtattttc tactaaacca gaaattggta gaaggattta | 1380 |
| aataagtaaa agctactatg tactgcctta gtgctgatgc ctgtgtactg ccttaaatgt | 1440 |
| acctatggca atttagctct cttgggttcc caaatccctc tcacaagaat gtgcagaaga | 1500 |
| aatcataaag gatcagagat tctg | 1524 |

<210> SEQ ID NO 36
<211> LENGTH: 1964
<212> TYPE: DNA
<213> ORGANISM: Homo Sapien

<400> SEQUENCE: 36

| | |
|---|---|
| atcactgtag tagtagctgg aaagagaaat ctgtgactcc aattagccag ttcctgcaga | 60 |
| ccttgtgagg actagaggaa gaatgctcct ggctgttttg tactgcctgc tgtggagttt | 120 |
| ccagacctcc gctggccatt tccctagagc ctgtgtctcc tctaagaacc tgatggagaa | 180 |
| ggaatgctgt ccaccgtgga gcggggacag gagtccctgt ggccagcttt caggcagagg | 240 |

-continued

| | | |
|---|---|---|
| ttcctgtcag aatatccttc tgtccaatgc accacttggg cctcaatttc ccttcacagg | 300 | |
| ggtggatgac cgggagtcgt ggccttccgt cttttataat aggacctgcc agtgctctgg | 360 | |
| caacttcatg ggattcaact gtggaaactg caagtttggc ttttggggac caaactgcac | 420 | |
| agagagacga ctcttggtga gaagaaacat cttcgatttg agtgcccag agaaggacaa | 480 | |
| attttttgcc tacctcactt tagcaaagca taccatcagc tcagactatg tcatccccat | 540 | |
| agggacctat ggccaaatga aaatggatc aacacccatg tttaacgaca tcaatattta | 600 | |
| tgacctcttt gtctggatgc attattatgt gtcaatggat gcactgcttg ggggatctga | 660 | |
| aatctggaga gacattgatt ttgcccatga agcaccagct tttctgcctt ggcatagact | 720 | |
| cttcttgttg cggtgggaac aagaaatcca gaagctgaca ggagatgaaa acttcactat | 780 | |
| tccatattgg gactggcggg atgcagaaaa gtgtgacatt tgcacagatg agtacatggg | 840 | |
| aggtcagcac cccacaaatc ctaacttact cagcccagca tcattcttct cctcttggca | 900 | |
| gattgtctgt agccgattgg aggagtacaa cagccatcag tctttatgca atggaacgcc | 960 | |
| cgagggacct ttacggcgta atcctggaaa ccatgacaaa tccagaaccc caaggctccc | 1020 | |
| ctcttcagct gatgtagaat tttgcctgag tttgacccaa tatgaatctg gttccatgga | 1080 | |
| taaagctgcc aatttcagct ttagaaatac actggaagga tttgctagtc cacttactgg | 1140 | |
| gatagcggat gcctctcaaa gcagcatgca caatgccttg cacatctata tgaatggaac | 1200 | |
| aatgtcccag gtacagggat ctgccaacga tcctatcttc cttcttcacc atgcatttgt | 1260 | |
| tgacagtatt tttgagcagt ggctccgaag gcaccgtcct cttcaagaag tttatccaga | 1320 | |
| agccaatgca cccattggac ataaccggga atcctacatg gttccttta taccactgta | 1380 | |
| cagaaatggt gatttcttta tttcatccaa agatctgggc tatgactata gctatctaca | 1440 | |
| agattcagac ccagactctt ttcaagacta cattaagtcc tatttggaac aagcgagtcg | 1500 | |
| gatctggtca tggctccttg gggcggcgat ggtaggggcc gtcctcactg ccctgctggc | 1560 | |
| agggcttgtg agcttgctgt gtcgtcacaa gagaaagcag cttcctgaag aaaagcagcc | 1620 | |
| actcctcatg gagaaagagg attaccacag cttgtatcag agccatttat aaaaggctta | 1680 | |
| ggcaatagag tagggccaaa aagcctgacc tcactctaac tcaaagtaat gtccaggttc | 1740 | |
| ccagagaata tctgctggta tttttctgta aagaccattt gcaaaattgt aacctaatac | 1800 | |
| aaagtgtagc cttcttccaa ctcaggtaga acacacctgt ctttgtcttg ctgttttcac | 1860 | |
| tcagcccttt taacattttc ccctaagccc atatgtctaa ggaaaggatg ctatttggta | 1920 | |
| atgaggaact gttatttgta tgtgaattaa agtgctctta tttt | 1964 | |

<210> SEQ ID NO 37
<211> LENGTH: 752
<212> TYPE: DNA
<213> ORGANISM: Homo Sapien

<400> SEQUENCE: 37

| | | |
|---|---|---|
| atcctcgtgg gccctgacct tctctctgag agccgggcag aggctccgga gccatgcagg | 60 | |
| ccgaaggccg gggcacaggg ggttcgacgg gcgatgctga tggcccagga ggccctggca | 120 | |
| ttcctgatgg cccaggggc aatgctggcg gcccaggaga ggcgggtgcc acgggcggca | 180 | |
| gaggtccccg gggcgcaggg gcagcaaggg cctcggggcc gggaggaggc gccccgcggg | 240 | |
| gtccgcatgg cggcgcggct tcagggctga atggatgctg cagatgcggg gccaggggc | 300 | |
| cggagagccg cctgcttgag ttctacctcg ccatgccttt cgcgacaccc atggaagcag | 360 | |
| agctggcccg caggagcctg gcccaggatg ccccaccgct tcccgtgcca gggtgcttc | 420 | |

-continued

```
tgaaggagtt cactgtgtcc ggcaacatac tgactatccg actgactgct gcagaccacc    480
gccaactgca gctctccatc agctcctgtc tccagcagct ttccctgttg atgtggatca    540
cgcagtgctt tctgcccgtg tttttggctc agcctccctc agggcagagg cgctaagccc    600
agcctggcgc cccttcctag gtcatgcctc ctcccctagg gaatggtccc agcacgagtg    660
gccagttcat tgtgggggcc tgattgtttg tcgctggagg aggacggctt acatgtttgt    720
ttctgtagaa aataaaactg agctacgaaa aa                                  752
```

<210> SEQ ID NO 38
<211> LENGTH: 750
<212> TYPE: PRT
<213> ORGANISM: Homo Sapien

<400> SEQUENCE: 38

```
Met Trp Asn Leu Leu His Glu Thr Asp Ser Ala Val Ala Thr Ala Arg
 1               5                  10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
             35                  40                  45

Ala Thr Asn Ile Thr Pro Lys His Asn Met Lys Ala Phe Leu Asp Glu
         50                  55                  60

Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320
```

```
Gly Ser Leu Lys Val Pro Tyr Asn Val Gly Pro Phe Thr Gly Asn
            325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
            450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
            485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
            565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
            725                 730                 735

Phe Thr Val Gln Ala Ala Ala Glu Thr Leu Ser Glu Val Ala
            740                 745                 750
```

<210> SEQ ID NO 39
<211> LENGTH: 2653
<212> TYPE: DNA
<213> ORGANISM: Homo Sapien

<400> SEQUENCE: 39

| | | | | | |
|---|---|---|---|---|---|
| ctcaaaaggg | gccggatttc | cttctcctgg | aggcagatgt | tgcctctctc | tctcgctcgg | 60 |
| attggttcag | tgcactctag | aaacactgct | gtggtggaga | aactggaccc | caggtctgga | 120 |
| gcgaattcca | gcctgcaggg | ctgataagcg | aggcattagt | gagattgaga | gagactttac | 180 |
| cccgccgtgg | tggttggagg | gcgcgcagta | gagcagcagc | acaggcgcgg | gtcccgggag | 240 |
| gccggctctg | ctcgcgccga | gatgtggaat | ctccttcacg | aaaccgactc | ggctgtggcc | 300 |
| accgcgcgcc | gcccgcgctg | gctgtgcgct | ggggcgctgg | tgctggcggg | tggcttcttt | 360 |
| ctcctcggct | tcctcttcgg | gtggtttata | aaatcctcca | atgaagctac | taacattact | 420 |
| ccaaagcata | atatgaaagc | attttttggat | gaattgaaag | ctgagaacat | caagaagttc | 480 |
| ttatataatt | ttacacagat | accacattta | gcaggaacag | aacaaaactt | tcagcttgca | 540 |
| aagcaaattc | aatcccagtg | gaaagaattt | ggcctggatt | ctgttgagct | agcacattat | 600 |
| gatgtcctgt | tgtcctaccc | aaataagact | catcccaact | acatctcaat | aattaatgaa | 660 |
| gatgaaaatg | agattttcaa | cacatcatta | tttgaaccac | ctcctccagg | atatgaaaat | 720 |
| gtttcggata | ttgtaccacc | tttcagtgct | ttctctcctc | aaggaatgcc | agagggcgat | 780 |
| ctagtgtatg | ttaactatgc | acgaactgaa | gacttcttta | aattggaacg | ggacatgaaa | 840 |
| atcaattgct | ctgggaaaat | tgtaattgcc | agatatggga | aagttttcag | aggaaataag | 900 |
| gttaaaaatg | cccagctggc | aggggccaaa | ggagtcattc | tctactccga | ccctgctgac | 960 |
| tactttgctc | ctgggggtgaa | gtcctatcca | gatggttgga | atcttcctgg | aggtggtgtc | 1020 |
| cagcgtggaa | atatcctaaa | tctgaatggt | gcaggagacc | ctctcacacc | aggttaccca | 1080 |
| gcaaatgaat | atgcttatag | gcgtggaatt | gcagaggctg | ttggtcttcc | aagtattcct | 1140 |
| gttcatccaa | ttggatacta | tgatgcacag | aagctcctag | aaaaaatggg | tggctcagca | 1200 |
| ccaccagata | gcagctggag | aggaagtctc | aaagtgccct | acaatgttgg | acctggcttt | 1260 |
| actggaaact | tttctacaca | aaaagtcaag | atgcacatcc | actctaccaa | tgaagtgaca | 1320 |
| agaatttaca | atgtgatagg | tactctcaga | ggagcagtgg | aaccagacag | atatgtcatt | 1380 |
| ctgggaggtc | accgggactc | atgggtgttt | ggtggtattg | accctcagag | tggagcagct | 1440 |
| gttgttcatg | aaattgtgag | gagctttgga | acactgaaaa | aggaagggtg | gagacctaga | 1500 |
| agaacaattt | tgtttgcaag | ctgggatgca | gaagaatttg | gtcttcttgg | ttctactgag | 1560 |
| tgggcagagg | agaattcaag | actccttcaa | gagcgtggcg | tggcttatat | taatgctgac | 1620 |
| tcatctatag | aaggaaacta | cactctgaga | gttgattgta | caccgctgat | gtacagcttg | 1680 |
| gtacacaacc | taacaaaaga | gctgaaaagc | cctgatgaag | ctttgaagg | caaatctctt | 1740 |
| tatgaaagtt | ggactaaaaa | aagtccttcc | ccagagttca | gtggcatgcc | caggataagc | 1800 |
| aaattgggat | ctggaaatga | ttttgaggtg | ttcttccaac | gacttggaat | tgcttcaggc | 1860 |
| agagcacggt | atactaaaaa | ttgggaaaca | aacaaattca | gcggctatcc | actgtatcac | 1920 |
| agtgtctatg | aaacatatga | gttggtgaa | agtttttatg | atccaatgtt | taaatatcac | 1980 |
| ctcactgtgg | cccaggttcg | aggagggatg | gtgtttgagc | tagccaattc | catagtgctc | 2040 |
| cctttttgatt | gtcgagatta | tgctgtagtt | ttaagaaagt | atgctgacaa | aatctacagt | 2100 |
| atttctatga | aacatccaca | ggaaatgaag | acatacagtg | tatcatttga | ttcacttttt | 2160 |

```
tctgcagtaa agaattttac agaaattgct tccaagttca gtgagagact ccaggacttt      2220
gacaaaagca acccaatagt attaagaatg atgaatgatc aactcatgtt tctggaaaga      2280
gcatttattg atccattagg gttaccagac aggccttttt ataggcatgt catctatgct      2340
ccaagcagcc acaacaagta tgcaggggag tcattcccag gaatttatga tgctctgttt      2400
gatattgaaa gcaaagtgga cccttccaag gcctggggag aagtgaagag acagatttat      2460
gttgcagcct tcacagtgca ggcagctgca gagactttga gtgaagtagc ctaagaggat      2520
tctttagaga atccgtattg aatttgtgtg gtatgtcact cagaaagaat cgtaatgggt      2580
atattgataa atttaaaat tggtatattt gaaataaagt tgaatattat atataaaaaa      2640
aaaaaaaaaa aaa                                                        2653

<210> SEQ ID NO 40
<211> LENGTH: 188
<212> TYPE: PRT
<213> ORGANISM: Homo Sapien

<400> SEQUENCE: 40

Met Asn Gly Asp Asp Ala Phe Ala Arg Arg Pro Thr Val Gly Ala Gln
 1               5                  10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185

<210> SEQ ID NO 41
<211> LENGTH: 766
<212> TYPE: DNA
<213> ORGANISM: Homo Sapien

<400> SEQUENCE: 41
ctctctttcg attcttccat actcagagta cgcacggtct gattttctct ttggattctt       60
ccaaaatcag agtcagactg ctcccggtgc catgaacgga gacgacgcct ttgcaaggag      120
acccacggtt ggtgctcaaa taccagaaaa gatccaaaag gccttcgatg atattgccaa      180
atacttctct aaggaagagt gggaaaagat gaaagcctcg gagaaaatct ctatgtgta      240 tatgaagaga aagtatgagg ctatgactaa actaggtttc aaggccaccc tcccacctt       300
```

```
catgtgtaat aaacgggccg aagacttcca ggggaatgat ttggataatg accctaaccg    360
tgggaatcag gttgaacgtc ctcagatgac tttcggcagg ctccagggaa tctccccgaa    420
gatcatgccc aagaagccag cagaggaagg aaatgattcg gaggaagtgc agaagcatc     480 tggcccacaa aatgatggga aagagctgtg ccccccggga aaaccaacta cctctgagaa    540
gattcacgag agatctggac ccaaaagggg ggaacatgcc tggacccaca gactgcgtga    600
gagaaaacag ctggtgattt atgaagagat cagcgaccct gaggaagatg acgagtaact    660
cccctcaggg atacgacaca tgcccatgat gagaagcaga acgtggtgac ctttcacgaa    720
catgggcatg gctgcggacc cctcgtcatc aggtgcatag caagtg                   766

<210> SEQ ID NO 42
<211> LENGTH: 903
<212> TYPE: DNA
<213> ORGANISM: Herpes Simplex Virus

<400> SEQUENCE: 42
atgacctctc gccgctccgt gaagtcgggt ccgcgggagg ttccgcgcga tgagtacgag     60
gatctgtact acacccgtc ttcaggtatg gcgagtccg atagtccgcc tgacacctcc      120
cgccgtggcg ccctacagac acgctcgcgc cagaggggcg aggtccgttt cgtccagtac    180
gacgagtcgg attatgccct ctacggggc tcgtcatccg aagacgacga acacccggag     240
gtcccccgga cgcggcgtcc cgtttccggg gcggttttgt ccggcccggg gcctgcgcgg    300
gcgcctccgc caccgctgg gtccggaggg gccggacgca cacccaccac cgcccccgg     360 gccccccgaa cccagcgggt ggcgactaag gccccgcgg cccggcggc ggagaccacc     420 cgcggcagga aatcggccca gccagaatcc gccgcactcc cagacgcccc cgcgtcgacg    480
gcgccaaccc gatccaagac acccgcgcag gggctggcca gaaagctgca ctttagcacc    540
gcccccccaa accccgacgc gccatggacc ccccgggtgg ccggctttaa caagcgcgtc    600
ttctgcgccg cggtcgggcg cctggcggcc atgcatgccc ggatggcggc ggtccagctc    660
tgggacatgt cgcgtccgcg cacagacgaa gacctcaacg aactccttgg catcaccacc    720
atccgcgtga cggtctgcga gggcaaaaac ctgcttcagc gcgccaacga gttggtgaat    780
ccagacgtgg tgcaggacgt cgacgcggcc acggcgactc gagggcgttc tgcggcgtcg    840
cgccccaccg agcgacctcg agcccagcc cgctccgctt ctcgccccag acggcccgtc    900
gag                                                                  903

<210> SEQ ID NO 43
<211> LENGTH: 311
<212> TYPE: PRT
<213> ORGANISM: Herpes Simplex Virus

<400> SEQUENCE: 43

Met Thr Ser Arg Arg Ser Val Lys Ser Gly Pro Arg Glu Val Pro Arg
  1               5                  10                  15

Asp Glu Tyr Glu Asp Leu Tyr Tyr Thr Pro Ser Ser Gly Met Ala Ser
             20                  25                  30

Pro Asp Ser Pro Pro Asp Thr Ser Arg Arg Gly Ala Leu Phe Thr Gln
         35                  40                  45

Thr Arg Ser Arg Gln Arg Gly Glu Val Arg Phe Val Gln Tyr Asp Glu
     50                  55                  60

Ser Asp Tyr Ala Leu Tyr Gly Gly Ser Ser Ser Glu Asp Asp Glu His
 65                  70                  75                  80
```

```
Pro Glu Val Pro Arg Thr Arg Pro Val Ser Gly Ala Val Leu Ser
                85                  90                  95

Gly Pro Gly Pro Ala Arg Ala Pro Pro Phe Thr Pro Ala Gly Ser
            100                 105                 110

Gly Gly Ala Gly Arg Thr Pro Thr Ala Pro Arg Ala Pro Arg Thr
            115                 120                 125

Gln Arg Val Ala Thr Lys Ala Pro Ala Ala Pro Ala Ala Glu Thr Thr
130                 135                 140

Arg Gly Arg Lys Ser Ala Gln Pro Glu Ser Ala Ala Leu Pro Asp Ala
145                 150                 155                 160

Pro Ala Ser Thr Ala Pro Thr Phe Thr Arg Ser Lys Thr Pro Ala Gln
                165                 170                 175

Gly Leu Ala Arg Lys Leu His Phe Ser Thr Ala Pro Pro Asn Pro Asp
            180                 185                 190

Ala Pro Trp Thr Pro Arg Val Ala Gly Phe Asn Lys Arg Val Phe Cys
            195                 200                 205

Ala Ala Val Gly Arg Leu Ala Ala Met His Ala Arg Met Ala Ala Val
            210                 215                 220

Gln Leu Trp Asp Phe Thr Met Ser Arg Pro Arg Thr Asp Glu Asp Leu
225                 230                 235                 240

Asn Glu Leu Leu Gly Ile Thr Thr Ile Arg Val Thr Val Cys Glu Gly
                245                 250                 255

Lys Asn Leu Leu Gln Arg Ala Asn Glu Leu Val Asn Pro Asp Val Val
                260                 265                 270

Gln Asp Val Asp Ala Ala Thr Ala Thr Arg Gly Arg Ser Ala Ala Ser
            275                 280                 285

Arg Phe Thr Pro Thr Glu Arg Pro Arg Ala Pro Ala Arg Ser Ala Ser
290                 295                 300

Arg Pro Arg Arg Pro Val Glu
305                 310

<210> SEQ ID NO 44
<211> LENGTH: 9
<212> TYPE: PRT
<213> ORGANISM: Adenovirus 3

<400> SEQUENCE: 44

Leu Ile Val Ile Gly Ile Leu Ile Leu
1               5

<210> SEQ ID NO 45
<211> LENGTH: 10
<212> TYPE: PRT
<213> ORGANISM: Adenovirus 5

<400> SEQUENCE: 45

Ser Gly Pro Ser Asn Thr Pro Pro Glu Ile
1               5                   10

<210> SEQ ID NO 46
<211> LENGTH: 8
<212> TYPE: PRT
<213> ORGANISM: Adenovirus 5

<400> SEQUENCE: 46

Val Asn Ile Arg Asn Cys Cys Tyr
1               5

<210> SEQ ID NO 47
```

```
<211> LENGTH: 10
<212> TYPE: PRT
<213> ORGANISM: Adenovirus 5

<400> SEQUENCE: 47

Ser Gly Pro Ser Asn Ile Pro Pro Glu Ile
1               5                   10

<210> SEQ ID NO 48
<211> LENGTH: 9
<212> TYPE: PRT
<213> ORGANISM: Classical Swine Fever Virus

<400> SEQUENCE: 48

Glu Asn Ala Leu Leu Val Ala Leu Phe
1               5

<210> SEQ ID NO 49
<211> LENGTH: 9
<212> TYPE: PRT
<213> ORGANISM: Dengue Virus 4

<400> SEQUENCE: 49

Thr Pro Glu Gly Ile Ile Pro Thr Leu
1               5

<210> SEQ ID NO 50
<211> LENGTH: 9
<212> TYPE: PRT
<213> ORGANISM: Epstein-Barr Virus

<400> SEQUENCE: 50

Cys Leu Gly Gly Leu Leu Thr Met Val
1               5

<210> SEQ ID NO 51
<211> LENGTH: 9
<212> TYPE: PRT
<213> ORGANISM: Epstein-Barr Virus

<400> SEQUENCE: 51

Asn Ile Ala Glu Gly Leu Arg Ala Leu
1               5

<210> SEQ ID NO 52
<211> LENGTH: 9
<212> TYPE: PRT
<213> ORGANISM: Epstein-Barr Virus

<400> SEQUENCE: 52

Asn Leu Arg Arg Gly Thr Ala Leu Ala
1               5

<210> SEQ ID NO 53
<211> LENGTH: 9
<212> TYPE: PRT
<213> ORGANISM: Epstein-Barr Virus

<400> SEQUENCE: 53

Ala Leu Ala Ile Pro Gln Cys Arg Leu
1               5

<210> SEQ ID NO 54
<211> LENGTH: 9
<212> TYPE: PRT
<213> ORGANISM: Epstein-Barr Virus
```

```
<400> SEQUENCE: 54

Val Leu Lys Asp Ala Ile Lys Asp Leu
 1               5

<210> SEQ ID NO 55
<211> LENGTH: 9
<212> TYPE: PRT
<213> ORGANISM: Epstein-Barr Virus

<400> SEQUENCE: 55

Phe Met Val Phe Leu Gln Thr His Ile
 1               5

<210> SEQ ID NO 56
<211> LENGTH: 9
<212> TYPE: PRT
<213> ORGANISM: Epstein-Barr Virus

<400> SEQUENCE: 56

His Leu Ile Val Asp Thr Asp Ser Leu
 1               5

<210> SEQ ID NO 57
<211> LENGTH: 9
<212> TYPE: PRT
<213> ORGANISM: Epstein-Barr Virus

<400> SEQUENCE: 57

Ser Leu Gly Asn Pro Ser Leu Ser Val
 1               5

<210> SEQ ID NO 58
<211> LENGTH: 9
<212> TYPE: PRT
<213> ORGANISM: Epstein-Barr Virus

<400> SEQUENCE: 58

Pro Leu Ala Ser Ala Met Arg Met Leu
 1               5

<210> SEQ ID NO 59
<211> LENGTH: 8
<212> TYPE: PRT
<213> ORGANISM: Epstein-Barr Virus

<400> SEQUENCE: 59

Arg Met Leu Trp Met Ala Asn Tyr
 1               5

<210> SEQ ID NO 60
<211> LENGTH: 9
<212> TYPE: PRT
<213> ORGANISM: Epstein-Barr Virus

<400> SEQUENCE: 60

Met Leu Trp Met Ala Asn Tyr Ile Val
 1               5

<210> SEQ ID NO 61
<211> LENGTH: 9
<212> TYPE: PRT
<213> ORGANISM: Epstein-Barr Virus

<400> SEQUENCE: 61
```

Ile Leu Pro Gln Gly Pro Gln Thr Ala
1               5

<210> SEQ ID NO 62
<211> LENGTH: 9
<212> TYPE: PRT
<213> ORGANISM: Epstein-Barr Virus

<400> SEQUENCE: 62

Pro Leu Arg Pro Thr Ala Pro Thr Ile
1               5

<210> SEQ ID NO 63
<211> LENGTH: 9
<212> TYPE: PRT
<213> ORGANISM: Epstein-Barr Virus

<400> SEQUENCE: 63

Pro Leu Pro Pro Ala Thr Leu Thr Val
1               5

<210> SEQ ID NO 64
<211> LENGTH: 9
<212> TYPE: PRT
<213> ORGANISM: Epstein-Barr Virus

<400> SEQUENCE: 64

Arg Met His Leu Pro Val Leu His Val
1               5

<210> SEQ ID NO 65
<211> LENGTH: 9
<212> TYPE: PRT
<213> ORGANISM: Epstein-Barr Virus

<400> SEQUENCE: 65

Pro Met Pro Leu Pro Pro Ser Gln Leu
1               5

<210> SEQ ID NO 66
<211> LENGTH: 9
<212> TYPE: PRT
<213> ORGANISM: Epstein-Barr Virus

<400> SEQUENCE: 66

Gln Leu Pro Pro Pro Ala Ala Pro Ala
1               5

<210> SEQ ID NO 67
<211> LENGTH: 9
<212> TYPE: PRT
<213> ORGANISM: Epstein-Barr Virus

<400> SEQUENCE: 67

Ser Met Pro Glu Leu Ser Pro Val Leu
1               5

<210> SEQ ID NO 68
<211> LENGTH: 9
<212> TYPE: PRT
<213> ORGANISM: Epstein-Barr Virus

<400> SEQUENCE: 68

Asp Leu Asp Glu Ser Trp Asp Tyr Ile
1               5

```
<210> SEQ ID NO 69
<211> LENGTH: 9
<212> TYPE: PRT
<213> ORGANISM: Epstein-Barr Virus

<400> SEQUENCE: 69

Pro Leu Pro Cys Val Leu Trp Pro Val
1               5

<210> SEQ ID NO 70
<211> LENGTH: 9
<212> TYPE: PRT
<213> ORGANISM: Epstein-Barr Virus

<400> SEQUENCE: 70

Ser Leu Glu Glu Cys Asp Ser Glu Leu
1               5

<210> SEQ ID NO 71
<211> LENGTH: 9
<212> TYPE: PRT
<213> ORGANISM: Epstein-Barr Virus

<400> SEQUENCE: 71

Glu Ile Lys Arg Tyr Lys Asn Arg Val
1               5

<210> SEQ ID NO 72
<211> LENGTH: 9
<212> TYPE: PRT
<213> ORGANISM: Epstein-Barr Virus

<400> SEQUENCE: 72

Gln Leu Leu Gln His Tyr Arg Glu Val
1               5

<210> SEQ ID NO 73
<211> LENGTH: 9
<212> TYPE: PRT
<213> ORGANISM: Epstein-Barr Virus

<400> SEQUENCE: 73

Leu Leu Gln His Tyr Arg Glu Val Ala
1               5

<210> SEQ ID NO 74
<211> LENGTH: 9
<212> TYPE: PRT
<213> ORGANISM: Epstein-Barr Virus

<400> SEQUENCE: 74

Leu Leu Lys Gln Met Cys Pro Ser Leu
1               5

<210> SEQ ID NO 75
<211> LENGTH: 9
<212> TYPE: PRT
<213> ORGANISM: Epstein-Barr Virus

<400> SEQUENCE: 75

Ser Ile Ile Pro Arg Thr Pro Asp Val
1               5

<210> SEQ ID NO 76
<211> LENGTH: 10
```

```
<212> TYPE: PRT
<213> ORGANISM: Epstein-Barr Virus

<400> SEQUENCE: 76

Leu Leu Asp Phe Val Arg Phe Met Gly Val
 1               5                  10

<210> SEQ ID NO 77
<211> LENGTH: 9
<212> TYPE: PRT
<213> ORGANISM: Epstein-Barr Virus

<400> SEQUENCE: 77

Ser Val Arg Asp Arg Leu Ala Arg Leu
 1               5

<210> SEQ ID NO 78
<211> LENGTH: 9
<212> TYPE: PRT
<213> ORGANISM: Epstein-Barr Virus

<400> SEQUENCE: 78

Ile Val Thr Asp Phe Ser Val Ile Lys
 1               5

<210> SEQ ID NO 79
<211> LENGTH: 10
<212> TYPE: PRT
<213> ORGANISM: Epstein-Barr Virus

<400> SEQUENCE: 79

Ala Val Phe Asp Arg Lys Ser Asp Ala Lys
 1               5                  10

<210> SEQ ID NO 80
<211> LENGTH: 8
<212> TYPE: PRT
<213> ORGANISM: Epstein-Barr Virus

<400> SEQUENCE: 80

Arg Tyr Ser Ile Phe Phe Asp Tyr
 1               5

<210> SEQ ID NO 81
<211> LENGTH: 9
<212> TYPE: PRT
<213> ORGANISM: Epstein-Barr Virus

<400> SEQUENCE: 81

Gln Pro Arg Ala Pro Ile Arg Pro Ile
 1               5

<210> SEQ ID NO 82
<211> LENGTH: 9
<212> TYPE: PRT
<213> ORGANISM: Epstein-Barr Virus

<400> SEQUENCE: 82

Arg Pro Pro Ile Phe Ile Arg Arg Ile
 1               5

<210> SEQ ID NO 83
<211> LENGTH: 9
<212> TYPE: PRT
<213> ORGANISM: Epstein-Barr Virus
```

```
<400> SEQUENCE: 83

Glu Pro Asp Val Pro Pro Gly Ala Ile
1               5

<210> SEQ ID NO 84
<211> LENGTH: 9
<212> TYPE: PRT
<213> ORGANISM: Epstein-Barr Virus

<400> SEQUENCE: 84

Ile Pro Gln Cys Arg Leu Thr Pro Leu
1               5

<210> SEQ ID NO 85
<211> LENGTH: 9
<212> TYPE: PRT
<213> ORGANISM: Epstein-Barr Virus

<400> SEQUENCE: 85

Gly Pro Gly Pro Gln Pro Gly Pro Leu
1               5

<210> SEQ ID NO 86
<211> LENGTH: 9
<212> TYPE: PRT
<213> ORGANISM: Epstein-Barr Virus

<400> SEQUENCE: 86

Gln Pro Gly Pro Leu Arg Glu Ser Ile
1               5

<210> SEQ ID NO 87
<211> LENGTH: 9
<212> TYPE: PRT
<213> ORGANISM: Epstein-Barr Virus

<400> SEQUENCE: 87

Arg Pro Gln Lys Arg Pro Ser Cys Ile
1               5

<210> SEQ ID NO 88
<211> LENGTH: 9
<212> TYPE: PRT
<213> ORGANISM: Epstein-Barr Virus

<400> SEQUENCE: 88

Pro Pro Thr Pro Leu Leu Thr Val Leu
1               5

<210> SEQ ID NO 89
<211> LENGTH: 9
<212> TYPE: PRT
<213> ORGANISM: Epstein-Barr Virus

<400> SEQUENCE: 89

Thr Pro Ser Pro Pro Arg Met His Leu
1               5

<210> SEQ ID NO 90
<211> LENGTH: 9
<212> TYPE: PRT
<213> ORGANISM: Epstein-Barr Virus

<400> SEQUENCE: 90

Pro Pro Arg Met His Leu Pro Val Leu
```

<210> SEQ ID NO 91
<211> LENGTH: 9
<212> TYPE: PRT
<213> ORGANISM: Epstein-Barr Virus

<400> SEQUENCE: 91

Val Pro Asp Gln Ser Met His Pro Leu
1               5

<210> SEQ ID NO 92
<211> LENGTH: 9
<212> TYPE: PRT
<213> ORGANISM: Epstein-Barr Virus

<400> SEQUENCE: 92

Pro Pro Ser Ile Asp Pro Ala Asp Leu
1               5

<210> SEQ ID NO 93
<211> LENGTH: 9
<212> TYPE: PRT
<213> ORGANISM: Epstein-Barr Virus

<400> SEQUENCE: 93

Leu Pro Cys Val Leu Trp Pro Val Leu
1               5

<210> SEQ ID NO 94
<211> LENGTH: 10
<212> TYPE: PRT
<213> ORGANISM: Epstein-Barr Virus

<400> SEQUENCE: 94

Cys Pro Ser Leu Asp Val Asp Ser Ile Ile
1               5                   10

<210> SEQ ID NO 95
<211> LENGTH: 9
<212> TYPE: PRT
<213> ORGANISM: Epstein-Barr Virus

<400> SEQUENCE: 95

Thr Pro Asp Val Leu His Glu Asp Leu
1               5

<210> SEQ ID NO 96
<211> LENGTH: 9
<212> TYPE: PRT
<213> ORGANISM: Epstein-Barr Virus

<400> SEQUENCE: 96

Phe Leu Arg Gly Arg Ala Tyr Gly Leu
1               5

<210> SEQ ID NO 97
<211> LENGTH: 9
<212> TYPE: PRT
<213> ORGANISM: Epstein-Barr Virus

<400> SEQUENCE: 97

Gln Ala Lys Trp Arg Leu Gln Thr Leu
1               5

```
<210> SEQ ID NO 98
<211> LENGTH: 9
<212> TYPE: PRT
<213> ORGANISM: Epstein-Barr Virus

<400> SEQUENCE: 98

Ala Tyr Pro Leu His Glu Gln His Gly
 1               5

<210> SEQ ID NO 99
<211> LENGTH: 9
<212> TYPE: PRT
<213> ORGANISM: Epstein-Barr Virus

<400> SEQUENCE: 99

Tyr Leu Lys Ser Phe Val Ser Asp Ala
 1               5

<210> SEQ ID NO 100
<211> LENGTH: 9
<212> TYPE: PRT
<213> ORGANISM: Epstein-Barr Virus

<400> SEQUENCE: 100

Arg Arg Arg Trp Arg Arg Leu Thr Val
 1               5

<210> SEQ ID NO 101
<211> LENGTH: 9
<212> TYPE: PRT
<213> ORGANISM: Epstein-Barr Virus

<400> SEQUENCE: 101

Arg Arg Ile Tyr Asp Leu Ile Glu Leu
 1               5

<210> SEQ ID NO 102
<211> LENGTH: 9
<212> TYPE: PRT
<213> ORGANISM: Epstein-Barr Virus

<400> SEQUENCE: 102

Tyr Pro Leu His Glu Gln His Gly Met
 1               5

<210> SEQ ID NO 103
<211> LENGTH: 9
<212> TYPE: PRT
<213> ORGANISM: Epstein-Barr Virus

<400> SEQUENCE: 103

Tyr Pro Leu His Glu Gln His Gly Met
 1               5

<210> SEQ ID NO 104
<211> LENGTH: 9
<212> TYPE: PRT
<213> ORGANISM: Hepatitis C Virus

<400> SEQUENCE: 104

His Ser Lys Lys Lys Cys Asp Glu Leu
 1               5

<210> SEQ ID NO 105
<211> LENGTH: 8
<212> TYPE: PRT
```

<213> ORGANISM: Hepatitis C Virus

<400> SEQUENCE: 105

Ala Ser Arg Cys Trp Val Ala Met
1               5

<210> SEQ ID NO 106
<211> LENGTH: 9
<212> TYPE: PRT
<213> ORGANISM: Hepatitis C Virus

<400> SEQUENCE: 106

Gly Gln Ile Val Gly Gly Val Tyr Leu
1               5

<210> SEQ ID NO 107
<211> LENGTH: 10
<212> TYPE: PRT
<213> ORGANISM: Hepatitis C Virus

<400> SEQUENCE: 107

Pro Pro Leu Thr Asp Phe Asp Gln Gly Trp
1               5                   10

<210> SEQ ID NO 108
<211> LENGTH: 10
<212> TYPE: PRT
<213> ORGANISM: Hepatitis C Virus

<400> SEQUENCE: 108

Leu Met Gly Tyr Ile Pro Leu Val Gly Ala
1               5                   10

<210> SEQ ID NO 109
<211> LENGTH: 10
<212> TYPE: PRT
<213> ORGANISM: Hepatitis C Virus

<400> SEQUENCE: 109

Ala Asp Leu Met Gly Tyr Ile Pro Leu Val
1               5                   10

<210> SEQ ID NO 110
<211> LENGTH: 16
<212> TYPE: PRT
<213> ORGANISM: Hepatitis C Virus

<400> SEQUENCE: 110

Met Ser Tyr Ser Trp Thr Gly Ala Leu Val Thr Pro Cys Ala Glu Glu
1               5                   10                  15

<210> SEQ ID NO 111
<211> LENGTH: 9
<212> TYPE: PRT
<213> ORGANISM: Hepatitis C Virus

<400> SEQUENCE: 111

Lys His Pro Asp Ala Thr Tyr Ser Arg
1               5

<210> SEQ ID NO 112
<211> LENGTH: 10
<212> TYPE: PRT
<213> ORGANISM: Hepatitis C Virus 1

<400> SEQUENCE: 112

Lys Leu Val Ala Leu Gly Ile Asn Ala Val
1               5                   10

<210> SEQ ID NO 113
<211> LENGTH: 9
<212> TYPE: PRT
<213> ORGANISM: Hepatitis C Virus 1

<400> SEQUENCE: 113

Gly Asp Phe Asp Ser Val Ile Asp Cys
1               5

<210> SEQ ID NO 114
<211> LENGTH: 9
<212> TYPE: PRT
<213> ORGANISM: Hepatitis C Virus 1

<400> SEQUENCE: 114

Gly Asn Ala Ser Arg Cys Trp Val Ala
1               5

<210> SEQ ID NO 115
<211> LENGTH: 9
<212> TYPE: PRT
<213> ORGANISM: Hepatitis C Virus 1

<400> SEQUENCE: 115

Thr Arg Pro Pro Leu Gly Asn Trp Phe
1               5

<210> SEQ ID NO 116
<211> LENGTH: 9
<212> TYPE: PRT
<213> ORGANISM: Hepatitis C Virus 1

<400> SEQUENCE: 116

Val Pro His Pro Asn Ile Glu Glu Val
1               5

<210> SEQ ID NO 117
<211> LENGTH: 9
<212> TYPE: PRT
<213> ORGANISM: Hepatitis C Virus 1

<400> SEQUENCE: 117

Tyr Thr Gly Asp Phe Asp Ser Val Ile
1               5

<210> SEQ ID NO 118
<211> LENGTH: 8
<212> TYPE: PRT
<213> ORGANISM: Hepatitis C Virus 1

<400> SEQUENCE: 118

Ser Trp Ala Ile Lys Trp Glu Tyr
1               5

<210> SEQ ID NO 119
<211> LENGTH: 9
<212> TYPE: PRT
<213> ORGANISM: Hepatitis C Virus 1

<400> SEQUENCE: 119

Lys His Pro Asp Ala Thr Tyr Ser Arg
1               5

```
<210> SEQ ID NO 120
<211> LENGTH: 9
<212> TYPE: PRT
<213> ORGANISM: Hepatitis C Virus 1

<400> SEQUENCE: 120

Gly Asp Phe Asp Ser Val Ile Asp Cys
1               5

<210> SEQ ID NO 121
<211> LENGTH: 9
<212> TYPE: PRT
<213> ORGANISM: Human Immunodeficiency Virus

<400> SEQUENCE: 121

Arg Tyr Leu Lys Asp Gln Gln Leu Leu
1               5

<210> SEQ ID NO 122
<211> LENGTH: 9
<212> TYPE: PRT
<213> ORGANISM: Human Immunodeficiency Virus

<400> SEQUENCE: 122

Ile Val Gly Leu Asn Lys Ile Val Arg
1               5

<210> SEQ ID NO 123
<211> LENGTH: 9
<212> TYPE: PRT
<213> ORGANISM: Human Immunodeficiency Virus

<400> SEQUENCE: 123

Glu Ile Tyr Lys Arg Trp Ile Ile Leu
1               5

<210> SEQ ID NO 124
<211> LENGTH: 8
<212> TYPE: PRT
<213> ORGANISM: Human Immunodeficiency Virus

<400> SEQUENCE: 124

Gly Glu Leu Tyr Lys Arg Trp Ile
1               5

<210> SEQ ID NO 125
<211> LENGTH: 9
<212> TYPE: PRT
<213> ORGANISM: Human Immunodeficiency Virus

<400> SEQUENCE: 125

Glu Ile Lys Asp Thr Lys Glu Ala Leu
1               5

<210> SEQ ID NO 126
<211> LENGTH: 8
<212> TYPE: PRT
<213> ORGANISM: Human Immunodeficiency Virus

<400> SEQUENCE: 126

Tyr Leu Lys Asp Gln Gln Leu Leu
1               5

<210> SEQ ID NO 127
```

```
<211> LENGTH: 11
<212> TYPE: PRT
<213> ORGANISM: Human Immunodeficiency Virus

<400> SEQUENCE: 127

Ile Leu Gly Leu Asn Lys Ile Val Arg Met Tyr
 1               5                  10

<210> SEQ ID NO 128
<211> LENGTH: 9
<212> TYPE: PRT
<213> ORGANISM: Human Immunodeficiency Virus

<400> SEQUENCE: 128

Glu Arg Tyr Leu Lys Asp Gln Gln Leu
 1               5

<210> SEQ ID NO 129
<211> LENGTH: 11
<212> TYPE: PRT
<213> ORGANISM: Human Immunodeficiency Virus

<400> SEQUENCE: 129

Tyr His Thr Gln Gly Tyr Phe Pro Gln Trp Gln
 1               5                  10

<210> SEQ ID NO 130
<211> LENGTH: 12
<212> TYPE: PRT
<213> ORGANISM: Human Immunodeficiency Virus

<400> SEQUENCE: 130

Thr Gln Gly Tyr Phe Pro Gln Trp Gln Asn Tyr Thr
 1               5                  10

<210> SEQ ID NO 131
<211> LENGTH: 9
<212> TYPE: PRT
<213> ORGANISM: Human Immunodeficiency Virus

<400> SEQUENCE: 131

Gly Arg Ala Phe Val Thr Leu Gly Lys
 1               5

<210> SEQ ID NO 132
<211> LENGTH: 9
<212> TYPE: PRT
<213> ORGANISM: Human Immunodeficiency Virus

<400> SEQUENCE: 132

Lys Arg Trp Ile Ile Leu Gly Leu Asn
 1               5

<210> SEQ ID NO 133
<211> LENGTH: 10
<212> TYPE: PRT
<213> ORGANISM: Human Immunodeficiency Virus

<400> SEQUENCE: 133

Gln Val Pro Leu Arg Pro Met Thr Tyr Lys
 1               5                  10

<210> SEQ ID NO 134
<211> LENGTH: 9
<212> TYPE: PRT
<213> ORGANISM: Human Immunodeficiency Virus
```

```
<400> SEQUENCE: 134

Thr Gln Gly Tyr Phe Pro Gln Trp Gln
 1               5

<210> SEQ ID NO 135
<211> LENGTH: 9
<212> TYPE: PRT
<213> ORGANISM: Human Immunodeficiency Virus

<400> SEQUENCE: 135

His Gln Ala Ile Ser Pro Arg Thr Ile
 1               5

<210> SEQ ID NO 136
<211> LENGTH: 12
<212> TYPE: PRT
<213> ORGANISM: Human Immunodeficiency Virus

<400> SEQUENCE: 136

Gln Met Val His Gln Ala Ile Ser Pro Arg Thr Leu
 1               5                  10

<210> SEQ ID NO 137
<211> LENGTH: 10
<212> TYPE: PRT
<213> ORGANISM: Human Immunodeficiency Virus

<400> SEQUENCE: 137

Met Tyr Ala Pro Pro Ile Gly Gly Gln Ile
 1               5                  10

<210> SEQ ID NO 138
<211> LENGTH: 10
<212> TYPE: PRT
<213> ORGANISM: Human Immunodeficiency Virus

<400> SEQUENCE: 138

Arg Gly Pro Gly Arg Ala Phe Val Thr Ile
 1               5                  10

<210> SEQ ID NO 139
<211> LENGTH: 9
<212> TYPE: PRT
<213> ORGANISM: Human Immunodeficiency Virus

<400> SEQUENCE: 139

Met Pro Gly Arg Ala Phe Val Thr Ile
 1               5

<210> SEQ ID NO 140
<211> LENGTH: 9
<212> TYPE: PRT
<213> ORGANISM: Human Immunodeficiency Virus 1

<400> SEQUENCE: 140

Ile Leu Lys Glu Pro Val His Gly Val
 1               5

<210> SEQ ID NO 141
<211> LENGTH: 9
<212> TYPE: PRT
<213> ORGANISM: Human Immunodeficiency Virus 1

<400> SEQUENCE: 141
```

```
Ala Phe His His Val Ala Arg Glu Leu
1               5

<210> SEQ ID NO 142
<211> LENGTH: 9
<212> TYPE: PRT
<213> ORGANISM: Human Immunodeficiency Virus 1

<400> SEQUENCE: 142

Lys Leu Thr Pro Leu Cys Val Thr Leu
1               5

<210> SEQ ID NO 143
<211> LENGTH: 10
<212> TYPE: PRT
<213> ORGANISM: Human Immunodeficiency Virus 1

<400> SEQUENCE: 143

Ser Leu Leu Asn Ala Thr Asp Ile Ala Val
1               5                   10

<210> SEQ ID NO 144
<211> LENGTH: 9
<212> TYPE: PRT
<213> ORGANISM: Human Immunodeficiency Virus 1

<400> SEQUENCE: 144

Val Ile Tyr Gln Tyr Met Asp Asp Leu
1               5

<210> SEQ ID NO 145
<211> LENGTH: 9
<212> TYPE: PRT
<213> ORGANISM: Human Immunodeficiency Virus 1

<400> SEQUENCE: 145

Ser Leu Tyr Asn Thr Val Ala Thr Leu
1               5

<210> SEQ ID NO 146
<211> LENGTH: 9
<212> TYPE: PRT
<213> ORGANISM: Human Immunodeficiency Virus 1

<400> SEQUENCE: 146

Arg Gly Pro Gly Arg Ala Phe Val Thr
1               5

<210> SEQ ID NO 147
<211> LENGTH: 11
<212> TYPE: PRT
<213> ORGANISM: Human Immunodeficiency Virus 1

<400> SEQUENCE: 147

Arg Leu Arg Asp Leu Leu Leu Ile Val Thr Arg
1               5                   10

<210> SEQ ID NO 148
<211> LENGTH: 10
<212> TYPE: PRT
<213> ORGANISM: Human Immunodeficiency Virus 1

<400> SEQUENCE: 148

Gln Val Pro Leu Arg Pro Met Thr Tyr Lys
1               5                   10
```

```
<210> SEQ ID NO 149
<211> LENGTH: 10
<212> TYPE: PRT
<213> ORGANISM: Human Immunodeficiency Virus 1

<400> SEQUENCE: 149

Thr Val Tyr Tyr Gly Val Pro Val Trp Lys
1               5                   10

<210> SEQ ID NO 150
<211> LENGTH: 9
<212> TYPE: PRT
<213> ORGANISM: Human Immunodeficiency Virus 1

<400> SEQUENCE: 150

Arg Leu Arg Pro Gly Gly Lys Lys Lys
1               5

<210> SEQ ID NO 151
<211> LENGTH: 9
<212> TYPE: PRT
<213> ORGANISM: Human Immunodeficiency Virus 1

<400> SEQUENCE: 151

Val Tyr Tyr Gly Val Pro Val Trp Lys
1               5

<210> SEQ ID NO 152
<211> LENGTH: 9
<212> TYPE: PRT
<213> ORGANISM: Human Immunodeficiency Virus 1

<400> SEQUENCE: 152

Val Pro Leu Arg Pro Met Thr Tyr Lys
1               5

<210> SEQ ID NO 153
<211> LENGTH: 9
<212> TYPE: PRT
<213> ORGANISM: Human Immunodeficiency Virus 1

<400> SEQUENCE: 153

Ala Ile Phe Gln Ser Ser Met Thr Lys
1               5

<210> SEQ ID NO 154
<211> LENGTH: 10
<212> TYPE: PRT
<213> ORGANISM: Human Immunodeficiency Virus 1

<400> SEQUENCE: 154

Gln Val Pro Leu Arg Pro Met Thr Tyr Lys
1               5                   10

<210> SEQ ID NO 155
<211> LENGTH: 12
<212> TYPE: PRT
<213> ORGANISM: Human Immunodeficiency Virus 1

<400> SEQUENCE: 155

Ala Ala Val Asp Leu Ser His Phe Leu Lys Glu Lys
1               5                   10

<210> SEQ ID NO 156
<211> LENGTH: 12
```

```
<212> TYPE: PRT
<213> ORGANISM: Human Immunodeficiency Virus 1

<400> SEQUENCE: 156

Ala Cys Gln Gly Val Gly Pro Gly Gly His Lys
 1               5                  10

<210> SEQ ID NO 157
<211> LENGTH: 10
<212> TYPE: PRT
<213> ORGANISM: Human Immunodeficiency Virus 1

<400> SEQUENCE: 157

Glu Thr Ile Asn Glu Glu Ala Ala Glu Trp
 1               5                  10

<210> SEQ ID NO 158
<211> LENGTH: 10
<212> TYPE: PRT
<213> ORGANISM: Human Immunodeficiency Virus 1

<400> SEQUENCE: 158

Thr Pro Gly Pro Gly Val Arg Tyr Pro Leu
 1               5                  10

<210> SEQ ID NO 159
<211> LENGTH: 8
<212> TYPE: PRT
<213> ORGANISM: Human Immunodeficiency Virus 1

<400> SEQUENCE: 159

Gly Gly Lys Lys Lys Tyr Lys Leu
 1               5

<210> SEQ ID NO 160
<211> LENGTH: 9
<212> TYPE: PRT
<213> ORGANISM: Human Immunodeficiency Virus 1

<400> SEQUENCE: 160

Arg Val Lys Glu Lys Tyr Gln His Leu
 1               5

<210> SEQ ID NO 161
<211> LENGTH: 9
<212> TYPE: PRT
<213> ORGANISM: Human Immunodeficiency Virus 1

<400> SEQUENCE: 161

Asp Arg Phe Tyr Lys Thr Leu Arg Ala
 1               5

<210> SEQ ID NO 162
<211> LENGTH: 16
<212> TYPE: PRT
<213> ORGANISM: Human Immunodeficiency Virus 1

<400> SEQUENCE: 162

Gly Val Arg Tyr Pro Leu Thr Phe Gly Trp Cys Tyr Lys Leu Val Pro
 1               5                  10                  15

<210> SEQ ID NO 163
<211> LENGTH: 10
<212> TYPE: PRT
<213> ORGANISM: Human Immunodeficiency Virus 1
```

```
<400> SEQUENCE: 163

Lys Arg Trp Ile Ile Leu Gly Leu Asn Lys
1               5                   10

<210> SEQ ID NO 164
<211> LENGTH: 9
<212> TYPE: PRT
<213> ORGANISM: Human Immunodeficiency Virus 1

<400> SEQUENCE: 164

Ala Phe His His Val Ala Arg Glu Leu
1               5

<210> SEQ ID NO 165
<211> LENGTH: 9
<212> TYPE: PRT
<213> ORGANISM: Epstein-Barr Virus

<400> SEQUENCE: 165

Lys Glu His Val Ile Gln Asn Ala Phe
1               5

<210> SEQ ID NO 166
<211> LENGTH: 10
<212> TYPE: PRT
<213> ORGANISM: Epstein-Barr Virus

<400> SEQUENCE: 166

Glu Glu Asn Leu Leu Asp Phe Val Arg Phe
1               5                   10

<210> SEQ ID NO 167
<211> LENGTH: 10
<212> TYPE: PRT
<213> ORGANISM: Epstein-Barr Virus

<400> SEQUENCE: 167

Asp Thr Pro Leu Ile Pro Leu Thr Ile Phe
1               5                   10

<210> SEQ ID NO 168
<211> LENGTH: 10
<212> TYPE: PRT
<213> ORGANISM: Epstein-Barr Virus

<400> SEQUENCE: 168

Gln Asn Gly Ala Leu Ala Ile Asn Thr Phe
1               5                   10

<210> SEQ ID NO 169
<211> LENGTH: 9
<212> TYPE: PRT
<213> ORGANISM: Epstein-Barr Virus

<400> SEQUENCE: 169

Arg Leu Arg Ala Glu Ala Gly Val Lys
1               5

<210> SEQ ID NO 170
<211> LENGTH: 10
<212> TYPE: PRT
<213> ORGANISM: Hepatitis B Virus

<400> SEQUENCE: 170

Gly Leu Ser Pro Thr Val Trp Leu Ser Val
```

```
<210> SEQ ID NO 171
<211> LENGTH: 9
<212> TYPE: PRT
<213> ORGANISM: Hepatitis B Virus

<400> SEQUENCE: 171

Trp Leu Ser Leu Leu Val Pro Phe Val
 1               5

<210> SEQ ID NO 172
<211> LENGTH: 10
<212> TYPE: PRT
<213> ORGANISM: Hepatitis B Virus

<400> SEQUENCE: 172

Phe Leu Pro Ser Asp Phe Phe Pro Ser Val
 1               5                  10

<210> SEQ ID NO 173
<211> LENGTH: 10
<212> TYPE: PRT
<213> ORGANISM: Hepatitis B Virus

<400> SEQUENCE: 173

Phe Leu Pro Ser Asp Phe Phe Pro Ser Val
 1               5                  10

<210> SEQ ID NO 174
<211> LENGTH: 10
<212> TYPE: PRT
<213> ORGANISM: Hepatitis B Virus

<400> SEQUENCE: 174

Phe Leu Pro Ser Asp Phe Phe Pro Ser Val
 1               5                  10

<210> SEQ ID NO 175
<211> LENGTH: 10
<212> TYPE: PRT
<213> ORGANISM: Hepatitis B Virus

<400> SEQUENCE: 175

Phe Leu Pro Ser Asp Phe Phe Pro Ser Val
 1               5                  10

<210> SEQ ID NO 176
<211> LENGTH: 9
<212> TYPE: PRT
<213> ORGANISM: Hepatitis B Virus

<400> SEQUENCE: 176

Phe Leu Leu Ser Leu Gly Ile His Leu
 1               5

<210> SEQ ID NO 177
<211> LENGTH: 9
<212> TYPE: PRT
<213> ORGANISM: Hepatitis B Virus

<400> SEQUENCE: 177

Ser Leu Tyr Ala Asp Ser Pro Ser Val
 1               5
```

```
<210> SEQ ID NO 178
<211> LENGTH: 9
<212> TYPE: PRT
<213> ORGANISM: Hepatitis B Virus

<400> SEQUENCE: 178

Gly Leu Ser Arg Tyr Val Ala Arg Leu
1               5

<210> SEQ ID NO 179
<211> LENGTH: 10
<212> TYPE: PRT
<213> ORGANISM: Hepatitis B Virus

<400> SEQUENCE: 179

Leu Leu Val Pro Phe Val Gln Trp Phe Val
1               5                   10

<210> SEQ ID NO 180
<211> LENGTH: 9
<212> TYPE: PRT
<213> ORGANISM: Hepatitis B Virus

<400> SEQUENCE: 180

Ala Leu Met Pro Leu Tyr Ala Cys Ile
1               5

<210> SEQ ID NO 181
<211> LENGTH: 10
<212> TYPE: PRT
<213> ORGANISM: Hepatitis B Virus

<400> SEQUENCE: 181

Leu Leu Pro Ile Phe Phe Cys Leu Trp Val
1               5                   10

<210> SEQ ID NO 182
<211> LENGTH: 9
<212> TYPE: PRT
<213> ORGANISM: Hepatitis B Virus

<400> SEQUENCE: 182

Tyr Met Asp Asp Val Val Leu Gly Ala
1               5

<210> SEQ ID NO 183
<211> LENGTH: 9
<212> TYPE: PRT
<213> ORGANISM: Hepatitis B Virus

<400> SEQUENCE: 183

Leu Leu Leu Cys Leu Ile Phe Leu Leu
1               5

<210> SEQ ID NO 184
<211> LENGTH: 10
<212> TYPE: PRT
<213> ORGANISM: Hepatitis B Virus

<400> SEQUENCE: 184

Leu Leu Asp Tyr Gln Gly Met Leu Pro Val
1               5                   10

<210> SEQ ID NO 185
<211> LENGTH: 10
<212> TYPE: PRT
```

<213> ORGANISM: Hepatitis B Virus

<400> SEQUENCE: 185

Ser Ile Val Ser Pro Phe Ile Pro Leu Leu
1               5                   10

<210> SEQ ID NO 186
<211> LENGTH: 9
<212> TYPE: PRT
<213> ORGANISM: Hepatitis B Virus

<400> SEQUENCE: 186

Phe Leu Leu Thr Arg Ile Leu Thr Ile
1               5

<210> SEQ ID NO 187
<211> LENGTH: 9
<212> TYPE: PRT
<213> ORGANISM: Hepatitis B Virus

<400> SEQUENCE: 187

Tyr Val Asn Val Asn Met Gly Leu Lys
1               5

<210> SEQ ID NO 188
<211> LENGTH: 11
<212> TYPE: PRT
<213> ORGANISM: Hepatitis B Virus

<400> SEQUENCE: 188

Ser Thr Leu Pro Glu Thr Thr Val Val Arg Arg
1               5                   10

<210> SEQ ID NO 189
<211> LENGTH: 11
<212> TYPE: PRT
<213> ORGANISM: Hepatitis B Virus

<400> SEQUENCE: 189

Ser Thr Leu Pro Glu Thr Thr Val Val Arg Arg
1               5                   10

<210> SEQ ID NO 190
<211> LENGTH: 10
<212> TYPE: PRT
<213> ORGANISM: Hepatitis B Virus

<400> SEQUENCE: 190

Phe Leu Pro Ser Asp Phe Phe Pro Ser Val
1               5                   10

<210> SEQ ID NO 191
<211> LENGTH: 12
<212> TYPE: PRT
<213> ORGANISM: Hepatitis B Virus

<400> SEQUENCE: 191

Ile Pro Gln Ser Leu Asp Ser Trp Trp Thr Ser Leu
1               5                   10

<210> SEQ ID NO 192
<211> LENGTH: 8
<212> TYPE: PRT
<213> ORGANISM: Hepatitis B Virus

<400> SEQUENCE: 192

Met Gly Leu Lys Phe Arg Gln Leu
1               5

<210> SEQ ID NO 193
<211> LENGTH: 9
<212> TYPE: PRT
<213> ORGANISM: Hepatitis B Virus
<220> FEATURE:
<221> NAME/KEY: VARIANT
<222> LOCATION: 4, 8
<223> OTHER INFORMATION: Xaa = Any Amino Acid

<400> SEQUENCE: 193

Ser Thr Asx Xaa Gln Ser Gly Xaa Gln
1               5

<210> SEQ ID NO 194
<211> LENGTH: 11
<212> TYPE: PRT
<213> ORGANISM: Human Cytomegalovirus

<400> SEQUENCE: 194

Phe Ile Ala Gly Asn Ser Ala Tyr Glu Tyr Val
1               5                   10

<210> SEQ ID NO 195
<211> LENGTH: 12
<212> TYPE: PRT
<213> ORGANISM: Human Cytomegalovirus

<400> SEQUENCE: 195

Ser Asp Glu Glu Phe Ala Ile Val Ala Tyr Thr Leu
1               5                   10

<210> SEQ ID NO 196
<211> LENGTH: 15
<212> TYPE: PRT
<213> ORGANISM: Human Cytomegalovirus

<400> SEQUENCE: 196

Asp Asp Val Trp Thr Ser Gly Ser Asp Ser Asp Glu Glu Leu Val
1               5                   10                  15

<210> SEQ ID NO 197
<211> LENGTH: 9
<212> TYPE: PRT
<213> ORGANISM: Human Cytomegalovirus

<400> SEQUENCE: 197

Ile Pro Ser Ile Asn Val His His Tyr
1               5

<210> SEQ ID NO 198
<211> LENGTH: 9
<212> TYPE: PRT
<213> ORGANISM: Human Cytomegalovirus

<400> SEQUENCE: 198

Asn Leu Val Pro Met Val Ala Thr Val
1               5

<210> SEQ ID NO 199
<211> LENGTH: 9
<212> TYPE: PRT
<213> ORGANISM: Human Cytomegalovirus

```
<400> SEQUENCE: 199

Asp Leu Met Gly Tyr Ile Pro Leu Val
1               5

<210> SEQ ID NO 200
<211> LENGTH: 9
<212> TYPE: PRT
<213> ORGANISM: Hepatitis C Virus

<400> SEQUENCE: 200

Asp Leu Met Gly Tyr Ile Pro Leu Val
1               5

<210> SEQ ID NO 201
<211> LENGTH: 10
<212> TYPE: PRT
<213> ORGANISM: Hepatitis C Virus

<400> SEQUENCE: 201

Leu Leu Ala Leu Leu Ser Cys Leu Thr Val
1               5                   10

<210> SEQ ID NO 202
<211> LENGTH: 8
<212> TYPE: PRT
<213> ORGANISM: Hepatitis C Virus

<400> SEQUENCE: 202

Ile Leu His Thr Pro Gly Cys Val
1               5

<210> SEQ ID NO 203
<211> LENGTH: 10
<212> TYPE: PRT
<213> ORGANISM: Hepatitis C Virus

<400> SEQUENCE: 203

Gln Leu Arg Arg His Ile Asp Leu Leu Val
1               5                   10

<210> SEQ ID NO 204
<211> LENGTH: 9
<212> TYPE: PRT
<213> ORGANISM: Hepatitis C Virus

<400> SEQUENCE: 204

Asp Leu Cys Gly Ser Val Phe Leu Val
1               5

<210> SEQ ID NO 205
<211> LENGTH: 9
<212> TYPE: PRT
<213> ORGANISM: Hepatitis C Virus

<400> SEQUENCE: 205

Ser Met Val Gly Asn Trp Ala Lys Val
1               5

<210> SEQ ID NO 206
<211> LENGTH: 10
<212> TYPE: PRT
<213> ORGANISM: Hepatitis C Virus

<400> SEQUENCE: 206

His Leu Ile Ile Gln Asn Ile Val Asp Val
```

<210> SEQ ID NO 207
<211> LENGTH: 9
<212> TYPE: PRT
<213> ORGANISM: Hepatitis C Virus

<400> SEQUENCE: 207

Phe Leu Leu Leu Ala Asp Ala Arg Val
 1               5

<210> SEQ ID NO 208
<211> LENGTH: 13
<212> TYPE: PRT
<213> ORGANISM: Hepatitis C Virus

<400> SEQUENCE: 208

Gly Leu Arg Asp Leu Ala Val Ala Val Glu Pro Val Val
 1               5                  10

<210> SEQ ID NO 209
<211> LENGTH: 11
<212> TYPE: PRT
<213> ORGANISM: Hepatitis C Virus

<400> SEQUENCE: 209

Ser Leu Leu Ala Pro Gly Ala Lys Gln Asn Val
 1               5                  10

<210> SEQ ID NO 210
<211> LENGTH: 10
<212> TYPE: PRT
<213> ORGANISM: Hepatitis C Virus

<400> SEQUENCE: 210

Leu Leu Ala Pro Gly Ala Lys Gln Asn Val
 1               5                  10

<210> SEQ ID NO 211
<211> LENGTH: 10
<212> TYPE: PRT
<213> ORGANISM: Hepatitis C Virus

<400> SEQUENCE: 211

Leu Leu Phe Asn Ile Leu Gly Gly Trp Val
 1               5                  10

<210> SEQ ID NO 212
<211> LENGTH: 9
<212> TYPE: PRT
<213> ORGANISM: Hepatitis C Virus

<400> SEQUENCE: 212

Tyr Leu Val Ala Tyr Gln Ala Thr Val
 1               5

<210> SEQ ID NO 213
<211> LENGTH: 10
<212> TYPE: PRT
<213> ORGANISM: Hepatitis C Virus

<400> SEQUENCE: 213

Tyr Leu Leu Pro Arg Arg Gly Pro Arg Leu
 1               5                  10

```
<210> SEQ ID NO 214
<211> LENGTH: 10
<212> TYPE: PRT
<213> ORGANISM: Hepatitis C Virus

<400> SEQUENCE: 214

Leu Leu Ala Leu Leu Ser Cys Leu Thr Ile
1               5                   10

<210> SEQ ID NO 215
<211> LENGTH: 9
<212> TYPE: PRT
<213> ORGANISM: Hepatitis C Virus

<400> SEQUENCE: 215

Ser Leu Met Ala Phe Thr Ala Ala Val
1               5

<210> SEQ ID NO 216
<211> LENGTH: 9
<212> TYPE: PRT
<213> ORGANISM: Hepatitis C Virus

<400> SEQUENCE: 216

Cys Ile Asn Gly Val Cys Trp Thr Val
1               5

<210> SEQ ID NO 217
<211> LENGTH: 9
<212> TYPE: PRT
<213> ORGANISM: Hepatitis C Virus

<400> SEQUENCE: 217

Leu Leu Cys Pro Ala Gly His Ala Val
1               5

<210> SEQ ID NO 218
<211> LENGTH: 9
<212> TYPE: PRT
<213> ORGANISM: Hepatitis C Virus

<400> SEQUENCE: 218

Ile Leu Asp Ser Phe Asp Pro Leu Val
1               5

<210> SEQ ID NO 219
<211> LENGTH: 9
<212> TYPE: PRT
<213> ORGANISM: Hepatitis C Virus

<400> SEQUENCE: 219

Ile Leu Ala Gly Tyr Gly Ala Gly Val
1               5

<210> SEQ ID NO 220
<211> LENGTH: 9
<212> TYPE: PRT
<213> ORGANISM: Hepatitis C Virus

<400> SEQUENCE: 220

Gly Leu Gln Asp Cys Thr Met Leu Val
1               5

<210> SEQ ID NO 221
<211> LENGTH: 10
<212> TYPE: PRT
```

<213> ORGANISM: Hepatitis C Virus

<400> SEQUENCE: 221

Thr Gly Ala Pro Val Thr Tyr Ser Thr Tyr
1               5                   10

<210> SEQ ID NO 222
<211> LENGTH: 9
<212> TYPE: PRT
<213> ORGANISM: Hepatitis C Virus

<400> SEQUENCE: 222

His Met Trp Asn Phe Ile Ser Gly Ile
1 5

<210> SEQ ID NO 223
<211> LENGTH: 9
<212> TYPE: PRT
<213> ORGANISM: Hepatitis C Virus

<400> SEQUENCE: 223

Arg Val Cys Glu Lys Met Ala Leu Tyr
1 5

<210> SEQ ID NO 224
<211> LENGTH: 8
<212> TYPE: PRT
<213> ORGANISM: Hepatitis C Virus

<400> SEQUENCE: 224

Thr Ile Asn Tyr Thr Ile Phe Lys
1 5

<210> SEQ ID NO 225
<211> LENGTH: 8
<212> TYPE: PRT
<213> ORGANISM: Hepatitis C Virus

<400> SEQUENCE: 225

Tyr Ile Ser Trp Cys Leu Trp Trp
1 5

<210> SEQ ID NO 226
<211> LENGTH: 9
<212> TYPE: PRT
<213> ORGANISM: Hepatitis C Virus

<400> SEQUENCE: 226

Gly Pro Arg Leu Gly Val Arg Ala Thr
1 5

<210> SEQ ID NO 227
<211> LENGTH: 9
<212> TYPE: PRT
<213> ORGANISM: Human Immunodeficiency Virus 1

<400> SEQUENCE: 227

Ser Phe Asn Cys Gly Gly Glu Phe Phe
1 5

<210> SEQ ID NO 228
<211> LENGTH: 9
<212> TYPE: PRT
<213> ORGANISM: Human Immunodeficiency Virus 1

<400> SEQUENCE: 228

```
Thr Glu Met Glu Lys Glu Gly Lys Ile
1               5
```

<210> SEQ ID NO 229
<211> LENGTH: 9
<212> TYPE: PRT
<213> ORGANISM: Human Immunodeficiency Virus 1

<400> SEQUENCE: 229

```
Lys Ile Arg Leu Arg Pro Gly Gly Lys
1               5
```

<210> SEQ ID NO 230
<211> LENGTH: 10
<212> TYPE: PRT
<213> ORGANISM: Human Immunodeficiency Virus 1

<400> SEQUENCE: 230

```
Arg Leu Arg Pro Gly Gly Lys Lys Lys Tyr
1               5                   10
```

<210> SEQ ID NO 231
<211> LENGTH: 9
<212> TYPE: PRT
<213> ORGANISM: Human Immunodeficiency Virus 1

<400> SEQUENCE: 231

```
Ala Ile Phe Gln Ser Ser Met Thr Lys
1               5
```

<210> SEQ ID NO 232
<211> LENGTH: 9
<212> TYPE: PRT
<213> ORGANISM: Human Immunodeficiency Virus 1

<400> SEQUENCE: 232

```
Thr Leu Tyr Cys Val His Gln Arg Ile
1               5
```

<210> SEQ ID NO 233
<211> LENGTH: 10
<212> TYPE: PRT
<213> ORGANISM: Human Immunodeficiency Virus 1

<400> SEQUENCE: 233

```
Ile Tyr Gln Glu Pro Phe Lys Asn Leu Lys
1               5                   10
```

<210> SEQ ID NO 234
<211> LENGTH: 9
<212> TYPE: PRT
<213> ORGANISM: Human Immunodeficiency Virus 1

<400> SEQUENCE: 234

```
Lys Tyr Lys Leu Lys His Ile Val Trp
1               5
```

<210> SEQ ID NO 235
<211> LENGTH: 10
<212> TYPE: PRT
<213> ORGANISM: Human Immunodeficiency Virus 1

<400> SEQUENCE: 235

```
Leu Phe Cys Ala Ser Asp Ala Lys Ala Tyr
1               5                   10
```

<210> SEQ ID NO 236
<211> LENGTH: 11
<212> TYPE: PRT
<213> ORGANISM: Human Immunodeficiency Virus 1

<400> SEQUENCE: 236

Gln Ala Ile Ser Pro Arg Thr Leu Asn Ala Trp
1               5                   10

<210> SEQ ID NO 237
<211> LENGTH: 9
<212> TYPE: PRT
<213> ORGANISM: Human Immunodeficiency Virus 1

<400> SEQUENCE: 237

Glu Val Ile Pro Met Phe Ser Ala Leu
1               5

<210> SEQ ID NO 238
<211> LENGTH: 11
<212> TYPE: PRT
<213> ORGANISM: Human Immunodeficiency Virus 1

<400> SEQUENCE: 238

Glu Thr Phe Tyr Val Asp Gly Ala Ala Asn Arg
1               5                   10

<210> SEQ ID NO 239
<211> LENGTH: 11
<212> TYPE: PRT
<213> ORGANISM: Human Immunodeficiency Virus 1

<400> SEQUENCE: 239

Arg Leu Arg Asp Leu Leu Leu Ile Val Thr Arg
1               5                   10

<210> SEQ ID NO 240
<211> LENGTH: 10
<212> TYPE: PRT
<213> ORGANISM: Human Immunodeficiency Virus 1

<400> SEQUENCE: 240

Pro Ile Gln Lys Glu Thr Trp Glu Thr Trp
1               5                   10

<210> SEQ ID NO 241
<211> LENGTH: 9
<212> TYPE: PRT
<213> ORGANISM: Human Immunodeficiency Virus 1

<400> SEQUENCE: 241

Arg Ile Lys Gln Ile Ile Asn Met Trp
1               5

<210> SEQ ID NO 242
<211> LENGTH: 9
<212> TYPE: PRT
<213> ORGANISM: Human Immunodeficiency Virus 1

<400> SEQUENCE: 242

Ile Thr Leu Trp Gln Arg Pro Leu Val
1               5

<210> SEQ ID NO 243

```
<211> LENGTH: 9
<212> TYPE: PRT
<213> ORGANISM: Human Immunodeficiency Virus 1

<400> SEQUENCE: 243

Asp Thr Val Leu Glu Glu Met Asn Leu
1               5

<210> SEQ ID NO 244
<211> LENGTH: 9
<212> TYPE: PRT
<213> ORGANISM: Human Immunodeficiency Virus 1

<400> SEQUENCE: 244

Ile Thr Leu Trp Gln Arg Pro Leu Val
1               5

<210> SEQ ID NO 245
<211> LENGTH: 9
<212> TYPE: PRT
<213> ORGANISM: Human Immunodeficiency Virus 1

<400> SEQUENCE: 245

Ser Pro Arg Thr Leu Asn Ala Trp Val
1               5

<210> SEQ ID NO 246
<211> LENGTH: 9
<212> TYPE: PRT
<213> ORGANISM: Human Immunodeficiency Virus 1

<400> SEQUENCE: 246

Ala Thr Pro Gln Asp Leu Asn Thr Met
1               5

<210> SEQ ID NO 247
<211> LENGTH: 10
<212> TYPE: PRT
<213> ORGANISM: Human Immunodeficiency Virus 1

<400> SEQUENCE: 247

Arg Pro Asn Asn Asn Thr Arg Lys Ser Ile
1               5                   10

<210> SEQ ID NO 248
<211> LENGTH: 9
<212> TYPE: PRT
<213> ORGANISM: Human Immunodeficiency Virus 1

<400> SEQUENCE: 248

Ile Pro Arg Arg Ile Arg Gln Gly Leu
1               5

<210> SEQ ID NO 249
<211> LENGTH: 9
<212> TYPE: PRT
<213> ORGANISM: Human Immunodeficiency Virus 1

<400> SEQUENCE: 249

Glu Leu Arg Ser Leu Tyr Asn Thr Val
1               5

<210> SEQ ID NO 250
<211> LENGTH: 8
<212> TYPE: PRT
<213> ORGANISM: Human Immunodeficiency Virus 1
```

```
<400> SEQUENCE: 250

Trp Pro Thr Val Arg Glu Arg Met
1               5

<210> SEQ ID NO 251
<211> LENGTH: 8
<212> TYPE: PRT
<213> ORGANISM: Human Immunodeficiency Virus 1

<400> SEQUENCE: 251

Phe Leu Lys Glu Lys Gly Gly Leu
1               5

<210> SEQ ID NO 252
<211> LENGTH: 9
<212> TYPE: PRT
<213> ORGANISM: Human Immunodeficiency Virus 1

<400> SEQUENCE: 252

Asp Leu Asn Thr Met Leu Asn Thr Val
1               5

<210> SEQ ID NO 253
<211> LENGTH: 10
<212> TYPE: PRT
<213> ORGANISM: Human Immunodeficiency Virus 1

<400> SEQUENCE: 253

Lys Ile Arg Leu Arg Pro Gly Gly Lys Lys
1               5                   10

<210> SEQ ID NO 254
<211> LENGTH: 9
<212> TYPE: PRT
<213> ORGANISM: Human Immunodeficiency Virus 1

<400> SEQUENCE: 254

Ile Arg Leu Arg Pro Gly Gly Lys Lys
1               5

<210> SEQ ID NO 255
<211> LENGTH: 10
<212> TYPE: PRT
<213> ORGANISM: Human Immunodeficiency Virus 1

<400> SEQUENCE: 255

Gly Arg Arg Gly Trp Glu Ala Leu Lys Tyr
1               5                   10

<210> SEQ ID NO 256
<211> LENGTH: 10
<212> TYPE: PRT
<213> ORGANISM: Human Immunodeficiency Virus 1

<400> SEQUENCE: 256

Gln Val Pro Leu Arg Pro Met Thr Tyr Lys
1               5                   10

<210> SEQ ID NO 257
<211> LENGTH: 8
<212> TYPE: PRT
<213> ORGANISM: Human Immunodeficiency Virus 1

<400> SEQUENCE: 257
```

Arg Tyr Leu Lys Asp Gln Gln Leu
1               5

<210> SEQ ID NO 258
<211> LENGTH: 10
<212> TYPE: PRT
<213> ORGANISM: Human Immunodeficiency Virus 1

<400> SEQUENCE: 258

Arg Arg Gln Asp Ile Leu Asp Leu Trp Ile
1               5                   10

<210> SEQ ID NO 259
<211> LENGTH: 8
<212> TYPE: PRT
<213> ORGANISM: Human Immunodeficiency Virus 1

<400> SEQUENCE: 259

Arg Tyr Pro Leu Thr Phe Gly Trp
1               5

<210> SEQ ID NO 260
<211> LENGTH: 9
<212> TYPE: PRT
<213> ORGANISM: Human Immunodeficiency Virus 1

<400> SEQUENCE: 260

Trp Ala Ser Arg Glu Leu Glu Arg Phe
1               5

<210> SEQ ID NO 261
<211> LENGTH: 9
<212> TYPE: PRT
<213> ORGANISM: Human Immunodeficiency Virus 1

<400> SEQUENCE: 261

Thr Val Leu Asp Val Gly Asp Ala Tyr
1               5

<210> SEQ ID NO 262
<211> LENGTH: 11
<212> TYPE: PRT
<213> ORGANISM: Human Immunodeficiency Virus 1

<400> SEQUENCE: 262

Val Pro Val Trp Lys Glu Ala Thr Thr Thr Leu
1               5                   10

<210> SEQ ID NO 263
<211> LENGTH: 9
<212> TYPE: PRT
<213> ORGANISM: Human Immunodeficiency Virus 1

<400> SEQUENCE: 263

Asn Ser Ser Lys Val Ser Gln Asn Tyr
1               5

<210> SEQ ID NO 264
<211> LENGTH: 9
<212> TYPE: PRT
<213> ORGANISM: Human Immunodeficiency Virus 1

<400> SEQUENCE: 264

Pro Pro Ile Pro Val Gly Asp Ile Tyr
1               5

```
<210> SEQ ID NO 265
<211> LENGTH: 9
<212> TYPE: PRT
<213> ORGANISM: Human Immunodeficiency Virus 1

<400> SEQUENCE: 265

His Pro Asp Ile Val Ile Tyr Gln Tyr
1               5

<210> SEQ ID NO 266
<211> LENGTH: 9
<212> TYPE: PRT
<213> ORGANISM: Human Immunodeficiency Virus 1

<400> SEQUENCE: 266

Thr Ala Val Pro Trp Asn Ala Ser Trp
1               5

<210> SEQ ID NO 267
<211> LENGTH: 9
<212> TYPE: PRT
<213> ORGANISM: Human Immunodeficiency Virus 1

<400> SEQUENCE: 267

Asn Pro Val Pro Val Gly Asn Leu Tyr
1               5

<210> SEQ ID NO 268
<211> LENGTH: 9
<212> TYPE: PRT
<213> ORGANISM: Human Immunodeficiency Virus 1

<400> SEQUENCE: 268

Tyr Phe Pro Asp Trp Gln Asn Tyr Thr
1               5

<210> SEQ ID NO 269
<211> LENGTH: 9
<212> TYPE: PRT
<213> ORGANISM: Human Immunodeficiency Virus 1

<400> SEQUENCE: 269

Gly His Gln Ala Ala Met Gln Met Leu
1               5

<210> SEQ ID NO 270
<211> LENGTH: 10
<212> TYPE: PRT
<213> ORGANISM: Human Immunodeficiency Virus 1

<400> SEQUENCE: 270

Arg Leu Arg Pro Gly Gly Lys Lys Lys Tyr
1               5                   10

<210> SEQ ID NO 271
<211> LENGTH: 9
<212> TYPE: PRT
<213> ORGANISM: Human Immunodeficiency Virus 1

<400> SEQUENCE: 271

Tyr Pro Gly Ile Lys Val Arg Gln Leu
1               5

<210> SEQ ID NO 272
<211> LENGTH: 10
```

```
<212> TYPE: PRT
<213> ORGANISM: Human Immunodeficiency Virus 1

<400> SEQUENCE: 272

Gly Ala Glu Thr Phe Tyr Val Asp Gly Ala
1               5                   10

<210> SEQ ID NO 273
<211> LENGTH: 9
<212> TYPE: PRT
<213> ORGANISM: Human Immunodeficiency Virus 1

<400> SEQUENCE: 273

Asn Ala Asn Pro Asp Cys Lys Thr Ile
1               5

<210> SEQ ID NO 274
<211> LENGTH: 8
<212> TYPE: PRT
<213> ORGANISM: Human Immunodeficiency Virus 1

<400> SEQUENCE: 274

Arg Met Tyr Ser Pro Thr Ser Ile
1               5

<210> SEQ ID NO 275
<211> LENGTH: 10
<212> TYPE: PRT
<213> ORGANISM: Human Immunodeficiency Virus 1

<400> SEQUENCE: 275

Val Pro Val Trp Lys Glu Ala Thr Thr Thr
1               5                   10

<210> SEQ ID NO 276
<211> LENGTH: 9
<212> TYPE: PRT
<213> ORGANISM: Human Immunodeficiency Virus 1

<400> SEQUENCE: 276

Ile Ser Pro Arg Thr Leu Asn Ala Trp
1               5

<210> SEQ ID NO 277
<211> LENGTH: 10
<212> TYPE: PRT
<213> ORGANISM: Human Immunodeficiency Virus 1

<400> SEQUENCE: 277

Thr Ser Thr Leu Gln Glu Gln Ile Gly Trp
1               5                   10

<210> SEQ ID NO 278
<211> LENGTH: 11
<212> TYPE: PRT
<213> ORGANISM: Human Immunodeficiency Virus 1

<400> SEQUENCE: 278

Lys Ala Phe Ser Pro Glu Val Ile Pro Met Phe
1               5                   10

<210> SEQ ID NO 279
<211> LENGTH: 9
<212> TYPE: PRT
<213> ORGANISM: Human Immunodeficiency Virus 1
```

```
<400> SEQUENCE: 279

Gln Ala Ser Gln Glu Val Lys Asn Trp
1               5

<210> SEQ ID NO 280
<211> LENGTH: 9
<212> TYPE: PRT
<213> ORGANISM: Human Immunodeficiency Virus 1

<400> SEQUENCE: 280

Gln Ala Ser Gln Asp Val Lys Asn Trp
1               5

<210> SEQ ID NO 281
<211> LENGTH: 10
<212> TYPE: PRT
<213> ORGANISM: Human Immunodeficiency Virus 1

<400> SEQUENCE: 281

His Thr Gln Gly Tyr Phe Pro Asp Trp Gln
1               5                   10

<210> SEQ ID NO 282
<211> LENGTH: 9
<212> TYPE: PRT
<213> ORGANISM: Human Immunodeficiency Virus 1

<400> SEQUENCE: 282

Tyr Phe Pro Asp Trp Gln Asn Tyr Thr
1               5

<210> SEQ ID NO 283
<211> LENGTH: 10
<212> TYPE: PRT
<213> ORGANISM: Human Immunodeficiency Virus 1

<400> SEQUENCE: 283

Thr Ser Thr Leu Gln Glu Gln Ile Gly Trp
1               5                   10

<210> SEQ ID NO 284
<211> LENGTH: 10
<212> TYPE: PRT
<213> ORGANISM: Human Immunodeficiency Virus 1

<400> SEQUENCE: 284

Arg Leu Arg Pro Gly Gly Lys Lys Lys Tyr
1               5                   10

<210> SEQ ID NO 285
<211> LENGTH: 9
<212> TYPE: PRT
<213> ORGANISM: Human Immunodeficiency Virus 1

<400> SEQUENCE: 285

Leu Gly Leu Asn Lys Val Arg Met Tyr
1               5

<210> SEQ ID NO 286
<211> LENGTH: 12
<212> TYPE: PRT
<213> ORGANISM: Human Immunodeficiency Virus 1

<400> SEQUENCE: 286

Leu Val Gly Lys Leu Asn Trp Ala Ser Gln Ile Tyr
```

```
<210> SEQ ID NO 287
<211> LENGTH: 10
<212> TYPE: PRT
<213> ORGANISM: Human Immunodeficiency Virus 1

<400> SEQUENCE: 287

Ile Leu Lys Glu Pro Val His Gly Val Tyr
1               5                   10

<210> SEQ ID NO 288
<211> LENGTH: 11
<212> TYPE: PRT
<213> ORGANISM: Human Immunodeficiency Virus 1

<400> SEQUENCE: 288

Thr Gln Gly Tyr Phe Pro Asp Trp Gln Asn Tyr
1               5                   10

<210> SEQ ID NO 289
<211> LENGTH: 8
<212> TYPE: PRT
<213> ORGANISM: Human Immunodeficiency Virus 1

<400> SEQUENCE: 289

Ala Val Asp Leu Ser His Phe Leu
1               5

<210> SEQ ID NO 290
<211> LENGTH: 8
<212> TYPE: PRT
<213> ORGANISM: Human Immunodeficiency Virus 1

<400> SEQUENCE: 290

Val Ile Pro Met Phe Ser Ala Leu
1               5

<210> SEQ ID NO 291
<211> LENGTH: 9
<212> TYPE: PRT
<213> ORGANISM: Human Immunodeficiency Virus 1

<400> SEQUENCE: 291

Phe Asn Cys Gly Gly Glu Phe Phe Tyr
1               5

<210> SEQ ID NO 292
<211> LENGTH: 9
<212> TYPE: PRT
<213> ORGANISM: Human Immunodeficiency Virus 1

<400> SEQUENCE: 292

Ser Phe Asn Cys Gly Gly Glu Phe Phe
1               5

<210> SEQ ID NO 293
<211> LENGTH: 10
<212> TYPE: PRT
<213> ORGANISM: Human Immunodeficiency Virus 1

<400> SEQUENCE: 293

Pro Leu Thr Phe Gly Trp Cys Tyr Lys Leu
1               5                   10
```

```
<210> SEQ ID NO 294
<211> LENGTH: 10
<212> TYPE: PRT
<213> ORGANISM: Human Immunodeficiency Virus 1

<400> SEQUENCE: 294

Val Leu Glu Trp Arg Phe Asp Ser Arg Leu
 1               5                  10

<210> SEQ ID NO 295
<211> LENGTH: 10
<212> TYPE: PRT
<213> ORGANISM: Human Immunodeficiency Virus 1

<400> SEQUENCE: 295

Phe Pro Val Thr Pro Gln Val Pro Leu Arg
 1               5                  10

<210> SEQ ID NO 296
<211> LENGTH: 10
<212> TYPE: PRT
<213> ORGANISM: Human Immunodeficiency Virus 1

<400> SEQUENCE: 296

Thr Pro Gly Pro Gly Val Arg Tyr Pro Leu
 1               5                  10

<210> SEQ ID NO 297
<211> LENGTH: 9
<212> TYPE: PRT
<213> ORGANISM: Human Immunodeficiency Virus 1

<400> SEQUENCE: 297

Gln Ala Ser Gln Glu Val Lys Asn Trp
 1               5

<210> SEQ ID NO 298
<211> LENGTH: 10
<212> TYPE: PRT
<213> ORGANISM: Human Immunodeficiency Virus 1 IIIB

<400> SEQUENCE: 298

Val Pro Leu Asp Glu Asp Phe Arg Lys Tyr
 1               5                  10

<210> SEQ ID NO 299
<211> LENGTH: 9
<212> TYPE: PRT
<213> ORGANISM: Human Immunodeficiency Virus 1 IIIB

<400> SEQUENCE: 299

Asn Pro Asp Ile Val Ile Tyr Gln Tyr
 1               5

<210> SEQ ID NO 300
<211> LENGTH: 9
<212> TYPE: PRT
<213> ORGANISM: Human Immunodeficiency Virus 1 IIIB

<400> SEQUENCE: 300

Arg Ala Ile Glu Ala Gln Ala His Leu
 1               5

<210> SEQ ID NO 301
<211> LENGTH: 8
<212> TYPE: PRT
```

<213> ORGANISM: Human Immunodeficiency Virus 1 IIIB

<400> SEQUENCE: 301

Thr Ala Phe Thr Ile Pro Ser Ile
1 5

<210> SEQ ID NO 302
<211> LENGTH: 10
<212> TYPE: PRT
<213> ORGANISM: Human Immunodeficiency Virus 1 IIIB

<400> SEQUENCE: 302

Val His Pro Val His Ala Gly Pro Ile Ala
1 5 10

<210> SEQ ID NO 303
<211> LENGTH: 10
<212> TYPE: PRT
<213> ORGANISM: Human Immunodeficiency Virus 1 IIIB

<400> SEQUENCE: 303

Asn Cys Ser Phe Asn Ile Ser Thr Ser Ile
1 5 10

<210> SEQ ID NO 304
<211> LENGTH: 9
<212> TYPE: PRT
<213> ORGANISM: Human Immunodeficiency Virus 1 IIIB

<400> SEQUENCE: 304

Cys Thr Asn Val Ser Thr Val Gln Cys
1 5

<210> SEQ ID NO 305
<211> LENGTH: 9
<212> TYPE: PRT
<213> ORGANISM: Human Immunodeficiency Virus 1 5F2

<400> SEQUENCE: 305

Ile Gly Pro Gly Arg Ala Phe His Thr
1 5

<210> SEQ ID NO 306
<211> LENGTH: 9
<212> TYPE: PRT
<213> ORGANISM: Human Immunodeficiency Virus 1 5F2

<400> SEQUENCE: 306

Asn Pro Asp Ile Val Ile Tyr Gln Tyr
1 5

<210> SEQ ID NO 307
<211> LENGTH: 10
<212> TYPE: PRT
<213> ORGANISM: Human Immunodeficiency Virus 1 5F2

<400> SEQUENCE: 307

Glu Pro Ile Val Gly Ala Glu Thr Phe Tyr
1 5 10

<210> SEQ ID NO 308
<211> LENGTH: 9
<212> TYPE: PRT
<213> ORGANISM: Human Immunodeficiency Virus 1 5F2

<400> SEQUENCE: 308

```
Glu Pro Ile Val Gly Ala Glu Thr Phe
1               5
```

<210> SEQ ID NO 309
<211> LENGTH: 9
<212> TYPE: PRT
<213> ORGANISM: Human Immunodeficiency Virus 1 5F2

<400> SEQUENCE: 309

```
Ser Pro Ala Ile Phe Gln Ser Ser Met
1               5
```

<210> SEQ ID NO 310
<211> LENGTH: 10
<212> TYPE: PRT
<213> ORGANISM: Human Immunodeficiency Virus 1 5F2

<400> SEQUENCE: 310

```
Val Pro Leu Asp Lys Asp Phe Arg Lys Tyr
1               5                   10
```

<210> SEQ ID NO 311
<211> LENGTH: 9
<212> TYPE: PRT
<213> ORGANISM: Human Immunodeficiency Virus 1 5F2

<400> SEQUENCE: 311

```
Ile Pro Leu Thr Glu Glu Ala Glu Leu
1               5
```

<210> SEQ ID NO 312
<211> LENGTH: 11
<212> TYPE: PRT
<213> ORGANISM: Human Immunodeficiency Virus 1 5F2

<400> SEQUENCE: 312

```
Arg Pro Gln Val Pro Leu Arg Pro Met Thr Tyr
1               5                   10
```

<210> SEQ ID NO 313
<211> LENGTH: 9
<212> TYPE: PRT
<213> ORGANISM: Human Immunodeficiency Virus 1 5F2

<400> SEQUENCE: 313

```
Phe Pro Val Arg Pro Gln Val Pro Leu
1               5
```

<210> SEQ ID NO 314
<211> LENGTH: 9
<212> TYPE: PRT
<213> ORGANISM: Human Immunodeficiency Virus 1 5F2

<400> SEQUENCE: 314

```
Asp Pro Asn Pro Gln Glu Val Val Leu
1               5
```

<210> SEQ ID NO 315
<211> LENGTH: 9
<212> TYPE: PRT
<213> ORGANISM: Human Immunodeficiency Virus 1 5F2

<400> SEQUENCE: 315

```
Arg Pro Ile Val Ser Thr Gln Leu Leu
1               5
```

```
<210> SEQ ID NO 316
<211> LENGTH: 9
<212> TYPE: PRT
<213> ORGANISM: Human Immunodeficiency Virus 1 5F2

<400> SEQUENCE: 316

Ile Pro Leu Thr Glu Glu Ala Glu Leu
1               5

<210> SEQ ID NO 317
<211> LENGTH: 9
<212> TYPE: PRT
<213> ORGANISM: Human Immunodeficiency Virus 1 5F2

<400> SEQUENCE: 317

Asp Pro Asn Pro Gln Glu Val Val Leu
1               5

<210> SEQ ID NO 318
<211> LENGTH: 9
<212> TYPE: PRT
<213> ORGANISM: Human Immunodeficiency Virus 1 5F2

<400> SEQUENCE: 318

Ala Met Gln Met Leu Lys Glu Thr Ile
1               5

<210> SEQ ID NO 319
<211> LENGTH: 9
<212> TYPE: PRT
<213> ORGANISM: Human Immunodeficiency Virus 2

<400> SEQUENCE: 319

Thr Pro Tyr Asp Arg Asn Gln Met Leu
1               5

<210> SEQ ID NO 320
<211> LENGTH: 11
<212> TYPE: PRT
<213> ORGANISM: Human Immunodeficiency Virus 2

<400> SEQUENCE: 320

Arg Arg Trp Ile Gln Leu Gly Leu Gln Lys Val
1               5                   10

<210> SEQ ID NO 321
<211> LENGTH: 15
<212> TYPE: PRT
<213> ORGANISM: Human Immunodeficiency Virus 1 5F2

<400> SEQUENCE: 321

Gly Ile Trp Gly Cys Ser Gly Lys Leu Ile Cys Thr Thr Ala Val
1               5                   10                  15

<210> SEQ ID NO 322
<211> LENGTH: 15
<212> TYPE: PRT
<213> ORGANISM: Human Immunodeficiency Virus 1 5F2

<400> SEQUENCE: 322

Ala Leu Ile Trp Glu Asp Leu Arg Ser Leu Cys Leu Phe Ser Tyr
1               5                   10                  15

<210> SEQ ID NO 323
```

```
<211> LENGTH: 9
<212> TYPE: PRT
<213> ORGANISM: Human Papillomavirus 6b

<400> SEQUENCE: 323

Gly Leu His Cys Tyr Glu Gln Leu Val
 1               5

<210> SEQ ID NO 324
<211> LENGTH: 9
<212> TYPE: PRT
<213> ORGANISM: Human Papillomavirus 6b

<400> SEQUENCE: 324

Pro Leu Lys Gln His Phe Gln Ile Val
 1               5

<210> SEQ ID NO 325
<211> LENGTH: 9
<212> TYPE: PRT
<213> ORGANISM: Human Papillomavirus 11

<400> SEQUENCE: 325

Arg Leu Val Thr Leu Lys Asp Ile Val
 1               5

<210> SEQ ID NO 326
<211> LENGTH: 9
<212> TYPE: PRT
<213> ORGANISM: Human Papillomavirus 16

<400> SEQUENCE: 326

Thr Leu Gly Ile Val Cys Pro Ile Cys
 1               5

<210> SEQ ID NO 327
<211> LENGTH: 9
<212> TYPE: PRT
<213> ORGANISM: Human Papillomavirus 16

<400> SEQUENCE: 327

Gly Thr Leu Gly Ile Val Cys Pro Ile
 1               5

<210> SEQ ID NO 328
<211> LENGTH: 9
<212> TYPE: PRT
<213> ORGANISM: Human Papillomavirus 16

<400> SEQUENCE: 328

Met Leu Asp Leu Gln Pro Glu Thr Thr
 1               5

<210> SEQ ID NO 329
<211> LENGTH: 10
<212> TYPE: PRT
<213> ORGANISM: Human Papillomavirus 16

<400> SEQUENCE: 329

Tyr Met Leu Asp Leu Gln Pro Glu Thr Thr
 1               5                  10

<210> SEQ ID NO 330
<211> LENGTH: 8
<212> TYPE: PRT
<213> ORGANISM: Human Papillomavirus 16
```

<400> SEQUENCE: 330

Arg Pro Arg Lys Leu Pro Gln Leu
1               5

<210> SEQ ID NO 331
<211> LENGTH: 9
<212> TYPE: PRT
<213> ORGANISM: Human Papillomavirus 16

<400> SEQUENCE: 331

Arg Ala His Tyr Asn Ile Val Thr Phe
1               5

<210> SEQ ID NO 332
<211> LENGTH: 8
<212> TYPE: PRT
<213> ORGANISM: Herpes Simplex Virus

<400> SEQUENCE: 332

Ser Ser Ile Glu Phe Ala Arg Leu
1               5

<210> SEQ ID NO 333
<211> LENGTH: 9
<212> TYPE: PRT
<213> ORGANISM: Herpes Simplex Virus 1

<400> SEQUENCE: 333

Gly Ile Gly Ile Gly Val Leu Ala Ala
1               5

<210> SEQ ID NO 334
<211> LENGTH: 9
<212> TYPE: PRT
<213> ORGANISM: Herpes Simplex Virus 1

<400> SEQUENCE: 334

Asp Tyr Ala Thr Leu Gly Val Gly Val
1               5

<210> SEQ ID NO 335
<211> LENGTH: 11
<212> TYPE: PRT
<213> ORGANISM: Herpes Simplex Virus 1

<400> SEQUENCE: 335

Leu Tyr Arg Thr Phe Ala Gly Asn Pro Arg Ala
1               5                   10

<210> SEQ ID NO 336
<211> LENGTH: 8
<212> TYPE: PRT
<213> ORGANISM: Herpes Simplex Virus 1

<400> SEQUENCE: 336

Gln Thr Phe Asp Phe Gly Arg Leu
1               5

<210> SEQ ID NO 337
<211> LENGTH: 9
<212> TYPE: PRT
<213> ORGANISM: Herpes Simplex Virus 2

<400> SEQUENCE: 337

```
Gly Ala Gly Ile Gly Val Ala Val Leu
1               5
```

<210> SEQ ID NO 338
<211> LENGTH: 9
<212> TYPE: PRT
<213> ORGANISM: Human T-lymphotropic Virus 1

<400> SEQUENCE: 338

```
Leu Leu Phe Gly Tyr Pro Val Tyr Val
1               5
```

<210> SEQ ID NO 339
<211> LENGTH: 9
<212> TYPE: PRT
<213> ORGANISM: Influenza

<400> SEQUENCE: 339

```
Gly Ile Leu Gly Phe Val Phe Thr Leu
1               5
```

<210> SEQ ID NO 340
<211> LENGTH: 10
<212> TYPE: PRT
<213> ORGANISM: Influenza

<400> SEQUENCE: 340

```
Ile Leu Gly Phe Val Phe Thr Leu Thr Val
1               5                   10
```

<210> SEQ ID NO 341
<211> LENGTH: 9
<212> TYPE: PRT
<213> ORGANISM: Influenza

<400> SEQUENCE: 341

```
Ile Leu Arg Gly Ser Val Ala His Lys
1               5
```

<210> SEQ ID NO 342
<211> LENGTH: 9
<212> TYPE: PRT
<213> ORGANISM: Influenza

<400> SEQUENCE: 342

```
Lys Thr Gly Gly Pro Ile Tyr Lys Arg
1               5
```

<210> SEQ ID NO 343
<211> LENGTH: 9
<212> TYPE: PRT
<213> ORGANISM: Influenza

<400> SEQUENCE: 343

```
Glu Leu Arg Ser Arg Tyr Trp Ala Ile
1               5
```

<210> SEQ ID NO 344
<211> LENGTH: 8
<212> TYPE: PRT
<213> ORGANISM: Influenza

<400> SEQUENCE: 344

```
Leu Arg Ser Arg Tyr Trp Ala Ile
1               5
```

```
<210> SEQ ID NO 345
<211> LENGTH: 9
<212> TYPE: PRT
<213> ORGANISM: Influenza

<400> SEQUENCE: 345

Glu Asp Leu Arg Val Leu Ser Phe Ile
1               5

<210> SEQ ID NO 346
<211> LENGTH: 9
<212> TYPE: PRT
<213> ORGANISM: Influenza

<400> SEQUENCE: 346

Gly Glu Ile Ser Pro Leu Pro Ser Leu
1               5

<210> SEQ ID NO 347
<211> LENGTH: 9
<212> TYPE: PRT
<213> ORGANISM: Influenza

<400> SEQUENCE: 347

Phe Glu Asp Leu Arg Val Leu Ser Phe
1               5

<210> SEQ ID NO 348
<211> LENGTH: 9
<212> TYPE: PRT
<213> ORGANISM: Influenza

<400> SEQUENCE: 348

Gly Glu Ile Ser Pro Leu Pro Ser Leu
1               5

<210> SEQ ID NO 349
<211> LENGTH: 9
<212> TYPE: PRT
<213> ORGANISM: Influenza

<400> SEQUENCE: 349

Phe Glu Asp Leu Arg Val Leu Ser Phe
1               5

<210> SEQ ID NO 350
<211> LENGTH: 9
<212> TYPE: PRT
<213> ORGANISM: Influenza

<400> SEQUENCE: 350

Val Ser Asp Gly Gly Pro Lys Leu Tyr
1               5

<210> SEQ ID NO 351
<211> LENGTH: 9
<212> TYPE: PRT
<213> ORGANISM: Influenza A

<400> SEQUENCE: 351

Cys Thr Glu Leu Lys Leu Ser Asp Tyr
1               5

<210> SEQ ID NO 352
<211> LENGTH: 9
```

```
<212> TYPE: PRT
<213> ORGANISM: Influenza

<400> SEQUENCE: 352

Ala Ile Met Asp Lys Asn Ile Ile Leu
 1               5

<210> SEQ ID NO 353
<211> LENGTH: 10
<212> TYPE: PRT
<213> ORGANISM: Influenza A

<400> SEQUENCE: 353

Ile Met Asp Lys Asn Ile Ile Leu Lys Ala
 1               5                  10

<210> SEQ ID NO 354
<211> LENGTH: 9
<212> TYPE: PRT
<213> ORGANISM: Influenza A

<400> SEQUENCE: 354

Ser Arg Tyr Trp Ala Ile Arg Thr Arg
 1               5

<210> SEQ ID NO 355
<211> LENGTH: 9
<212> TYPE: PRT
<213> ORGANISM: Influenza A

<400> SEQUENCE: 355

Thr Tyr Gln Arg Thr Arg Ala Leu Val
 1               5

<210> SEQ ID NO 356
<211> LENGTH: 10
<212> TYPE: PRT
<213> ORGANISM: Influenza A

<400> SEQUENCE: 356

Thr Tyr Val Ser Val Ser Thr Ser Thr Leu
 1               5                  10

<210> SEQ ID NO 357
<211> LENGTH: 9
<212> TYPE: PRT
<213> ORGANISM: Influenza A

<400> SEQUENCE: 357

Ile Tyr Ser Thr Val Ala Ser Ser Leu
 1               5

<210> SEQ ID NO 358
<211> LENGTH: 8
<212> TYPE: PRT
<213> ORGANISM: Influenza A

<400> SEQUENCE: 358

Phe Glu Ala Asn Gly Asn Leu Ile
 1               5

<210> SEQ ID NO 359
<211> LENGTH: 9
<212> TYPE: PRT
<213> ORGANISM: Influenza A
```

```
<400> SEQUENCE: 359

Ile Glu Gly Gly Trp Thr Gly Met Leu
1               5

<210> SEQ ID NO 360
<211> LENGTH: 8
<212> TYPE: PRT
<213> ORGANISM: Influenza A

<400> SEQUENCE: 360

Ser Asp Tyr Glu Gly Arg Leu Ile
1               5

<210> SEQ ID NO 361
<211> LENGTH: 9
<212> TYPE: PRT
<213> ORGANISM: Influenza A

<400> SEQUENCE: 361

Glu Glu Gly Ala Ile Val Gly Glu Ile
1               5

<210> SEQ ID NO 362
<211> LENGTH: 9
<212> TYPE: PRT
<213> ORGANISM: Influenza A34

<400> SEQUENCE: 362

Ala Ser Asn Glu Asn Met Glu Thr Met
1               5

<210> SEQ ID NO 363
<211> LENGTH: 9
<212> TYPE: PRT
<213> ORGANISM: Influenza A68

<400> SEQUENCE: 363

Ala Ser Asn Glu Asn Met Asp Ala Met
1               5

<210> SEQ ID NO 364
<211> LENGTH: 10
<212> TYPE: PRT
<213> ORGANISM: Influenza B

<400> SEQUENCE: 364

Lys Leu Gly Glu Phe Tyr Asn Gln Met Met
1               5                   10

<210> SEQ ID NO 365
<211> LENGTH: 10
<212> TYPE: PRT
<213> ORGANISM: Influenza B

<400> SEQUENCE: 365

Lys Ala Gly Glu Phe Tyr Asn Gln Met Met
1               5                   10

<210> SEQ ID NO 366
<211> LENGTH: 9
<212> TYPE: PRT
<213> ORGANISM: Influenza JAP

<400> SEQUENCE: 366

Leu Tyr Gln Asn Val Gly Thr Tyr Val
```

<210> SEQ ID NO 367
<211> LENGTH: 10
<212> TYPE: PRT
<213> ORGANISM: Influenza JAP

<400> SEQUENCE: 367

Thr Tyr Val Ser Val Gly Thr Ser Thr Leu
1               5                   10

<210> SEQ ID NO 368
<211> LENGTH: 9
<212> TYPE: PRT
<213> ORGANISM: Influenza JAP

<400> SEQUENCE: 368

Val Tyr Gln Ile Leu Ala Thr Tyr Ala
1               5

<210> SEQ ID NO 369
<211> LENGTH: 9
<212> TYPE: PRT
<213> ORGANISM: Influenza JAP

<400> SEQUENCE: 369

Ile Tyr Ala Thr Val Ala Gly Ser Leu
1               5

<210> SEQ ID NO 370
<211> LENGTH: 10
<212> TYPE: PRT
<213> ORGANISM: Influenza JAP

<400> SEQUENCE: 370

Thr Tyr Val Ser Val Gly Thr Ser Thr Ile
1               5                   10

<210> SEQ ID NO 371
<211> LENGTH: 8
<212> TYPE: PRT
<213> ORGANISM: Influenza JAP

<400> SEQUENCE: 371

Phe Glu Ser Thr Gly Asn Leu Ile
1               5

<210> SEQ ID NO 372
<211> LENGTH: 9
<212> TYPE: PRT
<213> ORGANISM: Mouse Hepatitis Virus Strain JHM

<400> SEQUENCE: 372

Ala Pro Thr Ala Gly Ala Phe Phe Phe
1               5

<210> SEQ ID NO 373
<211> LENGTH: 9
<212> TYPE: PRT
<213> ORGANISM: Lymphocytic Choriomeningitis Virus

<400> SEQUENCE: 373

Arg Pro Gln Ala Ser Gly Val Tyr Met
1               5

```
<210> SEQ ID NO 374
<211> LENGTH: 9
<212> TYPE: PRT
<213> ORGANISM: Lymphocytic Choriomeningitis Virus

<400> SEQUENCE: 374

Phe Gln Pro Gln Asn Gly Gln Phe Ile
 1               5

<210> SEQ ID NO 375
<211> LENGTH: 11
<212> TYPE: PRT
<213> ORGANISM: Lymphocytic Choriomeningitis Virus

<400> SEQUENCE: 375

Ser Gly Val Glu Asn Pro Gly Gly Tyr Cys Leu
 1               5                  10

<210> SEQ ID NO 376
<211> LENGTH: 10
<212> TYPE: PRT
<213> ORGANISM: Lymphocytic Choriomeningitis Virus

<400> SEQUENCE: 376

Lys Ala Val Tyr Asn Phe Ala Thr Cys Gly
 1               5                  10

<210> SEQ ID NO 377
<211> LENGTH: 9
<212> TYPE: PRT
<213> ORGANISM: Murine Cytomegalovirus

<400> SEQUENCE: 377

Tyr Pro His Phe Met Pro Thr Asn Leu
 1               5

<210> SEQ ID NO 378
<211> LENGTH: 9
<212> TYPE: PRT
<213> ORGANISM: Mouse Hepatitis Virus

<400> SEQUENCE: 378

Cys Leu Ser Trp Asn Gly Pro His Leu
 1               5

<210> SEQ ID NO 379
<211> LENGTH: 9
<212> TYPE: PRT
<213> ORGANISM: Mouse Mammarytumor Virus

<400> SEQUENCE: 379

Ser Phe Ala Val Ala Thr Thr Ala Leu
 1               5

<210> SEQ ID NO 380
<211> LENGTH: 9
<212> TYPE: PRT
<213> ORGANISM: Mouse Mammarytumor Virus

<400> SEQUENCE: 380

Ser Tyr Glu Thr Phe Ile Ser Arg Leu
 1               5

<210> SEQ ID NO 381
<211> LENGTH: 8
<212> TYPE: PRT
```

<213> ORGANISM: Mouse Mammarytumor Virus

<400> SEQUENCE: 381

Ala Asn Tyr Asp Phe Ile Cys Val
1               5

<210> SEQ ID NO 382
<211> LENGTH: 8
<212> TYPE: PRT
<213> ORGANISM: Murine Leukemia Virus

<400> SEQUENCE: 382

Lys Ser Pro Trp Phe Thr Thr Leu
1               5

<210> SEQ ID NO 383
<211> LENGTH: 8
<212> TYPE: PRT
<213> ORGANISM: Murine Leukemia Virus

<400> SEQUENCE: 383

Ser Ser Trp Asp Phe Ile Thr Val
1               5

<210> SEQ ID NO 384
<211> LENGTH: 9
<212> TYPE: PRT
<213> ORGANISM: Murine Leukemia Virus

<400> SEQUENCE: 384

Cys Cys Leu Cys Leu Thr Val Phe Leu
1               5

<210> SEQ ID NO 385
<211> LENGTH: 9
<212> TYPE: PRT
<213> ORGANISM: Murine Leukemia Virus

<400> SEQUENCE: 385

Ser Pro Ser Tyr Val Tyr His Gln Phe
1               5

<210> SEQ ID NO 386
<211> LENGTH: 11
<212> TYPE: PRT
<213> ORGANISM: Measles Virus

<400> SEQUENCE: 386

Ser Arg Arg Tyr Pro Asp Ala Val Tyr Leu His
1               5                   10

<210> SEQ ID NO 387
<211> LENGTH: 9
<212> TYPE: PRT
<213> ORGANISM: Measles Virus

<400> SEQUENCE: 387

Arg Arg Tyr Pro Asp Ala Val Tyr Leu
1               5

<210> SEQ ID NO 388
<211> LENGTH: 9
<212> TYPE: PRT
<213> ORGANISM: Measles Virus

<400> SEQUENCE: 388

Tyr Pro Ala Leu Gly Leu His Glu Phe
1               5

<210> SEQ ID NO 389
<211> LENGTH: 9
<212> TYPE: PRT
<213> ORGANISM: Measles Virus

<400> SEQUENCE: 389

Asp Pro Val Ile Asp Arg Leu Tyr Leu
1               5

<210> SEQ ID NO 390
<211> LENGTH: 9
<212> TYPE: PRT
<213> ORGANISM: Measles Virus

<400> SEQUENCE: 390

Ser Pro Gly Arg Ser Phe Ser Tyr Phe
1               5

<210> SEQ ID NO 391
<211> LENGTH: 8
<212> TYPE: PRT
<213> ORGANISM: Poliovirus

<400> SEQUENCE: 391

Thr Tyr Lys Asp Thr Val Gln Leu
1               5

<210> SEQ ID NO 392
<211> LENGTH: 10
<212> TYPE: PRT
<213> ORGANISM: Poliovirus

<400> SEQUENCE: 392

Phe Tyr Asp Gly Phe Ser Lys Val Pro Leu
1               5                   10

<210> SEQ ID NO 393
<211> LENGTH: 9
<212> TYPE: PRT
<213> ORGANISM: Pseudorabies virus gp

<400> SEQUENCE: 393

Ile Ala Gly Ile Gly Ile Leu Ala Ile
1               5

<210> SEQ ID NO 394
<211> LENGTH: 9
<212> TYPE: PRT
<213> ORGANISM: Rabiesvirus

<400> SEQUENCE: 394

Val Glu Ala Glu Ile Ala His Gln Ile
1               5

<210> SEQ ID NO 395
<211> LENGTH: 8
<212> TYPE: PRT
<213> ORGANISM: Rotavirus

<400> SEQUENCE: 395

Leu Leu Tyr Arg Phe Leu Leu Leu
1               5

<210> SEQ ID NO 396
<211> LENGTH: 9
<212> TYPE: PRT
<213> ORGANISM: Rotavirus

<400> SEQUENCE: 396

Val Gly Pro Val Phe Pro Pro Gly Met
1               5

<210> SEQ ID NO 397
<211> LENGTH: 9
<212> TYPE: PRT
<213> ORGANISM: Rotavirus

<400> SEQUENCE: 397

Tyr Ser Gly Tyr Ile Phe Arg Asp Leu
1               5

<210> SEQ ID NO 398
<211> LENGTH: 9
<212> TYPE: PRT
<213> ORGANISM: Respiratory Syncytial Virus

<400> SEQUENCE: 398

Ser Tyr Ile Gly Ser Ile Asn Asn Ile
1               5

<210> SEQ ID NO 399
<211> LENGTH: 12
<212> TYPE: PRT
<213> ORGANISM: Simian Immunodeficiency Virus

<400> SEQUENCE: 399

Glu Gly Cys Thr Pro Tyr Asp Thr Asn Gln Met Leu
1               5                   10

<210> SEQ ID NO 400
<211> LENGTH: 9
<212> TYPE: PRT
<213> ORGANISM: Sendai Virus

<400> SEQUENCE: 400

Phe Ala Pro Gly Asn Tyr Pro Ala Leu
1               5

<210> SEQ ID NO 401
<211> LENGTH: 10
<212> TYPE: PRT
<213> ORGANISM: Sendai Virus

<400> SEQUENCE: 401

Phe Ala Pro Cys Thr Asn Tyr Pro Ala Leu
1               5                   10

<210> SEQ ID NO 402
<211> LENGTH: 8
<212> TYPE: PRT
<213> ORGANISM: Sendai Virus 40

<400> SEQUENCE: 402

Val Val Tyr Asp Phe Leu Lys Cys
1               5

<210> SEQ ID NO 403

```
<211> LENGTH: 10
<212> TYPE: PRT
<213> ORGANISM: Sendai Virus 40

<400> SEQUENCE: 403

Ser Ala Ile Asn Asn Tyr Ala Gln Lys Leu
1               5                   10

<210> SEQ ID NO 404
<211> LENGTH: 9
<212> TYPE: PRT
<213> ORGANISM: Sendai Virus 40

<400> SEQUENCE: 404

Cys Lys Gly Val Asn Lys Glu Tyr Leu
1               5

<210> SEQ ID NO 405
<211> LENGTH: 9
<212> TYPE: PRT
<213> ORGANISM: Sendai Virus 40

<400> SEQUENCE: 405

Gln Gly Ile Asn Asn Leu Asp Asn Leu
1               5

<210> SEQ ID NO 406
<211> LENGTH: 10
<212> TYPE: PRT
<213> ORGANISM: Sendai Virus 40

<400> SEQUENCE: 406

Asn Asn Leu Asp Asn Leu Arg Asp Tyr Leu
1               5                   10

<210> SEQ ID NO 407
<211> LENGTH: 9
<212> TYPE: PRT
<213> ORGANISM: Sendai Virus 40

<400> SEQUENCE: 407

Ser Glu Phe Leu Leu Glu Lys Arg Ile
1               5

<210> SEQ ID NO 408
<211> LENGTH: 8
<212> TYPE: PRT
<213> ORGANISM: Vesicular Stomatitis Virus

<400> SEQUENCE: 408

Arg Gly Tyr Val Tyr Gln Gly Leu
1               5

<210> SEQ ID NO 409
<211> LENGTH: 9
<212> TYPE: PRT
<213> ORGANISM: Homo Sapiens

<400> SEQUENCE: 409

Glu Ala Asp Pro Thr Gly His Ser Tyr
1               5

<210> SEQ ID NO 410
<211> LENGTH: 9
<212> TYPE: PRT
<213> ORGANISM: Influenza
```

```
<400> SEQUENCE: 410

Val Ser Asp Gly Gly Pro Asn Leu Tyr
 1               5

<210> SEQ ID NO 411
<211> LENGTH: 9
<212> TYPE: PRT
<213> ORGANISM: Influenza

<400> SEQUENCE: 411

Cys Thr Glu Leu Lys Leu Ser Asp Tyr
 1               5

<210> SEQ ID NO 412
<211> LENGTH: 9
<212> TYPE: PRT
<213> ORGANISM: Homo Sapiens

<400> SEQUENCE: 412

Glu Val Asp Pro Ile Gly His Leu Tyr
 1               5

<210> SEQ ID NO 413
<211> LENGTH: 10
<212> TYPE: PRT
<213> ORGANISM: Homo Sapien (Calreticulin)

<400> SEQUENCE: 413

Met Leu Leu Ser Val Pro Leu Leu Leu Gly
 1               5                  10

<210> SEQ ID NO 414
<211> LENGTH: 9
<212> TYPE: PRT
<213> ORGANISM: Hepatitis B Virus
<220> FEATURE:
<221> NAME/KEY: VARIANT
<222> LOCATION: 4, 8
<223> OTHER INFORMATION: Xaa = Any Amino Acid

<400> SEQUENCE: 414

Ser Thr Asx Xaa Gln Ser Gly Xaa Gln
 1               5

<210> SEQ ID NO 415
<211> LENGTH: 9
<212> TYPE: PRT
<213> ORGANISM: Homo Sapiens

<400> SEQUENCE: 415

Tyr Met Asp Gly Thr Met Ser Gln Val
 1               5

<210> SEQ ID NO 416
<211> LENGTH: 9
<212> TYPE: PRT
<213> ORGANISM: Human Immunodeficiency Virus 1

<400> SEQUENCE: 416

Ile Leu Lys Glu Pro Val His Gly Val
 1               5

<210> SEQ ID NO 417
<211> LENGTH: 10
<212> TYPE: PRT
```

<213> ORGANISM: Influenza MP

<400> SEQUENCE: 417

Leu Leu Gly Phe Val Phe Thr Leu Thr Val
 1 5 10

<210> SEQ ID NO 418
<211> LENGTH: 10
<212> TYPE: PRT
<213> ORGANISM: Human T-lymphotropic Virus 1

<400> SEQUENCE: 418

Leu Leu Phe Gly Tyr Pro Val Tyr Val Val
1 5 10

<210> SEQ ID NO 419
<211> LENGTH: 10
<212> TYPE: PRT
<213> ORGANISM: Hepatitis B Virus

<400> SEQUENCE: 419

Gly Leu Ser Pro Thr Val Trp Leu Ser Val
1 5 10

<210> SEQ ID NO 420
<211> LENGTH: 9
<212> TYPE: PRT
<213> ORGANISM: Hepatitis B Virus

<400> SEQUENCE: 420

Trp Leu Ser Leu Leu Val Pro Phe Val
1 5

<210> SEQ ID NO 421
<211> LENGTH: 10
<212> TYPE: PRT
<213> ORGANISM: Hepatitis B Virus

<400> SEQUENCE: 421

Phe Leu Pro Ser Asp Phe Phe Pro Ser Val
1 5 10

<210> SEQ ID NO 422
<211> LENGTH: 8
<212> TYPE: PRT
<213> ORGANISM: Epstein-Barr Virus

<400> SEQUENCE: 422

Cys Leu Gly Leu Leu Thr Met Val
1 5

<210> SEQ ID NO 423
<211> LENGTH: 11
<212> TYPE: PRT
<213> ORGANISM: Human Cytomegalovirus

<400> SEQUENCE: 423

Phe Leu Ala Gly Asn Ser Ala Tyr Glu Tyr Val
1 5 10

<210> SEQ ID NO 424
<211> LENGTH: 10
<212> TYPE: PRT
<213> ORGANISM: Influenza

<400> SEQUENCE: 424

Lys Leu Gly Glu Phe Tyr Asn Gln Met Met
1               5                   10

<210> SEQ ID NO 425
<211> LENGTH: 10
<212> TYPE: PRT
<213> ORGANISM: Hepatitis C Virus 1

<400> SEQUENCE: 425

Lys Leu Val Ala Leu Gly Ile Asn Ala Val
1               5                   10

<210> SEQ ID NO 426
<211> LENGTH: 9
<212> TYPE: PRT
<213> ORGANISM: Hepatitis C Virus

<400> SEQUENCE: 426

Asp Leu Met Gly Tyr Ile Pro Leu Val
1               5

<210> SEQ ID NO 427
<211> LENGTH: 9
<212> TYPE: PRT
<213> ORGANISM: Human Papillomavirus

<400> SEQUENCE: 427

Arg Leu Val Thr Leu Lys Asp Ile Val
1               5

<210> SEQ ID NO 428
<211> LENGTH: 9
<212> TYPE: PRT
<213> ORGANISM: Homo Sapien

<400> SEQUENCE: 428

Met Leu Leu Ala Val Leu Tyr Cys Leu
1               5

<210> SEQ ID NO 429
<211> LENGTH: 9
<212> TYPE: PRT
<213> ORGANISM: Homo Sapien

<400> SEQUENCE: 429

Ala Ala Gly Ile Gly Ile Leu Thr Val
1               5

<210> SEQ ID NO 430
<211> LENGTH: 9
<212> TYPE: PRT
<213> ORGANISM: Homo Sapien

<400> SEQUENCE: 430

Tyr Leu Glu Pro Gly Pro Val Thr Ala
1               5

<210> SEQ ID NO 431
<211> LENGTH: 10
<212> TYPE: PRT
<213> ORGANISM: Homo Sapien

<400> SEQUENCE: 431

Ile Leu Asp Gly Thr Ala Thr Leu Arg Leu
1               5                   10

<210> SEQ ID NO 432
<211> LENGTH: 10
<212> TYPE: PRT
<213> ORGANISM: Homo Sapien

<400> SEQUENCE: 432

Leu Leu Asp Gly Thr Ala Thr Leu Arg Leu
1               5                   10

<210> SEQ ID NO 433
<211> LENGTH: 9
<212> TYPE: PRT
<213> ORGANISM: Homo Sapien

<400> SEQUENCE: 433

Ile Thr Asp Gln Val Pro Phe Ser Val
1               5

<210> SEQ ID NO 434
<211> LENGTH: 9
<212> TYPE: PRT
<213> ORGANISM: Homo Sapien

<400> SEQUENCE: 434

Lys Thr Trp Gly Gln Tyr Trp Gln Val
1               5

<210> SEQ ID NO 435
<211> LENGTH: 10
<212> TYPE: PRT
<213> ORGANISM: Homo Sapien

<400> SEQUENCE: 435

Thr Ile Thr Asp Gln Val Pro Phe Ser Val
1               5                   10

<210> SEQ ID NO 436
<211> LENGTH: 10
<212> TYPE: PRT
<213> ORGANISM: Human Immunodeviciency Virus 1

<400> SEQUENCE: 436

Ala Phe His Ile Ile Val Ala Arg Glu Leu
1               5                   10

<210> SEQ ID NO 437
<211> LENGTH: 9
<212> TYPE: PRT
<213> ORGANISM: Plasmodium Falciparum

<400> SEQUENCE: 437

Tyr Leu Asn Lys Ile Gln Asn Ser Leu
1               5

<210> SEQ ID NO 438
<211> LENGTH: 10
<212> TYPE: PRT
<213> ORGANISM: Plasmodium Falciparum

<400> SEQUENCE: 438

Met Met Arg Lys Leu Ala Ile Leu Ser Val
1               5                   10

<210> SEQ ID NO 439

```
<211> LENGTH: 10
<212> TYPE: PRT
<213> ORGANISM: Influenza

<400> SEQUENCE: 439

Lys Ala Gly Glu Phe Tyr Asn Gln Met Met
1               5                   10

<210> SEQ ID NO 440
<211> LENGTH: 9
<212> TYPE: PRT
<213> ORGANISM: Epstein-Barr Virus (EBNA)

<400> SEQUENCE: 440

Asn Ile Ala Glu Gly Leu Arg Ala Leu
1               5

<210> SEQ ID NO 441
<211> LENGTH: 9
<212> TYPE: PRT
<213> ORGANISM: Epstein-Barr Virus (EBNA)

<400> SEQUENCE: 441

Asn Leu Arg Arg Gly Thr Ala Leu Ala
1               5

<210> SEQ ID NO 442
<211> LENGTH: 9
<212> TYPE: PRT
<213> ORGANISM: Epstein-Barr Virus (EBNA)

<400> SEQUENCE: 442

Ala Leu Ala Ile Pro Gln Cys Arg Leu
1               5

<210> SEQ ID NO 443
<211> LENGTH: 9
<212> TYPE: PRT
<213> ORGANISM: Epstein-Barr Virus (EBNA)

<400> SEQUENCE: 443

Val Leu Lys Asp Ala Ile Lys Asp Leu
1               5

<210> SEQ ID NO 444
<211> LENGTH: 9
<212> TYPE: PRT
<213> ORGANISM: Epstein-Barr Virus (EBNA)

<400> SEQUENCE: 444

Phe Met Val Phe Leu Gln Thr His Ile
1               5

<210> SEQ ID NO 445
<211> LENGTH: 9
<212> TYPE: PRT
<213> ORGANISM: Epstein-Barr Virus (EBNA)

<400> SEQUENCE: 445

His Leu Ile Val Asp Thr Asp Ser Leu
1               5

<210> SEQ ID NO 446
<211> LENGTH: 9
<212> TYPE: PRT
<213> ORGANISM: Epstein-Barr Virus (EBNA)
```

<400> SEQUENCE: 446

Ser Leu Gly Asn Pro Ser Leu Ser Val
1               5

<210> SEQ ID NO 447
<211> LENGTH: 9
<212> TYPE: PRT
<213> ORGANISM: Epstein-Barr Virus (EBNA)

<400> SEQUENCE: 447

Pro Leu Ala Ser Ala Met Arg Met Leu
1               5

<210> SEQ ID NO 448
<211> LENGTH: 9
<212> TYPE: PRT
<213> ORGANISM: Epstein-Barr Virus (EBNA)

<400> SEQUENCE: 448

Arg Met Leu Trp Met Ala Asn Tyr Ile
1               5

<210> SEQ ID NO 449
<211> LENGTH: 9
<212> TYPE: PRT
<213> ORGANISM: Epstein-Barr Virus (EBNA)

<400> SEQUENCE: 449

Met Leu Trp Met Ala Asn Tyr Ile Val
1               5

<210> SEQ ID NO 450
<211> LENGTH: 9
<212> TYPE: PRT
<213> ORGANISM: Epstein-Barr Virus (EBNA)

<400> SEQUENCE: 450

Ile Leu Pro Gln Gly Pro Gln Thr Ala
1               5

<210> SEQ ID NO 451
<211> LENGTH: 10
<212> TYPE: PRT
<213> ORGANISM: Epstein-Barr Virus (EBNA)

<400> SEQUENCE: 451

Pro Leu Arg Pro Thr Ala Pro Thr Thr Ile
1               5                   10

<210> SEQ ID NO 452
<211> LENGTH: 9
<212> TYPE: PRT
<213> ORGANISM: Epstein-Barr Virus (EBNA)

<400> SEQUENCE: 452

Pro Leu Pro Pro Ala Thr Leu Thr Val
1               5

<210> SEQ ID NO 453
<211> LENGTH: 9
<212> TYPE: PRT
<213> ORGANISM: Epstein-Barr Virus (EBNA)

<400> SEQUENCE: 453

Arg Met His Leu Pro Val Leu His Val
1               5

<210> SEQ ID NO 454
<211> LENGTH: 9
<212> TYPE: PRT
<213> ORGANISM: Epstein-Barr Virus (EBNA)

<400> SEQUENCE: 454

Pro Met Pro Leu Pro Pro Ser Gln Leu
1               5

<210> SEQ ID NO 455
<211> LENGTH: 9
<212> TYPE: PRT
<213> ORGANISM: Epstein-Barr Virus (EBNA)

<400> SEQUENCE: 455

Gln Leu Pro Pro Pro Ala Ala Pro Ala
1               5

<210> SEQ ID NO 456
<211> LENGTH: 9
<212> TYPE: PRT
<213> ORGANISM: Epstein-Barr Virus (EBNA)

<400> SEQUENCE: 456

Ser Met Pro Glu Leu Ser Pro Val Leu
1               5

<210> SEQ ID NO 457
<211> LENGTH: 9
<212> TYPE: PRT
<213> ORGANISM: Epstein-Barr Virus (EBNA)

<400> SEQUENCE: 457

Asp Leu Asp Glu Ser Trp Asp Tyr Leu
1               5

<210> SEQ ID NO 458
<211> LENGTH: 10
<212> TYPE: PRT
<213> ORGANISM: Epstein-Barr Virus (EBNA)

<400> SEQUENCE: 458

Pro Leu Pro Cys Val Leu Trp Pro Val Val
1               5                   10

<210> SEQ ID NO 459
<211> LENGTH: 9
<212> TYPE: PRT
<213> ORGANISM: Epstein-Barr Virus (EBNA)

<400> SEQUENCE: 459

Ser Leu Glu Glu Cys Asp Ser Glu Leu
1               5

<210> SEQ ID NO 460
<211> LENGTH: 9
<212> TYPE: PRT
<213> ORGANISM: Epstein-Barr Virus (EBNA)

<400> SEQUENCE: 460

Glu Ile Lys Arg Tyr Lys Asn Arg Val
1               5

<210> SEQ ID NO 461
<211> LENGTH: 10
<212> TYPE: PRT
<213> ORGANISM: Epstein-Barr Virus (EBNA)

<400> SEQUENCE: 461

Gln Leu Leu Gln Phe Ile Tyr Arg Glu Val
1               5                   10

<210> SEQ ID NO 462
<211> LENGTH: 9
<212> TYPE: PRT
<213> ORGANISM: Epstein-Barr Virus (EBNA)

<400> SEQUENCE: 462

Leu Leu Gln His Tyr Arg Glu Val Ala
1               5

<210> SEQ ID NO 463
<211> LENGTH: 9
<212> TYPE: PRT
<213> ORGANISM: Epstein-Barr Virus (EBNA)

<400> SEQUENCE: 463

Leu Leu Lys Gln Met Cys Pro Ser Leu
1               5

<210> SEQ ID NO 464
<211> LENGTH: 9
<212> TYPE: PRT
<213> ORGANISM: Epstein-Barr Virus (EBNA)

<400> SEQUENCE: 464

Ser Ile Ile Pro Arg Thr Pro Asp Val
1               5

<210> SEQ ID NO 465
<211> LENGTH: 9
<212> TYPE: PRT
<213> ORGANISM: Influenza A

<400> SEQUENCE: 465

Ala Ile Met Asp Lys Asn Ile Ile Leu
1               5

<210> SEQ ID NO 466
<211> LENGTH: 10
<212> TYPE: PRT
<213> ORGANISM: Influenza A

<400> SEQUENCE: 466

Ile Met Asp Lys Asn Ile Ile Leu Lys Ala
1               5                   10

<210> SEQ ID NO 467
<211> LENGTH: 10
<212> TYPE: PRT
<213> ORGANISM: Hepatitis C Virus

<400> SEQUENCE: 467

Leu Leu Ala Leu Leu Ser Cys Leu Thr Val
1               5                   10

<210> SEQ ID NO 468
<211> LENGTH: 8

```
<212> TYPE: PRT
<213> ORGANISM: Hepatitis C Virus

<400> SEQUENCE: 468

Ile Leu His Thr Pro Gly Cys Val
 1               5

<210> SEQ ID NO 469
<211> LENGTH: 10
<212> TYPE: PRT
<213> ORGANISM: Hepatitis C Virus

<400> SEQUENCE: 469

Gln Leu Arg Arg His Ile Asp Leu Leu Val
 1               5                  10

<210> SEQ ID NO 470
<211> LENGTH: 9
<212> TYPE: PRT
<213> ORGANISM: Hepatitis C Virus

<400> SEQUENCE: 470

Asp Leu Cys Gly Ser Val Phe Leu Val
 1               5

<210> SEQ ID NO 471
<211> LENGTH: 9
<212> TYPE: PRT
<213> ORGANISM: Hepatitis C Virus

<400> SEQUENCE: 471

Ser Met Val Gly Asn Trp Ala Lys Val
 1               5

<210> SEQ ID NO 472
<211> LENGTH: 9
<212> TYPE: PRT
<213> ORGANISM: Hepatitis C Virus

<400> SEQUENCE: 472

His Leu His Gln Asn Ile Val Asp Val
 1               5

<210> SEQ ID NO 473
<211> LENGTH: 9
<212> TYPE: PRT
<213> ORGANISM: Hepatitis C Virus

<400> SEQUENCE: 473

Phe Leu Leu Leu Ala Asp Ala Arg Val
 1               5

<210> SEQ ID NO 474
<211> LENGTH: 13
<212> TYPE: PRT
<213> ORGANISM: Hepatitis C Virus

<400> SEQUENCE: 474

Gly Leu Arg Asp Leu Ala Val Ala Val Glu Pro Val Val
 1               5                  10

<210> SEQ ID NO 475
<211> LENGTH: 11
<212> TYPE: PRT
<213> ORGANISM: Hepatitis C Virus
```

```
<400> SEQUENCE: 475

Ser Leu Leu Ala Pro Gly Ala Lys Gln Asn Val
1               5                   10

<210> SEQ ID NO 476
<211> LENGTH: 10
<212> TYPE: PRT
<213> ORGANISM: Hepatitis C Virus

<400> SEQUENCE: 476

Leu Leu Ala Pro Gly Ala Lys Gln Asn Val
1               5                   10

<210> SEQ ID NO 477
<211> LENGTH: 9
<212> TYPE: PRT
<213> ORGANISM: Hepatitis B Virus

<400> SEQUENCE: 477

Phe Leu Leu Ser Leu Gly Ile His Leu
1               5

<210> SEQ ID NO 478
<211> LENGTH: 9
<212> TYPE: PRT
<213> ORGANISM: Hepatitis B Virus

<400> SEQUENCE: 478

Ser Leu Tyr Ala Asp Ser Pro Ser Val
1               5

<210> SEQ ID NO 479
<211> LENGTH: 9
<212> TYPE: PRT
<213> ORGANISM: Hepatitis B Virus

<400> SEQUENCE: 479

Gly Leu Ser Arg Tyr Val Ala Arg Leu
1               5

<210> SEQ ID NO 480
<211> LENGTH: 9
<212> TYPE: PRT
<213> ORGANISM: Homo Sapien

<400> SEQUENCE: 480

Lys Ile Phe Gly Ser Leu Ala Phe Leu
1               5

<210> SEQ ID NO 481
<211> LENGTH: 9
<212> TYPE: PRT
<213> ORGANISM: Homo Sapien

<400> SEQUENCE: 481

Glu Leu Val Ser Glu Phe Ser Arg Met
1               5

<210> SEQ ID NO 482
<211> LENGTH: 9
<212> TYPE: PRT
<213> ORGANISM: Human Immunodeficiency Virus 1

<400> SEQUENCE: 482

Lys Leu Thr Pro Leu Cys Val Thr Leu
```

```
                              1               5

<210> SEQ ID NO 483
<211> LENGTH: 10
<212> TYPE: PRT
<213> ORGANISM: Human Immunodeficiency Virus 1

<400> SEQUENCE: 483

Ser Leu Leu Asn Ala Thr Asp Ile Ala Val
 1               5                  10

<210> SEQ ID NO 484
<211> LENGTH: 10
<212> TYPE: PRT
<213> ORGANISM: Homo Sapien

<400> SEQUENCE: 484

Val Leu Tyr Arg Tyr Gly Ser Phe Ser Val
 1               5                  10

<210> SEQ ID NO 485
<211> LENGTH: 9
<212> TYPE: PRT
<213> ORGANISM: Homo Sapien

<400> SEQUENCE: 485

Tyr Ile Gly Glu Val Leu Val Ser Val
 1               5

<210> SEQ ID NO 486
<211> LENGTH: 10
<212> TYPE: PRT
<213> ORGANISM: Hepatitis C Virus

<400> SEQUENCE: 486

Leu Leu Phe Asn Ile Leu Gly Gly Trp Val
 1               5                  10

<210> SEQ ID NO 487
<211> LENGTH: 10
<212> TYPE: PRT
<213> ORGANISM: Hepatitis B Virus

<400> SEQUENCE: 487

Leu Leu Val Pro Phe Val Gln Trp Phe Trp
 1               5                  10

<210> SEQ ID NO 488
<211> LENGTH: 9
<212> TYPE: PRT
<213> ORGANISM: Hepatitis B Virus

<400> SEQUENCE: 488

Ala Leu Met Pro Leu Tyr Ala Cys Ile
 1               5

<210> SEQ ID NO 489
<211> LENGTH: 9
<212> TYPE: PRT
<213> ORGANISM: Hepatitis C Virus

<400> SEQUENCE: 489

Tyr Leu Val Ala Tyr Gln Ala Thr Val
 1               5
```

```
<210> SEQ ID NO 490
<211> LENGTH: 9
<212> TYPE: PRT
<213> ORGANISM: Himetobi P Virus (HiPV)

<400> SEQUENCE: 490

Thr Leu Gly Ile Val Cys Pro Ile Cys
1               5

<210> SEQ ID NO 491
<211> LENGTH: 10
<212> TYPE: PRT
<213> ORGANISM: Hepatitis C Virus

<400> SEQUENCE: 491

Tyr Leu Leu Pro Arg Arg Gly Pro Arg Leu
1               5                   10

<210> SEQ ID NO 492
<211> LENGTH: 10
<212> TYPE: PRT
<213> ORGANISM: Hepatitis B Virus

<400> SEQUENCE: 492

Leu Leu Pro Ile Phe Phe Cys Leu Trp Val
1               5                   10

<210> SEQ ID NO 493
<211> LENGTH: 9
<212> TYPE: PRT
<213> ORGANISM: Hepatitis B Virus

<400> SEQUENCE: 493

Tyr Met Asp Asp Val Val Leu Gly Ala
1               5

<210> SEQ ID NO 494
<211> LENGTH: 9
<212> TYPE: PRT
<213> ORGANISM: Human Papillomavirus

<400> SEQUENCE: 494

Gly Thr Leu Gly Ile Val Cys Pro Ile
1               5

<210> SEQ ID NO 495
<211> LENGTH: 10
<212> TYPE: PRT
<213> ORGANISM: Hepatitis C Virus

<400> SEQUENCE: 495

Leu Leu Ala Leu Leu Ser Cys Leu Thr Ile
1               5                   10

<210> SEQ ID NO 496
<211> LENGTH: 9
<212> TYPE: PRT
<213> ORGANISM: Human Papillomavirus

<400> SEQUENCE: 496

Met Leu Asp Leu Gln Pro Glu Thr Thr
1               5

<210> SEQ ID NO 497
<211> LENGTH: 9
<212> TYPE: PRT
```

<213> ORGANISM: Hepatitis C Virus

<400> SEQUENCE: 497

Ser Leu Met Ala Phe Thr Ala Ala Val
1               5

<210> SEQ ID NO 498
<211> LENGTH: 9
<212> TYPE: PRT
<213> ORGANISM: Hepatitis C Virus

<400> SEQUENCE: 498

Cys Ile Asn Gly Val Cys Trp Thr Val
1 5

<210> SEQ ID NO 499
<211> LENGTH: 10
<212> TYPE: PRT
<213> ORGANISM: Homo Sapien

<400> SEQUENCE: 499

Val Met Asn Ile Leu Leu Gln Tyr Val Val
1 5 10

<210> SEQ ID NO 500
<211> LENGTH: 9
<212> TYPE: PRT
<213> ORGANISM: Homo Sapien

<400> SEQUENCE: 500

Ile Leu Thr Val Ile Leu Gly Val Leu
1 5

<210> SEQ ID NO 501
<211> LENGTH: 9
<212> TYPE: PRT
<213> ORGANISM: Homo Sapien

<400> SEQUENCE: 501

Phe Leu Trp Gly Pro Arg Ala Leu Val
1 5

<210> SEQ ID NO 502
<211> LENGTH: 9
<212> TYPE: PRT
<213> ORGANISM: Hepatitis C Virus

<400> SEQUENCE: 502

Leu Leu Cys Pro Ala Gly His Ala Val
1 5

<210> SEQ ID NO 503
<211> LENGTH: 9
<212> TYPE: PRT
<213> ORGANISM: Hepatitis C Virus

<400> SEQUENCE: 503

Ile Leu Asp Ser Phe Asp Pro Leu Val
1 5

<210> SEQ ID NO 504
<211> LENGTH: 9
<212> TYPE: PRT
<213> ORGANISM: Hepatitis B Virus

<400> SEQUENCE: 504

Leu Leu Leu Cys Leu Ile Phe Leu Leu
1               5

<210> SEQ ID NO 505
<211> LENGTH: 10
<212> TYPE: PRT
<213> ORGANISM: Hepatitis B Virus

<400> SEQUENCE: 505

Leu Ile Asp Tyr Gln Gly Met Leu Pro Val
1               5                   10

<210> SEQ ID NO 506
<211> LENGTH: 10
<212> TYPE: PRT
<213> ORGANISM: Hepatitis B Virus

<400> SEQUENCE: 506

Ser Ile Val Ser Pro Phe Ile Pro Leu Leu
1               5                   10

<210> SEQ ID NO 507
<211> LENGTH: 9
<212> TYPE: PRT
<213> ORGANISM: Hepatitis B Virus

<400> SEQUENCE: 507

Phe Leu Leu Thr Arg Ile Leu Thr Ile
1               5

<210> SEQ ID NO 508
<211> LENGTH: 9
<212> TYPE: PRT
<213> ORGANISM: Plasmodium Faciparum

<400> SEQUENCE: 508

His Leu Gly Asn Val Lys Tyr Leu Val
1               5

<210> SEQ ID NO 509
<211> LENGTH: 9
<212> TYPE: PRT
<213> ORGANISM: Plasmodium Faciparum

<400> SEQUENCE: 509

Gly Ile Ala Gly Gly Leu Ala Leu Leu
1               5

<210> SEQ ID NO 510
<211> LENGTH: 9
<212> TYPE: PRT
<213> ORGANISM: Hepatitis C Virus

<400> SEQUENCE: 510

Ile Leu Ala Gly Tyr Gly Ala Gly Val
1               5

<210> SEQ ID NO 511
<211> LENGTH: 9
<212> TYPE: PRT
<213> ORGANISM: Hepatitis C Virus

<400> SEQUENCE: 511

Gly Leu Gln Asp Cys Thr Met Leu Val
1               5

```
<210> SEQ ID NO 512
<211> LENGTH: 10
<212> TYPE: PRT
<213> ORGANISM: Hepatitis C Virus

<400> SEQUENCE: 512

Thr Gly Ala Pro Val Thr Tyr Ser Thr Tyr
1               5                   10

<210> SEQ ID NO 513
<211> LENGTH: 10
<212> TYPE: PRT
<213> ORGANISM: Human Immunodeficiency Virus 1

<400> SEQUENCE: 513

Val Ile Tyr Gln Tyr Met Asp Asp Leu Val
1               5                   10

<210> SEQ ID NO 514
<211> LENGTH: 10
<212> TYPE: PRT
<213> ORGANISM: Homo Sapien

<400> SEQUENCE: 514

Val Leu Pro Asp Val Phe Ile Arg Cys Val
1               5                   10

<210> SEQ ID NO 515
<211> LENGTH: 9
<212> TYPE: PRT
<213> ORGANISM: Homo Sapien

<400> SEQUENCE: 515

Val Leu Pro Asp Val Phe Ile Arg Cys
1               5

<210> SEQ ID NO 516
<211> LENGTH: 9
<212> TYPE: PRT
<213> ORGANISM: Homo Sapien

<400> SEQUENCE: 516

Ala Val Gly Ile Gly Ile Ala Val Val
1               5

<210> SEQ ID NO 517
<211> LENGTH: 9
<212> TYPE: PRT
<213> ORGANISM: Homo Sapien

<400> SEQUENCE: 517

Leu Val Val Leu Gly Leu Leu Ala Val
1               5

<210> SEQ ID NO 518
<211> LENGTH: 9
<212> TYPE: PRT
<213> ORGANISM: Homo Sapien

<400> SEQUENCE: 518

Ala Leu Gly Leu Gly Leu Leu Pro Val
1               5

<210> SEQ ID NO 519
```

```
<211> LENGTH: 9
<212> TYPE: PRT
<213> ORGANISM: Herpes Simplex Virus I

<400> SEQUENCE: 519

Gly Ile Gly Ile Gly Val Leu Ala Ala
1               5

<210> SEQ ID NO 520
<211> LENGTH: 9
<212> TYPE: PRT
<213> ORGANISM: Herpes Simplex Virus 2

<400> SEQUENCE: 520

Gly Ala Gly Ile Gly Val Ala Val Leu
1               5

<210> SEQ ID NO 521
<211> LENGTH: 9
<212> TYPE: PRT
<213> ORGANISM: Pseudorabies Virus

<400> SEQUENCE: 521

Ile Ala Gly Ile Gly Ile Leu Ala Ile
1               5

<210> SEQ ID NO 522
<211> LENGTH: 9
<212> TYPE: PRT
<213> ORGANISM: Adenovirus

<400> SEQUENCE: 522

Leu Ile Val Ile Gly Ile Leu Ile Leu
1               5

<210> SEQ ID NO 523
<211> LENGTH: 9
<212> TYPE: PRT
<213> ORGANISM: Streptomyces Lincolnensis

<400> SEQUENCE: 523

Leu Ala Gly Ile Gly Leu Ile Ala Ala
1               5

<210> SEQ ID NO 524
<211> LENGTH: 9
<212> TYPE: PRT
<213> ORGANISM: Yeast (YSA-1)

<400> SEQUENCE: 524

Val Asp Gly Ile Gly Ile Leu Thr Ile
1               5

<210> SEQ ID NO 525
<211> LENGTH: 9
<212> TYPE: PRT
<213> ORGANISM: Bacillus Polymyxa

<400> SEQUENCE: 525

Gly Ala Gly Ile Gly Val Leu Thr Ala
1               5

<210> SEQ ID NO 526
<211> LENGTH: 9
<212> TYPE: PRT
<213> ORGANISM: Escherichia Coli
```

-continued

<400> SEQUENCE: 526

Ala Ala Gly Ile Gly Ile Ile Gln Ile
1               5

<210> SEQ ID NO 527
<211> LENGTH: 9
<212> TYPE: PRT
<213> ORGANISM: Escherichia Coli

<400> SEQUENCE: 527

Gln Ala Gly Ile Gly Ile Leu Leu Ala
1               5

<210> SEQ ID NO 528
<211> LENGTH: 11
<212> TYPE: PRT
<213> ORGANISM: Homo Sapien

<400> SEQUENCE: 528

Lys Ala Arg Asp Pro His Ser Gly His Phe Val
1               5                   10

<210> SEQ ID NO 529
<211> LENGTH: 13
<212> TYPE: PRT
<213> ORGANISM: Homo Sapien

<400> SEQUENCE: 529

Lys Ala Cys Asp Pro Ile Ile Ser Gly Ile Ile Phe Val
1               5                   10

<210> SEQ ID NO 530
<211> LENGTH: 11
<212> TYPE: PRT
<213> ORGANISM: Homo Sapien

<400> SEQUENCE: 530

Ala Cys Asp Pro Phe Ile Ser Gly His Phe Val
1               5                   10

<210> SEQ ID NO 531
<211> LENGTH: 9
<212> TYPE: PRT
<213> ORGANISM: Human Immunodeficiency Virus I

<400> SEQUENCE: 531

Ser Leu Tyr Asn Thr Val Ala Thr Leu
1               5

<210> SEQ ID NO 532
<211> LENGTH: 9
<212> TYPE: PRT
<213> ORGANISM: Homo Sapien

<400> SEQUENCE: 532

Glu Leu Val Ser Glu Phe Ser Arg Val
1               5

<210> SEQ ID NO 533
<211> LENGTH: 10
<212> TYPE: PRT
<213> ORGANISM: Human Immunodeficiency Virus I

<400> SEQUENCE: 533

```
Arg Gly Pro Gly Arg Ala Phe Val Thr Ile
 1               5                  10

<210> SEQ ID NO 534
<211> LENGTH: 9
<212> TYPE: PRT
<213> ORGANISM: Hepatitis C Virus

<400> SEQUENCE: 534

His Met Trp Asn Phe Ile Ser Gly Ile
 1               5

<210> SEQ ID NO 535
<211> LENGTH: 10
<212> TYPE: PRT
<213> ORGANISM: Human Cytomegalovirus

<400> SEQUENCE: 535

Asn Leu Val Pro Met Val Ala Thr Val Gln
 1               5                  10

<210> SEQ ID NO 536
<211> LENGTH: 9
<212> TYPE: PRT
<213> ORGANISM: Human Papillomavirus

<400> SEQUENCE: 536

Gly Leu His Cys Tyr Glu Gln Leu Val
 1               5

<210> SEQ ID NO 537
<211> LENGTH: 9
<212> TYPE: PRT
<213> ORGANISM: Human Papillomavirus

<400> SEQUENCE: 537

Pro Leu Lys Gln His Phe Gln Ile Val
 1               5

<210> SEQ ID NO 538
<211> LENGTH: 10
<212> TYPE: PRT
<213> ORGANISM: Epstein-Barr Virus (EBNA)

<400> SEQUENCE: 538

Leu Leu Asp Phe Val Arg Phe Met Gly Val
 1               5                  10

<210> SEQ ID NO 539
<211> LENGTH: 9
<212> TYPE: PRT
<213> ORGANISM: Influenza

<400> SEQUENCE: 539

Ala Ile Met Glu Lys Asn Ile Met Leu
 1               5

<210> SEQ ID NO 540
<211> LENGTH: 9
<212> TYPE: PRT
<213> ORGANISM: Plasmodium Falciparum

<400> SEQUENCE: 540

Tyr Leu Lys Thr Ile Gln Asn Ser Leu
 1               5
```

```
<210> SEQ ID NO 541
<211> LENGTH: 9
<212> TYPE: PRT
<213> ORGANISM: Plasmodium Falciparum

<400> SEQUENCE: 541

Tyr Leu Asn Lys Ile Gln Asn Ser Leu
1               5

<210> SEQ ID NO 542
<211> LENGTH: 10
<212> TYPE: PRT
<213> ORGANISM: Human Papillomavirus

<400> SEQUENCE: 542

Tyr Met Leu Asp Leu Gln Pro Glu Thr Thr
1               5                   10

<210> SEQ ID NO 543
<211> LENGTH: 9
<212> TYPE: PRT
<213> ORGANISM: Human Papillomavirus

<400> SEQUENCE: 543

Leu Leu Met Gly Thr Leu Gly Ile Val
1               5

<210> SEQ ID NO 544
<211> LENGTH: 8
<212> TYPE: PRT
<213> ORGANISM: Human Papillomavirus

<400> SEQUENCE: 544

Thr Leu Gly Ile Val Cys Pro Ile
1               5

<210> SEQ ID NO 545
<211> LENGTH: 9
<212> TYPE: PRT
<213> ORGANISM: Human Immunodeficiency Virus 1

<400> SEQUENCE: 545

Thr Leu Thr Ser Cys Asn Thr Ser Val
1               5

<210> SEQ ID NO 546
<211> LENGTH: 9
<212> TYPE: PRT
<213> ORGANISM: Human Papillomavirus

<400> SEQUENCE: 546

Lys Leu Pro Gln Leu Cys Thr Glu Leu
1               5

<210> SEQ ID NO 547
<211> LENGTH: 9
<212> TYPE: PRT
<213> ORGANISM: Human Papillomavirus 16

<400> SEQUENCE: 547

Thr Ile His Asp Ile Ile Leu Glu Cys
1               5

<210> SEQ ID NO 548
<211> LENGTH: 9
```

<212> TYPE: PRT
<213> ORGANISM: Human Papillomavirus 16

<400> SEQUENCE: 548

Leu Gly Ile Val Cys Pro Ile Cys Ser
1               5

<210> SEQ ID NO 549
<211> LENGTH: 9
<212> TYPE: PRT
<213> ORGANISM: Homo Sapien

<400> SEQUENCE: 549

Val Ile Leu Gly Val Leu Leu Leu Ile
1               5

<210> SEQ ID NO 550
<211> LENGTH: 9
<212> TYPE: PRT
<213> ORGANISM: Homo Sapien

<400> SEQUENCE: 550

Ala Leu Met Asp Lys Ser Leu His Val
1               5

<210> SEQ ID NO 551
<211> LENGTH: 9
<212> TYPE: PRT
<213> ORGANISM: Homo Sapien

<400> SEQUENCE: 551

Gly Ile Leu Thr Val Ile Leu Gly Val
1               5

<210> SEQ ID NO 552
<211> LENGTH: 9
<212> TYPE: PRT
<213> ORGANISM: Plasmodium Falciparum

<400> SEQUENCE: 552

Met Ile Asn Ala Tyr Leu Asp Lys Leu
1               5

<210> SEQ ID NO 553
<211> LENGTH: 9
<212> TYPE: PRT
<213> ORGANISM: Homo Sapien

<400> SEQUENCE: 553

Ala Ala Gly Ile Gly Ile Leu Thr Val
1               5

<210> SEQ ID NO 554
<211> LENGTH: 10
<212> TYPE: PRT
<213> ORGANISM: Hepatitis B Virus

<400> SEQUENCE: 554

Phe Leu Pro Ser Asp Phe Phe Pro Ser Val
1               5                   10

<210> SEQ ID NO 555
<211> LENGTH: 9
<212> TYPE: PRT
<213> ORGANISM: Epstein-Barr Virus (EBNA)

```
<400> SEQUENCE: 555

Ser Val Arg Asp Arg Leu Ala Arg Leu
1               5

<210> SEQ ID NO 556
<211> LENGTH: 9
<212> TYPE: PRT
<213> ORGANISM: Homo Sapien

<400> SEQUENCE: 556

Ala Ala Gly Ile Gly Ile Leu Thr Val
1               5

<210> SEQ ID NO 557
<211> LENGTH: 9
<212> TYPE: PRT
<213> ORGANISM: Homo Sapien

<400> SEQUENCE: 557

Phe Ala Tyr Asp Gly Lys Asp Tyr Ile
1               5

<210> SEQ ID NO 558
<211> LENGTH: 9
<212> TYPE: PRT
<213> ORGANISM: Homo Sapien

<400> SEQUENCE: 558

Ala Ala Gly Ile Gly Ile Leu Thr Val
1               5

<210> SEQ ID NO 559
<211> LENGTH: 10
<212> TYPE: PRT
<213> ORGANISM: Hepatitis B Virus

<400> SEQUENCE: 559

Phe Leu Pro Ser Asp Phe Phe Pro Ser Val
1               5                   10

<210> SEQ ID NO 560
<211> LENGTH: 9
<212> TYPE: PRT
<213> ORGANISM: Homo Sapien

<400> SEQUENCE: 560

Ala Ala Gly Ile Gly Ile Leu Thr Val
1               5

<210> SEQ ID NO 561
<211> LENGTH: 10
<212> TYPE: PRT
<213> ORGANISM: Hepatitis B Virus

<400> SEQUENCE: 561

Phe Leu Pro Ser Asp Phe Phe Pro Ser Val
1               5                   10

<210> SEQ ID NO 562
<211> LENGTH: 9
<212> TYPE: PRT
<213> ORGANISM: Homo Sapien

<400> SEQUENCE: 562

Ala Ala Gly Ile Gly Ile Leu Thr Val
```

-continued

```
1               5
```

<210> SEQ ID NO 563
<211> LENGTH: 9
<212> TYPE: PRT
<213> ORGANISM: Homo Sapien

<400> SEQUENCE: 563

```
Ala Leu Leu Ala Val Gly Ala Thr Lys
 1               5
```

<210> SEQ ID NO 564
<211> LENGTH: 11
<212> TYPE: PRT
<213> ORGANISM: Human Immunodeficiency Virus 1

<400> SEQUENCE: 564

```
Arg Leu Arg Asp Leu Leu Leu Ile Val Thr Arg
 1               5                   10
```

<210> SEQ ID NO 565
<211> LENGTH: 10
<212> TYPE: PRT
<213> ORGANISM: Human Immunodeficiency Virus 1

<400> SEQUENCE: 565

```
Gln Val Pro Leu Arg Pro Met Thr Tyr Lys
 1               5                   10
```

<210> SEQ ID NO 566
<211> LENGTH: 10
<212> TYPE: PRT
<213> ORGANISM: Human Immunodeficiency Virus 1

<400> SEQUENCE: 566

```
Thr Val Tyr Tyr Gly Val Pro Val Trp Lys
 1               5                   10
```

<210> SEQ ID NO 567
<211> LENGTH: 9
<212> TYPE: PRT
<213> ORGANISM: Human Immunodeficiency Virus 1

<400> SEQUENCE: 567

```
Arg Leu Arg Pro Gly Gly Lys Lys Lys
 1               5
```

<210> SEQ ID NO 568
<211> LENGTH: 9
<212> TYPE: PRT
<213> ORGANISM: Influenza

<400> SEQUENCE: 568

```
Ile Leu Arg Gly Ser Val Ala His Lys
 1               5
```

<210> SEQ ID NO 569
<211> LENGTH: 9
<212> TYPE: PRT
<213> ORGANISM: Epstein-Barr Virus (EBNA)

<400> SEQUENCE: 569

```
Arg Leu Arg Ala Glu Ala Gly Val Lys
 1               5
```

-continued

```
<210> SEQ ID NO 570
<211> LENGTH: 11
<212> TYPE: PRT
<213> ORGANISM: Human Immunodeficiency Virus 1

<400> SEQUENCE: 570

Arg Leu Arg Asp Leu Leu Leu Ile Val Thr Arg
1               5                   10

<210> SEQ ID NO 571
<211> LENGTH: 9
<212> TYPE: PRT
<213> ORGANISM: Human Immunodeficiency Virus 1

<400> SEQUENCE: 571

Val Tyr Tyr Gly Val Pro Val Trp Lys
1               5

<210> SEQ ID NO 572
<211> LENGTH: 9
<212> TYPE: PRT
<213> ORGANISM: Hepatitis C Virus

<400> SEQUENCE: 572

Arg Val Cys Glu Lys Met Ala Leu Tyr
1               5

<210> SEQ ID NO 573
<211> LENGTH: 9
<212> TYPE: PRT
<213> ORGANISM: Homo Sapien

<400> SEQUENCE: 573

Lys Ile Phe Ser Glu Val Thr Leu Lys
1               5

<210> SEQ ID NO 574
<211> LENGTH: 9
<212> TYPE: PRT
<213> ORGANISM: Hepatitis B Virus

<400> SEQUENCE: 574

Tyr Val Asn Val Asn Met Gly Leu Lys
1               5

<210> SEQ ID NO 575
<211> LENGTH: 9
<212> TYPE: PRT
<213> ORGANISM: Epstein-Barr Virus (EBNA)

<400> SEQUENCE: 575

Ile Val Thr Asp Phe Ser Val Ile Lys
1               5

<210> SEQ ID NO 576
<211> LENGTH: 9
<212> TYPE: PRT
<213> ORGANISM: Homo Sapien

<400> SEQUENCE: 576

Glu Leu Asn Glu Ala Leu Glu Leu Lys
1               5

<210> SEQ ID NO 577
<211> LENGTH: 9
<212> TYPE: PRT
```

-continued

<213> ORGANISM: Human Immunodeficiency Virus 1

<400> SEQUENCE: 577

Val Pro Leu Arg Pro Met Thr Tyr Lys
1               5

<210> SEQ ID NO 578
<211> LENGTH: 9
<212> TYPE: PRT
<213> ORGANISM: Human Immunodeficiency Virus 1

<400> SEQUENCE: 578

Ala Ile Phe Gln Ser Ser Met Thr Lys
1               5

<210> SEQ ID NO 579
<211> LENGTH: 10
<212> TYPE: PRT
<213> ORGANISM: Human Immunodeficiency Virus 1

<400> SEQUENCE: 579

Gln Val Pro Leu Arg Pro Met Thr Tyr Lys
1               5                   10

<210> SEQ ID NO 580
<211> LENGTH: 11
<212> TYPE: PRT
<213> ORGANISM: Influenza

<400> SEQUENCE: 580

Thr Ile Asn Tyr Thr Ile Phe Lys His Cys Val
1               5                   10

<210> SEQ ID NO 581
<211> LENGTH: 12
<212> TYPE: PRT
<213> ORGANISM: Human Immunodeficiency Virus 1

<400> SEQUENCE: 581

Ala Ala Val Asp Leu Ser His Phe Leu Lys Glu Lys
1               5                   10

<210> SEQ ID NO 582
<211> LENGTH: 12
<212> TYPE: PRT
<213> ORGANISM: Human Immunodeficiency Virus 1

<400> SEQUENCE: 582

Ala Cys Gln Gly Val Gly Gly Pro Gly Gly His Lys
1               5                   10

<210> SEQ ID NO 583
<211> LENGTH: 9
<212> TYPE: PRT
<213> ORGANISM: Homo Sapien

<400> SEQUENCE: 583

Ser Tyr Leu Asp Ser Gly Ile His Phe
1               5

<210> SEQ ID NO 584
<211> LENGTH: 9
<212> TYPE: PRT
<213> ORGANISM: Human Immunodeficiency Virus 1

<400> SEQUENCE: 584

Arg Tyr Leu Lys Asp Gln Gln Leu Leu
1               5

<210> SEQ ID NO 585
<211> LENGTH: 9
<212> TYPE: PRT
<213> ORGANISM: Homo Sapien

<400> SEQUENCE: 585

Ala Tyr Gly Leu Asp Phe Tyr Ile Leu
1               5

<210> SEQ ID NO 586
<211> LENGTH: 10
<212> TYPE: PRT
<213> ORGANISM: Homo Sapien

<400> SEQUENCE: 586

Ala Phe Leu Pro Trp His Arg Leu Phe Leu
1               5                   10

<210> SEQ ID NO 587
<211> LENGTH: 9
<212> TYPE: PRT
<213> ORGANISM: Homo Sapien

<400> SEQUENCE: 587

Ala Phe Leu Pro Trp His Arg Leu Phe
1               5

<210> SEQ ID NO 588
<211> LENGTH: 8
<212> TYPE: PRT
<213> ORGANISM: Epstein-Barr Virus (EBNA)

<400> SEQUENCE: 588

Arg Tyr Ser Ile Phe Phe Asp Tyr
1               5

<210> SEQ ID NO 589
<211> LENGTH: 10
<212> TYPE: PRT
<213> ORGANISM: Human Immunodeficiency Virus 1

<400> SEQUENCE: 589

Glu Thr Ile Asn Glu Glu Ala Ala Glu Trp
1               5                   10

<210> SEQ ID NO 590
<211> LENGTH: 11
<212> TYPE: PRT
<213> ORGANISM: Hepatitis B Virus

<400> SEQUENCE: 590

Ser Thr Leu Pro Glu Thr Thr Val Val Arg Arg
1               5                   10

<210> SEQ ID NO 591
<211> LENGTH: 9
<212> TYPE: PRT
<213> ORGANISM: Homo Sapien

<400> SEQUENCE: 591

Met Ser Leu Gln Arg Gln Phe Leu Arg
1               5

-continued

```
<210> SEQ ID NO 592
<211> LENGTH: 9
<212> TYPE: PRT
<213> ORGANISM: Homo Sapien

<400> SEQUENCE: 592

Leu Leu Pro Gly Gly Arg Pro Tyr Arg
 1               5

<210> SEQ ID NO 593
<211> LENGTH: 9
<212> TYPE: PRT
<213> ORGANISM: Human Immunodeficiency Virus

<400> SEQUENCE: 593

Ile Val Gly Leu Asn Lys Ile Val Arg
 1               5

<210> SEQ ID NO 594
<211> LENGTH: 9
<212> TYPE: PRT
<213> ORGANISM: Homo Sapien

<400> SEQUENCE: 594

Ala Ala Gly Ile Gly Ile Leu Thr Val
 1               5

<210> SEQ ID NO 595
<211> LENGTH: 9
<212> TYPE: PRT
<213> ORGANISM: Homo Sapien

<400> SEQUENCE: 595

Glu Val Asp Pro Thr Ser Asn Thr Tyr
 1               5

<210> SEQ ID NO 596
<211> LENGTH: 9
<212> TYPE: PRT
<213> ORGANISM: Homo Sapien

<400> SEQUENCE: 596

Glu Ala Asp Pro Thr Ser Asn Thr Tyr
 1               5

<210> SEQ ID NO 597
<211> LENGTH: 9
<212> TYPE: PRT
<213> ORGANISM: Homo Sapien

<400> SEQUENCE: 597

Glu Ala Asp Pro Thr Ser Asn Thr Tyr
 1               5

<210> SEQ ID NO 598
<211> LENGTH: 9
<212> TYPE: PRT
<213> ORGANISM: Homo Sapien

<400> SEQUENCE: 598

Glu Val Asp Pro Ile Gly His Val Tyr
 1               5

<210> SEQ ID NO 599
```

-continued

```
<211> LENGTH: 10
<212> TYPE: PRT
<213> ORGANISM: Homo Sapien

<400> SEQUENCE: 599

Met Leu Leu Ala Val Leu Tyr Cys Leu Leu
1               5                   10

<210> SEQ ID NO 600
<211> LENGTH: 9
<212> TYPE: PRT
<213> ORGANISM: Homo Sapien

<400> SEQUENCE: 600

Met Leu Leu Ala Val Leu Tyr Cys Leu
1               5

<210> SEQ ID NO 601
<211> LENGTH: 10
<212> TYPE: PRT
<213> ORGANISM: Homo Sapien

<400> SEQUENCE: 601

Ser Glu Ile Trp Arg Asp Ile Asp Phe Ala
1               5                   10

<210> SEQ ID NO 602
<211> LENGTH: 9
<212> TYPE: PRT
<213> ORGANISM: Homo Sapien

<400> SEQUENCE: 602

Ser Glu Ile Trp Arg Asp Ile Asp Phe
1               5

<210> SEQ ID NO 603
<211> LENGTH: 9
<212> TYPE: PRT
<213> ORGANISM: Homo Sapien
<220> FEATURE:
<221> NAME/KEY: VARIANT
<222> LOCATION: 1
<223> OTHER INFORMATION: Xaa = Any Amino Acid

<400> SEQUENCE: 603

Xaa Glu Ile Trp Arg Asp Ile Asp Phe
1               5

<210> SEQ ID NO 604
<211> LENGTH: 10
<212> TYPE: PRT
<213> ORGANISM: Homo Sapien

<400> SEQUENCE: 604

Ser Thr Leu Val Glu Val Thr Leu Gly Val
1               5                   10

<210> SEQ ID NO 605
<211> LENGTH: 9
<212> TYPE: PRT
<213> ORGANISM: Homo Sapien

<400> SEQUENCE: 605

Leu Val Glu Val Thr Leu Gly Glu Val
1               5
```

```
<210> SEQ ID NO 606
<211> LENGTH: 10
<212> TYPE: PRT
<213> ORGANISM: Homo Sapien

<400> SEQUENCE: 606

Val Ile Phe Ser Lys Ala Ser Glu Tyr Leu
 1               5                  10

<210> SEQ ID NO 607
<211> LENGTH: 9
<212> TYPE: PRT
<213> ORGANISM: Homo Sapien

<400> SEQUENCE: 607

Ile Ile Val Leu Ala Ile Ile Ala Ile
 1               5

<210> SEQ ID NO 608
<211> LENGTH: 11
<212> TYPE: PRT
<213> ORGANISM: Homo Sapien

<400> SEQUENCE: 608

Lys Ile Trp Glu Glu Leu Ser Met Leu Glu Tyr
 1               5                  10

<210> SEQ ID NO 609
<211> LENGTH: 9
<212> TYPE: PRT
<213> ORGANISM: Homo Sapien

<400> SEQUENCE: 609

Leu Ile Glu Thr Ser Tyr Val Lys Val
 1               5

<210> SEQ ID NO 610
<211> LENGTH: 9
<212> TYPE: PRT
<213> ORGANISM: Homo Sapien

<400> SEQUENCE: 610

Phe Leu Trp Gly Pro Arg Ala Leu Val
 1               5

<210> SEQ ID NO 611
<211> LENGTH: 10
<212> TYPE: PRT
<213> ORGANISM: Homo Sapien

<400> SEQUENCE: 611

Thr Leu Val Glu Val Thr Leu Gly Glu Val
 1               5                  10

<210> SEQ ID NO 612
<211> LENGTH: 10
<212> TYPE: PRT
<213> ORGANISM: Homo Sapien

<400> SEQUENCE: 612

Ala Leu Val Glu Thr Ser Tyr Val Lys Val
 1               5                  10

<210> SEQ ID NO 613
<211> LENGTH: 9
<212> TYPE: PRT
```

```
<213> ORGANISM: Homo Sapien

<400> SEQUENCE: 613

Lys Ile Trp Glu Glu Leu Ser Val Leu
  1               5

<210> SEQ ID NO 614
<211> LENGTH: 9
<212> TYPE: PRT
<213> ORGANISM: Homo Sapien

<400> SEQUENCE: 614

Glu Val Asp Pro Ile Gly His Leu Tyr
  1               5

<210> SEQ ID NO 615
<211> LENGTH: 9
<212> TYPE: PRT
<213> ORGANISM: Homo Sapien
<220> FEATURE:
<221> NAME/KEY: VARIANT
<222> LOCATION: 2, 4, 5, 6, 7, 8
<223> OTHER INFORMATION: Xaa = Any Amino Acid

<400> SEQUENCE: 615

Glu Xaa Asp Xaa Xaa Xaa Xaa Xaa Tyr
  1               5

<210> SEQ ID NO 616
<211> LENGTH: 9
<212> TYPE: PRT
<213> ORGANISM: Homo Sapien

<400> SEQUENCE: 616

Glu Ala Asp Pro Thr Gly His Ser Tyr
  1               5

<210> SEQ ID NO 617
<211> LENGTH: 9
<212> TYPE: PRT
<213> ORGANISM: Homo Sapien
<220> FEATURE:
<221> NAME/KEY: VARIANT
<222> LOCATION: 4, 5, 6, 7, 8
<223> OTHER INFORMATION: Xaa = Any Amino Acid
<220> FEATURE:
<221> NAME/KEY: VARIANT
<222> LOCATION: 2
<223> OTHER INFORMATION: Xaa = A or V

<400> SEQUENCE: 617

Glu Xaa Asp Xaa Xaa Xaa Xaa Xaa Tyr
  1               5

<210> SEQ ID NO 618
<211> LENGTH: 9
<212> TYPE: PRT
<213> ORGANISM: Homo Sapien
<220> FEATURE:
<221> NAME/KEY: VARIANT
<222> LOCATION: 5, 6, 7, 8
<223> OTHER INFORMATION: Xaa = Any Amino Acid
<220> FEATURE:
<221> NAME/KEY: VARIANT
<222> LOCATION: 2
<223> OTHER INFORMATION: Xaa = A or V

<400> SEQUENCE: 618

Glu Xaa Asp Pro Xaa Xaa Xaa Xaa Tyr
```

```
<210> SEQ ID NO 619
<211> LENGTH: 9
<212> TYPE: PRT
<213> ORGANISM: Homo Sapien
<220> FEATURE:
<221> NAME/KEY: VARIANT
<222> LOCATION: 6, 7, 8
<223> OTHER INFORMATION: Xaa = Any Amino Acid
<220> FEATURE:
<221> NAME/KEY: VARIANT
<222> LOCATION: 2
<223> OTHER INFORMATION: Xaa = A or V
<220> FEATURE:
<221> NAME/KEY: VARIANT
<222> LOCATION: 5
<223> OTHER INFORMATION: Xaa = I or A or T

<400> SEQUENCE: 619

Glu Xaa Asp Pro Xaa Xaa Xaa Xaa Tyr
 1               5

<210> SEQ ID NO 620
<211> LENGTH: 9
<212> TYPE: PRT
<213> ORGANISM: Homo Sapien
<220> FEATURE:
<221> NAME/KEY: VARIANT
<222> LOCATION: 7, 8
<223> OTHER INFORMATION: Xaa = Any Amino Acid
<220> FEATURE:
<221> NAME/KEY: VARIANT
<222> LOCATION: 2
<223> OTHER INFORMATION: Xaa = A or V
<220> FEATURE:
<221> NAME/KEY: VARIANT
<222> LOCATION: 5
<223> OTHER INFORMATION: Xaa = I or A or T
<220> FEATURE:
<221> NAME/KEY: VARIANT
<222> LOCATION: 6
<223> OTHER INFORMATION: Xaa = G or S

<400> SEQUENCE: 620

Glu Xaa Asp Pro Xaa Xaa Xaa Xaa Tyr
 1               5

<210> SEQ ID NO 621
<211> LENGTH: 9
<212> TYPE: PRT
<213> ORGANISM: Homo Sapien
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 2
<223> OTHER INFORMATION: Xaa = A or V
<220> FEATURE:
<221> NAME/KEY: VARIANT
<222> LOCATION: 5
<223> OTHER INFORMATION: Xaa = I or A or T
<220> FEATURE:
<221> NAME/KEY: VARIANT
<222> LOCATION: 6
<223> OTHER INFORMATION: Xaa = G or S
<220> FEATURE:
<221> NAME/KEY: VARIANT
<222> LOCATION: 7
<223> OTHER INFORMATION: Xaa = H or N

<400> SEQUENCE: 621
```

```
Glu Xaa Asp Pro Xaa Xaa Xaa Xaa Tyr
1               5
```

<210> SEQ ID NO 622
<211> LENGTH: 9
<212> TYPE: PRT
<213> ORGANISM: Homo Sapien
<220> FEATURE:
<221> NAME/KEY: VARIANT
<222> LOCATION: 2
<223> OTHER INFORMATION: Xaa = A or V
<220> FEATURE:
<221> NAME/KEY: VARIANT
<222> LOCATION: 5
<223> OTHER INFORMATION: Xaa = I or A or T
<220> FEATURE:
<221> NAME/KEY: VARIANT
<222> LOCATION: 6
<223> OTHER INFORMATION: Xaa = G or S
<220> FEATURE:
<221> NAME/KEY: VARIANT
<222> LOCATION: 7
<223> OTHER INFORMATION: Xaa = H or N
<220> FEATURE:
<221> NAME/KEY: VARIANT
<222> LOCATION: 8
<223> OTHER INFORMATION: Xaa = L or T or V

<400> SEQUENCE: 622

```
Glu Xaa Asp Pro Xaa Xaa Xaa Xaa Tyr
1               5
```

<210> SEQ ID NO 623
<211> LENGTH: 16
<212> TYPE: PRT
<213> ORGANISM: Homo Sapien

<400> SEQUENCE: 623

```
Glu Leu His Ser Ala Tyr Gly Glu Pro Arg Lys Leu Leu Thr Gln Asp
1               5                   10                  15
```

<210> SEQ ID NO 624
<211> LENGTH: 12
<212> TYPE: PRT
<213> ORGANISM: Homo Sapien

<400> SEQUENCE: 624

```
Glu His Ser Ala Tyr Gly Glu Pro Arg Lys Leu Leu
1               5                   10
```

<210> SEQ ID NO 625
<211> LENGTH: 9
<212> TYPE: PRT
<213> ORGANISM: Homo Sapien

<400> SEQUENCE: 625

```
Ser Ala Tyr Gly Glu Pro Arg Lys Leu
1               5
```

<210> SEQ ID NO 626
<211> LENGTH: 9
<212> TYPE: PRT
<213> ORGANISM: Homo Sapien

<400> SEQUENCE: 626

```
Glu Ala Asp Pro Thr Gly His Ser Tyr
1               5
```

<210> SEQ ID NO 627

```
<211> LENGTH: 22
<212> TYPE: PRT
<213> ORGANISM: Homo Sapien

<400> SEQUENCE: 627

Met Ala Ala Arg Ala Val Phe Leu Ala Leu Ser Ala Gln Leu Leu Gln
 1               5                  10                  15
Ala Arg Leu Met Lys Glu
            20

<210> SEQ ID NO 628
<211> LENGTH: 16
<212> TYPE: PRT
<213> ORGANISM: Homo Sapien

<400> SEQUENCE: 628

Met Ala Ala Arg Ala Val Phe Leu Ala Leu Ser Ala Gln Leu Leu Gln
 1               5                  10                  15

<210> SEQ ID NO 629
<211> LENGTH: 9
<212> TYPE: PRT
<213> ORGANISM: Homo Sapien

<400> SEQUENCE: 629

Ala Ala Arg Ala Val Phe Leu Ala Leu
 1               5

<210> SEQ ID NO 630
<211> LENGTH: 8
<212> TYPE: PRT
<213> ORGANISM: Homo Sapien

<400> SEQUENCE: 630

Tyr Arg Pro Arg Pro Arg Arg Tyr
 1               5

<210> SEQ ID NO 631
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 631

Ala Leu Phe Ala Ala Ala Ala Ala Val
 1               5

<210> SEQ ID NO 632
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 632

Gly Ile Phe Gly Gly Val Gly Gly Val
 1               5

<210> SEQ ID NO 633
<211> LENGTH: 8
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 633
```

Gly Leu Asp Lys Gly Gly Gly Val
1               5

<210> SEQ ID NO 634
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 634

Gly Leu Phe Gly Gly Phe Gly Gly Val
1               5

<210> SEQ ID NO 635
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 635

Gly Leu Phe Gly Gly Gly Ala Gly Val
1               5

<210> SEQ ID NO 636
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 636

Gly Leu Phe Gly Gly Gly Glu Gly Val
1               5

<210> SEQ ID NO 637
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 637

Gly Leu Phe Gly Gly Gly Phe Gly Val
1               5

<210> SEQ ID NO 638
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 638

Gly Leu Phe Gly Gly Gly Gly Gly Leu
1               5

<210> SEQ ID NO 639
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 639

Gly Leu Phe Gly Gly Gly Gly Gly Val

-continued

```
<210> SEQ ID NO 640
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 640

Gly Leu Phe Gly Gly Gly Val Gly Val
 1               5

<210> SEQ ID NO 641
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 641

Gly Leu Phe Gly Gly Val Gly Gly Val
 1               5

<210> SEQ ID NO 642
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 642

Gly Leu Phe Gly Gly Val Gly Lys Val
 1               5

<210> SEQ ID NO 643
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 643

Gly Leu Phe Lys Gly Val Gly Gly Val
 1               5

<210> SEQ ID NO 644
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 644

Gly Leu Gly Gly Gly Gly Phe Gly Val
 1               5

<210> SEQ ID NO 645
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 645

Gly Leu Leu Gly Gly Gly Val Gly Val
 1               5
```

<210> SEQ ID NO 646
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 646

Gly Leu Tyr Gly Gly Gly Gly Gly Val
 1               5

<210> SEQ ID NO 647
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 647

Gly Met Phe Gly Gly Gly Gly Gly Val
 1               5

<210> SEQ ID NO 648
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 648

Gly Met Phe Gly Gly Val Gly Gly Val
 1               5

<210> SEQ ID NO 649
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 649

Gly Gln Phe Gly Gly Val Gly Gly Val
 1               5

<210> SEQ ID NO 650
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 650

Gly Val Phe Gly Gly Val Gly Gly Val
 1               5

<210> SEQ ID NO 651
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 651

Lys Leu Phe Gly Gly Gly Gly Gly Val
 1               5

<210> SEQ ID NO 652

```
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 652

Lys Leu Phe Gly Gly Val Gly Gly Val
 1               5

<210> SEQ ID NO 653
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 653

Ala Ile Leu Gly Phe Val Phe Thr Leu
 1               5

<210> SEQ ID NO 654
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 654

Gly Ala Ile Gly Phe Val Phe Thr Leu
 1               5

<210> SEQ ID NO 655
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 655

Gly Ala Leu Gly Phe Val Phe Thr Leu
 1               5

<210> SEQ ID NO 656
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 656

Gly Glu Leu Gly Phe Val Phe Thr Leu
 1               5

<210> SEQ ID NO 657
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 657

Gly Ile Ala Gly Phe Val Phe Thr Leu
 1               5

<210> SEQ ID NO 658
<211> LENGTH: 9
<212> TYPE: PRT
```

```
<213> ORGANISM: Artificial Sequence
<220> FEATURE:
<223> OTHER INFORMATION: Synthetic HLA-A2 binding nonamer peptide

<400> SEQUENCE: 658

Gly Ile Glu Gly Phe Val Phe Thr Leu
 1               5

<210> SEQ ID NO 659
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 659

Gly Ile Leu Ala Phe Val Phe Thr Leu
 1               5

<210> SEQ ID NO 660
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 660

Gly Ile Leu Gly Ala Val Phe Thr Leu
 1               5

<210> SEQ ID NO 661
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 661

Gly Ile Leu Gly Glu Val Phe Thr Leu
 1               5

<210> SEQ ID NO 662
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 662

Gly Ile Leu Phe Gly Ala Phe Thr Leu
 1               5

<210> SEQ ID NO 663
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 663

Gly Ile Leu Gly Phe Glu Phe Thr Leu
 1               5

<210> SEQ ID NO 664
<211> LENGTH: 9
<212> TYPE: PRT
<213> ORGANISM: Artificial Sequence
<220> FEATURE:
```

<223> OTHER INFORMATION: Synthetic HLA-A2 binding nonamer peptide

<400> SEQUENCE: 664

Gly Ile Leu Gly Phe Lys Phe Thr Leu
 1               5

<210> SEQ ID NO 665
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 665

Gly Ile Leu Gly Phe Val Ala Thr Leu
 1               5

<210> SEQ ID NO 666
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 666

Gly Ile Leu Gly Phe Val Glu Thr Leu
 1               5

<210> SEQ ID NO 667
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 667

Gly Ile Leu Gly Phe Val Phe Ala Leu
 1               5

<210> SEQ ID NO 668
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 668

Gly Ile Leu Gly Phe Val Phe Glu Leu
 1               5

<210> SEQ ID NO 669
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 669

Gly Ile Leu Gly Phe Val Phe Lys Leu
 1               5

<210> SEQ ID NO 670
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

```
<400> SEQUENCE: 670

Gly Ile Leu Gly Phe Val Phe Thr Ala
1               5

<210> SEQ ID NO 671
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 671

Gly Ile Leu Gly Phe Val Phe Thr Leu
1               5

<210> SEQ ID NO 672
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 672

Gly Ile Leu Gly Phe Val Phe Val Leu
1               5

<210> SEQ ID NO 673
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 673

Gly Ile Leu Gly Phe Val Lys Thr Leu
1               5

<210> SEQ ID NO 674
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 674

Gly Ile Leu Gly Lys Val Phe Thr Leu
1               5

<210> SEQ ID NO 675
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 675

Gly Ile Leu Lys Phe Val Phe Thr Leu
1               5

<210> SEQ ID NO 676
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 676
```

```
Gly Ile Leu Pro Phe Val Phe Thr Leu
 1               5

<210> SEQ ID NO 677
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 677

Gly Ile Val Gly Phe Val Phe Thr Leu
 1               5

<210> SEQ ID NO 678
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 678

Gly Lys Leu Gly Phe Val Phe Thr Leu
 1               5

<210> SEQ ID NO 679
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 679

Gly Leu Leu Gly Phe Val Phe Thr Leu
 1               5

<210> SEQ ID NO 680
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 680

Gly Gln Leu Gly Phe Val Phe Thr Leu
 1               5

<210> SEQ ID NO 681
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 681

Lys Ala Leu Gly Phe Val Phe Thr Leu
 1               5

<210> SEQ ID NO 682
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 682

Lys Ile Leu Gly Phe Val Phe Thr Leu
 1               5
```

<210> SEQ ID NO 683
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 683

Lys Ile Leu Gly Lys Val Phe Thr Leu
1               5

<210> SEQ ID NO 684
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 684

Ala Ile Leu Leu Gly Val Phe Met Leu
1               5

<210> SEQ ID NO 685
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 685

Ala Ile Tyr Lys Arg Trp Ile Ile Leu
1               5

<210> SEQ ID NO 686
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 686

Ala Leu Phe Phe Phe Asp Ile Asp Leu
1               5

<210> SEQ ID NO 687
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 687

Ala Thr Val Glu Leu Leu Ser Glu Leu
1               5

<210> SEQ ID NO 688
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 688

Cys Leu Phe Gly Tyr Pro Val Tyr Val
1               5

```
<210> SEQ ID NO 689
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 689

Phe Ile Phe Pro Asn Tyr Thr Ile Val
 1               5

<210> SEQ ID NO 690
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 690

Ile Ile Ser Leu Trp Asp Ser Gln Leu
 1               5

<210> SEQ ID NO 691
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 691

Ile Leu Ala Ser Leu Phe Ala Ala Val
 1               5

<210> SEQ ID NO 692
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 692

Ile Leu Glu Ser Leu Phe Ala Ala Val
 1               5

<210> SEQ ID NO 693
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 693

Lys Leu Gly Glu Phe Phe Asn Gln Met
 1               5

<210> SEQ ID NO 694
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 694

Lys Leu Gly Glu Phe Tyr Asn Gln Met
 1               5

<210> SEQ ID NO 695
<211> LENGTH: 9
```

```
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 695

Leu Leu Phe Gly Tyr Pro Val Tyr Val
 1               5

<210> SEQ ID NO 696
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 696

Leu Leu Trp Lys Gly Glu Gly Ala Val
 1               5

<210> SEQ ID NO 697
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 697

Leu Met Phe Gly Tyr Pro Val Tyr Val
 1               5

<210> SEQ ID NO 698
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 698

Leu Asn Phe Gly Tyr Pro Val Tyr Val
 1               5

<210> SEQ ID NO 699
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 699

Leu Gln Phe Gly Tyr Pro Val Tyr Val
 1               5

<210> SEQ ID NO 700
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 700

Asn Ile Val Ala His Thr Phe Lys Val
 1               5

<210> SEQ ID NO 701
<211> LENGTH: 8
<212> TYPE: PRT
<213> ORGANISM: Artificial Sequence
```

```
<220> FEATURE:
<223> OTHER INFORMATION: Synthetic HLA-A2 binding nonamer peptide

<400> SEQUENCE: 701

Asn Leu Pro Met Val Ala Thr Val
 1               5

<210> SEQ ID NO 702
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 702

Gln Met Leu Leu Ala Ile Ala Arg Leu
 1               5

<210> SEQ ID NO 703
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 703

Gln Met Trp Gln Ala Arg Leu Thr Val
 1               5

<210> SEQ ID NO 704
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 704

Arg Leu Leu Gln Thr Gly Ile His Val
 1               5

<210> SEQ ID NO 705
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 705

Arg Leu Val Asn Gly Ser Leu Ala Leu
 1               5

<210> SEQ ID NO 706
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 706

Ser Leu Tyr Asn Thr Val Ala Thr Leu
 1               5

<210> SEQ ID NO 707
<211> LENGTH: 9
<212> TYPE: PRT
<213> ORGANISM: Artificial Sequence
<220> FEATURE:
<223> OTHER INFORMATION: Synthetic HLA-A2 binding nonamer peptide
```

```
<400> SEQUENCE: 707

Thr Leu Asn Ala Trp Val Lys Val Val
1               5

<210> SEQ ID NO 708
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 708

Trp Leu Tyr Arg Glu Thr Cys Asn Leu
1               5

<210> SEQ ID NO 709
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 709

Tyr Leu Phe Lys Arg Met Ile Asp Leu
1               5

<210> SEQ ID NO 710
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 710

Gly Ala Phe Gly Gly Val Gly Gly Val
1               5

<210> SEQ ID NO 711
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 711

Gly Ala Phe Gly Gly Val Gly Gly Tyr
1               5

<210> SEQ ID NO 712
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 712

Gly Glu Phe Gly Gly Val Gly Gly Val
1               5

<210> SEQ ID NO 713
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 713
```

Gly Gly Phe Gly Gly Val Gly Gly Val
1               5

<210> SEQ ID NO 714
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 714

Gly Ile Phe Gly Gly Gly Gly Gly Val
1               5

<210> SEQ ID NO 715
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 715

Gly Ile Gly Gly Phe Gly Gly Gly Leu
1               5

<210> SEQ ID NO 716
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 716

Gly Ile Gly Gly Gly Gly Gly Gly Leu
1               5

<210> SEQ ID NO 717
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 717

Gly Leu Asp Gly Gly Gly Gly Gly Val
1               5

<210> SEQ ID NO 718
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 718

Gly Leu Asp Gly Lys Gly Gly Gly Val
1               5

<210> SEQ ID NO 719
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 719

Gly Leu Asp Lys Lys Gly Gly Gly Val

<210> SEQ ID NO 720
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 720

Gly Leu Phe Gly Gly Gly Phe Gly Phe
1               5

<210> SEQ ID NO 721
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 721

Gly Leu Phe Gly Gly Gly Phe Gly Gly
1               5

<210> SEQ ID NO 722
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 722

Gly Leu Phe Gly Gly Gly Phe Gly Asn
1               5

<210> SEQ ID NO 723
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 723

Gly Leu Phe Gly Gly Gly Phe Gly Ser
1               5

<210> SEQ ID NO 724
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 724

Gly Leu Phe Gly Gly Gly Gly Gly Ile
1               5

<210> SEQ ID NO 725
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 725

Gly Leu Phe Gly Gly Gly Gly Gly Met
1               5

```
<210> SEQ ID NO 726
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 726

Gly Leu Phe Gly Gly Gly Gly Gly Thr
1               5

<210> SEQ ID NO 727
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 727

Gly Leu Phe Gly Gly Gly Gly Gly Tyr
1               5

<210> SEQ ID NO 728
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 728

Gly Leu Gly Phe Gly Gly Gly Gly Val
1               5

<210> SEQ ID NO 729
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 729

Gly Leu Gly Gly Phe Gly Gly Gly Val
1               5

<210> SEQ ID NO 730
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 730

Gly Leu Gly Gly Gly Phe Gly Gly Val
1               5

<210> SEQ ID NO 731
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 731

Gly Leu Gly Gly Gly Gly Gly Phe Val
1               5

<210> SEQ ID NO 732
```

-continued

```
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 732

Gly Leu Gly Gly Gly Gly Gly Gly Tyr
 1               5

<210> SEQ ID NO 733
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 733

Gly Leu Gly Gly Gly Val Gly Gly Val
 1               5

<210> SEQ ID NO 734
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 734

Gly Leu Leu Gly Gly Gly Gly Gly Val
 1               5

<210> SEQ ID NO 735
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 735

Gly Leu Pro Gly Gly Gly Gly Gly Val
 1               5

<210> SEQ ID NO 736
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 736

Gly Asn Phe Gly Gly Val Gly Gly Val
 1               5

<210> SEQ ID NO 737
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 737

Gly Ser Phe Gly Gly Val Gly Gly Val
 1               5

<210> SEQ ID NO 738
<211> LENGTH: 9
<212> TYPE: PRT
```

<213> ORGANISM: Artificial Sequence
<220> FEATURE:
<223> OTHER INFORMATION: Synthetic HLA-A2 binding nonamer peptide

<400> SEQUENCE: 738

Gly Thr Phe Gly Gly Val Gly Gly Val
1               5

<210> SEQ ID NO 739
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 739

Ala Gly Asn Ser Ala Tyr Glu Tyr Val
1               5

<210> SEQ ID NO 740
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 740

Gly Leu Phe Pro Gly Gln Phe Ala Tyr
1               5

<210> SEQ ID NO 741
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 741

His Ile Leu Leu Gly Val Phe Met Leu
1               5

<210> SEQ ID NO 742
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 742

Ile Leu Glu Ser Leu Phe Arg Ala Val
1               5

<210> SEQ ID NO 743
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 743

Lys Lys Lys Tyr Lys Leu Lys His Ile
1               5

<210> SEQ ID NO 744
<211> LENGTH: 9
<212> TYPE: PRT
<213> ORGANISM: Artificial Sequence
<220> FEATURE:

<223> OTHER INFORMATION: Synthetic HLA-A2 binding nonamer peptide

<400> SEQUENCE: 744

Met Leu Ala Ser Ile Asp Leu Lys Tyr
1               5

<210> SEQ ID NO 745
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 745

Met Leu Glu Arg Glu Leu Val Arg Lys
1               5

<210> SEQ ID NO 746
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 746

Lys Leu Phe Gly Phe Val Phe Thr Val
1               5

<210> SEQ ID NO 747
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 747

Ile Leu Asp Lys Lys Val Glu Lys Val
1               5

<210> SEQ ID NO 748
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 748

Ile Leu Lys Glu Pro Val His Gly Val
1               5

<210> SEQ ID NO 749
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 749

Ala Leu Phe Ala Ala Ala Ala Ala Tyr
1               5

<210> SEQ ID NO 750
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

```
<400> SEQUENCE: 750

Gly Ile Gly Phe Gly Gly Gly Gly Leu
1               5

<210> SEQ ID NO 751
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 751

Gly Lys Phe Gly Gly Val Gly Gly Val
1               5

<210> SEQ ID NO 752
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 752

Gly Leu Phe Gly Gly Gly Gly Gly Lys
1               5

<210> SEQ ID NO 753
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 753

Glu Ile Leu Gly Phe Val Phe Thr Leu
1               5

<210> SEQ ID NO 754
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 754

Gly Ile Lys Gly Phe Val Phe Thr Leu
1               5

<210> SEQ ID NO 755
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 755

Gly Gln Leu Gly Phe Val Phe Thr Lys
1               5

<210> SEQ ID NO 756
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 756
```

```
Ile Leu Gly Phe Val Phe Thr Leu Thr
1               5

<210> SEQ ID NO 757
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 757

Lys Ile Leu Gly Phe Val Phe Thr Lys
1               5

<210> SEQ ID NO 758
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 758

Lys Lys Leu Gly Phe Val Phe Thr Leu
1               5

<210> SEQ ID NO 759
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 759

Lys Leu Phe Glu Lys Val Tyr Asn Tyr
1               5

<210> SEQ ID NO 760
<211> LENGTH: 9
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 760

Leu Arg Phe Gly Tyr Pro Val Tyr Val
1               5

<210> SEQ ID NO 761
<211> LENGTH: 9
<212> TYPE: PRT
<213> ORGANISM: Homo Sapien

<400> SEQUENCE: 761

Ile Arg Arg Gly Val Met Leu Ala Val
1               5

<210> SEQ ID NO 762
<211> LENGTH: 9
<212> TYPE: PRT
<213> ORGANISM: Homo Sapien

<400> SEQUENCE: 762

Lys Arg Ile Gln Glu Ile Ile Glu Gln
1               5

<210> SEQ ID NO 763
<211> LENGTH: 9
```

<212> TYPE: PRT
<213> ORGANISM: Homo Sapien

<400> SEQUENCE: 763

Lys Arg Thr Leu Lys Ile Pro Ala Met
1 5

<210> SEQ ID NO 764
<211> LENGTH: 9
<212> TYPE: PRT
<213> ORGANISM: Yersenia Pestis

<400> SEQUENCE: 764

Gly Arg Asn Val Val Leu Asp Lys Ser
1 5

<210> SEQ ID NO 765
<211> LENGTH: 9
<212> TYPE: PRT
<213> ORGANISM: Yersenia Pestis

<400> SEQUENCE: 765

Lys Arg Gly Ile Asp Lys Ala Val Ile
1 5

<210> SEQ ID NO 766
<211> LENGTH: 9
<212> TYPE: PRT
<213> ORGANISM: Yersenia Pestis

<400> SEQUENCE: 766

Ile Arg Ala Ala Ser Ala Ile Thr Ala
1 5

<210> SEQ ID NO 767
<211> LENGTH: 9
<212> TYPE: PRT
<213> ORGANISM: Yersenia Pestis

<400> SEQUENCE: 767

Arg Arg Lys Ala Met Phe Glu Asp Ile
1 5

<210> SEQ ID NO 768
<211> LENGTH: 8
<212> TYPE: PRT
<213> ORGANISM: Plasmodium Falciparum

<400> SEQUENCE: 768

Lys Pro Lys Asp Glu Leu Asp Tyr
1 5

<210> SEQ ID NO 769
<211> LENGTH: 9
<212> TYPE: PRT
<213> ORGANISM: Influenza

<400> SEQUENCE: 769

Leu Glu Leu Arg Ser Arg Tyr Trp Ala
1 5

<210> SEQ ID NO 770
<211> LENGTH: 10
<212> TYPE: PRT
<213> ORGANISM: Homo Sapien

```
<400> SEQUENCE: 770

Gly Pro Pro His Ser Asn Asn Phe Gly Tyr
1               5                   10

<210> SEQ ID NO 771
<211> LENGTH: 8
<212> TYPE: PRT
<213> ORGANISM: Rotavirus

<400> SEQUENCE: 771

Ile Ile Tyr Arg Phe Leu Leu Ile
1               5

<210> SEQ ID NO 772
<211> LENGTH: 9
<212> TYPE: PRT
<213> ORGANISM: Homo Sapien

<400> SEQUENCE: 772

Gln Leu Ser Pro Tyr Pro Phe Asp Leu
1               5

<210> SEQ ID NO 773
<211> LENGTH: 8
<212> TYPE: PRT
<213> ORGANISM: Homo Sapien

<400> SEQUENCE: 773

Val Tyr Asp Phe Phe Val Trp Leu
1               5

<210> SEQ ID NO 774
<211> LENGTH: 8
<212> TYPE: PRT
<213> ORGANISM: Homo Sapien

<400> SEQUENCE: 774

Ser Asn Phe Val Phe Ala Gly Ile
1               5

<210> SEQ ID NO 775
<211> LENGTH: 8
<212> TYPE: PRT
<213> ORGANISM: Rotavirus

<400> SEQUENCE: 775

Ser Val Val Glu Phe Ser Ser Leu
1               5

<210> SEQ ID NO 776
<211> LENGTH: 8
<212> TYPE: PRT
<213> ORGANISM: Artificial Sequence
<220> FEATURE:
<223> OTHER INFORMATION: Epitope mimic of natural tumor Ag

<400> SEQUENCE: 776

Ala His Tyr Leu Phe Arg Asn Leu
1               5

<210> SEQ ID NO 777
<211> LENGTH: 8
<212> TYPE: PRT
<213> ORGANISM: Artificial Sequence
<220> FEATURE:
<223> OTHER INFORMATION: Epitope mimic of natural tumor Ag
```

```
<400> SEQUENCE: 777

Thr His Tyr Leu Phe Arg Asn Leu
1               5

<210> SEQ ID NO 778
<211> LENGTH: 8
<212> TYPE: PRT
<213> ORGANISM: Artificial Sequence
<220> FEATURE:
<223> OTHER INFORMATION: Epitope Mimic of H-3 miHAg

<400> SEQUENCE: 778

Leu Ile Val Ile Tyr Asn Thr Leu
1               5

<210> SEQ ID NO 779
<211> LENGTH: 8
<212> TYPE: PRT
<213> ORGANISM: Artificial Sequence
<220> FEATURE:
<223> OTHER INFORMATION: Epitope Mimic of H-3 miHAg

<400> SEQUENCE: 779

Leu Ile Tyr Glu Phe Asn Thr Leu
1               5

<210> SEQ ID NO 780
<211> LENGTH: 8
<212> TYPE: PRT
<213> ORGANISM: Artificial Sequence
<220> FEATURE:
<223> OTHER INFORMATION: Epitope Mimic of H-3 miHAg

<400> SEQUENCE: 780

Ile Pro Tyr Ile Tyr Asn Thr Leu
1               5

<210> SEQ ID NO 781
<211> LENGTH: 8
<212> TYPE: PRT
<213> ORGANISM: Artificial Sequence
<220> FEATURE:
<223> OTHER INFORMATION: Epitope Mimic of H-3 miHAg

<400> SEQUENCE: 781

Ile Ile Tyr Ile Tyr His Arg Leu
1               5

<210> SEQ ID NO 782
<211> LENGTH: 8
<212> TYPE: PRT
<213> ORGANISM: Artificial Sequence
<220> FEATURE:
<223> OTHER INFORMATION: Epitope Mimic of H-3 miHAg

<400> SEQUENCE: 782

Leu Ile Tyr Ile Phe Asn Thr Leu
1               5

<210> SEQ ID NO 783
<211> LENGTH: 8
<212> TYPE: PRT
<213> ORGANISM: Hepatitis B Virus

<400> SEQUENCE: 783

Met Gly Leu Lys Phe Arg Gln Leu
```

<210> SEQ ID NO 784
<211> LENGTH: 9
<212> TYPE: PRT
<213> ORGANISM: Homo Sapien

<400> SEQUENCE: 784

Ile Met Ile Lys Phe Arg Asn Arg Leu
1               5

<210> SEQ ID NO 785
<211> LENGTH: 9
<212> TYPE: PRT
<213> ORGANISM: Mus Musculus

<400> SEQUENCE: 785

Trp Met His His Asn Met Asp Leu Ile
1               5

<210> SEQ ID NO 786
<211> LENGTH: 9
<212> TYPE: PRT
<213> ORGANISM: Mus Musculus

<400> SEQUENCE: 786

Lys Tyr Met Cys Asn Ser Ser Cys Met
1               5

<210> SEQ ID NO 787
<211> LENGTH: 9
<212> TYPE: PRT
<213> ORGANISM: Mus Musculus

<400> SEQUENCE: 787

Gly Arg Pro Lys Asn Gly Cys Ile Val
1               5

<210> SEQ ID NO 788
<211> LENGTH: 9
<212> TYPE: PRT
<213> ORGANISM: Artificial Sequence
<220> FEATURE:
<223> OTHER INFORMATION: Epitope mimic of natural tumor Ag

<400> SEQUENCE: 788

Ala Gln His Pro Asn Ala Glu Leu Leu
1               5

<210> SEQ ID NO 789
<211> LENGTH: 9
<212> TYPE: PRT
<213> ORGANISM: Murine Leukemia Virus

<400> SEQUENCE: 789

Cys Cys Leu Cys Leu Thr Val Phe Leu
1               5

<210> SEQ ID NO 790
<211> LENGTH: 8
<212> TYPE: PRT
<213> ORGANISM: Plasmodium Falciparum

<400> SEQUENCE: 790

Tyr Glu Asn Asp Ile Glu Lys Lys
1               5

```
<210> SEQ ID NO 791
<211> LENGTH: 9
<212> TYPE: PRT
<213> ORGANISM: Plasmodium Falciparum

<400> SEQUENCE: 791

Asp Glu Leu Asp Tyr Glu Asn Asp Ile
1               5

<210> SEQ ID NO 792
<211> LENGTH: 9
<212> TYPE: PRT
<213> ORGANISM: Human Immunodeficiency Virus

<400> SEQUENCE: 792

Thr Glu Met Glu Lys Glu Gly Lys Ile
1               5

<210> SEQ ID NO 793
<211> LENGTH: 9
<212> TYPE: PRT
<213> ORGANISM: Rabies

<400> SEQUENCE: 793

Val Glu Ala Glu Ile Ala His Gln Ile
1               5

<210> SEQ ID NO 794
<211> LENGTH: 9
<212> TYPE: PRT
<213> ORGANISM: Influenza A

<400> SEQUENCE: 794

Glu Glu Gly Ala Ile Val Gly Glu Ile
1               5

<210> SEQ ID NO 795
<211> LENGTH: 8
<212> TYPE: PRT
<213> ORGANISM: Mus Musculus

<400> SEQUENCE: 795

Thr Glu Asn Ser Gly Lys Asp Ile
1               5

<210> SEQ ID NO 796
<211> LENGTH: 9
<212> TYPE: PRT
<213> ORGANISM: Artificial Sequence
<220> FEATURE:
<223> OTHER INFORMATION: MHC Class I Leader

<400> SEQUENCE: 796

Ala Met Ala Pro Arg Thr Leu Leu Leu
1               5

<210> SEQ ID NO 797
<211> LENGTH: 11
<212> TYPE: PRT
<213> ORGANISM: Homo Sapien

<400> SEQUENCE: 797

Phe Phe Ile Asn Ile Leu Thr Leu Leu Val Pro
1               5                   10
```

<210> SEQ ID NO 798
<211> LENGTH: 11
<212> TYPE: PRT
<213> ORGANISM: Homo Sapien

<400> SEQUENCE: 798

Phe Phe Ile Asn Ile Leu Thr Leu Leu Val Pro
1               5                   10

<210> SEQ ID NO 799
<211> LENGTH: 16
<212> TYPE: PRT
<213> ORGANISM: Homo Sapien

<400> SEQUENCE: 799

Phe Phe Ile Asn Ile Leu Thr Leu Leu Val Pro Ile Leu Ile Ala Met
1               5                   10                  15

<210> SEQ ID NO 800
<211> LENGTH: 16
<212> TYPE: PRT
<213> ORGANISM: Homo Sapien

<400> SEQUENCE: 800

Phe Phe Ile Asn Ala Leu Thr Leu Leu Val Pro Ile Leu Ile Ala Met
1               5                   10                  15

<210> SEQ ID NO 801
<211> LENGTH: 5
<212> TYPE: PRT
<213> ORGANISM: Homo Sapien

<400> SEQUENCE: 801

Phe Ile Asn Arg Trp
1               5

<210> SEQ ID NO 802
<211> LENGTH: 5
<212> TYPE: PRT
<213> ORGANISM: Listeria Monocytogenes

<400> SEQUENCE: 802

Ile Gly Trp Ile Ile
1               5

<210> SEQ ID NO 803
<211> LENGTH: 12
<212> TYPE: PRT
<213> ORGANISM: Simian Immunodeficiency Virus

<400> SEQUENCE: 803

Glu Gly Cys Thr Pro Tyr Asp Ile Asn Gln Met Leu
1               5                   10

<210> SEQ ID NO 804
<211> LENGTH: 9
<212> TYPE: PRT
<213> ORGANISM: Homo Sapien

<400> SEQUENCE: 804

Ala Leu Ser Arg Lys Val Ala Glu Leu
1               5

<210> SEQ ID NO 805
<211> LENGTH: 9

```
<212> TYPE: PRT
<213> ORGANISM: Homo Sapien

<400> SEQUENCE: 805

Ile Met Pro Lys Ala Gly Leu Leu Ile
1               5

<210> SEQ ID NO 806
<211> LENGTH: 9
<212> TYPE: PRT
<213> ORGANISM: Homo Sapien

<400> SEQUENCE: 806

Lys Ile Trp Glu Glu Leu Ser Val Leu
1               5

<210> SEQ ID NO 807
<211> LENGTH: 10
<212> TYPE: PRT
<213> ORGANISM: Homo Sapien

<400> SEQUENCE: 807

Ala Leu Val Glu Thr Ser Tyr Val Lys Val
1               5                   10

<210> SEQ ID NO 808
<211> LENGTH: 10
<212> TYPE: PRT
<213> ORGANISM: Homo Sapien

<400> SEQUENCE: 808

Thr Leu Val Glu Val Thr Leu Gly Glu Val
1               5                   10

<210> SEQ ID NO 809
<211> LENGTH: 9
<212> TYPE: PRT
<213> ORGANISM: Homo Sapien

<400> SEQUENCE: 809

Ala Leu Ser Arg Lys Val Ala Glu Leu
1               5

<210> SEQ ID NO 810
<211> LENGTH: 9
<212> TYPE: PRT
<213> ORGANISM: Homo Sapien

<400> SEQUENCE: 810

Ile Met Pro Lys Ala Gly Leu Leu Ile
1               5

<210> SEQ ID NO 811
<211> LENGTH: 9
<212> TYPE: PRT
<213> ORGANISM: Homo Sapien

<400> SEQUENCE: 811

Lys Ile Trp Glu Glu Leu Ser Val Leu
1               5

<210> SEQ ID NO 812
<211> LENGTH: 10
<212> TYPE: PRT
<213> ORGANISM: Homo Sapien
```

```
<400> SEQUENCE: 812

Ala Leu Val Glu Thr Ser Tyr Val Lys Val
1               5                   10

<210> SEQ ID NO 813
<211> LENGTH: 12
<212> TYPE: PRT
<213> ORGANISM: Homo Sapien

<400> SEQUENCE: 813

Lys Gly Ile Leu Gly Phe Val Phe Thr Leu Thr Val
1               5                   10

<210> SEQ ID NO 814
<211> LENGTH: 9
<212> TYPE: PRT
<213> ORGANISM: Homo Sapien

<400> SEQUENCE: 814

Gly Ile Ile Gly Phe Val Phe Thr Ile
1               5

<210> SEQ ID NO 815
<211> LENGTH: 9
<212> TYPE: PRT
<213> ORGANISM: Homo Sapien

<400> SEQUENCE: 815

Gly Ile Ile Gly Phe Val Phe Thr Leu
1               5

<210> SEQ ID NO 816
<211> LENGTH: 9
<212> TYPE: PRT
<213> ORGANISM: Homo Sapien

<400> SEQUENCE: 816

Gly Ile Leu Gly Phe Val Phe Thr Leu
1               5

<210> SEQ ID NO 817
<211> LENGTH: 9
<212> TYPE: PRT
<213> ORGANISM: Homo Sapien

<400> SEQUENCE: 817

Gly Leu Leu Gly Phe Val Phe Thr Leu
1               5

<210> SEQ ID NO 818
<211> LENGTH: 9
<212> TYPE: PRT
<213> ORGANISM: Homo Sapien
<220> FEATURE:
<221> NAME/KEY: VARIANT
<222> LOCATION: 1, 2, 5, 6, 9
<223> OTHER INFORMATION: Xaa = Any Amino Acid

<400> SEQUENCE: 818

Xaa Xaa Thr Val Xaa Xaa Gly Val Xaa
1               5

<210> SEQ ID NO 819
<211> LENGTH: 9
<212> TYPE: PRT
<213> ORGANISM: Homo Sapien
```

<400> SEQUENCE: 819

Ile Leu Thr Val Ile Leu Gly Val Leu
1               5

<210> SEQ ID NO 820
<211> LENGTH: 9
<212> TYPE: PRT
<213> ORGANISM: Homo Sapien

<400> SEQUENCE: 820

Tyr Leu Glu Pro Gly Pro Val Thr Ala
1               5

<210> SEQ ID NO 821
<211> LENGTH: 10
<212> TYPE: PRT
<213> ORGANISM: Homo Sapien

<400> SEQUENCE: 821

Gln Val Pro Leu Arg Pro Met Thr Tyr Lys
1               5                   10

<210> SEQ ID NO 822
<211> LENGTH: 11
<212> TYPE: PRT
<213> ORGANISM: Homo Sapien

<400> SEQUENCE: 822

Asp Gly Leu Ala Pro Pro Gln His Leu Ile Arg
1               5                   10

<210> SEQ ID NO 823
<211> LENGTH: 9
<212> TYPE: PRT
<213> ORGANISM: Homo Sapien

<400> SEQUENCE: 823

Leu Leu Gly Arg Asn Ser Phe Glu Val
1               5

<210> SEQ ID NO 824
<211> LENGTH: 16
<212> TYPE: PRT
<213> ORGANISM: Homo Sapien

<400> SEQUENCE: 824

Glu His Ser Ala Tyr Gly Glu Pro Arg Lys Leu Leu Thr Gln Asp Leu
1               5                   10                  15

<210> SEQ ID NO 825
<211> LENGTH: 12
<212> TYPE: PRT
<213> ORGANISM: Homo Sapien

<400> SEQUENCE: 825

Glu His Ser Ala Tyr Gly Glu Pro Arg Lys Leu Leu
1               5                   10

<210> SEQ ID NO 826
<211> LENGTH: 9
<212> TYPE: PRT
<213> ORGANISM: Homo Sapien

<400> SEQUENCE: 826

```
Ser Ala Tyr Gly Glu Pro Arg Lys Leu
1               5
```

<210> SEQ ID NO 827
<211> LENGTH: 8
<212> TYPE: PRT
<213> ORGANISM: Homo Sapien

<400> SEQUENCE: 827

```
Tyr Arg Pro Arg Pro Arg Arg Tyr
1               5
```

<210> SEQ ID NO 828
<211> LENGTH: 9
<212> TYPE: PRT
<213> ORGANISM: Homo Sapien

<400> SEQUENCE: 828

```
Thr Tyr Arg Pro Arg Pro Arg Arg Tyr
1               5
```

<210> SEQ ID NO 829
<211> LENGTH: 9
<212> TYPE: PRT
<213> ORGANISM: Homo Sapien

<400> SEQUENCE: 829

```
Tyr Arg Pro Arg Pro Arg Arg Tyr Val
1               5
```

<210> SEQ ID NO 830
<211> LENGTH: 10
<212> TYPE: PRT
<213> ORGANISM: Homo Sapien

<400> SEQUENCE: 830

```
Thr Tyr Arg Pro Arg Pro Arg Arg Tyr Val
1               5                   10
```

<210> SEQ ID NO 831
<211> LENGTH: 9
<212> TYPE: PRT
<213> ORGANISM: Homo Sapien

<400> SEQUENCE: 831

```
Arg Pro Arg Pro Arg Arg Tyr Val Glu
1               5
```

<210> SEQ ID NO 832
<211> LENGTH: 15
<212> TYPE: PRT
<213> ORGANISM: Homo Sapien

<400> SEQUENCE: 832

```
Met Ser Trp Arg Gly Arg Ser Thr Tyr Arg Pro Arg Pro Arg Arg
1               5                   10                  15
```

<210> SEQ ID NO 833
<211> LENGTH: 16
<212> TYPE: PRT
<213> ORGANISM: Homo Sapien

<400> SEQUENCE: 833

```
Thr Tyr Arg Pro Arg Pro Arg Arg Tyr Val Glu Pro Pro Glu Met Ile
1               5                   10                  15
```

```
<210> SEQ ID NO 834
<211> LENGTH: 3
<212> TYPE: PRT
<213> ORGANISM: Homo Sapien

<400> SEQUENCE: 834

Glu Asp Tyr
1

<210> SEQ ID NO 835
<211> LENGTH: 9
<212> TYPE: PRT
<213> ORGANISM: Homo Sapien

<400> SEQUENCE: 835

Glu Val Val Pro Ile Ser His Leu Tyr
1               5

<210> SEQ ID NO 836
<211> LENGTH: 9
<212> TYPE: PRT
<213> ORGANISM: Homo Sapien

<400> SEQUENCE: 836

Glu Val Val Arg Ile Gly His Leu Tyr
1               5

<210> SEQ ID NO 837
<211> LENGTH: 9
<212> TYPE: PRT
<213> ORGANISM: Homo Sapien

<400> SEQUENCE: 837

Glu Val Asp Pro Ile Gly His Leu Tyr
1               5

<210> SEQ ID NO 838
<211> LENGTH: 9
<212> TYPE: PRT
<213> ORGANISM: Homo Sapien

<400> SEQUENCE: 838

Glu Val Asp Pro Ala Ser Asn Thr Tyr
1               5

<210> SEQ ID NO 839
<211> LENGTH: 9
<212> TYPE: PRT
<213> ORGANISM: Homo Sapien

<400> SEQUENCE: 839

Glu Val Asp Pro Thr Ser Asn Thr Tyr
1               5

<210> SEQ ID NO 840
<211> LENGTH: 9
<212> TYPE: PRT
<213> ORGANISM: Homo Sapien

<400> SEQUENCE: 840

Glu Ala Asp Pro Thr Ser Asn Thr Tyr
1               5

<210> SEQ ID NO 841
<211> LENGTH: 9
```

```
<212> TYPE: PRT
<213> ORGANISM: Homo Sapien

<400> SEQUENCE: 841

Glu Val Asp Pro Ile Gly His Val Tyr
 1               5

<210> SEQ ID NO 842
<211> LENGTH: 27
<212> TYPE: DNA
<213> ORGANISM: Homo Sapien

<400> SEQUENCE: 842
gaagtggtcc ccatcagcca cttgtac                                         27

<210> SEQ ID NO 843
<211> LENGTH: 27
<212> TYPE: DNA
<213> ORGANISM: Homo Sapien

<400> SEQUENCE: 843
gaagtggtcc gcatcggcca cttgtac                                         27

<210> SEQ ID NO 844
<211> LENGTH: 27
<212> TYPE: DNA
<213> ORGANISM: Homo Sapien

<400> SEQUENCE: 844
gaagtggacc ccatcggcca cttgtac                                         27

<210> SEQ ID NO 845
<211> LENGTH: 27
<212> TYPE: DNA
<213> ORGANISM: Homo Sapien

<400> SEQUENCE: 845
gaagtggacc ccgccagcaa cacctac                                         27

<210> SEQ ID NO 846
<211> LENGTH: 27
<212> TYPE: DNA
<213> ORGANISM: Homo Sapien

<400> SEQUENCE: 846
gaagtggacc ccaccagcaa cacctac                                         27

<210> SEQ ID NO 847
<211> LENGTH: 27
<212> TYPE: DNA
<213> ORGANISM: Homo Sapien

<400> SEQUENCE: 847
gaagcggacc ccaccagcaa cacctac                                         27

<210> SEQ ID NO 848
<211> LENGTH: 27
<212> TYPE: DNA
<213> ORGANISM: Homo Sapien

<400> SEQUENCE: 848
gaagcggacc ccaccagcaa cacctac                                         27

<210> SEQ ID NO 849
```

```
<211> LENGTH: 27
<212> TYPE: DNA
<213> ORGANISM: Homo Sapien

<400> SEQUENCE: 849
gaagtggacc ccatcggcca cgtgtac                                         27

<210> SEQ ID NO 850
<211> LENGTH: 8
<212> TYPE: PRT
<213> ORGANISM: Homo Sapien

<400> SEQUENCE: 850

Glu Ala Asp Pro Thr Gly His Ser
1               5

<210> SEQ ID NO 851
<211> LENGTH: 8
<212> TYPE: PRT
<213> ORGANISM: Homo Sapien

<400> SEQUENCE: 851

Ala Asp Pro Trp Gly His Ser Tyr
1               5

<210> SEQ ID NO 852
<211> LENGTH: 11
<212> TYPE: PRT
<213> ORGANISM: Homo Sapien

<400> SEQUENCE: 852

Ser Thr Leu Val Glu Val Thr Leu Gly Glu Val
1               5                   10

<210> SEQ ID NO 853
<211> LENGTH: 9
<212> TYPE: PRT
<213> ORGANISM: Homo Sapien

<400> SEQUENCE: 853

Leu Val Glu Val Thr Leu Gly Glu Val
1               5

<210> SEQ ID NO 854
<211> LENGTH: 9
<212> TYPE: PRT
<213> ORGANISM: Homo Sapien

<400> SEQUENCE: 854

Lys Met Val Glu Leu Val His Phe Leu
1               5

<210> SEQ ID NO 855
<211> LENGTH: 10
<212> TYPE: PRT
<213> ORGANISM: Homo Sapien

<400> SEQUENCE: 855

Val Ile Phe Ser Lys Ala Ser Glu Tyr Leu
1               5                   10

<210> SEQ ID NO 856
<211> LENGTH: 10
<212> TYPE: PRT
<213> ORGANISM: Homo Sapien
```

```
<400> SEQUENCE: 856

Tyr Leu Gln Leu Val Phe Gly Ile Glu Val
 1               5                  10

<210> SEQ ID NO 857
<211> LENGTH: 9
<212> TYPE: PRT
<213> ORGANISM: Homo Sapien

<400> SEQUENCE: 857

Gln Leu Val Phe Gly Ile Glu Val Val
 1               5

<210> SEQ ID NO 858
<211> LENGTH: 11
<212> TYPE: PRT
<213> ORGANISM: Homo Sapien

<400> SEQUENCE: 858

Gln Leu Val Phe Gly Ile Glu Val Val Glu Val
 1               5                  10

<210> SEQ ID NO 859
<211> LENGTH: 9
<212> TYPE: PRT
<213> ORGANISM: Homo Sapien

<400> SEQUENCE: 859

Ile Ile Val Leu Ala Ile Ile Ala Ile
 1               5

<210> SEQ ID NO 860
<211> LENGTH: 11
<212> TYPE: PRT
<213> ORGANISM: Homo Sapien

<400> SEQUENCE: 860

Lys Ile Trp Glu Glu Leu Ser Met Leu Glu Val
 1               5                  10

<210> SEQ ID NO 861
<211> LENGTH: 10
<212> TYPE: PRT
<213> ORGANISM: Homo Sapien

<400> SEQUENCE: 861

Ala Leu Ile Glu Thr Ser Tyr Val Lys Val
 1               5                  10

<210> SEQ ID NO 862
<211> LENGTH: 9
<212> TYPE: PRT
<213> ORGANISM: Homo Sapien

<400> SEQUENCE: 862

Leu Ile Glu Thr Ser Tyr Val Lys Val
 1               5

<210> SEQ ID NO 863
<211> LENGTH: 11
<212> TYPE: PRT
<213> ORGANISM: Homo Sapien

<400> SEQUENCE: 863

Gly Leu Glu Ala Arg Gly Glu Ala Leu Gly Leu
```

```
                                 1               5                    10
```

<210> SEQ ID NO 864
<211> LENGTH: 9
<212> TYPE: PRT
<213> ORGANISM: Homo Sapien

<400> SEQUENCE: 864

```
Gly Leu Glu Ala Arg Gly Glu Ala Leu
 1               5
```

<210> SEQ ID NO 865
<211> LENGTH: 9
<212> TYPE: PRT
<213> ORGANISM: Homo Sapien

<400> SEQUENCE: 865

```
Ala Leu Gly Leu Val Gly Ala Gln Ala
 1               5
```

<210> SEQ ID NO 866
<211> LENGTH: 9
<212> TYPE: PRT
<213> ORGANISM: Homo Sapien

<400> SEQUENCE: 866

```
Gly Leu Val Gly Ala Gln Ala Pro Ala
 1               5
```

<210> SEQ ID NO 867
<211> LENGTH: 9
<212> TYPE: PRT
<213> ORGANISM: Homo Sapien

<400> SEQUENCE: 867

```
Asp Leu Glu Ser Glu Phe Gln Ala Ala
 1               5
```

<210> SEQ ID NO 868
<211> LENGTH: 10
<212> TYPE: PRT
<213> ORGANISM: Homo Sapien

<400> SEQUENCE: 868

```
Asp Leu Glu Ser Glu Phe Gln Ala Ala Ile
 1               5                   10
```

<210> SEQ ID NO 869
<211> LENGTH: 10
<212> TYPE: PRT
<213> ORGANISM: Homo Sapien

<400> SEQUENCE: 869

```
Ala Ile Ser Arg Lys Met Val Glu Leu Val
 1               5                   10
```

<210> SEQ ID NO 870
<211> LENGTH: 9
<212> TYPE: PRT
<213> ORGANISM: Homo Sapien

<400> SEQUENCE: 870

```
Ala Ile Ser Arg Lys Met Val Glu Leu
 1               5
```

<210> SEQ ID NO 871
<211> LENGTH: 10
<212> TYPE: PRT
<213> ORGANISM: Homo Sapien

<400> SEQUENCE: 871

Lys Met Val Glu Leu Val His Phe Leu Leu
1               5                   10

<210> SEQ ID NO 872
<211> LENGTH: 11
<212> TYPE: PRT
<213> ORGANISM: Homo Sapien

<400> SEQUENCE: 872

Lys Met Val Glu Leu Val His Phe Leu Leu
1               5                   10

<210> SEQ ID NO 873
<211> LENGTH: 11
<212> TYPE: PRT
<213> ORGANISM: Homo Sapien

<400> SEQUENCE: 873

Leu Leu Leu Lys Tyr Arg Ala Arg Glu Pro Val
1               5                   10

<210> SEQ ID NO 874
<211> LENGTH: 10
<212> TYPE: PRT
<213> ORGANISM: Homo Sapien

<400> SEQUENCE: 874

Leu Leu Lys Tyr Arg Ala Arg Glu Pro Val
1               5                   10

<210> SEQ ID NO 875
<211> LENGTH: 11
<212> TYPE: PRT
<213> ORGANISM: Homo Sapien

<400> SEQUENCE: 875

Val Leu Arg Asn Cys Gln Asp Phe Phe Pro Val
1               5                   10

<210> SEQ ID NO 876
<211> LENGTH: 11
<212> TYPE: PRT
<213> ORGANISM: Homo Sapien

<400> SEQUENCE: 876

Tyr Leu Gln Leu Val Phe Gly Ile Glu Val Val
1               5                   10

<210> SEQ ID NO 877
<211> LENGTH: 10
<212> TYPE: PRT
<213> ORGANISM: Homo Sapien

<400> SEQUENCE: 877

Gly Ile Glu Val Val Glu Val Val Pro Ile
1               5                   10

<210> SEQ ID NO 878
<211> LENGTH: 9
<212> TYPE: PRT

<213> ORGANISM: Homo Sapien

<400> SEQUENCE: 878

Pro Ile Ser His Leu Tyr Ile Leu Val
1               5

<210> SEQ ID NO 879
<211> LENGTH: 9
<212> TYPE: PRT
<213> ORGANISM: Homo Sapien

<400> SEQUENCE: 879

His Leu Tyr Ile Leu Val Thr Cys Leu
1               5

<210> SEQ ID NO 880
<211> LENGTH: 11
<212> TYPE: PRT
<213> ORGANISM: Homo Sapien

<400> SEQUENCE: 880

His Leu Tyr Ile Leu Val Thr Cys Leu Gly Leu
1               5                   10

<210> SEQ ID NO 881
<211> LENGTH: 9
<212> TYPE: PRT
<213> ORGANISM: Homo Sapien

<400> SEQUENCE: 881

Tyr Ile Leu Val Thr Cys Leu Gly Leu
1               5

<210> SEQ ID NO 882
<211> LENGTH: 9
<212> TYPE: PRT
<213> ORGANISM: Homo Sapien

<400> SEQUENCE: 882

Cys Leu Gly Leu Ser Tyr Asp Gly Leu
1               5

<210> SEQ ID NO 883
<211> LENGTH: 10
<212> TYPE: PRT
<213> ORGANISM: Homo Sapien

<400> SEQUENCE: 883

Cys Leu Gly Leu Ser Tyr Asp Gly Leu Leu
1               5                   10

<210> SEQ ID NO 884
<211> LENGTH: 9
<212> TYPE: PRT
<213> ORGANISM: Homo Sapien

<400> SEQUENCE: 884

Val Met Pro Lys Thr Gly Leu Leu Ile
1               5

<210> SEQ ID NO 885
<211> LENGTH: 10
<212> TYPE: PRT
<213> ORGANISM: Homo Sapien

<400> SEQUENCE: 885

```
Val Met Pro Lys Thr Gly Leu Leu Ile Ile
1               5                   10
```

<210> SEQ ID NO 886
<211> LENGTH: 11
<212> TYPE: PRT
<213> ORGANISM: Homo Sapien

<400> SEQUENCE: 886

```
Val Met Pro Lys Thr Gly Leu Leu Ile Ile Val
1               5                   10
```

<210> SEQ ID NO 887
<211> LENGTH: 9
<212> TYPE: PRT
<213> ORGANISM: Homo Sapien

<400> SEQUENCE: 887

```
Gly Leu Leu Ile Ile Val Leu Ala Ile
1               5
```

<210> SEQ ID NO 888
<211> LENGTH: 10
<212> TYPE: PRT
<213> ORGANISM: Homo Sapien

<400> SEQUENCE: 888

```
Gly Leu Leu Ile Ile Val Leu Ala Ile Ile
1               5                   10
```

<210> SEQ ID NO 889
<211> LENGTH: 11
<212> TYPE: PRT
<213> ORGANISM: Homo Sapien

<400> SEQUENCE: 889

```
Gly Leu Leu Ile Ile Val Leu Ala Ile Ile Ala
1               5                   10
```

<210> SEQ ID NO 890
<211> LENGTH: 9
<212> TYPE: PRT
<213> ORGANISM: Homo Sapien

<400> SEQUENCE: 890

```
Leu Leu Ile Ile Val Leu Ala Ile Ile
1               5
```

<210> SEQ ID NO 891
<211> LENGTH: 10
<212> TYPE: PRT
<213> ORGANISM: Homo Sapien

<400> SEQUENCE: 891

```
Leu Leu Ile Ile Val Leu Ala Ile Ile Ala
1               5                   10
```

<210> SEQ ID NO 892
<211> LENGTH: 11
<212> TYPE: PRT
<213> ORGANISM: Homo Sapien

<400> SEQUENCE: 892

```
Leu Leu Ile Ile Val Leu Ala Ile Ile Ala Ile
1               5                   10
```

<210> SEQ ID NO 893
<211> LENGTH: 9
<212> TYPE: PRT
<213> ORGANISM: Homo Sapien

<400> SEQUENCE: 893

Leu Ile Ile Val Leu Ala Ile Ile Ala
1               5

<210> SEQ ID NO 894
<211> LENGTH: 10
<212> TYPE: PRT
<213> ORGANISM: Homo Sapien

<400> SEQUENCE: 894

Leu Ile Ile Val Leu Ala Ile Ile Ala Ile
1               5                   10

<210> SEQ ID NO 895
<211> LENGTH: 9
<212> TYPE: PRT
<213> ORGANISM: Homo Sapien

<400> SEQUENCE: 895

Ile Ile Ala Ile Glu Gly Asp Cys Ala
1               5

<210> SEQ ID NO 896
<211> LENGTH: 9
<212> TYPE: PRT
<213> ORGANISM: Homo Sapien

<400> SEQUENCE: 896

Lys Ile Trp Glu Glu Leu Ser Met Leu
1               5

<210> SEQ ID NO 897
<211> LENGTH: 11
<212> TYPE: PRT
<213> ORGANISM: Homo Sapien

<400> SEQUENCE: 897

Leu Met Gln Asp Leu Val Gln Glu Asn Tyr Leu
1               5                   10

<210> SEQ ID NO 898
<211> LENGTH: 9
<212> TYPE: PRT
<213> ORGANISM: Homo Sapien

<400> SEQUENCE: 898

Phe Leu Trp Gly Pro Arg Ala Leu Ile
1               5

<210> SEQ ID NO 899
<211> LENGTH: 9
<212> TYPE: PRT
<213> ORGANISM: Homo Sapien

<400> SEQUENCE: 899

Leu Ile Glu Thr Ser Tyr Val Lys Val
1               5

<210> SEQ ID NO 900

```
<211> LENGTH: 11
<212> TYPE: PRT
<213> ORGANISM: Homo Sapien

<400> SEQUENCE: 900

Ala Leu Ile Glu Thr Ser Tyr Val Lys Val Leu
1               5                   10

<210> SEQ ID NO 901
<211> LENGTH: 10
<212> TYPE: PRT
<213> ORGANISM: Homo Sapien

<400> SEQUENCE: 901

Thr Leu Lys Ile Gly Gly Glu Pro His Ile
1               5                   10

<210> SEQ ID NO 902
<211> LENGTH: 11
<212> TYPE: PRT
<213> ORGANISM: Homo Sapien

<400> SEQUENCE: 902

His Ile Ser Tyr Pro Pro Leu His Glu Arg Ala
1               5                   10

<210> SEQ ID NO 903
<211> LENGTH: 9
<212> TYPE: PRT
<213> ORGANISM: Homo Sapien

<400> SEQUENCE: 903

Gln Thr Ala Ser Ser Ser Ser Thr Leu
1               5

<210> SEQ ID NO 904
<211> LENGTH: 10
<212> TYPE: PRT
<213> ORGANISM: Homo Sapien

<400> SEQUENCE: 904

Gln Thr Ala Ser Ser Ser Ser Thr Leu Val
1               5                   10

<210> SEQ ID NO 905
<211> LENGTH: 9
<212> TYPE: PRT
<213> ORGANISM: Homo Sapien

<400> SEQUENCE: 905

Val Thr Leu Gly Glu Val Pro Ala Ala
1               5

<210> SEQ ID NO 906
<211> LENGTH: 10
<212> TYPE: PRT
<213> ORGANISM: Homo Sapien

<400> SEQUENCE: 906

Val Thr Lys Ala Glu Met Leu Glu Ser Val
1               5                   10

<210> SEQ ID NO 907
<211> LENGTH: 11
<212> TYPE: PRT
<213> ORGANISM: Homo Sapien
```

```
<400> SEQUENCE: 907

Val Thr Lys Ala Glu Met Leu Glu Ser Val Leu
1               5                   10

<210> SEQ ID NO 908
<211> LENGTH: 11
<212> TYPE: PRT
<213> ORGANISM: Homo Sapien

<400> SEQUENCE: 908

Val Thr Cys Leu Gly Leu Ser Tyr Asp Gly Leu
1               5                   10

<210> SEQ ID NO 909
<211> LENGTH: 9
<212> TYPE: PRT
<213> ORGANISM: Homo Sapien

<400> SEQUENCE: 909

Lys Thr Gly Leu Leu Ile Ile Val Leu
1               5

<210> SEQ ID NO 910
<211> LENGTH: 10
<212> TYPE: PRT
<213> ORGANISM: Homo Sapien

<400> SEQUENCE: 910

Lys Thr Gly Leu Leu Ile Ile Val Leu Ala
1               5                   10

<210> SEQ ID NO 911
<211> LENGTH: 11
<212> TYPE: PRT
<213> ORGANISM: Homo Sapien

<400> SEQUENCE: 911

Lys Thr Gly Leu Leu Ile Ile Val Leu Ala Ile
1               5                   10

<210> SEQ ID NO 912
<211> LENGTH: 11
<212> TYPE: PRT
<213> ORGANISM: Homo Sapien

<400> SEQUENCE: 912

His Thr Leu Lys Ile Gly Gly Glu Pro His Ile
1               5                   10

<210> SEQ ID NO 913
<211> LENGTH: 9
<212> TYPE: PRT
<213> ORGANISM: Homo Sapien

<400> SEQUENCE: 913

Met Leu Asp Leu Gln Pro Glu Thr Thr
1               5

<210> SEQ ID NO 914
<211> LENGTH: 9
<212> TYPE: PRT
<213> ORGANISM: Homo Sapien

<400> SEQUENCE: 914
```

Gly Leu Glu Ala Arg Gly Glu Ala Leu
1               5

<210> SEQ ID NO 915
<211> LENGTH: 9
<212> TYPE: PRT
<213> ORGANISM: Homo Sapien

<400> SEQUENCE: 915

Ala Leu Ser Arg Lys Val Ala Glu Leu
1               5

<210> SEQ ID NO 916
<211> LENGTH: 9
<212> TYPE: PRT
<213> ORGANISM: Homo Sapien

<400> SEQUENCE: 916

Phe Leu Trp Gly Pro Arg Ala Leu Val
1               5

<210> SEQ ID NO 917
<211> LENGTH: 10
<212> TYPE: PRT
<213> ORGANISM: Homo Sapien

<400> SEQUENCE: 917

Thr Leu Val Glu Val Thr Leu Gly Glu Val
1               5                   10

<210> SEQ ID NO 918
<211> LENGTH: 10
<212> TYPE: PRT
<213> ORGANISM: Homo Sapien

<400> SEQUENCE: 918

Ala Leu Ser Arg Lys Val Ala Glu Leu Val
1               5                   10

<210> SEQ ID NO 919
<211> LENGTH: 10
<212> TYPE: PRT
<213> ORGANISM: Homo Sapien

<400> SEQUENCE: 919

Ala Leu Val Glu Thr Ser Tyr Val Lys Val
1               5                   10

<210> SEQ ID NO 920
<211> LENGTH: 9
<212> TYPE: PRT
<213> ORGANISM: Homo Sapien

<400> SEQUENCE: 920

Tyr Met Asn Gly Thr Met Ser Gln Val
1               5

<210> SEQ ID NO 921
<211> LENGTH: 10
<212> TYPE: PRT
<213> ORGANISM: Homo Sapien

<400> SEQUENCE: 921

Met Leu Leu Ala Val Leu Tyr Cys Leu Leu
1               5                   10

<210> SEQ ID NO 922
<211> LENGTH: 9
<212> TYPE: PRT
<213> ORGANISM: Homo Sapien

<400> SEQUENCE: 922

Met Leu Leu Ala Val Leu Tyr Cys Leu
1               5

<210> SEQ ID NO 923
<211> LENGTH: 9
<212> TYPE: PRT
<213> ORGANISM: Homo Sapien

<400> SEQUENCE: 923

Leu Leu Ala Val Leu Tyr Cys Leu Leu
1               5

<210> SEQ ID NO 924
<211> LENGTH: 13
<212> TYPE: PRT
<213> ORGANISM: Homo Sapien

<400> SEQUENCE: 924

Ser Glu Ile Trp Arg Asp Ile Asp Phe Ala His Glu Ala
1               5                   10

<210> SEQ ID NO 925
<211> LENGTH: 9
<212> TYPE: PRT
<213> ORGANISM: Homo Sapien

<400> SEQUENCE: 925

Ser Glu Ile Trp Arg Asp Ile Asp Phe
1               5

<210> SEQ ID NO 926
<211> LENGTH: 10
<212> TYPE: PRT
<213> ORGANISM: Homo Sapien

<400> SEQUENCE: 926

Glu Glu Asn Leu Leu Asp Phe Val Arg Phe
1               5                   10

<210> SEQ ID NO 927
<211> LENGTH: 10
<212> TYPE: PRT
<213> ORGANISM: Homo Sapien

<400> SEQUENCE: 927

Glu Ala Ala Gly Ile Gly Ile Leu Thr Val
1               5                   10

<210> SEQ ID NO 928
<211> LENGTH: 9
<212> TYPE: PRT
<213> ORGANISM: Homo Sapien

<400> SEQUENCE: 928

Met Leu Leu Ala Val Leu Tyr Cys Leu
1               5

<210> SEQ ID NO 929
<211> LENGTH: 9

```
<212> TYPE: PRT
<213> ORGANISM: Homo Sapien

<400> SEQUENCE: 929

Tyr Met Asp Gly Thr Met Ser Gln Val
1               5

<210> SEQ ID NO 930
<211> LENGTH: 9
<212> TYPE: PRT
<213> ORGANISM: Homo Sapien

<400> SEQUENCE: 930

Tyr Leu Glu Pro Gly Pro Val Thr Ala
1               5

<210> SEQ ID NO 931
<211> LENGTH: 10
<212> TYPE: PRT
<213> ORGANISM: Homo Sapien

<400> SEQUENCE: 931

Leu Leu Asp Gly Thr Ala Thr Leu Arg Leu
1               5                   10

<210> SEQ ID NO 932
<211> LENGTH: 9
<212> TYPE: PRT
<213> ORGANISM: Homo Sapien

<400> SEQUENCE: 932

Gly Ile Leu Gly Phe Val Phe Thr Leu
1               5

<210> SEQ ID NO 933
<211> LENGTH: 9
<212> TYPE: PRT
<213> ORGANISM: Homo Sapien

<400> SEQUENCE: 933

Glu Ala Asp Pro Thr Gly His Ser Tyr
1               5

<210> SEQ ID NO 934
<211> LENGTH: 9
<212> TYPE: PRT
<213> ORGANISM: Homo Sapien

<400> SEQUENCE: 934

Glu Ala Asp Pro Thr Gly His Ser Tyr
1               5

<210> SEQ ID NO 935
<211> LENGTH: 22
<212> TYPE: PRT
<213> ORGANISM: Homo Sapien

<400> SEQUENCE: 935

Met Ala Ala Arg Ala Val Phe Leu Ala Leu Ser Ala Gln Leu Leu Gln
1               5                   10                  15

Ala Arg Leu Met Lys Glu
            20

<210> SEQ ID NO 936
<211> LENGTH: 16
```

```
<212> TYPE: PRT
<213> ORGANISM: Homo Sapien

<400> SEQUENCE: 936

Met Ala Ala Arg Ala Val Phe Leu Ala Leu Ser Ala Gln Leu Leu Gln
1               5                   10                  15

<210> SEQ ID NO 937
<211> LENGTH: 9
<212> TYPE: PRT
<213> ORGANISM: Homo Sapien

<400> SEQUENCE: 937

Ala Ala Arg Ala Val Phe Leu Ala Leu
1               5

<210> SEQ ID NO 938
<211> LENGTH: 9
<212> TYPE: PRT
<213> ORGANISM: Influenza

<400> SEQUENCE: 938

Ile Tyr Gln Arg Ile Arg Ala Leu Val
1               5

<210> SEQ ID NO 939
<211> LENGTH: 9
<212> TYPE: PRT
<213> ORGANISM: Homo Sapien

<400> SEQUENCE: 939

Ser Tyr Phe Pro Glu Ile Thr His Ile
1               5

<210> SEQ ID NO 940
<211> LENGTH: 9
<212> TYPE: PRT
<213> ORGANISM: Influenza

<400> SEQUENCE: 940

Ile Tyr Ala Thr Val Ala Gly Ser Leu
1               5

<210> SEQ ID NO 941
<211> LENGTH: 9
<212> TYPE: PRT
<213> ORGANISM: Influenza

<400> SEQUENCE: 941

Val Tyr Gln Ile Leu Ala Ile Tyr Ala
1               5

<210> SEQ ID NO 942
<211> LENGTH: 9
<212> TYPE: PRT
<213> ORGANISM: Influenza

<400> SEQUENCE: 942

Ile Tyr Ser Thr Val Ala Ser Ser Leu
1               5

<210> SEQ ID NO 943
<211> LENGTH: 9
<212> TYPE: PRT
<213> ORGANISM: Influenza
```

```
<400> SEQUENCE: 943

Leu Tyr Gln Asn Val Gly Thr Tyr Val
  1               5

<210> SEQ ID NO 944
<211> LENGTH: 9
<212> TYPE: PRT
<213> ORGANISM: Homo Sapien

<400> SEQUENCE: 944

Arg Tyr Leu Glu Asn Gln Lys Arg Thr
  1               5

<210> SEQ ID NO 945
<211> LENGTH: 9
<212> TYPE: PRT
<213> ORGANISM: Homo Sapien

<400> SEQUENCE: 945

Arg Tyr Leu Lys Asn Gly Lys Glu Thr
  1               5

<210> SEQ ID NO 946
<211> LENGTH: 9
<212> TYPE: PRT
<213> ORGANISM: Homo Sapien

<400> SEQUENCE: 946

Lys Tyr Gln Ala Val Thr Thr Thr Leu
  1               5

<210> SEQ ID NO 947
<211> LENGTH: 9
<212> TYPE: PRT
<213> ORGANISM: Plasmodium Berghei

<400> SEQUENCE: 947

Ser Tyr Ile Pro Ser Ala Glu Lys Ile
  1               5

<210> SEQ ID NO 948
<211> LENGTH: 9
<212> TYPE: PRT
<213> ORGANISM: Plasmodium Yoelii

<400> SEQUENCE: 948

Ser Tyr Val Pro Ser Ala Phe Gln Ile
  1               5

<210> SEQ ID NO 949
<211> LENGTH: 8
<212> TYPE: PRT
<213> ORGANISM: Vesicular Stomatitis Virus

<400> SEQUENCE: 949

Arg Gly Tyr Val Tyr Gln Gly Leu
  1               5

<210> SEQ ID NO 950
<211> LENGTH: 8
<212> TYPE: PRT
<213> ORGANISM: Gallus Domesticus

<400> SEQUENCE: 950

Ser Ile Ile Asn Phe Glu Lys Leu
  1               5
```

```
<210> SEQ ID NO 951
<211> LENGTH: 8
<212> TYPE: PRT
<213> ORGANISM: Sendai Virus

<400> SEQUENCE: 951

Ala Pro Gly Asn Tyr Pro Ala Leu
 1               5

<210> SEQ ID NO 952
<211> LENGTH: 9
<212> TYPE: PRT
<213> ORGANISM: Homo Sapien

<400> SEQUENCE: 952

Val Pro Tyr Gly Ser Phe Lys His Val
 1               5

<210> SEQ ID NO 953
<211> LENGTH: 9
<212> TYPE: PRT
<213> ORGANISM: Influenza

<400> SEQUENCE: 953

Thr Tyr Gln Arg Thr Arg Ala Leu Val
 1               5

<210> SEQ ID NO 954
<211> LENGTH: 9
<212> TYPE: PRT
<213> ORGANISM: Homo Sapien

<400> SEQUENCE: 954

Ser Tyr Phe Pro Glu Ile Thr His Ile
 1               5

<210> SEQ ID NO 955
<211> LENGTH: 9
<212> TYPE: PRT
<213> ORGANISM: Influenza

<400> SEQUENCE: 955

Ile Tyr Ala Thr Val Ala Gly Ser Leu
 1               5

<210> SEQ ID NO 956
<211> LENGTH: 9
<212> TYPE: PRT
<213> ORGANISM: Influenza

<400> SEQUENCE: 956

Val Tyr Gln Ile Leu Ala Ile Tyr Ala
 1               5

<210> SEQ ID NO 957
<211> LENGTH: 9
<212> TYPE: PRT
<213> ORGANISM: Influenza

<400> SEQUENCE: 957

Ile Tyr Ser Thr Val Ala Ser Ser Leu
 1               5
```

<210> SEQ ID NO 958
<211> LENGTH: 9
<212> TYPE: PRT
<213> ORGANISM: Influenza

<400> SEQUENCE: 958

Leu Tyr Gln Asn Val Gly Thr Tyr Val
1 5

<210> SEQ ID NO 959
<211> LENGTH: 10
<212> TYPE: PRT
<213> ORGANISM: Homo Sapien

<400> SEQUENCE: 959

Arg Tyr Leu Glu Asn Gly Lys Glu Thr Leu
1 5 10

<210> SEQ ID NO 960
<211> LENGTH: 10
<212> TYPE: PRT
<213> ORGANISM: Homo Sapien

<400> SEQUENCE: 960

Arg Tyr Leu Lys Asn Gly Lys Glu Thr Leu
1 5 10

<210> SEQ ID NO 961
<211> LENGTH: 9
<212> TYPE: PRT
<213> ORGANISM: Homo Sapien

<400> SEQUENCE: 961

Lys Tyr Gln Ala Val Thr Thr Thr Leu
1 5

<210> SEQ ID NO 962
<211> LENGTH: 9
<212> TYPE: PRT
<213> ORGANISM: Plasmodium Berghei

<400> SEQUENCE: 962

Ser Tyr Ile Pro Ser Ala Glu Lys Ile
1 5

<210> SEQ ID NO 963
<211> LENGTH: 9
<212> TYPE: PRT
<213> ORGANISM: Plasmodium Yoelii

<400> SEQUENCE: 963

Ser Tyr Val Pro Ser Ala Glu Gln Ile
1 5

<210> SEQ ID NO 964
<211> LENGTH: 9
<212> TYPE: PRT
<213> ORGANISM: Influenza

<400> SEQUENCE: 964

Ala Ser Asn Glu Asn Met Glu Thr Met
1 5

<210> SEQ ID NO 965
<211> LENGTH: 10
<212> TYPE: PRT

<213> ORGANISM: Adenovirus

<400> SEQUENCE: 965

Ser Gly Pro Ser Asn Thr Pro Pro Glu Ile
1               5                   10

<210> SEQ ID NO 966
<211> LENGTH: 11
<212> TYPE: PRT
<213> ORGANISM: Lymphocytic Choriomeningitis Virus

<400> SEQUENCE: 966

Ser Gly Val Glu Asn Pro Gly Gly Tyr Cys Leu
1               5                   10

<210> SEQ ID NO 967
<211> LENGTH: 9
<212> TYPE: PRT
<213> ORGANISM: Simian Virus
<220> FEATURE:
<221> NAME/KEY: VARIANT
<222> LOCATION: 7, 8, 9
<223> OTHER INFORMATION: Xaa = Any Amino Acid

<400> SEQUENCE: 967

Ser Ala Ile Asn Asn Tyr Xaa Xaa Xaa
1               5

<210> SEQ ID NO 968
<211> LENGTH: 9
<212> TYPE: PRT
<213> ORGANISM: Human Immunodeficiency Virus

<400> SEQUENCE: 968

Ile Leu Lys Glu Pro Val His Gly Val
1               5

<210> SEQ ID NO 969
<211> LENGTH: 9
<212> TYPE: PRT
<213> ORGANISM: Influenza

<400> SEQUENCE: 969

Gly Ile Leu Gly Phe Val Phe Thr Leu
1               5

<210> SEQ ID NO 970
<211> LENGTH: 10
<212> TYPE: PRT
<213> ORGANISM: Influenza

<400> SEQUENCE: 970

Ile Leu Gly Phe Val Phe Thr Leu Thr Val
1               5                   10

<210> SEQ ID NO 971
<211> LENGTH: 9
<212> TYPE: PRT
<213> ORGANISM: Human Immunodeficiency Virus

<400> SEQUENCE: 971

Phe Leu Gln Ser Arg Pro Glu Pro Thr
1               5

<210> SEQ ID NO 972
<211> LENGTH: 9

```
<212> TYPE: PRT
<213> ORGANISM: Human Immunodeficiency Virus
<220> FEATURE:
<221> NAME/KEY: VARIANT
<222> LOCATION: 8, 9
<223> OTHER INFORMATION: Xaa = Any Amino Acid

<400> SEQUENCE: 972

Ala Met Gln Met Leu Lys Glu Xaa Xaa
 1               5

<210> SEQ ID NO 973
<211> LENGTH: 9
<212> TYPE: PRT
<213> ORGANISM: Human Immunodeficiency Virus

<400> SEQUENCE: 973

Pro Ile Ala Pro Gly Gln Met Arg Glu
 1               5

<210> SEQ ID NO 974
<211> LENGTH: 9
<212> TYPE: PRT
<213> ORGANISM: Human Immunodeficiency Virus

<400> SEQUENCE: 974

Gln Met Lys Asp Cys Thr Glu Arg Gln
 1               5

<210> SEQ ID NO 975
<211> LENGTH: 7
<212> TYPE: PRT
<213> ORGANISM: Human Immunodeficiency Virus

<400> SEQUENCE: 975

Val Tyr Gly Val Ile Gln Lys
 1               5

<210> SEQ ID NO 976
<211> LENGTH: 12
<212> TYPE: PRT
<213> ORGANISM: Artificial Sequence
<220> FEATURE:
<223> OTHER INFORMATION: Synthetic HLA-A2 binding nonamer peptide

<400> SEQUENCE: 976

Ser Asp Leu Arg Gly Tyr Val Tyr Gln Gly Leu Lys
 1               5                  10

<210> SEQ ID NO 977
<211> LENGTH: 15
<212> TYPE: PRT
<213> ORGANISM: Artificial Sequence
<220> FEATURE:
<223> OTHER INFORMATION: Epitope mimic of natural tumor Ag

<400> SEQUENCE: 977

Arg Pro Gln Ala Ser Gly Val Tyr Met Gly Asn Leu Thr Thr Gln
 1               5                  10                  15

<210> SEQ ID NO 978
<211> LENGTH: 9
<212> TYPE: PRT
<213> ORGANISM: Artificial Sequence
<220> FEATURE:
<223> OTHER INFORMATION: Epitope mimic of natural tumor Ag

<400> SEQUENCE: 978
```

Lys Ala Val Tyr Asn Phe Ala Thr Cys
1               5

<210> SEQ ID NO 979
<211> LENGTH: 9
<212> TYPE: PRT
<213> ORGANISM: Homo Sapien

<400> SEQUENCE: 979

Glu Val Asp Pro Ala Ser Asn Thr Tyr
1               5

<210> SEQ ID NO 980
<211> LENGTH: 75
<212> TYPE: PRT
<213> ORGANISM: Artificial Sequence
<220> FEATURE:
<223> OTHER INFORMATION: Chmeric amino acid sequence assembled from
      human tumor antigen epitopes

<400> SEQUENCE: 980

Met Ser Leu Leu Met Trp Ile Thr Gln Cys Lys Ala Ser Glu Lys Ile
1               5                   10                  15

Phe Tyr Val Gly Leu Pro Ser Ile Pro Val His Pro Ile Gly Leu Pro
                20                  25                  30

Ser Ile Pro Val His Pro Ile Lys Ala Ser Glu Lys Ile Phe Tyr Val
            35                  40                  45

Ser Leu Leu Met Trp Ile Thr Gln Cys Lys Ala Ser Glu Lys Ile Phe
        50                  55                  60

Tyr Val Lys Ala Ser Glu Lys Ile Phe Tyr Val
65                  70                  75

<210> SEQ ID NO 981
<211> LENGTH: 75
<212> TYPE: PRT
<213> ORGANISM: Artificial Sequence
<220> FEATURE:
<223> OTHER INFORMATION: Chmeric amino acid sequence assembled from
      human tumor antigen epitopes

<400> SEQUENCE: 981

Met Gly Leu Pro Ser Ile Pro Val His Pro Ile Lys Ala Ser Glu Lys
1               5                   10                  15

Ile Phe Tyr Val Ser Leu Leu Met Trp Ile Thr Gln Cys Lys Ala Ser
                20                  25                  30

Glu Lys Ile Phe Tyr Val Lys Ala Ser Glu Lys Ile Phe Tyr Val Gly
            35                  40                  45

Leu Pro Ser Ile Pro Val His Pro Ile Ser Leu Leu Met Trp Ile Thr
        50                  55                  60

Gln Cys Lys Ala Ser Glu Lys Ile Phe Tyr Val
65                  70                  75

<210> SEQ ID NO 982
<211> LENGTH: 77
<212> TYPE: PRT
<213> ORGANISM: Artificial Sequence
<220> FEATURE:
<223> OTHER INFORMATION: Chmeric amino acid sequence assembled from
      human tumor antigen epitopes

<400> SEQUENCE: 982

Met Ala Val Leu Tyr Cys Leu Lys Ala Ser Glu Lys Ile Phe Tyr Val
1               5                   10                  15

```
Gly Leu Pro Ser Ile Pro Val His Pro Ile Ser Leu Leu Met Trp Ile
            20                  25                  30

Thr Gln Cys Lys Ala Ser Glu Lys Ile Phe Tyr Val Ser Leu Leu Met
        35                  40                  45

Trp Ile Thr Gln Cys Ala Val Leu Tyr Cys Leu Lys Ala Ser Glu Lys
    50                  55                  60

Ile Phe Tyr Val Lys Ala Ser Glu Lys Ile Phe Tyr Val
65                  70                  75

<210> SEQ ID NO 983
<211> LENGTH: 73
<212> TYPE: PRT
<213> ORGANISM: Artificial Sequence
<220> FEATURE:
<223> OTHER INFORMATION: Chmeric amino acid sequence assembled from
      human tumor antigen epitopes

<400> SEQUENCE: 983

Met Ser Leu Leu Met Trp Ile Thr Gln Cys Lys Ala Ser Glu Lys Ile
1               5                   10                  15

Phe Tyr Val Thr Gln Cys Phe Leu Pro Val Phe Leu Ser Leu Leu Met
            20                  25                  30

Trp Ile Thr Gln Cys Lys Ala Ser Glu Lys Ile Phe Tyr Val Lys Ala
        35                  40                  45

Ser Glu Lys Ile Phe Tyr Val Thr Gln Cys Phe Leu Pro Val Phe Leu
    50                  55                  60

Lys Ala Ser Glu Lys Ile Phe Tyr Val
65                  70

<210> SEQ ID NO 984
<211> LENGTH: 73
<212> TYPE: PRT
<213> ORGANISM: Artificial Sequence
<220> FEATURE:
<223> OTHER INFORMATION: Chmeric amino acid sequence assembled from
      human tumor antigen epitopes

<400> SEQUENCE: 984

Met Thr Gln Cys Phe Leu Pro Val Phe Leu Lys Ala Ser Glu Lys Ile
1               5                   10                  15

Phe Tyr Val Ser Leu Leu Met Trp Ile Thr Gln Cys Thr Gln Cys Phe
            20                  25                  30

Leu Pro Val Phe Leu Lys Ala Ser Glu Lys Ile Phe Tyr Val Lys Ala
        35                  40                  45

Ser Glu Lys Ile Phe Tyr Val Ser Leu Leu Met Trp Ile Thr Gln Cys
    50                  55                  60

Lys Ala Ser Glu Lys Ile Phe Tyr Val
65                  70

<210> SEQ ID NO 985
<211> LENGTH: 70
<212> TYPE: PRT
<213> ORGANISM: Artificial Sequence
<220> FEATURE:
<223> OTHER INFORMATION: Chmeric amino acid sequence assembled from
      human tumor antigen epitopes

<400> SEQUENCE: 985

Met Ala Val Leu Tyr Cys Leu Lys Ala Ser Glu Lys Ile Phe Tyr Val
1               5                   10                  15

Lys Ala Ser Glu Lys Ile Phe Tyr Val Ser Leu Leu Met Trp Ile Thr
```

```
                    20                  25                  30
Gln Cys Thr Gln Cys Phe Leu Pro Val Phe Leu Ser Leu Leu Met Trp
        35                  40                  45

Ile Thr Gln Cys Lys Ala Ser Glu Lys Ile Phe Tyr Val Lys Ala Ser
    50                  55                  60

Glu Lys Ile Phe Tyr Val
65                  70

<210> SEQ ID NO 986
<211> LENGTH: 38
<212> TYPE: PRT
<213> ORGANISM: Homo sapien

<400> SEQUENCE: 986

Tyr Phe Ser Lys Glu Glu Trp Glu Lys Met Lys Ala Ser Glu Lys Ile
1               5                   10                  15

Phe Tyr Val Tyr Met Lys Arg Lys Tyr Glu Ala Met Thr Lys Leu Gly
            20                  25                  30

Phe Lys Ala Thr Leu Pro
        35
```

EXPRESSION VECTORS ENCODING EPITOPES OF TARGET-ASSOCIATED ANTIGENS AND METHODS FOR THEIR DESIGN

CROSS REFERENCE TO RELATED APPLICATIONS

This application is a continuation of U.S. application Ser. No. 10/292,413, filed on Nov. 7, 2002, entitled "EXPRESSION VECTORS ENCODING EPITOPES OF TARGET-ASSOCIATED ANTIGENS AND METHODS FOR THEIR DESIGN, which claims priority under 35 U.S.C. §119(e) to U.S. Provisional Application No. 60/336,968, filed on Nov. 7, 2001, having the same title; both of which are hereby incorporated by reference in their entirety.

BACKGROUND OF THE INVENTION

1. Field of the Invention

The invention disclosed herein is directed to methods for the design of epitope-encoding vectors, and epitope cluster regions, for use in compositions, including for example, pharmaceutical compositions capable of inducing an immune response in a subject to whom the compositions are administered. The invention is further directed to the vectors themselves. The epitope(s) expressed using such vectors can stimulate a cellular immune response against a target cell displaying the epitope(s).

2. Description of the Related Art

The immune system can be categorized into two discrete effector arms. The first is innate immunity, which involves numerous cellular components and soluble factors that respond to all infectious challenges. The other is the adaptive immune response, which is customized to respond specifically to precise epitopes from infectious agents. The adaptive immune response is further broken down into two effector arms known as the humoral and cellular immune systems. The humoral arm is centered on the production of antibodies by B-lymphocytes while the cellular arm involves the killer cell activity of cytotoxic T Lymphocytes.

Cytotoxic T Lymphocytes (CTL) do not recognize epitopes on the infectious agents themselves. Rather, CTL detect fragments of antigens derived from infectious agents that are displayed on the surface of infected cells. As a result antigens are visible to CTL only after they have been processed by the infected cell and thus displayed on the surface of the cell.

The antigen processing and display system on the surface of cells has been well established. CTL recognize short peptide antigens, which are displayed on the surface in non-covalent association with class I major histocompatibility complex molecules (MHC). These class I peptides are in turn derived from the degradation of cytosolic proteins.

SUMMARY OF THE INVENTION

The invention disclosed herein relates to the identification of epitope cluster regions that are used to generate pharmaceutical compositions capable of inducing an immune response from a subject to whom the compositions have been administered. One embodiment of the disclosed invention relates to an epitope cluster, the cluster being derived from an antigen associated with a target, the cluster including or encoding at least two sequences having a known or predicted affinity for an MHC receptor peptide binding cleft, wherein the cluster is an incomplete fragment of the antigen.

In one aspect of the invention, the target is a neoplastic cell.

In another aspect of the invention, the MHC receptor may be a class I HLA receptor.

In yet another aspect of the invention, the cluster includes or encodes a polypeptide having a length, wherein the length is at least 10 amino acids. Advantageously, the length of the polypeptide may be less than about 75 amino acids.

In still another aspect of the invention, there is provided an antigen having a length, wherein the cluster consists of or encodes a polypeptide having a length, wherein the length of the polypeptide is less than about 80% of the length of the antigen. Preferably, the length of the polypeptide is less than about 50% of the length of the antigen. Most preferably, the length of the polypeptide is less than about 20% of the length of the antigen.

Embodiments of the invention particularly relate to epitope clusters identified in the tumor-associated antigen NY-ESO (SEQ ID NO: 11). One embodiment of the invention relates to an isolated nucleic acid containing a reading frame with a first sequence encoding one or more segments of NY-ESO, wherein the whole antigen is not encoded, wherein each segment contains an epitope cluster, and wherein each cluster contains at least two amino acid sequences with a known or predicted affinity for a same MHC receptor peptide binding cleft. In various aspects of the invention the epitope cluster can be amino acids 79-104, 86-171, 108-140, 108-174, 144-171, and 148-167 of NY-ESO. In other aspects the segments can consist of an epitope cluster; the first sequence can be a fragment of NY-ESO. The fragment can consist of a polypeptide having a length, wherein the length of the polypeptide is less than about 90, 80, 60, 50, 25, or 10% of the length of NY-ESO; and/or the fragment can consist essentially of an amino acid sequence beginning at amino acid 79, 86, 108, 144 and 148 and ending at amino acid 104, 140, 167, 171 and 174 of NY-ESO. Also, the NY-ESO fragment can consist essentially of, for example, amino acids 79-140, 79-167, 79-171, or 79-174; amino acids 86-140, 86-167, 86-171 or 86-174; also, amino acids 86-140, 86-167, 86-171 or 86-174; amino acids 108-167 or 108-171; amino acids 144-167 or 144-174; amino acids 148-171 or 148-174; amino acids 79-174; and/or amino acids 77-180. Embodiments relate to a reading frame operably linked to a promoter. Further embodiments of the invention include a second sequence encoding essentially a housekeeping epitope. In one aspect of this embodiment the first and second sequences constitute a single reading frame. In aspects of the invention the reading frame is operably linked to a promoter. Other embodiments of the invention include the polypeptides encoded by the nucleic acid embodiments of the invention and immunogenic compositions containing the nucleic acids or polypeptides of the invention.

Embodiments of the invention provide expression cassettes, for example, for use in vaccine vectors, which encode one or more embedded housekeeping epitopes, and methods for designing and testing such expression cassettes. Housekeeping epitopes can be liberated from the translation product of such cassettes through proteolytic processing by the immunoproteasome of professional antigen presenting cells (pAPC). In one embodiment of the invention, sequences flanking the housekeeping epitope(s) can be altered to promote cleavage by the immunoproteasome at the desired location(s). Housekeeping epitopes, their uses, and identification are described in U.S. patent application Ser. Nos. 09/560,465 and 09/561,074 entitled EPITOPE SYNCHRONIZATION IN ANTIGEN PRESENTING CELLS, and METHOD OF EPITOPE DISCOVERY, respectively; both of which were filed on Apr. 28, 2000, and which are both incorporated herein by reference in their entireties.

Examples of housekeeping epitopes are disclosed in provisional U.S. patent applications entitled EPITOPE SEQUENCES, Nos. 60/282,211, filed on Apr. 6, 2001; 60/337,017, filed on Nov. 7, 2001; 60/363,210 filed Mar. 7, 2002; and 60/409,123, filed on Sep. 5, 2002; and U.S. application Ser. No. 10/117,937, filed on Apr. 4, 2002, which is also entitled EPITOPE SEQUENCES; which are all incorporated herein by reference in their entirety.

In other embodiments of the invention, the housekeeping epitope(s) can be flanked by arbitrary sequences or by sequences incorporating residues known to be favored in immunoproteasome cleavage sites. As used herein the term "arbitrary sequences" refers to sequences chosen without reference to the native sequence context of the epitope, their ability to promote processing or immunological function. In further embodiments of the invention multiple epitopes can be arrayed head-to-tail. These arrays can be made up entirely of housekeeping epitopes. Likewise, the arrays can include alternating housekeeping and immune epitopes. Alternatively, the arrays can include housekeeping epitopes flanked by immune epitopes, whether complete or distally truncated. Further, the arrays can be of any other similar arrangement. There is no restriction on placing a housekeeping epitope at the terminal positions of the array. The vectors can additionally contain authentic protein coding sequences or segments thereof containing epitope clusters as a source of immune epitopes. The term "authentic" refers to natural protein sequences.

Epitope clusters and their uses are described in U.S. patent application Ser. Nos. 09/561,571 entitled EPITOPE CLUSTERS, filed on Apr. 28, 2000; Ser. No. 10/005,905, entitled EPITOPE SYNCHRONIZATION IN ANTIGEN PRESENTING CELLS, filed on Nov. 7, 2001; and Ser. No. 10/026,066, filed on Dec. 7, 2001, also entitled EPITOPE SYNCHRONIZATION IN ANTIGEN PRESENTING CELLS; all of which are incorporated herein by reference in their entirety.

Embodiments of the invention can encompass screening the constructs to determine whether the housekeeping epitope is liberated. In constructs containing multiple housekeeping epitopes, embodiments can include screening to determine which epitopes are liberated. In a preferred embodiment, a vector containing an embedded epitope can be used to immunize HLA transgenic mice and the resultant CTL can be tested for their ability to recognize target cells presenting the mature epitope. In another embodiment, target cells expressing immunoproteasome can be transformed with the vector. The target cell may express immunoproteasome either constitutively, because of treatment with interferon (IFN), or through genetic manipulation, for example. CTL that recognize the mature epitope can be tested for their ability to recognize these target cells. In yet another embodiment, the embedded epitope can be prepared as a synthetic peptide. The synthetic peptide then can be subjected to digestion by an immunoproteasome preparation in vitro and the resultant fragments can be analyzed to determine the sites of cleavage. Such polypeptides, recombinant or synthetic, from which embedded epitopes can be successfully liberated, can also be incorporated into immunogenic compositions.

The invention disclosed herein relates to the identification of a polypeptide suitable for epitope liberation. One embodiment of the invention, relates to a method of identifying a polypeptide suitable for epitope liberation including, for example, the steps of identifying an epitope of interest; providing a substrate polypeptide sequence including the epitope, wherein the substrate polypeptide permits processing by a proteasome; contacting the substrate polypeptide with a composition including the proteasome, under conditions that support processing of the substrate polypeptide by the proteasome; and assaying for liberation of the epitope.

The epitope can be embedded in the substrate polypeptide, and in some aspects the substrate polypeptide can include more than one epitope, for example. Also, the epitope can be a housekeeping epitope.

In one aspect, the substrate polypeptide can be a synthetic peptide. Optionally, the substrate polypeptide can be included in a formulation promoting protein transfer. Alternatively, the substrate polypeptide can be a fusion protein. The fusion protein can further include a protein domain possessing protein transfer activity. Further, the contacting step can include immunization with the substrate polypeptide.

In another aspect, the substrate polypeptide can be encoded by a polynucleotide. The contacting step can include immunization with a vector including the polynucleotide, for example. The immunization can be carried out in an HLA-transgenic mouse or any other suitable animal, for example. Alternatively, the contacting step can include transforming a cell with a vector including the polynucleotide. In some embodiments the transformed cell can be a target cell that is targeted by CTL for purposes of assaying for proper liberation of epitope.

The proteasome processing can take place intracellularly, either in vitro or in vivo. Further, the proteasome processing can take place in a cell-free system.

The assaying step can include a technique selected from the group including, but not limited to, mass spectrometry, N-terminal pool sequencing, HPLC, and the like. Also, the assaying step can include a T cell target recognition assay. The T cell target recognition assay can be selected from the group including, but not limited to, a cytolytic activity assay, a chromium release assay, a cytokine assay, an ELISPOT assay, tetramer analysis, and the like.

In still another aspect, the amino acid sequence of the substrate polypeptide including the epitope can be arbitrary. Also, the substrate polypeptide in which the epitope is embedded can be derived from an authentic sequence of a target-associated antigen. Further, the substrate polypeptide in which the epitope is embedded can be conformed to a preferred immune proteasome cleavage site flanking sequence.

In another aspect, the substrate polypeptide can include an array of additional epitopes. Members of the array can be arranged head-to-tail, for example. The array can include more than one housekeeping epitope. The more than one housekeeping epitope can include copies of the same epitope. The array can include a housekeeping and an immune epitope, or alternating housekeeping and immune epitopes, for example. Also, the array can include a housekeeping epitope positioned between two immune epitopes in an epitope battery. The array can include multiple epitope batteries, so that there are two immune epitopes between each housekeeping epitope in the interior of the array. Optionally, at least one of the epitopes can be truncated distally to its junction with an adjacent epitope. The truncated epitopes can be immune epitopes, for example. The truncated epitopes can have lengths selected from the group including, but not limited to, 9, 8, 7, 6, 5, 4 amino acids, and the like.

In still another aspect, the substrate polypeptide can include an array of epitopes and epitope clusters. Members of the array can be arranged head-to-tail, for example.

In yet another aspect, the proteasome can be an immune proteasome.

Another embodiment of the disclosed invention relates to vectors including a housekeeping epitope expression cassette. The housekeeping epitope(s) can be derived from a target-associated antigen, and the housekeeping epitope can be liberatable, that is capable of liberation, from a translation product of the cassette by immunoproteasome processing.

In one aspect of the invention the expression cassette can encode an array of two or more epitopes or at least one epitope and at least one epitope cluster. The members of the array can be arranged head-to-tail, for example. Also, the members of the array can be arranged head-to-tail separated by spacing sequences, for example. Further, the array can include a plurality of housekeeping epitopes. The plurality of housekeeping epitopes can include more than one copy of the same epitope or single copies of distinct epitopes, for example. The array can include at least one housekeeping epitope and at least one immune epitope. Also, the array can include alternating housekeeping and immune epitopes. Further, the array includes a housekeeping epitope sandwiched between two immune epitopes so that there are two immune epitopes between each housekeeping epitope in the interior of the array. The immune epitopes can be truncated distally to their junction with the adjacent housekeeping epitope.

In another aspect, the expression cassette further encodes an authentic protein sequence, or segment thereof, including at least one immune epitope. Optionally, the segment can include at least one epitope cluster. The housekeeping epitope expression cassette and the authentic sequence including at least one immune epitope can be encoded in a single reading frame or transcribed as a single mRNA species, for example. Also, the housekeeping epitope expression cassette and the authentic sequence including at least one immune epitope may not be transcribed as a single mRNA species.

In yet another aspect, the vector can include a DNA molecule or an RNA molecule. The vector can encode, for example, SEQ ID NO. 4, SEQ ID NO. 17, SEQ ID NO. 20, SEQ ID NO. 26, SEQ ID NO. 27, SEQ ID NO. 29, SEQ ID NO. 33, and the like. Also, the vector can include SEQ ID NO. 9, SEQ ID NO. 19, SEQ ID NO. 21, SEQ ID NO. 30, SEQ ID NO. 34, and the like. Also, the vector can encode SEQ ID NO. 5 or SEQ ID NO. 18, for example.

In still another aspect, the target-associated antigen can be an antigen derived from or associated with a tumor or an intracellular parasite, and the intracellular parasite can be, for example, a virus, a bacterium, a protozoan, or the like.

Another embodiment of the invention relates to vectors including a housekeeping epitope identified according to any of the methods disclosed herein, claimed or otherwise. For example, embodiments can relate to vector encoding a substrate polypeptide that includes a housekeeping epitope by any of the methods described herein.

In one aspect, the housekeeping epitope can be liberated from the cassette translation product by immune proteasome processing.

Another embodiment of the disclosed invention relates to methods of activating a T cell. The methods can include, for example, the steps of contacting a vector including a housekeeping epitope expression cassette with an APC. The housekeeping epitope can be derived from a target-associated antigen, for example, and the housekeeping epitope can be liberatable from a translation product of the cassette by immunoproteasome processing. The methods can further include contacting the APC with a T cell. The contacting of the vector with the APC can occur in vitro or in vivo.

Another embodiment of the disclosed invention relates to a substrate polypeptide including a housekeeping epitope wherein the housekeeping epitope can be liberated by immunoproteasome processing in a pAPC.

Another embodiment of the disclosed invention relates to a method of activating a T cell comprising contacting a substrate polypeptide including a housekeeping epitope with an APC wherein the housekeeping epitope can be liberated by immunoproteasome processing and contacting the APC with a T cell.

BRIEF DESCRIPTION OF THE DRAWINGS

FIG. 1 depicts the sequence of Melan-A (SEQ ID NO: 2), showing clustering of class I HLA epitopes.

FIG. 2 depicts the sequence of SSX-2 (SEQ ID NO: 40), showing clustering of class I HLA epitopes.

FIG. 3 depicts the sequence of NY-ESO (SEQ ID NO: 11), showing clustering of class I HLA epitopes.

FIG. 4. An illustrative drawing depicting pMA2M.

DETAILED DESCRIPTION OF THE PREFERRED EMBODIMENT

Definitions

Figure 5:
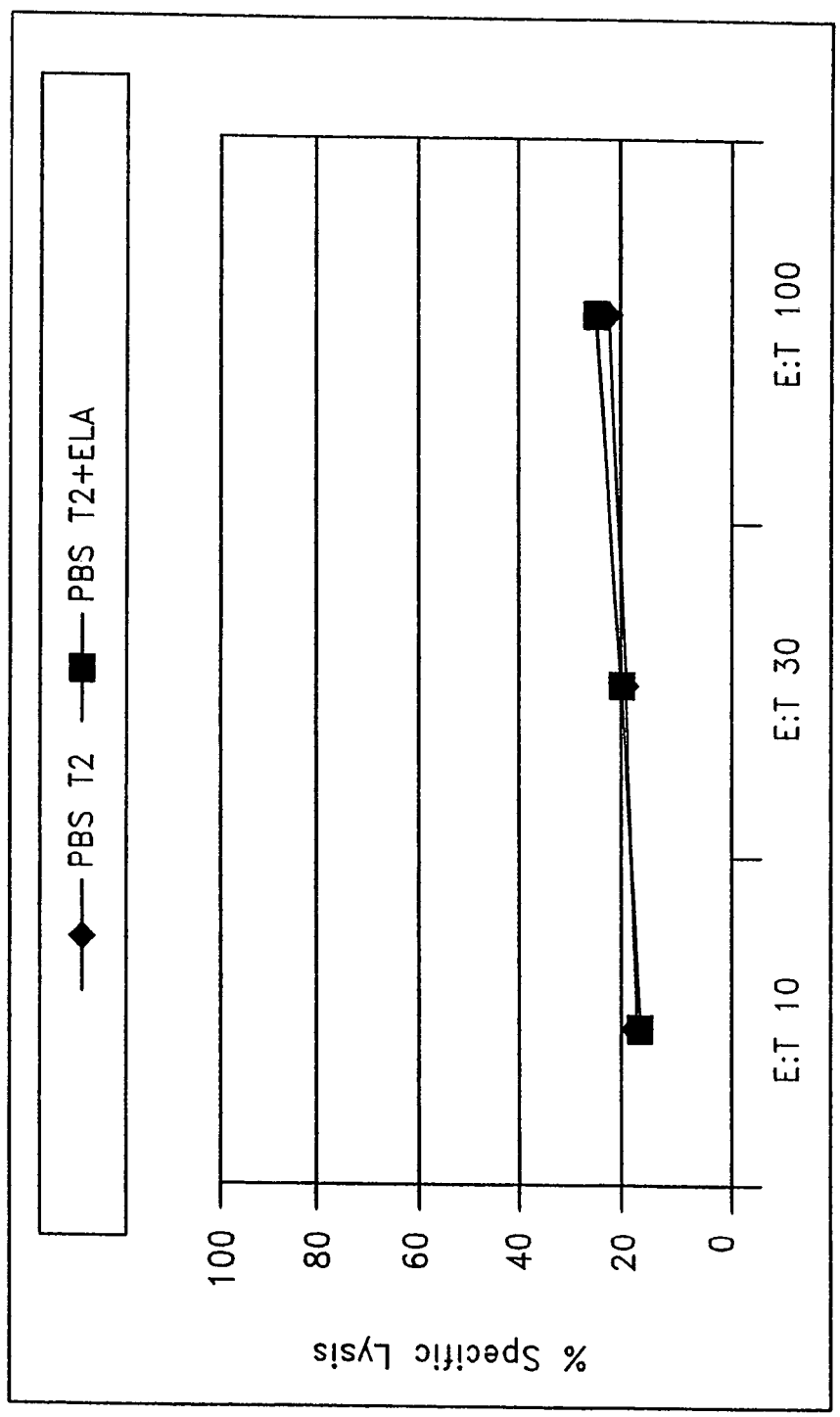
FIG. 5. Assay results showing the % of specific lysis of ELAGIGILTV (SEQ ID NO: 1) pulsed and unpulsed T2 target cells by mock immunized CTL.

Unless otherwise clear from the context of the use of a term herein, the following listed terms shall generally have the indicated meanings for purposes of this description.

PROFESSIONAL ANTIGEN-PRESENTING CELL (pAPC)—a cell that possesses T cell costimulatory molecules and is able to induce a T cell response. Well characterized pAPCs include dendritic cells, B cells, and macrophages.

PERIPHERAL CELL—a cell that is not a pAPC.

HOUSEKEEPING PROTEASOME—a proteasome normally active in peripheral cells, and generally not present or not strongly active in pAPCs.

IMMUNOPROTEASOME—a proteasome normally active in pAPCs; the immunoproteasome is also active in some peripheral cells in infected tissues or following exposure to interferon.

EPITOPE—a molecule or substance capable of stimulating an immune response. In preferred embodiments, epitopes according to this definition include but are not necessarily limited to a polypeptide and a nucleic acid encoding a polypeptide, wherein the polypeptide is capable of stimulating an immune response. In other preferred embodiments, epitopes according to this definition include but are not necessarily limited to peptides presented on the surface of cells, the peptides being non-covalently bound to the binding cleft of class I MHC, such that they can interact with T cell receptors (TCR). Epitopes presented by class I MHC may be in immature or mature form. "Mature" refers to an MHC epitope in distinction to any precursor ("immature") that may include or consist essentially of a housekeeping epitope, but also includes other sequences in a primary translation product that are removed by processing, including without limitation, alone or in any combination, proteasomal digestion, N-terminal trimming, or the action of exogenous enzymatic activities. Thus, a mature epitope may be provided embedded in a somewhat longer polypeptide, the immunological potential of which is due, at least in part, to the embedded epitope; or in its ultimate form that can bind in the MHC binding cleft to be recognized by TCR, respectively.

MHC EPITOPE—a polypeptide having a known or predicted binding affinity for a mammalian class I or class II major histocompatibility complex (MHC) molecule.

HOUSEKEEPING EPITOPE—In a preferred embodiment, a housekeeping epitope is defined as a polypeptide fragment that is an MHC epitope, and that is displayed on a cell in which housekeeping proteasomes are predominantly active. In another preferred embodiment, a housekeeping epitope is defined as a polypeptide containing a housekeeping epitope according to the foregoing definition, that is flanked by one to several additional amino acids. In another preferred embodiment, a housekeeping epitope is defined as a nucleic acid that encodes a housekeeping epitope according to the foregoing definitions. Exemplary housekeeping epitopes are provide in U.S. application Ser. No. 10/117,937, filed on Apr. 4, 2002; and U.S. Provisional Application No. 60/282,211, filed on Apr. 6, 2001; 60/337,017, filed on Nov. 7, 2001; 60/363,210 filed Mar. 7, 2002; and 60/409,123, filed on Sep. 5, 2002; all of which are entitled EPITOPE SEQUENCES, and all of which above were incorporated herein by reference in their entireties.

IMMUNE EPITOPE—In a preferred embodiment, an immune epitope is defined as a polypeptide fragment that is an MHC epitope, and that is displayed on a cell in which immunoproteasomes are predominantly active. In another preferred embodiment, an immune epitope is defined as a polypeptide containing an immune epitope according to the foregoing definition, that is flanked by one to several additional amino acids. In another preferred embodiment, an immune epitope is defined as a polypeptide including an epitope cluster sequence, having at least two polypeptide sequences having a known or predicted affinity for a class I MHC. In yet another preferred embodiment, an immune epitope is defined as a nucleic acid that encodes an immune epitope according to any of the foregoing definitions.

TARGET CELL—a cell to be targeted by the vaccines and methods of the invention. Examples of target cells according to this definition include but are not necessarily limited to: a neoplastic cell and a cell harboring an intracellular parasite, such as, for example, a virus, a bacterium, or a protozoan. Target cells can also include cells that are targeted by CTL as a part of assays to determine or confirm proper epitope liberation and processing by a cell expressing immunoproteasome, to determine T cell specificity or immunogenicity for a desired epitope. Such cells may be transformed to express the substrate or liberation sequence, or the cells can simply be pulsed with peptide/epitope.

TARGET-ASSOCIATED ANTIGEN (TAA)—a protein or polypeptide present in a target cell.

TUMOR-ASSOCIATED ANTIGENS (TuAA)—a TAA, wherein the target cell is a neoplastic cell.

HLA EPITOPE—a polypeptide having a known or predicted binding affinity for a human class I or class II HLA complex molecule.

ANTIBODY—a natural immunoglobulin (Ig), poly- or monoclonal, or any molecule composed in whole or in part of an Ig binding domain, whether derived biochemically or by use of recombinant DNA. Examples include inter alia, F(ab), single chain Fv, and Ig variable region-phage coat protein fusions.

ENCODE—an open-ended term such that a nucleic acid encoding a particular amino acid sequence can consist of codons specifying that (poly)peptide, but can also comprise additional sequences either translatable, or for the control of transcription, translation, or replication, or to facilitate manipulation of some host nucleic acid construct.

SUBSTANTIAL SIMILARITY—this term is used to refer to sequences that differ from a reference sequence in an inconsequential way as judged by examination of the sequence. Nucleic acid sequences encoding the same amino acid sequence are substantially similar despite differences in degenerate positions or modest differences in length or composition of any non-coding regions. Amino acid sequences differing only by conservative substitution or minor length variations are substantially similar. Additionally, amino acid sequences comprising housekeeping epitopes that differ in the number of N-terminal flanking residues, or immune epitopes and epitope clusters that differ in the number of flanking residues at either terminus, are substantially similar. Nucleic acids that encode substantially similar amino acid sequences are themselves also substantially similar.

FUNCTIONAL SIMILARITY—this term is used to refer to sequences that differ from a reference sequence in an inconsequential way as judged by examination of a biological or biochemical property, although the sequences may not be substantially similar. For example, two nucleic acids can be useful as hybridization probes for the same sequence but encode differing amino acid sequences. Two peptides that induce cross-reactive CTL responses are functionally similar even if they differ by non-conservative amino acid substitutions (and thus do not meet the substantial similarity definition). Pairs of antibodies, or TCRs, that recognize the same epitope can be functionally similar to each other despite whatever structural differences exist. In testing for functional similarity of immunogenicity one would generally immunize with the "altered" antigen and test the ability of the elicited response (Ab, CTL, cytokine production, etc.) to recognize the target antigen. Accordingly, two sequences may be designed to differ in certain respects while retaining the same function. Such designed sequence variants are among the embodiments of the present invention.

EXPRESSION CASSETTE—a polynucleotide sequence encoding a polypeptide, operably linked to a promoter and other transcription and translation control elements, including but not limited to enhancers, termination codons, internal ribosome entry sites, and polyadenylation sites. The cassette can also include sequences that facilitate moving it from one host molecule to another.

EMBEDDED EPITOPE—an epitope contained within a longer polypeptide, also can include an epitope in which either the N-terminus or the C-terminus is embedded such that the epitope is not in an interior position.

MATURE EPITOPE—a peptide with no additional sequence beyond that present when the epitope is bound in the MHC peptide-binding cleft.

EPITOPE CLUSTER—a polypeptide, or a nucleic acid sequence encoding it, that is a segment of a native protein sequence comprising two or more known or predicted epitopes with binding affinity for a shared MHC restriction element, wherein the density of epitopes within the cluster is greater than the density of all known or predicted epitopes with binding affinity for the shared MHC restriction element within the complete protein sequence, and as disclosed in U.S. patent application Ser. No. 09/561,571 entitled EPITOPE CLUSTERS.

SUBSTRATE OR LIBERATION SEQUENCE—a designed or engineered sequence comprising or encoding a housekeeping epitope (according to the first of the definitions offered above) embedded in a larger sequence that provides a context allowing the housekeeping epitope to be liberated by immunoproteasomal processing, directly or in combination with N-terminal trimming or other processes.

Epitope Clusters

Embodiments of the invention disclosed herein provide epitope cluster regions (ECRs) for use in vaccines and in vaccine design and epitope discovery. Specifically, embodiments of the invention relate to identifying epitope clusters for use in generating immunologically active compositions directed against target cell populations, and for use in the discovery of discrete housekeeping epitopes and immune epitopes. In many cases, numerous putative class I MHC epitopes may exist in a single target-associated antigen (TAA). Such putative epitopes are often found in clusters (ECRs), MHC epitopes distributed at a relatively high density within certain regions in the amino acid sequence of the parent TAA. Since these ECRs include multiple putative epitopes with potential useful biological activity in inducing an immune response, they represent an excellent material for in vitro or in vivo analysis to identify particularly useful epitopes for vaccine design. And, since the epitope clusters can themselves be processed inside a cell to produce active MHC epitopes, the clusters can be used directly in vaccines, with one or more putative epitopes in the cluster actually being processed into an active MHC epitope.

The use of ECRs in vaccines offers important technological advances in the manufacture of recombinant vaccines, and further offers crucial advantages in safety over existing nucleic acid vaccines that encode whole protein sequences. Recombinant vaccines generally rely on expensive and technically challenging production of whole proteins in microbial fermentors. ECRs offer the option of using chemically synthesized polypeptides, greatly simplifying development and manufacture, and obviating a variety of safety concerns. Similarly, the ability to use nucleic acid sequences encoding ECRs, which are typically relatively short regions of an entire sequence, allows the use of synthetic oligonucleotide chemistry processes in the development and manipulation of nucleic acid based vaccines, rather than the more expensive, time consuming, and potentially difficult molecular biology procedures involved with using whole gene sequences.

Since an ECR is encoded by a nucleic acid sequence that is relatively short compared to that which encodes the whole protein from which the ECR is found, this can greatly improve the safety of nucleic acid vaccines. An important issue in the field of nucleic acid vaccines is the fact that the extent of sequence homology of the vaccine with sequences in the animal to which it is administered determines the probability of integration of the vaccine sequence into the genome of the animal. A fundamental safety concern of nucleic acid vaccines is their potential to integrate into genomic sequences, which can cause deregulation of gene expression and tumor transformation. The Food and Drug Administration has advised that nucleic acid and recombinant vaccines should contain as little sequence homology with human sequences as possible. In the case of vaccines delivering tumor-associated antigens, it is inevitable that the vaccines contain nucleic acid sequences that are homologous to those which encode proteins that are expressed in the tumor cells of patients. It is, however, highly desirable to limit the extent of those sequences to that which is minimally essential to facilitate the expression of epitopes for inducing therapeutic immune responses. The use of ECRs thus offers the dual benefit of providing a minimal region of homology, while incorporating multiple epitopes that have potential therapeutic value.

Note that the following discussion sets forth the inventors' understanding of the operation of the invention. However, it is not intended that this discussion limit the patent to any particular theory of operation not set forth in the claims.

ECRs are Processed into MHC-Binding Epitopes in pAPCs

The immune system constantly surveys the body for the presence of foreign antigens, in part through the activity of pAPCs. The pAPCs endocytose matter found in the extracellular milieu, process that matter from a polypeptide form into shorter oligopeptides of about 3 to 23 amino acids in length, and display some of the resulting peptides to T cells via the MHC complex of the pAPCs. For example, a tumor cell upon lysis releases its cellular contents, including various proteins, into the extracellular milieu. Those released proteins can be endocytosed by pAPCs and processed into discrete peptides that are then displayed on the surface of the pAPCs via the MHC. By this mechanism, it is not the entire target protein that is presented on the surface of the pAPCs, but rather only one or more discrete fragments of that protein that are presented as MHC-binding epitopes. If a presented epitope is recognized by a T cell, that T cell is activated and an immune response results.

Similarly, the scavenger receptors on pAPC can take-up naked nucleic acid sequences or recombinant organisms containing target nucleic acid sequences. Uptake of the nucleic acid sequences into the pAPC subsequently results in the expression of the encoded products. As above, when an ECR can be processed into one or more useful epitopes, these products can be presented as MHC epitopes for recognition by T cells.

MHC-binding epitopes are often distributed unevenly throughout a protein sequence in clusters. Embodiments of the invention are directed to identifying epitope cluster regions (ECRs) in a particular region of a target protein. Candidate ECRs are likely to be natural substrates for various proteolytic enzymes and are likely to be processed into one or more epitopes for MHC display on the surface of an pAPC. In contrast to more traditional vaccines that deliver whole proteins or biological agents, ECRs can be administered as vaccines, resulting in a high probability that at least one epitope will be presented on MHC without requiring the use of a full length sequence.

The Use of ECRs in Identifying Discrete MHC-Binding Epitopes

Identifying putative MHC epitopes for use in vaccines often includes the use of available predictive algorithms that analyze the sequences of proteins or genes to predict binding affinity of peptide fragments for MHC. These algorithms rank putative epitopes according to predicted affinity or other characteristics associated with MHC binding. Exemplary algorithms for this kind of analysis include the Rammensee and NIH (Parker) algorithms. However, identifying epitopes that are naturally present on the surface of cells from among putative epitopes predicted using these algorithms has proven to be a difficult and laborious process. The use of ECRs in an epitope identification process can enormously simplify the task of identifying discrete MHC binding epitopes.

In a preferred embodiment, ECR polypeptides are synthesized on an automated peptide synthesizer and these ECRs are then subjected to in vitro digests using proteolytic enzymes involved in processing proteins for presentation of the epitopes. Mass spectrometry and/or analytical HPLC are then used to identify the digest products and in vitro MHC binding studies are used to assess the ability of these products to actually bind to MHC. Once epitopes contained in ECRs have been shown to bind MHC, they can be incorporated into vaccines or used as diagnostics, either as discrete epitopes or in the context of ECRs.

The use of an ECR (which because of its relatively short sequence can be produced through chemical synthesis) in this preferred embodiment is a significant improvement over what otherwise would require the use of whole protein. This is because whole proteins have to be produced using recombinant expression vector systems and/or complex purification procedures. The simplicity of using chemically synthesized ECRs enables the analysis and identification of large numbers of epitopes, while greatly reducing the time and expense of the process as compared to other currently used methods. The use of a defined ECR also greatly simplifies mass spectrum analysis of the digest, since the products of an ECR digest are a small fraction of the digest products of a whole protein.

In another embodiment, nucleic acid sequences encoding ECRs are used to express the polypeptides in cells or cell lines to assess which epitopes are presented on the surface. A variety of means can be used to detect the epitope on the surface. Preferred embodiments involve the lysis of the cells and affinity purification of the MHC, and subsequent elution and analysis of peptides from the MHC; or elution of epitopes from intact cells; (Falk, K. et al. Nature 351:290, 1991, and U.S. Pat. No. 5,989,565, respectively, both of which references are incorporated herein by reference in their entirety). A sensitive method for analyzing peptides eluted in this way from the MHC employs capillary or nanocapillary HPLC ESI mass spectrometry and on-line sequencing.

Target-Associated Antigens that Contain ECRs

TAAs from which ECRs may be defined include those from TuAAs, including oncofetal, cancer-testis, deregulated genes, fusion genes from errant translocations, differentiation antigens, embryonic antigens, cell cycle proteins, mutated tumor suppressor genes, and overexpressed gene products, including oncogenes. In addition, ECRs may be derived from virus gene products, particularly those associated with viruses that cause chronic diseases or are oncogenic, such as the herpes viruses, human papilloma viruses, human immunodeficiency virus, and human T cell leukemia virus. Also ECRs may be derived from gene products of parasitic organisms, such as *Trypanosoma, Leishmania*, and other intracellular or parasitic organisms.

Some of these TuAA include α-fetoprotein, carcinoembryonic antigen (CEA), esophageal cancer derived NY-ESO-1, and SSX genes, SCP-1, PRAME, MART-1/MelanA (MART-1), gp100 (Pmel 17), tyrosinase, TRP-1, TRP-2, MAGE-1, MAGE-2, MAGE-3, BAGE, GAGE-1, GAGE-2, p15; overexpressed oncogenes and mutated tumor-suppressor genes such as p53, Ras, HER-2/neu; unique tumor antigens resulting from chromosomal translocations such as BCR-ABL, E2A-PRL, H4-RET, IGH-IGK, MYL-RAR1 and viral antigens, EBNA1, EBNA2, HPV-E6, -E7; prostate specific antigen (PSA), prostate stem cell antigen (PSCA), MAAT-1, GP-100, TSP-180, MAGE-4, MAGE-5, MAGE-6, RAGE, p185erbB-2, p185erbB-3, c-met, nm-23H1, TAG-72, CA 19-9, CA 72-4, CAM 17.1, NuMa, K-ras, β-Catenin, CDK4, Mum-1, p15, and p16.

Numerous other TAAs are also contemplated for both pathogens and tumors. In terms of TuAAs, a variety of methods are available and well known in the art to identify genes and gene products that are differentially expressed in neoplastic cells as compared to normal cells. Examples of these techniques include differential hybridization, including the use of microarrays; subtractive hybridization cloning; differential display, either at the level of mRNA or protein expression; EST sequencing; and SAGE (sequential analysis of gene expression). These nucleic acid techniques have been reviewed by Carulli, J. P. et al., J. Cellular Biochem Suppl. 30/31:286-296, 1998 (hereby incorporated by reference). Differential display of proteins involves, for example, comparison of two-dimensional poly-acrylamide gel electrophoresis of cell lysates from tumor and normal tissue, location of protein spots unique or overexpressed in the tumor, recovery of the protein from the gel, and identification of the protein using traditional biochemical- or mass spectrometry-based sequencing. An additional technique for identification of TAAs is the Serex technique, discussed in Türeci, Ö., Sahin, U., and Pfreundschuh, M., "Serological analysis of human tumor antigens: molecular definition and implications", *Molecular Medicine Today,* 3:342, 1997, and hereby incorporated by reference.

Use of these and other methods provides one of skill in the art the techniques necessary to identify genes and gene products contained within a target cell that may be used as potential candidate proteins for generating the epitopes of the invention disclosed. However, it is not necessary, in practicing the invention, to identify a novel TuAA or TAA. Rather, embodiments of the invention make it possible to identify ECRs from any relevant protein sequence, whether the sequence is already known or is new.

Protein Sequence Analysis to Identify Epitope Clusters

In preferred embodiments of the invention, identification of ECRs involves two main steps: (1) identifying good putative epitopes; and (2) defining the limits of any clusters in which these putative epitopes are located. There are various preferred embodiments of each of these two steps, and a selected embodiment for the first step can be freely combined with a selected embodiment for the second step. The methods and embodiments that are disclosed herein for each of these steps are merely exemplary, and are not intended to limit the scope of the invention in any way. Persons of skill in the art will appreciate the specific tools that can be applied to the analysis of a specific TAA, and such analysis can be conducted in numerous ways in accordance with the invention.

Preferred embodiments for identifying good putative epitopes include the use of any available predictive algorithm that analyzes the sequences of proteins or genes to predict binding affinity of peptide fragments for MHC, or to rank putative epitopes according to predicted affinity or other characteristics associated with MHC binding. As described above, available exemplary algorithms for this kind of analysis include the Rammensee and NIH (Parker) algorithms. Likewise, good putative epitopes can be identified by direct or indirect assays of MHC binding. To choose "good" putative epitopes, it is necessary to set a cutoff point in terms of the score reported by the prediction software or in terms of the assayed binding affinity. In some embodiments, such a cutoff is absolute. For example, the cutoff can be based on the measured or predicted half time of dissociation between an epitope and a selected MHC allele. In such cases, embodiments of the cutoff can be any half time of dissociation longer than, for example, 0.5 minutes; in a preferred embodiment longer than 2.5 minutes; in a more preferred embodiment longer than 5 minutes; and in a highly stringent embodiment can be longer than 10, or 20, or 25 minutes. In these embodiments, the good putative epitopes are those that are predicted or identified to have good MHC binding characteristics, defined as being on the desirable side of the designated cutoff point. Likewise, the cutoff can be based on the measured or predicted binding affinity between an epitope and a selected MHC allele. Additionally, the absolute cutoff can be simply a selected number of putative epitopes.

In other embodiments, the cutoff is relative. For example, a selected percentage of the total number of putative epitopes can be used to establish the cutoff for defining a candidate sequence as a good putative epitope. Again the properties for ranking the epitopes are derived from measured or predicted MHC binding; the property used for such a determination can be any that is relevant to or indicative of binding. In preferred embodiments, identification of good putative epitopes can combine multiple methods of ranking candidate sequences. In such embodiments, the good epitopes are typically those that either represent a consensus of the good epitopes based on different methods and parameters, or that are particularly highly ranked by at least one of the methods.

When several good putative epitopes have been identified, their positions relative to each other can be analyzed to determine the optimal clusters for use in vaccines or in vaccine design. This analysis is based on the density of a selected epitope characteristic within the sequence of the TAA. The regions with the highest density of the characteristic, or with a density above a certain selected cutoff, are designated as ECRs. Various embodiments of the invention employ different characteristics for the density analysis. For example, one preferred characteristic is simply the presence of any good putative epitope (as defined by any appropriate method). In this embodiment, all putative epitopes above the cutoff are treated equally in the density analysis, and the best clusters are those with the highest density of good putative epitopes per amino acid residue. In another embodiment, the preferred characteristic is based on the parameter(s) previously used to score or rank the putative epitopes. In this embodiment, a putative epitope with a score that is twice as high as another putative epitope is doubly weighted in the density analysis, relative to the other putative epitope. Still other embodiments take the score or rank into account, but on a diminished scale, such as, for example, by using the log or the square root of the score to give more weight to some putative epitopes than to others in the density analysis.

Depending on the length of the TAA to be analyzed, the number of possible candidate epitopes, the number of good putative epitopes, the variability of the scoring of the good putative epitopes, and other factors that become evident in any given analysis, the various embodiments of the invention can be used alone or in combination to identify those ECRs that are most useful for a given application. Iterative or parallel analyses employing multiple approaches can be beneficial in many cases. ECRs are tools for increased efficiency of identifying true MHC epitopes, and for efficient "packaging" of MHC epitopes into vaccines. Accordingly, any of the embodiments described herein, or other embodiments that are evident to those of skill in the art based on this disclosure, are useful in enhancing the efficiency of these efforts by using ECRs instead of using complete TAAs in vaccines and vaccine design.

Since many or most TAAs have regions with low density of predicted MHC epitopes, using ECRs provides a valuable methodology that avoids the inefficiencies of including regions of low epitope density in vaccines and in epitope identification protocols. Thus, useful ECRs can also be defined as any portion of a TAA that is not the whole TAA, wherein the portion has a higher density of putative epitopes than the whole TAA, or than any regions of the TAA that have a particularly low density of putative epitopes. In this aspect of the invention, therefore, an ECR can be any fragment of a TAA with elevated epitope density. In some embodiments, an ECR can include a region up to about 80% of the length of the TAA. In a preferred embodiment, an ECR can include a region up to about 50% of the length of the TAA. In a more preferred embodiment, an ECR can include a region up to about 30% of the length of the TAA. And in a most preferred embodiment, an ECR can include a region of between 5 and 15% of the length of the TAA.

In another aspect of the invention, the ECR can be defined in terms of its absolute length. Accordingly, by this definition, the minimal cluster for 9-mer epitopes includes 10 amino acid residues and has two overlapping 9-mers with 8 amino acids in common. In a preferred embodiment, the cluster is between about 15 and 75 amino acids in length. In a more preferred embodiment, the cluster is between about 20 and 60 amino acids in length. In a most preferred embodiment, the cluster is between about 30 and 40 amino acids in length.

In practice, as described above, ECR identification can employ a simple density function such as the number of epitopes divided by the number of amino acids spanned by the those epitopes. It is not necessarily required that the epitopes overlap, but the value for a single epitope is not significant. If only a single value for a percentage cutoff is used and an absolute cutoff in the epitope prediction is not used, it is possible to set a single threshold at this step to define a cluster. However, using both an absolute cutoff and carrying out the first step using different percentage cutoffs, can produce variations in the global density of candidate epitopes. Such variations can require further accounting or manipulation. For example, an overlap of 2 epitopes is more significant if only 3 candidate epitopes were considered, than if 30 candidates were considered for any particular length protein. To take this feature into consideration, the weight given to a particular cluster can further be divided by the fraction of possible peptides actually being considered, in order to increase the significance of the calculation. This scales the result to the average density of predicted epitopes in the parent protein.

Similarly, some embodiments base the scoring of good putative epitopes on the average number of peptides considered per amino acid in the protein. The resulting ratio represents the factor by which the density of predicted epitopes in the putative cluster differs from the average density in the protein. Accordingly, an ECR is defined in one embodiment as any region containing two or more predicted epitopes for which this ratio exceeds 2, that is, any region with twice the average density of epitopes. In other embodiments, the region is defined as an ECR if the ratio exceeds 1.5, 3, 4, or 5, or more.

Considering the average number of peptides per amino acid in a target protein to calculate the presence of an ECR highlights densely populated ECRs without regard to the score/affinity of the individual constituents. This is most appropriate for use of score-based cutoffs. However, an ECR with only a small number of highly ranked candidates can be of more biological significance than a cluster with several densely packed but lower ranking candidates, particularly if only a small percentage of the total number of candidate peptides were designated as good putative epitopes. Thus in some embodiments it is appropriate to take into consideration the scores of the individual peptides. This is most readily accomplished by substituting the sum of the scores of the peptides in the putative cluster for the number of peptides in the putative cluster in the calculation described above.

This sum of scores method is more sensitive to sparsely populated clusters containing high scoring epitopes. Because the wide range of scores (i.e. half times of dissociation) produced by the BIMAS-NIH/Parker algorithm can lead to a single high scoring peptide dwarfing the contribution of other potential epitopes, the log of the score rather than the score itself is preferably used in this procedure.

Various other calculations can be devised under one or another condition. Generally speaking, the epitope density function is constructed so that it is proportional to the number of predicted epitopes, their scores, their ranks, and the like, within the putative cluster, and inversely proportional to the number of amino acids or fraction of protein contained within that putative cluster. Alternatively, the function can be evaluated for a window of a selected number of contiguous amino acids. In either case the function is also evaluated for all predicted epitopes in the whole protein. If the ratio of values for the putative cluster (or window) and the whole protein is greater than, for example, 1.5, 2, 3, 4, 5, or more, an ECR is defined.

Analysis of Target Gene Products For MHC Binding

Once a TAA has been identified, the protein sequence can be used to identify putative epitopes with known or predicted affinity to the MHC peptide binding cleft. Tests of peptide fragments can be conducted in vitro, or using the sequence can be computer analyzed to determine MHC receptor binding of the peptide fragments. In one embodiment of the invention, peptide fragments based on the amino acid sequence of the target protein are analyzed for their predicted ability to bind to the MHC peptide binding cleft. Examples of suitable computer algorithms for this purpose include that found at the world wide web page of Hans-Georg Rammensee, Jutta Bachmann, Niels Emmerich, Stefan Stevanovic: SYFPEITHI: An Internet Database for MHC Ligands and Peptide Motifs (access via hypertext transfer protocol: //134.2.96.221/scripts/hlaserver.dll/EpPredict.htm). Results obtained from this method are discussed in Rammensee, et al., "MHC Ligands and Peptide Motifs," Landes Bioscience Austin, Tex., 224-227, 1997, which is hereby incorporated by reference in its entirety. Another site of interest is found at hypertext transfer protocol: //bimas.dcrt.nih.gov/molbio/hla_bind, which also contains a suitable algorithm. The methods of this web site are discussed in Parker, et al., "Scheme for ranking potential HLA-A2 binding peptides based on independent binding of individual peptide side-chains," J. Immunol. 152:163-175, which is hereby incorporated by reference in its entirety.

As an alternative to predictive algorithms, a number of standard in vitro receptor binding affinity assays are available to identify peptides having an affinity for a particular allele of MHC. Accordingly, by the method of this aspect of the invention, the initial population of peptide fragments can be narrowed to include only putative epitopes having an actual or predicted affinity for the selected allele of MHC. Selected common alleles of MHC I, and their approximate frequencies, are reported in the tables below.

TABLE 1

Estimated gene frequencies of HLA-A antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| A1 | 15.1843 | 0.0489 | 5.7256 | 0.0771 | 4.4818 | 0.0846 | 7.4007 | 0.0978 | 12.0316 | 0.2533 |
| A2 | 28.6535 | 0.0619 | 18.8849 | 0.1317 | 24.6352 | 0.1794 | 28.1198 | 0.1700 | 29.3408 | 0.3585 |
| A3 | 13.3890 | 0.0463 | 8.4406 | 0.0925 | 2.6454 | 0.0655 | 8.0789 | 0.1019 | 11.0293 | 0.2437 |
| A28 | 4.4652 | 0.0280 | 9.9269 | 0.0997 | 1.7657 | 0.0537 | 8.9446 | 0.1067 | 5.3856 | 0.1750 |
| A36 | 0.0221 | 0.0020 | 1.8836 | 0.0448 | 0.0148 | 0.0049 | 0.1584 | 0.0148 | 0.1545 | 0.0303 |
| A23 | 1.8287 | 0.0181 | 10.2086 | 0.1010 | 0.3256 | 0.0231 | 2.9269 | 0.0628 | 1.9903 | 0.1080 |
| A24 | 9.3251 | 0.0395 | 2.9668 | 0.0560 | 22.0391 | 0.1722 | 13.2610 | 0.1271 | 12.6613 | 0.2590 |
| A9 unsplit | 0.0809 | 0.0038 | 0.0367 | 0.0063 | 0.0858 | 0.0119 | 0.0537 | 0.0086 | 0.0356 | 0.0145 |
| A9 total | 11.2347 | 0.0429 | 13.2121 | 0.1128 | 22.4505 | 0.1733 | 16.2416 | 0.1382 | 14.6872 | 0.2756 |
| A25 | 2.1157 | 0.0195 | 0.4329 | 0.0216 | 0.0990 | 0.0128 | 1.1937 | 0.0404 | 1.4520 | 0.0924 |
| A26 | 3.8795 | 0.0262 | 2.8284 | 0.0547 | 4.6628 | 0.0862 | 3.2612 | 0.0662 | 2.4292 | 0.1191 |
| A34 | 0.1508 | 0.0052 | 3.5228 | 0.0610 | 1.3529 | 0.0470 | 0.4928 | 0.0260 | 0.3150 | 0.0432 |
| A43 | 0.0018 | 0.0006 | 0.0334 | 0.0060 | 0.0231 | 0.0062 | 0.0055 | 0.0028 | 0.0059 | 0.0059 |
| A66 | 0.0173 | 0.0018 | 0.2233 | 0.0155 | 0.0478 | 0.0089 | 0.0399 | 0.0074 | 0.0534 | 0.0178 |
| A10 unsplit | 0.0790 | 0.0038 | 0.0939 | 0.0101 | 0.1255 | 0.0144 | 0.0647 | 0.0094 | 0.0298 | 0.0133 |
| A10 total | 6.2441 | 0.0328 | 7.1348 | 0.0850 | 6.3111 | 0.0993 | 5.0578 | 0.0816 | 4.2853 | 0.1565 |
| A29 | 3.5796 | 0.0252 | 3.2071 | 0.0582 | 1.1233 | 0.0429 | 4.5156 | 0.0774 | 3.4345 | 0.1410 |
| A30 | 2.5067 | 0.0212 | 13.0969 | 0.1129 | 2.2025 | 0.0598 | 4.4873 | 0.0772 | 2.5314 | 0.1215 |
| A31 | 2.7386 | 0.0221 | 1.6556 | 0.0420 | 3.6005 | 0.0761 | 4.8328 | 0.0800 | 6.0881 | 0.1855 |
| A32 | 3.6956 | 0.0256 | 1.5384 | 0.0405 | 1.0331 | 0.0411 | 2.7064 | 0.0604 | 2.5521 | 0.1220 |
| A33 | 1.2080 | 0.0148 | 6.5607 | 0.0822 | 9.2701 | 0.1191 | 2.6593 | 0.0599 | 1.0754 | 0.0796 |
| A74 | 0.0277 | 0.0022 | 1.9949 | 0.0461 | 0.0561 | 0.0096 | 0.2027 | 0.0167 | 0.1068 | 0.0252 |
| A19 unsplit | 0.0567 | 0.0032 | 0.2057 | 0.0149 | 0.0990 | 0.0128 | 0.1211 | 0.0129 | 0.0475 | 0.0168 |
| A19 total | 13.8129 | 0.0468 | 28.2593 | 0.1504 | 17.3846 | 0.1555 | 19.5252 | 0.1481 | 15.8358 | 0.2832 |
| AX | 0.8204 | 0.0297 | 4.9506 | 0.0963 | 2.9916 | 0.1177 | 1.6332 | 0.0878 | 1.8454 | 0.1925 |

[a]Gene frequency.

[b]Standard error.

TABLE 2

Estimated gene frequencies for HLA-B antigens

| Antigen | CAU Gf[a] | SE[b] | AFR Gf | SE | ASI Gf | SE | LAT Gf | SE | NAT Gf | SE |
|---|---|---|---|---|---|---|---|---|---|---|
| B7 | 12.1782 | 0.0445 | 10.5960 | 0.1024 | 4.2691 | 0.0827 | 6.4477 | 0.0918 | 10.9845 | 0.2432 |
| B8 | 9.4077 | 0.0397 | 3.8315 | 0.0634 | 1.3322 | 0.0467 | 3.8225 | 0.0715 | 8.5789 | 0.2176 |
| B13 | 2.3061 | 0.0203 | 0.8103 | 0.0295 | 4.9222 | 0.0886 | 1.2699 | 0.0416 | 1.7495 | 0.1013 |
| B14 | 4.3481 | 0.0277 | 3.0331 | 0.0566 | 0.5004 | 0.0287 | 5.4166 | 0.0846 | 2.9823 | 0.1316 |
| B18 | 4.7980 | 0.0290 | 3.2057 | 0.0582 | 1.1246 | 0.0429 | 4.2349 | 0.0752 | 3.3422 | 0.1391 |
| B27 | 4.3831 | 0.0278 | 1.2918 | 0.0372 | 2.2355 | 0.0603 | 2.3724 | 0.0567 | 5.1970 | 0.1721 |
| B35 | 9.6614 | 0.0402 | 8.5172 | 0.0927 | 8.1203 | 0.1122 | 14.6516 | 0.1329 | 10.1198 | 0.2345 |
| B37 | 1.4032 | 0.0159 | 0.5916 | 0.0252 | 1.2327 | 0.0449 | 0.7807 | 0.0327 | 0.9755 | 0.0759 |
| B41 | 0.9211 | 0.0129 | 0.8183 | 0.0296 | 0.1303 | 0.0147 | 1.2818 | 0.0418 | 0.4766 | 0.0531 |
| B42 | 0.0608 | 0.0033 | 5.6991 | 0.0768 | 0.0841 | 0.0118 | 0.5866 | 0.0284 | 0.2856 | 0.0411 |
| B46 | 0.0099 | 0.0013 | 0.0151 | 0.0040 | 4.9292 | 0.0886 | 0.0234 | 0.0057 | 0.0238 | 0.0119 |
| B47 | 0.2069 | 0.0061 | 0.1305 | 0.0119 | 0.0956 | 0.0126 | 0.1832 | 0.0159 | 0.2139 | 0.0356 |
| B48 | 0.0865 | 0.0040 | 0.1316 | 0.0119 | 2.0276 | 0.0575 | 1.5915 | 0.0466 | 1.0267 | 0.0778 |
| B53 | 0.4620 | 0.0092 | 10.9529 | 0.1039 | 0.4315 | 0.0266 | 1.6982 | 0.0481 | 1.0804 | 0.0798 |
| B59 | 0.0020 | 0.0006 | 0.0032 | 0.0019 | 0.4277 | 0.0265 | 0.0055 | 0.0028 | 0[c] | — |
| B67 | 0.0040 | 0.0009 | 0.0086 | 0.0030 | 0.2276 | 0.0194 | 0.0055 | 0.0028 | 0.0059 | 0.0059 |
| B70 | 0.3270 | 0.0077 | 7.3571 | 0.0866 | 0.8901 | 0.0382 | 1.9266 | 0.0512 | 0.6901 | 0.0639 |
| B73 | 0.0108 | 0.0014 | 0.0032 | 0.0019 | 0.0132 | 0.0047 | 0.0261 | 0.0060 | 0[c] | — |
| B51 | 5.4215 | 0.0307 | 2.5980 | 0.0525 | 7.4751 | 0.1080 | 6.8147 | 0.0943 | 6.9077 | 0.1968 |
| B52 | 0.9658 | 0.0132 | 1.3712 | 0.0383 | 3.5121 | 0.0752 | 2.2447 | 0.0552 | 0.6960 | 0.0641 |
| B5 unsplit | 0.1565 | 0.0053 | 0.1522 | 0.0128 | 0.1288 | 0.0146 | 0.1546 | 0.0146 | 0.1307 | 0.0278 |
| B5 total | 6.5438 | 0.0435 | 4.1214 | 0.0747 | 11.1160 | 0.1504 | 9.2141 | 0.1324 | 7.7344 | 0.2784 |
| B44 | 13.4838 | 0.0465 | 7.0137 | 0.0847 | 5.6807 | 0.0948 | 9.9253 | 0.1121 | 11.8024 | 0.2511 |
| B45 | 0.5771 | 0.0102 | 4.8069 | 0.0708 | 0.1816 | 0.0173 | 1.8812 | 0.0506 | 0.7603 | 0.0670 |
| B12 unsplit | 0.0788 | 0.0038 | 0.0280 | 0.0055 | 0.0049 | 0.0029 | 0.0193 | 0.0051 | 0.0654 | 0.0197 |
| B12 total | 14.1440 | 0.0474 | 11.8486 | 0.1072 | 5.8673 | 0.0963 | 11.8258 | 0.1210 | 12.6281 | 0.2584 |
| B62 | 5.9117 | 0.0320 | 1.5267 | 0.0404 | 9.2249 | 0.1190 | 4.1825 | 0.0747 | 6.9421 | 0.1973 |
| B63 | 0.4302 | 0.0088 | 1.8865 | 0.0448 | 0.4438 | 0.0270 | 0.8083 | 0.0333 | 0.3738 | 0.0471 |
| B75 | 0.0104 | 0.0014 | 0.0226 | 0.0049 | 1.9673 | 0.0566 | 0.1101 | 0.0123 | 0.0356 | 0.0145 |
| B76 | 0.0026 | 0.0007 | 0.0065 | 0.0026 | 0.0874 | 0.0120 | 0.0055 | 0.0028 | 0 | — |
| B77 | 0.0057 | 0.0010 | 0.0119 | 0.0036 | 0.0577 | 0.0098 | 0.0083 | 0.0034 | 0[c] | 0.0059 |
| B15 unsplit | 0.1305 | 0.0049 | 0.0691 | 0.0086 | 0.4301 | 0.0266 | 0.1820 | 0.0158 | 0.0059 | 0.0206 |
| B15 total | 6.4910 | 0.0334 | 3.5232 | 0.0608 | 12.2112 | 0.1344 | 5.2967 | 0.0835 | 7.4290 | 0.2035 |
| B38 | 2.4413 | 0.0209 | 0.3323 | 0.0189 | 3.2818 | 0.0728 | 1.9652 | 0.0517 | 1.1017 | 0.0806 |
| B39 | 1.9614 | 0.0188 | 1.2893 | 0.0371 | 2.0352 | 0.0576 | 6.3040 | 0.0909 | 4.5527 | 0.1615 |
| B16 unsplit | 0.0638 | 0.0034 | 0.0237 | 0.0051 | 0.0644 | 0.0103 | 0.1226 | 0.0130 | 0.0593 | 0.0188 |
| B16 total | 4.4667 | 0.0280 | 1.6453 | 0.0419 | 5.3814 | 0.0921 | 8.3917 | 0.1036 | 5.7137 | 0.1797 |
| B57 | 3.5955 | 0.0252 | 5.6746 | 0.0766 | 2.5782 | 0.0647 | 2.1800 | 0.0544 | 2.7265 | 0.1260 |
| B58 | 0.7152 | 0.0114 | 5.9546 | 0.0784 | 4.0189 | 0.0803 | 1.2481 | 0.0413 | 0.9398 | 0.0745 |
| B17 unsplit | 0.2845 | 0.0072 | 0.3248 | 0.0187 | 0.3751 | 0.0248 | 0.1446 | 0.0141 | 0.2674 | 0.0398 |
| B17 total | 4.5952 | 0.0284 | 11.9540 | 0.1076 | 6.9722 | 0.1041 | 3.5727 | 0.0691 | 3.9338 | 0.1503 |
| B49 | 1.6452 | 0.0172 | 2.6286 | 0.0528 | 0.2440 | 0.0200 | 2.3353 | 0.0562 | 1.5462 | 0.0953 |
| B50 | 1.0580 | 0.0138 | 0.8636 | 0.0304 | 0.4421 | 0.0270 | 1.8883 | 0.0507 | 0.7862 | 0.0681 |
| B21 unsplit | 0.0702 | 0.0036 | 0.0270 | 0.0054 | 0.0132 | 0.0047 | 0.0771 | 0.0103 | 0.0356 | 0.0145 |
| B21 total | 2.7733 | 0.0222 | 3.5192 | 0.0608 | 0.6993 | 0.0339 | 4.3007 | 0.0755 | 2.3680 | 0.1174 |
| B54 | 0.0124 | 0.0015 | 0.0183 | 0.0044 | 2.6873 | 0.0660 | 0.0289 | 0.0063 | 0.0534 | 0.0178 |
| B55 | 1.9046 | 0.0185 | 0.4895 | 0.0229 | 2.2444 | 0.0604 | 0.9515 | 0.0361 | 1.4054 | 0.0909 |
| B56 | 0.5527 | 0.0100 | 0.2686 | 0.0170 | 0.8260 | 0.0368 | 0.3596 | 0.0222 | 0.3387 | 0.0448 |
| B22 unsplit | 0.1682 | 0.0055 | 0.0496 | 0.0073 | 0.2730 | 0.0212 | 0.0372 | 0.0071 | 0.1246 | 0.0272 |
| B22 total | 2.0852 | 0.0217 | 0.8261 | 0.0297 | 6.0307 | 0.0971 | 1.3771 | 0.0433 | 1.9221 | 0.1060 |
| B60 | 5.2222 | 0.0302 | 1.5299 | 0.0404 | 8.3254 | 0.1135 | 2.2538 | 0.0553 | 5.7218 | 0.1801 |
| B61 | 1.1916 | 0.0147 | 0.4709 | 0.0225 | 6.2072 | 0.0989 | 4.6691 | 0.0788 | 2.6023 | 0.1231 |
| B40 unsplit | 0.2696 | 0.0070 | 0.0388 | 0.0065 | 0.3205 | 0.0230 | 0.2473 | 0.0184 | 0.2271 | 0.0367 |
| B40 total | 6.6834 | 0.0338 | 2.0396 | 0.0465 | 14.8531 | 0.1462 | 7.1702 | 0.0963 | 8.5512 | 0.2168 |
| BX | 1.0922 | 0.0252 | 3.5258 | 0.0802 | 3.8749 | 0.0988 | 2.5266 | 0.0807 | 1.9867 | 0.1634 |

[a]Gene frequency.
[b]Standard error.
[c]The observed gene count was zero.

TABLE 3

Estimated gene frequencies of HLA-DR antigens

| Antigen | CAU Gf[a] | SE[b] | AFR Gf | SE | ASI Gf | SE | LAT Gf | SE | NAT Gf | SE |
|---|---|---|---|---|---|---|---|---|---|---|
| DR1 | 10.2279 | 0.0413 | 6.8200 | 0.0832 | 3.4628 | 0.0747 | 7.9859 | 0.1013 | 8.2512 | 0.2139 |
| DR2 | 15.2408 | 0.0491 | 16.2373 | 0.1222 | 18.6162 | 0.1608 | 11.2389 | 0.1182 | 15.3932 | 0.2818 |

TABLE 3-continued

Estimated gene frequencies of HLA-DR antigens

| Antigen | CAU | | AFR | | ASI | | LAT | | NAT | |
|---|---|---|---|---|---|---|---|---|---|---|
| | Gf[a] | SE[b] | Gf | SE | Gf | SE | Gf | SE | Gf | SE |
| DR3 | 10.8708 | 0.0424 | 13.3080 | 0.1124 | 4.7223 | 0.0867 | 7.8998 | 0.1008 | 10.2549 | 0.2361 |
| DR4 | 16.7589 | 0.0511 | 5.7084 | 0.0765 | 15.4623 | 0.1490 | 20.5373 | 0.1520 | 19.8264 | 0.3123 |
| DR6 | 14.3937 | 0.0479 | 18.6117 | 0.1291 | 13.4471 | 0.1404 | 17.0265 | 0.1411 | 14.8021 | 0.2772 |
| DR7 | 13.2807 | 0.0463 | 10.1317 | 0.0997 | 6.9270 | 0.1040 | 10.6726 | 0.1155 | 10.4219 | 0.2378 |
| DR8 | 2.8820 | 0.0227 | 6.2673 | 0.0800 | 6.5413 | 0.1013 | 9.7731 | 0.1110 | 6.0059 | 0.1844 |
| DR9 | 1.0616 | 0.0139 | 2.9646 | 0.0559 | 9.7527 | 0.1218 | 1.0712 | 0.0383 | 2.8662 | 0.1291 |
| DR10 | 1.4790 | 0.0163 | 2.0397 | 0.0465 | 2.2304 | 0.0602 | 1.8044 | 0.0495 | 1.0896 | 0.0801 |
| DR11 | 9.3180 | 0.0396 | 10.6151 | 0.1018 | 4.7375 | 0.0869 | 7.0411 | 0.0955 | 5.3152 | 0.1740 |
| DR12 | 1.9070 | 0.0185 | 4.1152 | 0.0655 | 10.1365 | 0.1239 | 1.7244 | 0.0484 | 2.0132 | 0.1086 |
| DR5 unsplit | 1.2199 | 0.0149 | 2.2957 | 0.0493 | 1.4118 | 0.0480 | 1.8225 | 0.0498 | 1.6769 | 0.0992 |
| DR5 total | 12.4449 | 0.0045 | 17.0260 | 0.1243 | 16.2858 | 0.1516 | 10.5880 | 0.1148 | 9.0052 | 0.2218 |
| DRX | 1.3598 | 0.0342 | 0.8853 | 0.0760 | 2.5521 | 0.1089 | 1.4023 | 0.0930 | 2.0834 | 0.2037 |

[a]Gene frequency.
[b]Standard error.

It has been observed that predicted epitopes often cluster at one or more particular regions within the amino acid sequence of a TAA. The identification of such ECRs offers a simple and practicable solution to the problem of designing effective vaccines for stimulating cellular immunity. For vaccines in which immune epitopes are desired, an ECR is directly useful as a vaccine. This is because the immune proteasomes of the pAPCs can correctly process the cluster, liberating one or more of the contained MHC-binding peptides, in the same way a cell having immune proteasomes activity processes and presents peptides derived from the complete TAA. The cluster is also a useful a starting material for identification of housekeeping epitopes produced by the housekeeping proteasomes active in peripheral cells.

Identification of housekeeping epitopes using ECRs as a starting material is described in copending U.S. patent application Ser. No. 09/561,074 entitled "METHOD OF EPITOPE DISCOVERY," filed Apr. 28, 2000, which is incorporated herein by reference in its entirety. Epitope synchronization technology and vaccines for use in connection with this invention are disclosed in copending U.S. patent application Ser. No. 09/560,465 entitled "EPITOPE SYNCHRONIZATION IN ANTIGEN PRESENTING CELLS," filed Apr. 28, 2000, which is incorporated herein by reference in its entirety. Nucleic acid constructs useful as vaccines in accordance with the present invention are disclosed in copending U.S. patent application Ser. No. 09/561,572 entitled "EXPRESSION VECTORS ENCODING EPITOPES OF TARGET-ASSOCIATED ANTIGENS," filed Apr. 28, 2000, which is incorporated herein by reference in its entirety.

Vector Design and Vectors

Degradation of cytosolic proteins takes place via the ubiquitin-dependent multi-catalytic multi-subunit protease system known as the proteasome. The proteasome degrades cytosolic proteins generating fragments that can then be translocated from the cytosol into the endoplasmic reticulum (ER) for loading onto class I MHC. Such protein fragments shall be referred to as class I peptides. The peptide loaded MHC are subsequently transported to the cell surface where they can be detected by CTL.

The multi-catalytic activity of the proteasome is the result of its multi-subunit structure. Subunits are expressed from different genes and assembled post-translationally into the proteasome complex. A key feature of the proteasome is its bimodal activity, which enables it to exert its protease, or cleavage function, with two discrete kinds of cleavage patterns. This bimodal action of the proteasome is extremely fundamental to understanding how CTL are targeted to recognize peripheral cells in the body and how this targeting requires synchronization between the immune system and the targeted cells.

The housekeeping proteasome is constitutively active in all peripheral cells and tissues of the body. The first mode of operation for the housekeeping proteasome is to degrade cellular protein, recycling it into amino acids. Proteasome function is therefore a necessary activity for cell life. As a corollary to its housekeeping protease activity, however, class I peptides generated by the housekeeping proteasome are presented on all of the peripheral cells of the body.

The proteasome's second mode of function is highly exclusive and occurs specifically in pAPCs or as a consequence of a cellular response to interferons (IFNs). In its second mode of activity the proteasome incorporates unique subunits, which replace the catalytic subunits of the constitutive housekeeping proteasome. This "modified" proteasome has been called the immunoproteasome, owing to its expression in pAPC and as a consequence of induction by IFN in body cells.

APC define the repertoire of CTL that recirculate through the body and are potentially active as killer cells. CTL are activated by interacting with class I peptide presented on the surface of a pAPC. Activated CTL are induced to proliferate and caused to recirculate through the body in search of diseased cells. This is why the CTL response in the body is defined specifically by the class I peptides produced by the pAPC. It is important to remember that pAPCs express the immunoproteasome, and that as a consequence of the bimodal activity of the proteasome, the cleavage pattern of proteins (and the resultant class I peptides produced) are different from those in peripheral body cells which express housekeeping proteasome. The differential proteasome activity in pAPC and peripheral body cells, therefore, is important to consider during natural infection and with therapeutic CTL vaccination strategies.

All cells of the body are capable of producing IFN in the event that they are infected by a pathogen such as a virus. IFN production in turn results in the expression of the immunoproteasome in the infected cell. Viral antigens are thereby processed by the immunoproteasome of the infected cell and the consequent peptides are displayed with class I MHC on the cell surface. At the same time, pAPC are sequestering virus antigens and are processing class I peptides with their immunoproteasome activity, which is normal for the pAPC cell type. The CTL response in the body is being stimulated specifically by the class I peptides produced by the pAPC. Fortunately, the infected cell is also producing class I peptides from the immunoproteasome, rather than the normal housekeeping proteasome. Thus, virus-related class I peptides are being produced that enable detection by the ensuing CTL response. The CTL immune response is induced by pAPC, which normally produce different class I peptides compared to peripheral body cells, owing to different proteasome activity. Therefore, during infection there is epitope synchronization between the infected cell and the immune system.

This is not the case with tumors and chronic viruses, which block the interferon system. For tumors there is no infection in the tumor cell to induce the immunoproteasome expression, and chronic virus infection either directly or indirectly blocks immunoproteasome expression. In both cases the diseased cell maintains its display of class I peptides derived from housekeeping proteasome activity and avoids effective surveillance by CTL.

In the case of therapeutic vaccination to eradicate tumors or chronic infections, the bimodal function of the proteasome and its differential activity in APC and peripheral cells of the body is significant. Upon vaccination with protein antigen, and before a CTL response can occur, the antigen must be acquired and processed into peptides that are subsequently presented on class I MHC on the pAPC surface. The activated CTL recirculate in search of cells with similar class I peptide on the surface. Cells with this peptide will be subjected to destruction by the cytolytic activity of the CTL. If the targeted diseased cell does not express the immunoproteasome, which is present in the pAPC, then the epitopes are not synchronized and CTL fail to find the desired peptide target on the surface of the diseased cell.

Preferably, therapeutic vaccine design takes into account the class I peptide that is actually present on the target tissue. That is, effective antigens used to stimulate CTL to attack diseased tissue are those that are naturally processed and presented on the surface of the diseased tissue. For tumors and chronic infection this generally means that the CTL epitopes are those that have been processed by the housekeeping proteasome. In order to generate an effective therapeutic vaccine, CTL epitopes are identified based on the knowledge that such epitopes are, in fact, produced by the housekeeping proteasome system. Once identified, these epitopes, embodied as peptides, can be used to successfully immunize or induce therapeutic CTL responses against housekeeping proteasome expressing target cells in the host.

However, in the case of DNA vaccines, there can be an additional consideration. The immunization with DNA requires that APCs take up the DNA and express the encoded proteins or peptides. It is possible to encode a discrete class I peptide on the DNA. By immunizing with this construct, APCs can be caused to express a housekeeping epitope, which is then displayed on class I MHC on the surface of the cell for stimulating an appropriate CTL response. Constructs for generation of proper termini of housekeeping epitopes have been described in U.S. patent application Ser. No. 09/561,572 entitled EXPRESSION VECTORS ENCODING EPITOPES OF TARGET-ASSOCIATED ANTIGENS, filed on Apr. 28, 2000, which is incorporated herein by reference in its entirety.

Embodiments of the invention provide expression cassettes that encode one or more embedded housekeeping epitopes, and methods for designing and testing such expression cassettes. The expression cassettes and constructs can encode epitopes, including housekeeping epitopes, derived from antigens that are associated with targets. Housekeeping epitopes can be liberated from the translation product(s) of the cassettes. For example, in some embodiments of the invention, the housekeeping epitope(s) can be flanked by arbitrary sequences or by sequences incorporating residues known to be favored in immunoproteasome cleavage sites. In further embodiments of the invention multiple epitopes can be arrayed head-to-tail. In some embodiments, these arrays can be made up entirely of housekeeping epitopes. Likewise, the arrays can include alternating housekeeping and immune epitopes. Alternatively, the arrays can include housekeeping epitopes flanked by immune epitopes, whether complete or distally truncated. In some preferred embodiments, each housekeeping epitope can be flanked on either side by an immune epitope, such that an array of such arrangements has two immune epitopes between each housekeeping epitope. Further, the arrays can be of any other similar arrangement. There is no restriction on placing a housekeeping epitope at the terminal positions of the array. The vectors can additionally contain authentic protein coding sequences or segments thereof containing epitope clusters as a source of immune epitopes.

Several disclosures make reference to polyepitopes or string-of-bead arrays. See, for example, WO0119408A1, Mar. 22, 2001; WO9955730A2, Nov. 4, 1999; WO0040261A2, Jul. 13, 2000; WO9603144A1, Feb. 8, 1996; EP1181314A1, Feb. 27, 2002; WO0123577A3, April 5; U.S. Pat. No. 6,074,817, Jun. 13, 2000; U.S. Pat. No. 5,965,381, Oct. 12, 1999; WO9741440A1, Nov. 6, 1997; U.S. Pat. No. 6,130,066, Oct. 10, 2000; U.S. Pat. No. 6,004,777, Dec. 21, 1999; U.S. Pat. No. 5,990,091, Nov. 23, 1999; WO9840501A1, Sep. 17, 1998; WO9840500A1, Sep. 17, 1998; WO0118035A2, Mar. 15, 2001; WO02068654A2, Sep. 6, 2002; WO0189281A2, Nov. 29, 2001; WO0158478A, Aug. 16, 2001; EP1118860A1, Jul. 25, 2001; WO0111040A1, Feb. 15, 2001; WO0073438A1, Dec. 7, 2000; WO0071158A1, Nov. 30, 2000; WO0066727A1, Nov. 9, 2000; WO0052451A1, Sep. 8, 2000; WO0052157A1, Sep. 8, 2000; WO0029008A2, May 25, 2000; WO0006723A1, Feb. 10, 2000; all of which are incorporated by reference in their entirety. Additional disclosures, all of which are hereby incorporated by reference in their entirety, include Palmowski M J, et al—J Immunol 2002; 168(9):4391-8; Fang Z Y, et al—Virology 2001; 291(2):272-84; Firat H, et al—J Gene Med 2002; 4(1):38-45; Smith S G, et al—Clin Cancer Res 2001; 7(12):4253-61; Vonderheide R H, et al—Clin Cancer Res 2001; 7(11):3343-8; Firat H, et al—Eur J Immunol 2001; 31(10):3064-74; Le T T, et al—Vaccine 2001; 19(32): 4669-75; Fayolle C, et al—J Virol 2001; 75(16):7330-8; Smith SG—*Curr Opin Mol Ther* 1999; 1(1):10-5; Firat H, et al—Eur J Immunol 1999; 29(10):3112-21; Mateo L, et al—J Immunol 1999; 163(7):4058-63; Heemskerk M H, et al—Cell Immunol 1999; 195(1):10-7; Woodberry T, et al—J Virol 1999; 73(7):5320-5; Hanke T, et al—Vaccine 1998; 16(4):426-35; Thomson S A, et al—J Immunol 1998; 160(4): 1717-23; Toes R E, et al—Proc Natl Acad Sci USA 1997; 94(26):14660-5; Thomson S A, et al—J Immunol 1996; 157 (2):822-6; Thomson S A, et al—*Proc Natl Acad Sci USA* 1995; 92(13):5845-9; Street M D, et al—Immunology 2002; 106(4):526-36; Hirano K, et al—Histochem Cell Biol 2002; 117(1):41-53; Ward S M, et al—*Virus Genes* 2001; 23(1):97-104; Liu W J, et al—Virology 2000; 273(2):374-82; Gariglio P, et al—Arch Med Res 1998; 29(4):279-84; Suhrbier A—*Immunol Cell Biol* 1997; 75(4):402-8; Fomsgaard A, et al—Vaccine 1999; 18(7-8):681-91; An L L, et al—J Virol 1997; 71(3):2292-302; Whitton J L, et al—J Virol 1993; 67(1):348-

52; Ripalti A, et al—J Clin Microbiol 1994; 32(2):358-63; and Gilbert, S. C., et al., *Nat. Biotech.* 15:1280-1284, 1997.

One important feature that the disclosures in the preceding paragraph all share is their lack of appreciation for the desirability of regenerating housekeeping epitopes when the construct is expressed in a pAPC. This understanding was not apparent until the present invention. Embodiments of the invention include sequences, that when processed by an immune proteasome, liberate or generate a housekeeping epitope. Embodiments of the invention also can liberate or generate such epitopes in immunogenically effective amounts. Accordingly, while the preceding references contain disclosures relating to polyepitope arrays, none is enabling of the technology necessary to provide or select a polyepitope capable of liberating a housekeeping epitope by action of an immunoproteasome in a pAPC. In contrast, embodiments of the instant invention are based upon a recognition of the desirability of achieving this result. Accordingly, embodiments of the instant invention include any nucleic acid construct that encodes a polypeptide containing at least one housekeeping epitope provided in a context that promotes its generation via immunoproteasomal activity, whether the housekeeping epitope is embedded in a string-of-beads array or some other arrangement. Some embodiments of the invention include uses of one or more of the nucleic acid constructs or their products that are specifically disclosed in any one or more of the above-listed references. Such uses include, for example, screening a polyepitope for proper liberation context of a housekeeping epitope and/or an immune epitope, designing an effective immunogen capable of causing presentation of a housekeeping epitope and/or an immune epitope on a pAPC, immunizing a patient, and the like. Alternative embodiments include use of only a subset of such nucleic acid constructs or a single such construct, while specifically excluding one or more other such constructs, for any of the purposes disclosed herein. Some preferred embodiments employ these and/or other nucleic acid sequences encoding polyepitope arrays alone or in combination. For example, some embodiments exclude use of polyepitope arrays from one or more of the above-mentioned references. Other embodiments may exclude any combination or all of the polyepitope arrays from the above-mentioned references collectively. Some embodiments include viral and/or bacterial vectors encoding polyepitope arrays, while other embodiments specifically exclude such vectors. Such vectors can encode carrier proteins that may have some immunostimulatory effect. Some embodiments include such vectors with such immunostimulatory/immunopotentiating effects, as opposed to immunogenic effects, while in other embodiments such vectors may be included. Further, in some instances viral and bacterial vectors encode the desired epitope as a part of substantially complete proteins which are not associated with the target cell. Such vectors and products are included in some embodiments, while excluded from others. Some embodiments relate to repeated administration of vectors. In some of those embodiments, nonviral and nonbacterial vectors are included. Likewise, some embodiments include arrays that contain extra amino acids between epitopes, for example anywhere from 1-6 amino acids, or more, in some embodiments, while other embodiments specifically exclude such arrays.

Embodiments of the present invention also include methods, uses, therapies, and compositions directed to various types of targets. Such targets can include, for example, neoplastic cells such as those listed below, for example; and cells infected with any virus, bacterium, protozoan, fungus, or other agents, examples of which are listed below, in Tables 4-8, or which are disclosed in any of the references listed above. Alternative embodiments include the use of only a subset of such neoplastic cells and infected cells listed below, in Tables 4-8, or in any of the references disclosed herein, or a single one of the neoplastic cells or infected cells, while specifically excluding one or more other such neoplastic cells or infected cells, for any of the purposes disclosed herein. The following are examples of neoplastic cells that can be targeted: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non Hodgkin's disease), multiple myeloma, Waldenstrom's macroglobulinemia, heavy chain disease, hepatocellular cancer, brain cancer, stomach cancer, liver cancer, and the like. Examples of infectious agents that infect the target cells can include the following: adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, hepatitis C virus, measles virus, rubella virus, human immunodeficiency virus (HIV), human T cell leukemia virus I, human T cell leukemia virus II, *Chlamydia, Listeria, Salmonella, Legionella, Brucella, Coxiella, Rickettsia, Mycobacterium, Leishmania, Trypanasoma, Toxoplasma, Plasmodium*, and the like. Exemplary infectious agents and neoplastic cells are also included in Tables 4-8 below.

Furthermore the targets can include neoplastic cells described in or cells infected by agents that are described in any of the following references: Jäger, E. et al., "Granulocyte-macrophage-colony-stimulating factor enhances immune responses to melanoma-associated peptides in vivo," *Int. J. Cancer,* 67:54-62 (1996); Kündig, T. M., Althage, A., Hengartner, H. & Zinkernagel, R. M., "A skin test to assess CD8+ cytotoxic T cell activity," *Proc. Natl. Acad Sci. USA,* 89:7757-76 (1992); Bachmann, M. F. & Kundig, T. M., "In vitro vs. in vivo assays for the assessment of T- and B-cell function," *Curr. Opin. Immunol.,* 6:320-326 (1994); Kundig et al., "On the role of antigen in maintaining cytotoxic T cell memory," *Proceedings of the National Academy of Sciences of the United States of America,* 93:9716-23 (1996); Steinmann, R. M., "The dendritic cells system and its role in immunogenicity," *Annual Review of Immunology* 9:271-96 (1991); Inaba, K. et al., "Identification of proliferating dendritic cell precursors in mouse blood," *Journal of Experimental Medicine,* 175:1157-67 (1992); Young, J. W. & Inaba, K., "Dendritic cells as adjuvants for class I major histocompatibility complex-restricted anti-tumor immunity," *Journal of Experimental Medicine*, 183:7-11 (1996); Kuby, Janis, *Immunology*, Second Edition, Chapter 15, W.H. Freeman and Company (1991); Austenst, E., Stahl, T., and de Gruyter, Walter, *Insulin Pump Therapy*, Chapter 3, Berlin, New York (1990); Remington, *The Science and Practice of Pharmacy*, Nineteenth Edition, Chapters 86-88 (1985); Cleland, Jeffery L. and Langer, Robert (Editor), "Formulation and delivery of proteins and peptides," *American Chemical Society* (ACS Symposium Series, No. 567) (1994); Dickinson, Becton, which is fixed using Tegadenn transparent dressing Tegaderm™ 1624, 3M, St. Paul, Minn. 55144, USA; Santus, Giancarlo and Baker, Richard, "Osmotic drug delivery: A review of the patent literature," *Journal of Controlled Release*, 35:1-21 (1995); Rammensee, U.S. Pat. No. 5,747,269, issued May 5, 1998; Magruder, U.S. Pat. No. 5,059,423, issued Oct. 22, 1991; Sandbrook, U.S. Pat. No. 4,552,651, issued Nov. 25, 1985; Eckenhoff et al., U.S. Pat. No. 3,987,790, issued Oct. 26, 1976; Theeuwes, U.S. Pat. No. 4,455,145, issued Jun. 19, 1984; Roth et al. U.S. Pat. No. 4,929,233, issued May 29, 1990; van der Bruggen et al., U.S. Pat. No. 5,554,506, issued Sep. 10, 1996; Pfreundschuh, U.S. Pat. No. 5,698,396, issued Dec. 16, 1997; Magruder, U.S. Pat. No. 5,110,596, issued May 5, 1992; Eckenhoff, U.S. Pat. No. 4,619,652, issued Oct. 28, 1986; Higuchi et al., U.S. Pat. No. 3,995,631, issued Dec. 7, 1976; Maruyama, U.S. Pat. No. 5,017,381, issued May 21, 1991; Eckenhoff, U.S. Pat. No. 4,963,141, issued Oct. 16, 1990; van der Bruggen et al., U.S. Pat. No. 5,558,995, issued Sep. 24, 1996; Stolzenberg et al. U.S. Pat. No. 3,604,417, issued Sep. 14, 1971; Wong et al., U.S. Pat. No. 5,110,597, issued May 5, 1992; Eckenhoff, U.S. Pat. No. 4,753,651, issued Jun. 28, 1988; Theeuwes, U.S. Pat. No. 4,203,440, issued May 20, 1980; Wong et al. U.S. Pat. No. 5,023,088, issued Jun. 11, 1991; Wong et al., U.S. Pat. No. 4,976,966, issued Dec. 11, 1990; Van den Eynde et al., U.S. Pat. No. 5,648,226, issued Jul. 15, 1997; Baker et al., U.S. Pat. No. 4,838,862, issued Jun. 13, 1989; Magruder, U.S. Pat. No. 5,135,523, issued Aug. 4, 1992; Higuchi et al., U.S. Pat. No. 3,732,865, issued May 15, 1975; Theeuwes, U.S. Pat. No. 4,286,067, issued Aug. 25, 1981; Theeuwes et al., U.S. Pat. No. 5,030,216, issued Jul. 9, 1991; Boon et al., U.S. Pat. No. 5,405,940, issued Apr. 11, 1995; Faste, U.S. Pat. No. 4,898,582, issued Feb. 6, 1990; Eckenhoff, U.S. Pat. No. 5,137,727, issued Aug. 11, 1992; Higuchi et al. U.S. Pat. No. 3,760,804, issued Sep. 25, 1973; Eckenhoff et al., U.S. Pat. No. 4,300,558, issued Nov. 12, 1981; Magruder et al., U.S. Pat. No. 5,034,229, issued Jul. 23, 1991; Boon et al., U.S. Pat. No. 5,487,974, issued Jan. 30, 1996; Kam et al., U.S. Pat. No. 5,135,498, issued Aug. 4, 1992; Magruder et al., U.S. Pat. No. 5,174,999, issued Dec. 29, 1992; Higuchi, U.S. Pat. No. 3,760,805, Sep. 25, 1973; Michaels, U.S. Pat. No. 4,304,232, issued Dec. 8, 1981; Magruder et al., U.S. Pat. No. 5,037,420, issued Oct. 15, 1991; Wolfel et al., U.S. Pat. No. 5,530,096, issued Jun. 25, 1996; Athadye et al., U.S. Pat. No. 5,169,390, issued Dec. 8, 1992; Balaban et al., U.S. Pat. No. 5,209,746, issued May 11, 1993; Higuchi, U.S. Pat. No. 3,929,132, issued Dec. 30, 1975; Michaels, U.S. Pat. No. 4,340,054, issued Jul. 20, 1982; Magruder et al., U.S. Pat. No. 5,057,318, issued Oct. 15, 1991; Wolfel et al., U.S. Pat. No. 5,519,117, issued May 21, 1996; Athadye et al., U.S. Pat. No. 5,257,987, issued Nov. 2, 1993; Linkwitz et al., U.S. Pat. No. 5,221,278, issued Jun. 22, 1993; Nakano et al., U.S. Pat. No. 3,995,632, issued Dec. 7, 1976; Michaels, U.S. Pat. No. 4,367,741, issued Jan. 11, 1983; Eckenhoff, U.S. Pat. No. 4,865,598, issued Sep. 12, 1989; Lethe et al., U.S. Pat. No. 5,774,316, issued Apr. 28, 1998; Eckenhoff, U.S. Pat. No. 4,340,048, issued Jul. 20, 1982; Wong, U.S. Pat. No. 5,223,265, issued Jun. 29, 1993; Higuchi et al., U.S. Pat. No. 4,034,756, issued Jul. 12, 1977; Michaels, U.S. Pat. No. 4,450,198, issued May 22, 1984; Eckenhoff et al., U.S. Pat. No. 4,865,845, issued Sep. 12, 1989; Melief et. al., U.S. Pat. No. 5,554,724, issued Sep. 10, 1996; Eckenhoff et al., U.S. Pat. No. 4,474,575, issued Oct. 2, 1984; Theeuwes, U.S. Pat. No. 3,760,984, issued Sep. 25, 1983; Eckenhoff, U.S. Pat. No. 4,350,271, issued Sep. 21, 1982; Eckenhoff et al., U.S. Pat. No. 4,855,141, issued Aug. 8, 1989; Zingerman, U.S. Pat. No. 4,872,873, issued Oct. 10, 1989; Townsend et al., U.S. Pat. No. 5,585,461, issued Dec. 17, 1996; Carulli, J. P. et al., *J. Cellular Biochem Suppl.*, 30/31:286-96 (1998); Türeci, Ö., Sahin, U., and Pfreundschuh, M., "Serological analysis of human tumor antigens: molecular definition and implications," *Molecular Medicine Today*, 3:342 (1997); Rammensee et al., *MHC Ligands and Peptide Motifs*, Landes Bioscience Austin, Tex., 224-27, (1997); Parker et al., "Scheme for ranking potential HLA-A2 binding peptides based on independent binding of individual peptide side-chains," *J. Immunol.* 152: 163-175 (1994); Kido & Ohshita, *Anal. Biochem.*, 230:41-47 (1995); Yamada et al., *J. Biochem.* (Tokyo), 95:1155-60 (1984); Kawashima et al., *Kidney Int.*, 54:275-8 (1998); Nakabayshi & Ikezawa, *Biochem. Int* 16:1119-25 (1988); Kanaseki Ohkuma, *J. Biochem.* (Tokyo), 110:541-7 (1991); Wattiaux et al., *J. Cell Biol.*, 78:349-68 (1978); Lisman et al., *Biochem. J.*, 178:79-87 (1979); Dean, B., *Arch. Biochem. Biophys.*, 227:154-63 (1983); Overdijk et al., *Adv. Exp. Med. Biol.*, 101:601-10 (1978); Stromhaug et al., *Biochem. J.*, 335: 217-24 (1998); Escola et al., *J. Biol. Chem.*, 271:27360-05 (1996); Hammond et al., *Am. J. Physiol.*, 267:F516-27 (1994); Williams & Smith, *Arch. Biochem. Biophys.*, 305: 298-306 (1993); Marsh, M., *Methods Cell Biol.*, 31:319-34 (1989); Schmid & Mellman, *Prog. Clin. Biol. Res.*, 270:35-49 (1988); Falk, K. et al., *Nature*, 351:290, (1991); Ausubel et al., *Short Protocols in Molecular Biology*, Third Edition, Unit 11.2 (1997); hypertext transfer protocol address 134.2.96.221/scripts_/hlaserver.dll_/EpPredict.htm; Levy, Morel, S. et al., *Immunity* 12:107-117 (2000); Seipelt et al., "The structures of picornaviral proteinases," *Virus Research*, 62:159-68, 1999; Storkus et al., U.S. Pat. No. 5,989,565, issued Nov. 23, 1999; Morton, U.S. Pat. No. 5,993,828, issued Nov. 30, 1999; *Virus Research* 62:159-168, (1999); Simard et al., U.S. patent application Ser. No. 10/026,066, filed Dec. 7, 2001; Simard et al., U.S. patent application Ser. No. 09/561,571, filed Apr. 28, 2000; Simard et al., U.S. patent application Ser. No. 09/561,572, filed Apr. 28, 2000; Miura et al., WO 99/01283, Jan. 14, 1999; Simard et al., U.S. patent application Ser. No. 09/561,074, filed Apr. 28, 2000; Simard et al., U.S. patent application Ser. No. 10/225,568, filed Aug. 20, 2002; Simard et al., U.S. patent application Ser. No. 10/005,905, filed Nov. 7, 2001; Simard et al., U.S. patent application Ser. No. 09/561,074, filed Apr. 28, 2000.

Additional embodiments of the invention include methods, uses, therapies, and compositions relating to a particular antigen, whether the antigen is derived from, for example, a target cell or an infective agent, such as those mentioned above. Some preferred embodiments employ the antigens listed herein, in Tables 4-8, or in the list below, alone, as subsets, or in any combination. For example, some embodiments exclude use of one or more of those antigens. Other embodiments may exclude any combination or all of those antigens. Several examples of such antigens include MelanA (MART-I), gp100 (Pmel 17), tyrosinase, TRP-1, TRP-2, MAGE-1, MAGE-3, BAGE, GAGE-1, GAGE-2, CEA, RAGE, NY-ESO, SCP-1, Hom/Mel-40, PRAME, p53, H-Ras, HER-2/ neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CAM 17.1, NuMa, K-ras, β-Catenin, CDK4, Mum-1, p16, as well as any of those set forth in the above mentioned references. Other antigens are included in Tables 4-7 below.

Further embodiments include methods, uses, compositions, and therapies relating to epitopes, including, for example those epitopes listed in Tables 4-8. These epitopes can be useful to flank housekeeping epitopes in screening vectors, for example. Some embodiments include one or more epitopes from Tables 4-8, while other embodiments specifically exclude one or more of such epitopes or combinations thereof.

TABLE 4

| Virus | Protein | AA Position | T cell epitope MHC ligand (Antigen) | | MHC molecule |
|---|---|---|---|---|---|
| Adenovirus 3 | E3 9Kd | 30-38 | LIVIGILIL | (SEQ. ID NO.:44) | HLA-A*0201 |
| Adenovirus 5 | EIA | 234-243 | SGPSNTPPEI | (SEQ. ID NO.:45) | H2-Db |
| Adenovirus 5 | E1B | 192-200 | VNIRNCCY1 | (SEQ. ID NO.:46) | H2-Db |
| Adenovirus 5 | EIA | 234-243 | SGPSNIPPEI (T>I) | (SEQ. ID NO.:47) | H2-Db |
| CSFV | NS polyprotein | 2276-2284 | ENALLVALF | (SEQ. ID NO.:48) | SLA, haplotype d/d |
| Dengue virus 4 | NS3 | 500-508 | TPEGIIPTL | (SEQ. ID NO.:49) | HLA-B*3501 |
| EBV | LMP-2 | 426-434 | CLGGLLTMV | (SEQ. ID NO.:50) | HLA-A*0201 |
| EBV | EBNA-1 | 480-484 | NIAEGLRAL | (SEQ. ID NO.:51) | HLA-A*0201 |
| EBV | EBNA-1 | 519-527 | NLRRGTALA | (SEQ. ID NO.:52) | HLA-A*0201 |
| EBV | EBNA-1 | 525-533 | ALAIPQCRL | (SEQ. ID NO.:53) | HLA-A*0201 |
| EBV | EBNA-1 | 575-582 | VLKDAIKDL | (SEQ. ID NO.:54) | HLA-A*0201 |
| EBV | EBNA-1 | 562-570 | FMVFLQTHI | (SEQ. ID NO.:55) | HLA-A*0201 |
| EBV | EBNA-2 | 15-23 | HLIVDTDSL | (SEQ. ID NO.:56) | HLA-A*0201 |
| EBV | EBNA-2 | 22-30 | SLGNPSLSV | (SEQ. ID NO.:57) | HLA-A*0201 |
| EBV | EBNA-2 | 126-134 | PLASAMRML | (SEQ. ID NO.:58) | HLA-A*0201 |
| EBV | EBNA-2 | 132-140 | RMLWMANY1 | (SEQ. ID NO.:59) | HLA-A*0201 |
| EBV | EBNA-2 | 133-141 | MLWMANYIV | (SEQ. ID NO.:60) | HLA-A*0201 |
| EBV | EBNA-2 | 151-159 | ILPQGPQTA | (SEQ. ID NO.:61) | HLA-A*0201 |
| EBV | EBNA-2 | 171-179 | PLRPTAPTI | (SEQ. ID NO.:62) | HLA-A*0201 |
| EBV | EBNA-2 | 205-213 | PLPPATLTV | (SEQ. ID NO.:63) | HLA-A*0201 |
| EBV | EBNA-2 | 246-254 | RMHLPVLHV | (SEQ. ID NO.:64) | HLA-A*0201 |
| EBV | EBNA-2 | 287-295 | PMPLPPSQL | (SEQ. ID NO.:65) | HLA-A*0201 |
| EBV | EBNA-2 | 294-302 | QLPPPAAPA | (SEQ. ID NO.:66) | HLA-A*0201 |
| EBV | EBNA-2 | 381-389 | SMPELSPVL | (SEQ. ID NO.:67) | HLA-A*0201 |
| EBV | EBNA-2 | 453-461 | DLDESWDYI | (SEQ. ID NO.:68) | HLA-A*0201 |
| EBV | BZLF1 | 43-51 | PLPCVLWPV | (SEQ. ID NO.:69) | HLA-A*0201 |
| EBV | BZLF1 | 167-175 | SLEECDSEL | (SEQ. ID NO.:70) | HLA-A*0201 |
| EBV | BZLF1 | 176-184 | EIKRYKNRV | (SEQ. ID NO.:71) | HLA-A*0201 |
| EBV | BZLF1 | 195-203 | QLLQHYREV | (SEQ. ID NO.:72) | HLA-A*0201 |
| EBV | BZLF1 | 196-204 | LLQHYREVA | (SEQ. ID NO.:73) | HLA-A*0201 |
| EBV | BZLFI | 217-225 | LLKQMCPSL | (SEQ. ID NO.:74) | HLA-A*0201 |
| EBV | BZLF1 | 229-237 | SIIPRTPDV | (SEQ. ID NO.:75) | HLA-A*0201 |
| EBV | EBNA-6 | 284-293 | LLDFVRFMGV | (SEQ. ID NO.:76) | HLA-A*0201 |

TABLE 4-continued

| Virus | Protein | AA Position | T cell epitope MHC ligand (Antigen) | | MHC molecule |
|---|---|---|---|---|---|
| EBV | EBNA-3 | 464-472 | SVRDRLARL | (SEQ. ID NO.:77) | HLA-A*0203 |
| EBV | EBNA-4 | 416-424 | IVTDFSVIK | (SEQ. ID NO.:78) | HLA-A*1101 |
| EBV | EBNA-4 | 399-408 | AVFDRKSDAK | (SEQ. ID NO.:79) | HLA-A*0201 |
| EBV | EBNA-3 | 246-253 | RYSIFFDY | (SEQ. ID NO.:80) | HLA-A24 |
| EBV | EBNA-6 | 881-889 | QPRAPIRPI | (SEQ. ID NO.:81) | HLA-B7 |
| EBV | EBNA-3 | 379-387 | RPPIFIRRI. | (SEQ. ID NO.:82) | HLA-B7 |
| EBV | EBNA-1 | 426-434 | EPDVPPGAI | (SEQ. ID NO.:83) | HLA-B7 |
| EBV | EBNA-1 | 228-236 | IPQCRLTPL | (SEQ. ID NO.:84) | HLA-B7 |
| EBV | EBNA-1 | 546-554 | GPGPQPGPL | (SEQ. ID NO.:85) | HLA-B7 |
| EBV | EBNA-1 | 550-558 | QPGPLRESI | (SEQ. ID NO.:86) | HLA-B7 |
| EBV | EBNA-1 | 72-80 | R.PQKRPSCI | (SEQ. ID NO.:87) | HLA-B7 |
| EBV | EBNA-2 | 224-232 | PPTPLLTVL | (SEQ. ID NO.:88) | HLA-B7 |
| EBV | EBNA-2 | 241-249 | TPSPPRMHL | (SEQ. ID NO.:89) | HLA-B7 |
| EBV | EBNA-2 | 244-252 | PPRMHLPVL | (SEQ. ID NO.:90) | HLA-B7 |
| EBV | EBNA-2 | 254-262 | VPDQSMIHPL | (SEQ. ID NO.:91) | HLA-B7 |
| EBV | EBNA-2 | 446-454 | PPSIDPADL | (SEQ. ID NO.:92) | HLA-B7 |
| EBV | BZLFI | 44-52 | LPCVLWPVL | (SEQ. ID NO.:93) | HLA-B7 |
| EBV | BZLF1 | 222-231 | CPSLDVDSII | (SEQ. ID NO.:94) | HLA-B7 |
| EBV | BZLFI | 234-242 | TPDVLHEDL | (SEQ. ID NO.:95) | HLA-B7 |
| EBV | EBNA-3 | 339-347 | FLRGRAYGL | (SEQ. ID NO.:96) | HLA-B8 |
| EBV | EBNA-3 | 26-34 | QAKWRLQTL | (SEQ. ID NO.:97) | HLA-B8 |
| EBV | EBNA-3 | 325-333 | AYPLHEQHG | (SEQ. ID NO.:98) | HLA-B8 |
| EBV | EBNA-3 | 158-166 | YlKSFVSDA | (SEQ. ID NO.:99) | HLA-B8 |
| EBV | LMP-2 | 236-244 | RRRWRRLTV | (SEQ. ID NO.:100) | HLA-B*2704 |
| EBV | EBNA-6 | 258-266 | RRIYDLIEL | (SEQ. ID NO.:101) | HLA-B*2705 |
| EBV | EBNA-3 | 458-466 | YPLHEQHGM | (SEQ. ID NO.:102) | HLA-B*3501 |
| EBV | EBNA-3 | 458-466 | YPLHEQHGM | (SEQ. ID NO.:103) | HLA-B*3503 |
| HCV | NS3 | 389-397 | HSKKKCDEL | (SEQ. ID NO.:104) | HLA-B8 |
| HCV | env E | 44-51 | ASRCWVAM | (SEQ. ID NO.:105) | HLA-B*3501 |
| HCV | core protein | 27-35 | GQIVGGVYL | (SEQ. ID NO.:106) | HLA-B*40012 |
| HCV | NSI | 77-85 | PPLTDFDQGW | (SEQ. ID NO.:107) | HLA-B*5301 |
| HCV | core protein | 18-27 | LMGYIPLVGA | (SEQ. ID NO.:108) | H2-Dd |
| HCV | core protein | 16-25 | ADLMGYIPLV | (SEQ. ID NO.:109) | H2-Dd |
| HCV | NS5 | 409-424 | MSYSWTGALVTPCAEE | (SEQ. ID NO.:110) | H2-Dd |
| HCV | NS1 | 205-213 | KHPDATYSR | (SEQ. ID NO.:111) | Papa-A06 |
| HCV-1 | NS3 | 400-409 | KLVALGINAV | (SEQ. ID NO.:112) | HLA-A*0201 |
| HCV-1 | NS3 | 440-448 | GDFDSVIDC | (SEQ. ID NO.:113) | Patr-B16 |

TABLE 4-continued

| Virus | Protein | AA Position | T cell epitope MHC ligand (Antigen) | | MHC molecule |
|---|---|---|---|---|---|
| HCV-1 | env E | 118-126 | GNASRCWVA | (SEQ. ID NO.:114) | Patr-BI6 |
| HCV-1 | NSI | 159-167 | TRPPLGNWF | (SEQ. ID NO.:115) | Patr-B13 |
| HCV-1 | NS3 | 351-359 | VPHPNIEEV | (SEQ. ID NO.:116) | Patr-B13 |
| HCV-1 | NS3 | 438-446 | YTGDFDSVI | (SEQ. ID NO.:117) | Patr-B01 |
| HCV-1 | NS4 | 328-335 | SWAIKWEY | (SEQ. ID NO.:118) | Patr-A1 1 |
| HCV-1 | NSI | 205-213 | KHPDATYSR | (SEQ. ID NO.:119) | Patr-A04 |
| HCV-1 | NS3 | 440-448 | GDFDSVIDC | (SEQ. ID NO.:120) | Patr-A04 |
| HIV | gp41 | 583-591 | RYLKDQQLL | (SEQ. ID NO.:121) | HLA_A24 |
| HIV | gagp24 | 267-275 | IVGLNKLVR | (SEQ. ID NO.:122) | HLA-A*3302 |
| HIV | gagp24 | 262-270 | EIYKRWIIL | (SEQ. ID NO.:123) | HLA-B8 |
| HIV | gagp24 | 261-269 | GElYKRWI1 | (SEQ. ID NO.:124) | HLA-B8 |
| HIV | gagp17 | 93-101 | EIKDTKEAL | (SEQ. ID NO.:125) | HLA-B8 |
| HIV | gp41 | 586-593 | YLKDQQLL | (SEQ. ID NO.:126) | HLA-B8 |
| HIV | gagp24 | 267-277 | ILGLNKIVRMY | (SEQ. ID NO.:127) | HLA-B*1501 |
| HIV | gp41 | 584-592 | ERYLKDQQL | (SEQ. ID NO.:128) | HLA-B14 |
| HIV | nef | 115-125 | YHTQGYFPQWQ | (SEQ. ID NO.:129) | HLA-B17 |
| HIV | nef | 117-128 | TQGYFPQWQNYT | (SEQ. ID NO.:130) | HLA-B17 |
| HIV | gp120 | 314-322 | GRAFVT1GK | (SEQ. ID NO.:131) | HLA-B*2705 |
| HIV | gagp24 | 263-271 | KRWIILGLN | (SEQ. ID NO.:132) | HLA-B*2702 |
| HIV | nef | 72-82 | QVPLRPMTYK | (SEQ. ID NO.:133) | HLA-B*3501 |
| HIV | nef | 117-125 | TQGYFPQWQ | (SEQ. ID NO.:134) | HLA-B*3701 |
| HIV | gagp24 | 143-151 | HQAISPRTI, | (SEQ. ID NO.:135) | HLA-Cw*0301 |
| HIV | gagp24 | 140-151 | QMVHQAISPRTL | (SEQ. ID NO.:136) | HLA-Cw*0301 |
| HIV | gp120 | 431-440 | MYAPPIGGQI | (SEQ. ID NO.:137) | H2-Kd |
| HIV | gp160 | 318-327 | RGPGRAFVTI | (SEQ. ID NO.:138) | H2-Dd |
| HIV | gp120 | 17-29 | MPGRAFVTI | (SEQ. ID NO.:139) | H2-Ld |
| HIV-1 | RT | 476-484 | ILKEPVHGV | (SEQ. ID NO.:140) | HLA-A*0201 |
| HIV-1 | nef | 190-198 | AFHHVAREL | (SEQ. ID NO.:141) | HLA-A*0201 |
| HIV-1 | gpI60 | 120-128 | KLTPLCVTL | (SEQ. ID NO.:142) | HLA-A*0201 |
| HIV-1 | gp]60 | 814-823 | SLLNATDIAV | (SEQ. ID NO.:143) | HLA-A*0201 |
| HIV-1 | RT | 179-187 | VIYQYMDDL | (SEQ. ID NO.:144) | HLA-A*0201 |
| HIV-1 | gagp17 | 77-85 | SLYNTVATL | (SEQ. ID NO.:145) | HLA-A*0201 |
| HIV-1 | gp160 | 315-329 | RGPGRAFVT1 | (SEQ. ID NO.:146) | HLA-A*0201 |
| HIV-1 | gp41 | 768-778 | RLRDLLLIVTR | (SEQ. ID NO.:147) | HLA-A3 |
| HIV-1 | nef | 73-82 | QVPLRPMTYK | (SEQ. ID NO.:148) | HLA-A3 |
| HIV-1 | gp120 | 36-45 | TVYYGVPVWK | (SEQ. ID NO.:149) | HLA-A3 |
| HIV-1 | gagp17 | 20-29 | RLRPGGKKK | (SEQ. ID NO.:150) | HLA-A3 |
| HIV-1 | gp120 | 38-46 | VYYGVPVWK | (SEQ. ID NO.:151) | HLA-A3 |

TABLE 4-continued

| Virus | Protein | AA Position | T cell epitope MHC ligand (Antigen) | | MHC molecule |
|---|---|---|---|---|---|
| HIV-1 | nef | 74-82 | VPLRPMTYK | (SEQ. ID NO.:152) | HLA-a*1101 |
| HIV-1 | gagp24 | 325-333 | AIFQSSMTK | (SEQ. ID NO.:153) | HLA-A*1101 |
| HIV-1 | nef | 73-82 | QVPLRPMTYK | (SEQ. ID NO.:154) | HLA-A*1101 |
| HIV-1 | nef | 83-94 | AAVDLSHFLKEK | (SEQ. ID NO.:155) | HLA-A*1101 |
| HIV-1 | gagp24 | 349-359 | ACQGVGGPGGHK | (SEQ. ID NO.:156) | HLA-A*1101 |
| HIV-1 | gagp24 | 203-212 | ETINEEAAEW | (SEQ. ID NO.:157) | HLA-A25 |
| HIV-1 | nef | 128-137 | TPGPGVRYPL | (SEQ. ID NO.:158) | HLA-B7 |
| HIV-1 | gagp17 | 24-31 | GGKKKYKL | (SEQ. ID NO.:159) | HLA-B8 |
| HIV-1 | gp120 | 2-10 | RVKEKYQHL | (SEQ. ID NO.:160) | HLA-B8 |
| HIV-1 | gagp24 | 298-306 | DRFYKTLRA | (SEQ. ID NO.:161) | HLA-B14 |
| HIV-1 | NEF | 132-147 | GVRYPLTFGWCYKLVP | (SEQ. ID NO.:162) | HLA-B18 |
| HIV-1 | gagp24 | 265-24 | KRWIILGLNK | (SEQ. ID NO.:163) | HLA-B*2705 |
| HIV-1 | nef | 190-198 | AFHHVAREL | (SEQ. ID NO.:164) | HLA-B*5201 |
| EBV | EBNA-6 | 335-343 | KEHVIQNALF | (SEQ. ID NO.:165) | HLA-B44 |
| EBV | EBNA-6 | 130-139 | EENLLDFVRF | (SEQ. ID NO.:166) | HLA-B*4403 |
| EBV | EBNA-2 | 42-51 | DTPLIPLTIF | (SEQ. ID NO.:167) | HLA-B51 |
| EBV | EBNA-6 | 213-222 | QNGALAINTF | (SEQ. ID NO.:168) | HLA-1362 |
| EBV | EBNA-3 | 603-611 | RLRAEAGVK | (SEQ. ID NO.:169) | HLA-A3 |
| HBV | sAg | 348-357 | GLSPTVWLSV | (SEQ. ID NO.:170) | HLA-A*0201 |
| HBV | SAg | 335-343 | WLSLLVPFV | (SEQ. ID NO.:171) | HLA-A*0201 |
| HBV | cAg | 18-27 | FLPSDFFPSV | (SEQ. ID NO.:172) | HLA-A*0201 |
| HBV | cAg | 18-27 | FLPSDFFPSV | (SEQ. ID NO.:173) | HLA-A*0202 |
| HBV | cAg | 18-27 | FLPSDFFPSV | (SEQ. ID NO.:174) | HLA-A*0205 |
| HBV | cAg | 18-27 | FLPSDFFPSV | (SEQ. ID NO.:175) | HLA-A*0206 |
| HBV | pol | 575-583 | FLLSLGIHL | (SEQ. ID NO.:176) | HLA-A*0201 |
| HBV | pol | 816-824 | SLYADSPSV | (SEQ. ID NO.:177) | HLA-A*0201 |
| HBV | pol | 455-463 | GLSRYVARL | (SEQ. ID NO.:178) | HLA-A*0201 |
| HBV | env | 338-347 | LLVPFVQWFV | (SEQ. ID NO.:179) | HLA-A*0201 |
| HBV | pol | 642-650 | ALMPLYACI | (SEQ. ID NO.:180) | HLA-A*0201 |
| HBV | env | 378-387 | LLPIFFCLWV | (SEQ. ID NO.:181) | HLA-A*0201 |
| HBV | pol | 538-546 | YMDDVVLGA | (SEQ. ID NO.:182) | HLA-A*0201 |
| HBV | env | 250-258 | LLLCLIFLL | (SEQ. ID NO.:183) | HLA-A*0201 |
| HBV | env | 260-269 | LLDYQGMLPV | (SEQ. ID NO.:184) | HLA-A*0201 |
| HBV | env | 370-379 | SIVSPFIPLL | (SEQ. ID NO.:185) | HLA-A*0201 |
| HBV | env | 183-191 | FLLTRILTI | (SEQ. ID NO.:186) | HLA-A*0201 |
| HBV | cAg | 88-96 | YVNYNMGLK | (SEQ. ID NO.:187) | HLA-A*1101 |
| HBV | cAg | 141-151 | STLPETTVVRR | (SEQ. ID NO.:188) | HLA-A*3101 |
| HBV | cAg | 141-151 | STLPETTVVRR | (SEQ. ID NO.:189) | HLA-A*6801 |
| HBV | cAg | 18-27 | FLPSDFFPSV | (SEQ. ID NO.:190) | HLA-A*6801 |

TABLE 4-continued

| Virus | Protein | AA Position | T cell epitope MHC ligand (Antigen) | | MHC molecule |
|---|---|---|---|---|---|
| HBV | sAg | 28-39 | IPQSLDSWWTSL | (SEQ. ID NO.:191) | H2-Ld |
| HBV | cAg | 93-100 | MGLKFRQL | (SEQ. ID NO.:192) | H2-Kb |
| HBV | preS | 141-149 | STBXQSGXQ | (SEQ. ID NO.:193) | HLA-A*0201 |
| HCMV | gp B | 618-628 | FIAGNSAYEYV | (SEQ. ID NO.:194) | HLA-A*0201 |
| HCMV | E1 | 978-989 | SDEEFAIVAYTL | (SEQ. ID NO.:195) | HLA-B18 |
| HCMV | pp65 | 397-411 | DDVWTSGSDSDEELV | (SEQ. ID NO.:196) | HLA-b35 |
| HCMV | pp65 | 123-131 | IPSINVKHY | (SEQ. ID NO.:197) | HLA-B*3501 |
| HCMV | pp65 | 495-504 | NLVPMVATVO | (SEQ. ID NO.:198) | HLA-A*0201 |
| HCMV | pp65 | 415-429 | RKTPRVTOGGAMAGA | (SEQ. ID NO.:199) | HLA-B7 |
| HCV | MP | 17-25 | DLMGYIPLV | (SEQ. ID NO.:200) | HLA-A*0201 |
| HCV | MP | 63-72 | LLALLSCLTV | (SEQ. ID NO.:201) | HLA-A*0201 |
| HCV | MP | 105-112 | ILHTPGCV | (SEQ. ID NO.:202) | HLA-A*0201 |
| HCV | env E | 66-75 | QLRRHIDLLV | (SEQ. ID NO.:203) | HLA-A*0201 |
| HCV | env E | 88-96 | DLCGSVFLV | (SEQ. ID NO.:204) | HLA-A*0201 |
| HCV | env E | 172-180 | SMVGNWAKV | (SEQ. ID NO.:205) | HLA-A*0201 |
| HCV | NSI | 308-316 | HLIIQNIVDV | (SEQ. ID NO.:206) | HLA-A*0201 |
| HCV | NSI | 340-348 | FLLLADARV | (SEQ. ID NO.:207) | HLA-A*0201 |
| HCV | NS2 | 234-246 | GLRDLAVAVEPVV | (SEQ. ID NO.:208) | HLA-A*0201 |
| HCV | NSI | 18-28 | SLLAPGAKQNV | (SEQ. ID NO.:209) | HLA-A*0201 |
| HCV | NSI | 19-28 | LLAPGAKQNV | (SEQ. ID NO.:210) | HLA-A*0201 |
| HCV | NS4 | 192-201 | LLFNILGGWV | (SEQ. ID NO.:211) | HLA-A*0201 |
| HCV | NS3 | 579-587 | YLVAYQATV | (SEQ. ID NO.:212) | HLA-A*0201 |
| HCV | core protein | 34-43 | YLLPRRGPRL | (SEQ. ID NO.:213) | HLA-A*0201 |
| HCV | MP | 63-72 | LLALLSCLTI | (SEQ. ID NO.:214) | HLA-A*0201 |
| HCV | NS4 | 174-182 | SLMAFTAAV | (SEQ. ID NO.:215) | HLA-A*0201 |
| HCV | NS3 | 67-75 | CINGVCWTV | (SEQ. ID NO.:216) | HLA-A*0201 |
| HCV | NS3 | 163-171 | LLCPAGHAV | (SEQ. ID NO.:217) | HLA-A*0201 |
| HCV | NS5 | 239-247 | ILDSFDPLV | (SEQ. ID NO.:218) | HLA-A*0201 |
| HCV | NS4A | 236-244 | IAGYGAGV | (SEQ. ID NO.:219) | HLA-A*0201 |
| HCV | NS5 | 714-722 | GLQDCTMLV | (SEQ. ID NO.:220) | HLA-A*0201 |
| HCV | NS3 | 281-290 | TGAPVTYSTY | (SEQ. ID NO.:221) | HLA-A*0201 |
| HCV | NS4A | 149-157 | HMWNFISGI | (SEQ. ID NO.:222) | HLA-A*0201 |
| HCV | NS5 | 575-583 | RVCEKMALY | (SEQ. ID NO.:223) | HLA-A*0201-A3 |
| HCV | NS1 | 238-246 | TINYTIFK | (SEQ. ID NO.:224) | HLA-A*1101 |
| HCV | NS2 | 109-116 | YISWCLWW | (SEQ. ID NO.:225) | HLA-A23 |
| HCV | core protein | 40-48 | GPRLGVRAT | (SEQ. ID NO.:226) | HLA-B7 |
| HIV-1 | gp120 | 380-388 | SFNCGGEFF | (SEQ. ID NO.:227) | HLA-Cw*0401 |

TABLE 4-continued

| Virus | Protein | AA Position | T cell epitope MHC ligand (Antigen) | | MHC molecule |
|---|---|---|---|---|---|
| HIV-1 | RT | 206-214 | TEMEKEGKI | (SEQ. ID NO.:228) | H2-Kk |
| HIV-1 | p17 | 18-26 | KIRLRPGGK | (SEQ. ID NO.:229) | HLA-A*031 |
| HIV-1 | P17 | 20-29 | RLRPGGKKKY | (SEQ. ID NO.:230) | HLA-A*0301 |
| HIV-1 | RT | 325-333 | AIFQSSMTK | (SEQ. ID NO.:231) | HLA-A*0301 |
| HIV-1 | p17 | 84-92 | TLYCVHQRI | (SEQ. ID NO.:232) | HLA-A11 |
| HIV-1 | RT | 508-517 | IYQEPFKNLK | (SEQ. ID NO.:233) | HLA-A11 |
| HIV-1 | p17 | 28-36 | KYKLKHIVW | (SEQ. ID NO.:234) | HLA-A24 |
| HIV-1 | gp120 | 53-62 | LFCASDAKAY | (SEQ. ID NO.:235) | HLA-A24 |
| HIV-1 | gagp24 | 145-155 | QAISPRTLNAW | (SEQ. ID NO.:236) | HLA-A25 |
| HIV-1 | gagp24 | 167-175 | EVIPMFSAL | (SEQ. ID NO.:237) | HLA-A26 |
| HIV-1 | RT | 593-603 | ETFYVDGAANR | (SEQ. ID NO.:238) | HLA-A26 |
| HIV-1 | gp41 | 775-785 | RLRDLLLIVTR | (SEQ. ID NO.:239) | HLA-A31 |
| HIV-1 | RT | 559-568 | PIQKETWETW | (SEQ. ID NO.:240) | HLA-A32 |
| HIV-1 | gp120 | 419-427 | RIKQIINMW | (SEQ. ID NO.:241) | HLA-A32 |
| HIV-1 | RT | 71-79 | ITLWQRPLV | (SEQ. ID NO.:242) | HLA-A*6802 |
| HIV-1 | RT | 85-93 | DTVLEEMNL | (SEQ. ID NO.:243) | HLA-A*6802 |
| HIV-1 | RT | 71-79 | ITLWQRPLV | (SEQ. ID NO.:244) | HLA-A*7401 |
| HIV-1 | gag p24 | 148-156 | SPRTLNAWV | (SEQ. ID NO.:245) | HLA-B7 |
| HIV-1 | gagp24 | 179-187 | ATPQDLNTM | (SEQ. ID NO.:246) | HLA-B7 |
| HIV-1 | gp120 | 303-312 | RPNNNTRKSI | (SEQ. ID NO.:247) | HLA-B7 |
| HIV-1 | gp41 | 843-851 | IPRRIRQGL | (SEQ. ID NO.:248) | HLA-B7 |
| HIV-1 | p17 | 74-82 | ELRSLYNTV | (SEQ. ID NO.:249) | HLA-B8 |
| HIV-1 | nef | 13-20 | WPTVRERM | (SEQ. ID NO.:250) | HLA-B8 |
| HIV-1 | nef | 90-97 | FLKEKGGL | (SEQ. ID NO.:251) | HLA-B8 |
| HIV-1 | gag p24 | 183-191 | DLNTMLNTV | (SEQ. ID NO.:252) | HLA-B14 |
| HIV-1 | P17 | 18-27 | KIRLRPGGKK | (SEQ. ID NO.:253) | HLA-B27 |
| HIV-1 | p17 | 19-27 | IRLRPGGKK | (SEQ. ID NO.:254) | HLA-B27 |
| HIV-1 | gp41 | 791-799 | GRRGWEALKY | (SEQ. ID NO.:255) | HLA-B27 |
| HIV-1 | nef | 73-82 | QVPLRPMTYK | (SEQ. ID NO.:256) | HLA-B27 |
| HIV-1 | GP41 | 590-597 | RYLKDQQL | (SEQ. ID NO.:257) | HLA-B27 |
| HIV-1 | nef | 105-114 | RRQDILDLWI | (SEQ. ID NO.:258) | HLA-B*2705 |
| HIV-1 | nef | 134-141 | RYPLTFGW | (SEQ. ID NO.:259) | HLA-B*2705 |
| HIV-1 | p17 | 36-44 | WASRLELERF | (SEQ. ID NO.:260) | HLA-B35 |
| HIV-1 | GAG P24 | 262-270 | TVLDVGDAY | (SEQ. ID NO.:261) | HLA-B35 |
| HIV-1 | gp120 | 42-52 | VPVWKEATTTL | (SEQ. ID NO.:262) | HLA-B35 |
| HIV-1 | P17 | 36-44 | NSSKVSQNY | (SEQ. ID NO.:263) | HLA-B35 |
| HIV-1 | gag p24 | 254-262 | PPIPVGDIY | (SEQ. ID NO.:264) | HLA-B35 |
| HIV-1 | RT | 342-350 | HPDIVIYQY | (SEQ. ID NO.:265) | HLA-B35 |
| HIV-1 | gp41 | 611-619 | TAVPWNASW | (SEQ. ID NO.:266) | HLA-B35 |

TABLE 4-continued

| Virus | Protein | AA Position | T cell epitope MHC ligand (Antigen) | | MHC molecule |
|---|---|---|---|---|---|
| HIV-1 | gag | 245-253 | NPVPVGN1Y | (SEQ. ID NO.:267) | HLA-B35 |
| HIV-1 | nef | 120-128 | YFPDWQNYT | (SEQ. ID NO.:268) | HLA-B37 |
| HIV-1 | gag p24 | 193-201 | GHQAAMQML | (SEQ. ID NO.:269) | HLA-B42 |
| HIV-1 | p17 | 20-29 | RLRPGGKKKY | (SEQ. ID NO.:270) | HLA-B42 |
| HIV-1 | RT | 438-446 | YPGIKVRQL | (SEQ. ID NO.:271) | HLA-B42 |
| HIV-1 | RT | 591-600 | GAETFYVDGA | (SEQ. ID NO.:272) | HLA-B45 |
| HIV-1 | gag p24 | 325-333 | NANPDCKTI | (SEQ. ID NO.:273) | HLA-B51 |
| HIV-1 | gag p24 | 275-282 | RMYSPTSI | (SEQ. ID NO.:274) | HLA-B52 |
| HIV-1 | gp120 | 42-51 | VPVWKEATTT | (SEQ. ID NO.:275) | HLA-B*5501 |
| HIV-1 | gag p24 | 147-155 | ISPRTLNAW | (SEQ. ID NO.:276) | HLA-B57 |
| HIV-1 | gag p24 | 240-249 | TSTLQEQIGW | (SEQ. ID NO.:277) | HLA-B57 |
| HIV-1 | gag p24 | 162-172 | KAFSPEVIPMF | (SEQ. ID NO.:278) | HLA-B57 |
| HIV-1 | gagp24 | 311-319 | QASQEVKNW | (SEQ. ID NO.:279) | HLA-B57 |
| HIV-1 | gagp24 | 311-319 | QASQDVKNW | (SEQ. ID NO.:280) | HLA-B57 |
| HIV-1 | nef | 116-125 | HTQGYFPDWQ | (SEQ. ID NO.:281) | HLA-B57 |
| HIV-1 | nef | 120-128 | YFPDWQNYT | (SEQ. ID NO.:282) | HLA-B57 |
| HIV-1 | gag p24 | 240-249 | TSTLQEQIGW | (SEQ. ID NO.:283) | HLA-B58 |
| HIV-1 | p17 | 20-29 | RLRPGGKKKY | (SEQ. ID NO.:284) | HLA-B62 |
| HIV-1 | p24 | 268-277 | LGLNKJVRMY | (SEQ. ID NO.:285) | HLA-B62 |
| HIV-1 | RT | 415-426 | LVGKLNWASQIY | (SEQ. ID NO.:286) | HLA-B62 |
| HIV-1 | RT | 476-485 | ILKEPVHGVY | (SEQ. ID NO.:287) | HLA-B62 |
| HIV-1 | nef | 117-127 | TQGYFPDWQNY | (SEQ. ID NO.:288) | HLA-B62 |
| HIV-1 | nef | 84-91 | AVDLSHFL | (SEQ. ID NO.:289) | HLA-B62 |
| HIV-1 | gag p24 | 168-175 | VIPMIFSAL | (SEQ. ID NO.:290) | HLA-Cw*0102 |
| HIV-1 | gp120 | 376-384 | FNCGGEFFY | (SEQ. ID NO.:291) | HLA-A29 |
| HIV-1 | gp120 | 375-383 | SFNCGGEFF | (SEQ. ID NO.:292) | HLA-B15 |
| HIV-1 | nef | 136-145 | PLTFGWCYKL | (SEQ. ID NO.:293) | HLA-A*0201 |
| HIV-1 | nef | 180-189 | VLEWRFDSRL | (SEQ. ID NO.:294) | HLA-A*0201 |
| HIV-1 | nef | 68-77 | FPVTPQVPLR | (SEQ. ID NO.:295) | HLA-B7 |
| HIV-1 | nef | 128-137 | TPGPGVRYPL | (SEQ. ID NO.:296) | HLA-B7 |
| HIV-1 | gag p24 | 308-316 | QASQEVKNW | (SEQ. ID NO.:297) | HLA-Cw*0401 |
| HIV-1 IIIB | RT | 273-282 | VPLDEDFRKY | (SEQ. ID NO.:298) | HLA-B35 |
| HIV-1 IIIB | RT | 25-33 | NPDIVIYQY | (SEQ. ID NO.:299) | HLA-B35 |
| HIV-1 IIIB | gp41 | 557-565 | RAIEAQAHL | (SEQ. ID NO.:300) | HLA-B51 |
| HIV-1 IIIB | RT | 231-238 | TAFTIPSI | (SEQ. ID NO.:301) | HLA-B51 |
| HIV-1 IIIB | p24 | 215-223 | VHPVHAGPIA | (SEQ. ID NO.:302) | HLA-B*5501 |
| HIV-1 IIIB | gp120 | 156-165 | NCSFNISTSI | (SEQ. ID NO.:303) | HLA-Cw8 |
| HIV-1 IIIB | gp120 | 241-249 | CTNVSTVQC | (SEQ. ID NO.:304) | HLA-Cw8 |

TABLE 4-continued

| Virus | Protein | AA Position | T cell epitope MHC ligand (Antigen) | | MHC molecule |
|---|---|---|---|---|---|
| HIV-1 5F2 | gp120 | 312-320 | IGPGRAFHT | (SEQ. ID NO.:305) | H2-Dd |
| HIV-1 5F2 | pol | 25-33 | NPDIVIYQY | (SEQ. ID NO.:306) | HLA-B*3501 |
| HIV-1 5F2 | pol | 432-441 | EPIVGAETFY | (SEQ. ID NO.:307) | HLA-B*3501 |
| HIV-1 5F2 | pol | 432-440 | EPIVGAETF | (SEQ. ID NO.:308) | HLA-B*3501 |
| HIV-1 5F2 | pol | 6-14 | SPAIFQSSM | (SEQ. ID NO.:309) | HLA-B*3501 |
| HIV-1 5F2 | pol | 59-68 | VPLDKDFRKY | (SEQ. ID NO.:310) | HLA-B*3501 |
| HIV-1 5F2 | pol | 6-14 | IPLTEEAEL | (SEQ. ID NO.:311) | HLA-B*3501 |
| HIV-1 5F2 | nef | 69-79 | RPQVPLRPMTY | (SEQ. ID NO.:312) | HLA-B*3501 |
| HIV-1 5F2 | nef | 66-74 | FPVRPQVPL | (SEQ. ID NO.:313) | HLA-B*3501 |
| HIV-1 5F2 | env | 10-18 | DPNPQEVVL | (SEQ. ID NO.:314) | HLA-B*3501 |
| HIV-1 5F2 | env | 7-15 | RPIVSTQLL | (SEQ. ID NO.:315) | HLA-B*3501 |
| HIV-1 5F2 | pol | 6-14 | IPLTEEAEL | (SEQ. ID NO.:316) | HLA-B51 |
| HIV-1 5F2 | env | 10-18 | DPNPQEVVL | (SEQ. ID NO.:317) | HLA-B51 |
| HIV-1 5F2 | gagp24 | 199-207 | AMQMLKETI | (SEQ. ID NO.:318) | H2-Kd |
| HIV-2 | gagp24 | 182-190 | TPYDrNQML | (SEQ. ID NO.:319) | HLA-B*5301 |
| HIV-2 | gag | 260-269 | RRWIQLGLQKV | (SEQ. ID NO.:320) | HLA-B*2703 |
| HIV-1 5F2 | gp41 | 593-607 | GIWGCSGKLICTTAV | (SEQ. ID NO.:321) | HLA-B17 |
| HIV-1 5F2 | gp41 | 753-767 | ALIWEDLRSLCLFSY | (SEQ. ID NO.:322) | HLA-B22 |
| HPV 6b | E7 | 21-30 | GLHCYEQLV | (SEQ. ID NO.:323) | HLA-A*0201 |
| HPV 6b | E7 | 47-55 | PLKQHFQIV | (SEQ. ID NO.:324) | HLA-A*0201 |
| HPV11 | E7 | 4-12 | RLVTLKDIV | (SEQ. ID NO.:325) | HLA-A*0201 |
| HPV16 | E7 | 86-94 | TLGIVCPIC | (SEQ. ID NO.:326) | HLA-A*0201 |
| HPV16 | E7 | 85-93 | GTLGIVCPI | (SEQ. ID NO.:327) | HLA-A*0201 |
| HPV16 | E7 | 12-20 | MLDLQPETT | (SEQ. ID NO.:328) | HLA-A*0201 |
| HPV16 | E7 | 11-20 | YMLDLQPETT | (SEQ. ID NO.:329) | HLA-A*0201 |
| HPV16 | E6 | 15-22 | RPRKLPQL | (SEQ. ID NO.:330) | HLA-B7 |
| HPV16 | E6 | 49-57 | RAHYNIVTF | (SEQ. ID NO.:331) | HLA-Db |
| HSV | gp B | 498-505 | SSIEFARL | (SEQ. ID NO.:332) | H2-Kb |
| HSV-1 | gp C | 480-488 | GIGIGVLAA | (SEQ. ID NO.:333) | HLA-A*0201 |
| HSV-1 | ICP27 | 448-456 | DYATLGVGV | (SEQ. ID NO.:334) | H2-Kd |
| HSV-1 | ICP27 | 322-332 | LYRTFAGNPRA | (SEQ. ID NO.:335) | H2-Kd |
| HSV-1 | UL39 | 822-829 | QTFDFGRL | (SEQ. ID NO.:336) | H2-Kb |
| HSV-2 | gpC | 446-454 | GAGIGVAVL | (SEQ. ID NO.:337) | HLA-A*0201 |
| HLTV-1 | TAX | 11-19 | LLFGYPVYV | (SEQ. ID NO.:338) | HLA-A*0201 |
| Influenza | MP | 58-66 | GILGFVFTL | (SEQ. ID NO.:339) | HLA-A*0201 |
| Influenza | MP | 59-68 | ILGFVFTLTV | (SEQ. ID NO.:340) | HLA-A*0201 |
| Influenza | NP | 265-273 | ILRGSVAHK | (SEQ. ID NO.:341) | HLA-A3 |
| Influenza | NP | 91-99 | KTGGPIYKR | (SEQ. ID NO.:342) | HLA-A*6801 |
| Influenza | NP | 380-388 | ELRSRYWAI | (SEQ. ID NO.:343) | HLA-B8 |

TABLE 4-continued

| Virus | Protein | AA Position | T cell epitope MHC ligand (Antigen) | | MHC molecule |
|---|---|---|---|---|---|
| Influenza | NP | 381-388 | LRSRYWAI | (SEQ. ID NO.:344) | HLA-B*2702 |
| Influenza | NP | 339-347 | EDLRVLSFI | (SEQ. ID NO.:345) | HLA-B*3701 |
| Influenza | NSI | 158-166 | GEISPLPSL | (SEQ. ID NO.:346) | HLA-B44 |
| Influenza | NP | 338-346 | FEDLRVLSF | (SEQ. ID NO.:347) | HLA-B44 |
| Influenza | NSI | 158-166 | GEISPLPSL | (SEQ. ID NO.:348) | HLA-B*4402 |
| Influenza | NP | 338-346 | FEDLRVLSF | (SEQ. ID NO.:349) | HLA-B*4402 |
| Influenza | PBI | 591-599 | VSDGGPKLY | (SEQ. ID NO.:350) | HLA-A1 |
| Influenza A | NP | 44-52 | CTELKLSDY | (SEQ. ID NO.:351) | HLA-A1 |
| Influenza | NSI | 122-130 | AIMDKNIIL | (SEQ. ID NO.:352) | HLA-A*0201 |
| Influenza A | NSI | 123-132 | IMDKNIILKA | (SEQ. ID NO.:353) | HLA-A*0201 |
| Influenza A | NP | 383-391 | SRYWAIRTR | (SEQ. ID NO.:354) | HLA-B*2705 |
| Influenza A | NP | 147-155 | TYQRTRALV | (SEQ. ID NO.:355) | H2-Kd |
| Influenza A | HA | 210-219 | TYVSVSTSTL | (SEQ. ID NO.:356) | H2-Kd |
| Influenza A | HA | 518-526 | IYSTVASSL | (SEQ. ID NO.:357) | H2-Kd |
| Influenza A | HA | 259-266 | FEANGNLI | (SEQ. ID NO.:358) | H2-Kk |
| Influenza A | HA | 10-18 | IEGGWTGM1 | (SEQ. ID NO.:359) | H2-Kk |
| Influenza A | NP | 50-57 | SDYEGRLI | (SEQ. ID NO.:360) | H2-Kk |
| Influenza a | NSI | 152-160 | EEGAIVGEI | (SEQ. ID NO.:361) | H2-Kk |
| Influenza A34 | NP | 336-374 | ASNENMETM | (SEQ. ID NO.:362) | H2Db |
| Influenza A68 | NP | 366-374 | ASNENMDAM | (SEQ. ID NO.:363) | H2Db |
| Influenza B | NP | 85-94 | KLGEFYNQMM | (SEQ. ID NO.:364) | HLA-A*0201 |
| Influenza B | NP | 85-94 | KAGEFYNQMM | (SEQ. ID NO.:365) | HLA-A*0201 |
| Influenza JAP | HA | 204-212 | LYQNVGTYV | (SEQ. ID NO.:366) | H2Kd |
| Influenza JAP | HA | 210-219 | TYVSVGTSTL | (SEQ. ID NO.:367) | H2-Kd |
| Influenza JAP | HA | 523-531 | VYQILATYA | (SEQ. ID NO.:368) | H2-Kd |
| Influenza JAP | HA | 529-537 | IYATVAGSL | (SEQ. ID NO.:369) | H2-Kd |
| Influenza JAP | HA | 210-219 | TYVSVGTSTI (L>I) | (SEQ. ID NO.:370) | H2-Kd |
| Influenza JAP | HA | 255-262 | FESTGNLI | (SEQ. ID NO.:371) | H2-Kk |
| JHMV | cAg | 318-326 | APTAGAFFF | (SEQ. ID NO.:372) | H2-Ld |
| LCMV | NP | 118-126 | RPQASGVYM | (SEQ. ID NO.:373) | H2-Ld |
| LCMV | NP | 396-404 | FQPQNGQFI | (SEQ. ID NO.:374) | H2-Db |
| LCMV | GP | 276-286 | SGVENPGGYCL | (SEQ. ID NO.:375) | H2-Db |
| LCMV | GP | 33-42 | KAVYNFATCG | (SEQ. ID NO.:376) | H2-Db |
| MCMV | pp89 | 168-176 | YPHFMPTNL | (SEQ. ID NO.:377) | H2-Ld |
| MHV | spike protein | 510-518 | CLSWNGPHL | (SEQ. ID NO.:378) | H2-Db |
| MMTV | env gp 36 | 474-482 | SFAVATTAL | (SEQ. ID NO.:379) | H2-Kd |
| MMTV | gag p27 | 425-433 | SYETFISRL | (SEQ. ID NO.:380) | H2-Kd |
| MMTV | env gp73 | 544-551 | ANYDFICV | (SEQ. ID NO.:381) | H2-Kb |

TABLE 4-continued

| Virus | Protein | AA Position | T cell epitope MHC ligand (Antigen) | | MHC molecule |
|---|---|---|---|---|---|
| MuLV | env p15E | 574-581 | KSPWFTTL | (SEQ. ID NO.:382) | H2-Kb |
| MuLV | env gp70 | 189-196 | SSWDFITV | (SEQ. ID NO.:383) | H2-Kb |
| MuLV | gag 75K | 75-83 | CCLCLTVFL | (SEQ. ID NO.:384) | H2-Db |
| MuLV | env gp70 | 423-431 | SPSYVYHQF | (SEQ. ID NO.:385) | H2Ld |
| MV | F protein | 437-447 | SRRYPDAVYLH | (SEQ. ID NO.:386) | HLA-B*2705 |
| Mv | F protein | 438-446 | RRYPDAVYL | (SEQ. ID NO.:387) | HLA-B*2705 |
| Mv | NP | 281-289 | YPALGLHEF | (SEQ. ID NO.:388) | H2-Ld |
| Mv | HA | 343-351 | DPVIDRLYL | (SEQ. ID NO.:389) | H2-Ld |
| MV | HA | 544-552 | SPGRSFSYF | (SEQ. ID NO.:390) | H2-Ld |
| Poliovirus | VP1 | 111-118 | TYKDTVQL | (SEQ. ID NO.:391) | H2-kd |
| Poliovirus | VP1 | 208-217 | FYDGFSKVPL | (SEQ. ID NO.:392) | H2-Kd |
| Pseudorabies virus gp | G111 | 455-463 | IAGIGILAI | (SEQ. ID NO.:393) | HLA-A*0201 |
| Rabiesvirus | NS | 197-205 | VEAEIAHQI | (SEQ. ID NO.:394) | H2-Kk |
| Rotavirus | VP7 | 33-40 | llYRFLLl | (SEQ. ID NO.:395) | H2-Kb |
| Rotavirus | VP6 | 376-384 | VGPVFPPGM | (SEQ. ID NO.:396) | H2-Kb |
| Rotavirus | VP3 | 585-593 | YSGYIFRDL | (SEQ. ID NO.:397) | H2-Kb |
| RSV | M2 | 82-90 | SYIGSINNI | (SEQ. ID NO.:398) | H2-Kd |
| SIV | gagp11C | 179-190 | EGCTPYDTNQML | (SEQ. ID NO.:399) | Mamu-A*01 |
| SV | NP | 324-332 | FAPGNYPAL | (SEQ. ID NO.:400) | H2-Db |
| SV | NP | 324-332 | FAPCTNYPAL | (SEQ. ID NO.:401) | H2-Kb |
| SV40 | T | 404-411 | VVYDFLKC | (SEQ. ID NO.:402) | H2-Kb |
| SV40 | T | 206-215 | SAINNYAQKL | (SEQ. ID NO.:403) | H2-Db |
| SV40 | T | 223-231 | CKGVNKEYL | (SEQ. ID NO.:404) | H2-Db |
| SV40 | T | 489-497 | QGINNLDNL | (SEQ. ID NO.:405) | H2-Db |
| SV40 | T | 492-500 (501) | NNLDNLRDY(L) | (SEQ. ID NO.:406) | H2-Db |
| SV40 | T | 560-568 | SEFLLEKRI | (SEQ. ID NO.:407) | H2-Kk |
| VSV | NP | 52-59 | RGYVYQGL | (SEQ. ID NO.:408) | H2-Kb |

TABLE 5

| HLA-A1 | | Position (Antigen) | | Source |
|---|---|---|---|---|
| T cell epitopes | EADPTGHSY | | (SEQ. ID NO.:409) | MAGE-1 161-169 |
| | VSDGGPNLY | | (SEQ. ID NO.:410) | Influenza A PB 1591-599 |
| | CTELKLSDY | | (SEQ. ID NO.:411) | Influenza A NP 44-52 |
| | EVDPIGHLY | | (SEQ. ID NO.:412) | MAGE-3 168-176 |
| HLA-A201 | MLLSVPLLLG | | (SEQ. ID NO.:413) | Calreticulin signal sequence 1-10 |
| | STBXQSGXQ | | (SEQ. ID NO.:414) | HBV PRE-S PROTEIN 141-149 |
| | YMDGTMSQV | | (SEQ. ID NO.:415) | Tyrosinase 369-377 |

TABLE 5-continued

| HLA-A1 | Position (Antigen) | Source |
|---|---|---|
| ILKEPVHGV | (SEQ. ID NO.:416) | HIV-I RT 476-484 |
| LLGFVFTLTV | (SEQ. ID NO.:417) | Influenza MP 59-68 |
| LLFGYPVYVV | (SEQ. ID NO.:418) | HTLV-1 tax 11-19 |
| GLSPTVWLSV | (SEQ. ID NO.:419) | HBV sAg 348-357 |
| WLSLLVPFV | (SEQ. ID NO.:420) | HBV sAg 335-343 |
| FLPSDFFPSV | (SEQ. ID NO.:421) | HBV cAg 18-27 |
| C L G 0 L L T M V | (SEQ. ID NO.:422) | EBV LMP-2 426-434 |
| FLAGNSAYEYV | (SEQ. ID NO.:423) | HCMV gp 618-628B |
| KLGEFYNQMM | (SEQ. ID NO.:424) | Influenza BNP 85-94 |
| KLVALGINAV | (SEQ. ID NO.:425) | HCV-1 NS3 400-409 |
| DLMGYIPLV | (SEQ. ID NO.:426) | HCV MP 17-25 |
| RLVTLKDIV | (SEQ. ID NO.:427) | HPV 11 EZ 4-12 |
| MLLAVLYCL | (SEQ. ID NO.:428) | Tyrosinase 1-9 |
| AAGIGILTV | (SEQ. ID NO.:429) | Melan A\Mart-127-35 |
| YLEPGPVTA | (SEQ. ID NO.:430) | Pmel 17/gp 100 480-488 |
| ILDGTATLRL | (SEQ. ID NO.:431) | Pmel 17/gp 100 457-466 |
| LLDGTATLRL | (SEQ. ID NO.:432) | Pmel gp100 457-466 |
| ITDQVPFSV | (SEQ. ID NO.:433) | Pmel gp 100 209-217 |
| KTWGQYWQV | (SEQ. ID NO.:434) | Pmel gp 100 154-162 |
| TITDQVPFSV | (SEQ. ID NO.:435) | Pmel gp 100 208-217 |
| AFHIIVAREL | (SEQ. ID NO.:436) | HIV-I nef 190-198 |
| YLNKIQNSL | (SEQ. ID NO.:437) | *P. falciparum* CSP 334-342 |
| MMRKLAILSV | (SEQ. ID NO.:438) | *P. falciparum* CSP 1-10 |
| KAGEFYNQMM | (SEQ. ID NO.:439) | Influenza BNP 85-94 |
| NIAEGLRAL | (SEQ. ID NO.:440) | EBNA-1 480-488 |
| NLRRGTALA | (SEQ. ID NO.:441) | EBNA-1 519-527 |
| ALAIPQCRL | (SEQ. ID NO.:442) | EBNA-1 525-533 |
| VLKDAIKDL | (SEQ. ID NO.:443) | EBNA-1 575-582 |
| FMVFLQTHI | (SEQ. ID NO.:444) | EBNA-1 562-570 |
| HLIVDTDSL | (SEQ. ID NO.:445) | EBNA-2 15-23 |
| SLGNPSLSV | (SEQ. ID NO.:446) | EBNA-2 22-30 |
| PLASAMRML | (SEQ. ID NO.:447) | EBNA-2 126-134 |
| RMLWMANYI | (SEQ. ID NO.:448) | EBNA-2 132-140 |
| MLWMANYIV | (SEQ. ID NO.:449) | EBNA-2 133-141 |
| ILPQGPQTA | (SEQ. ID NO.:450) | EBNA-2 151-159 |
| PLRPTAPTTI | (SEQ. ID NO.:451) | EBNA-2 171-179 |
| PLPPATLTV | (SEQ. ID NO.:452) | EBNA-2 205-213 |
| R M H L P V L H V | (SEQ. ID NO.:453) | EBNA-2 246-254 |
| PMPLPPSQL | (SEQ. ID NO.:454) | EBNA-2 287-295 |

TABLE 5-continued

| HLA-A1 | Position (Antigen) | | Source |
|---|---|---|---|
| QLPPPAAPA | (SEQ. ID NO.:455) | EBNA-2 294-302 |
| SMPELSPVL | (SEQ. ID NO.:456) | EBNA-2 381-389 |
| DLDESWDYl | (SEQ. ID NO.:457) | EBNA-2 453-461 |
| P L P C V L W P VV | (SEQ. ID NO.:458) | BZLF1 43-51 |
| SLEECDSEL | (SEQ. ID NO.:459) | BZLF1 167-175 |
| EIKRYKNRV | (SEQ. ID NO.:460) | BZLFI 176-184 |
| QLLQFIYREV | (SEQ. ID NO.:461) | BZLF1 195-203 |
| LLQHYREVA | (SEQ. ID NO.:462) | BZLFI 196-204 |
| LLKQMCPSL | (SEQ. ID NO.:463) | BZLFI 217-225 |
| SIIPRTPDV | (SEQ. ID NO.:464) | BZLFI 229-237 |
| AIMDKNIIL | (SEQ. ID NO.:465) | Influenza A NS1 122-130 |
| IMDKNIILKA | (SEQ. ID NO.:466) | Influenza A NS1 123-132 |
| LLALLSCLTV | (SEQ. ID NO.:467) | HCV MP 63-72 |
| ILHTPGCV | (SEQ. ID NO.:468) | HCV MP 105-112 |
| QLRRHIDLLV | (SEQ. ID NO.:469) | HCV env E 66-75 |
| DLCGSVFLV | (SEQ. ID NO.:470) | HCV env E 88-96 |
| SMVGNWAKV | (SEQ. ID NO.:471) | HCV env E 172-180 |
| HLHQNIVDV | (SEQ. ID NO.:472) | HCV NSI 308-316 |
| FLLLADARV | (SEQ. ID NO.:473) | HCV NSI 340-348 |
| GLRDLAVAVEPVV | (SEQ. ID NO.:474) | HCV NS2 234-246 |
| SLLAPGAKQNV | (SEQ. ID NO.:475) | HCV NS1 18-28 |
| LLAPGAKQNV | (SEQ. ID NO.:476) | HCV NS1 19-28 |
| FLLSLGIHL | (SEQ. ID NO.:477) | HBV pol 575-583 |
| SLYADSPSV | (SEQ. ID NO.:478) | HBV pol 816-824 |
| GLSRYVARL | (SEQ. ID NO.:479) | HBV POL 455-463 |
| KIFGSLAFL | (SEQ. ID NO.:480) | HER-2 369-377 |
| ELVSEFSRM | (SEQ. ID NO.:481) | HER-2 971-979 |
| KLTPLCVTL | (SEQ. ID NO.:482) | HIV-I gp 160 120-128 |
| SLLNATDIAV | (SEQ. ID NO.:483) | HIV-I GP 160 814-823 |
| VLYRYGSFSV | (SEQ. ID NO.:484) | Pmel gp100 476-485 |
| YIGEVLVSV | (SEQ. ID NO.:485) | Non-filament forming class I myosin family (HA-2)** |
| LLFNILGGWV | (SEQ. ID NO.:486) | HCV NS4 192-201 |
| LLVPFVQWFW | (SEQ. ID NO.:487) | HBV env 338-347 |
| ALMPLYACI | (SEQ. ID NO.:488) | HBV pol 642-650 |
| YLVAYQATV | (SEQ. ID NO.:489) | HCV NS3 579-587 |
| TLGIVCPIC | (SEQ. ID NO.:490) | HIPV 16 E7 86-94 |
| YLLPRRGPRL | (SEQ. ID NO.:491) | HCV core protein 34-43 |
| LLPIFFCLWV | (SEQ. ID NO.:492) | HBV env 378-387 |

TABLE 5-continued

| HLA-A1 | Position (Antigen) | Source |
|---|---|---|
| YMDDVVLGA | (SEQ. ID NO.:493) | HBV Pol 538-546 |
| GTLGIVCPI | (SEQ. ID NO.:494) | HPV16 E7 85-93 |
| LLALLSCLTI | (SEQ. ID NO.:495) | HCV MP 63-72 |
| MLDLQPETT | (SEQ. ID NO.:496) | HPV 16 E7 12-20 |
| SLMAFTAAV | (SEQ. ID NO.:497) | HCV NS4 174-182 |
| CINGVCWTV | (SEQ. ID NO.:498) | HCV NS3 67-75 |
| VMNILLQYVV | (SEQ. ID NO.:499) | Glutarnic acid decarboxylase 114-123 |
| ILTVILGVL | (SEQ. ID NO.:500) | Melan A/Mart-32-40 |
| FLWGPRALV | (SEQ. ID NO.:501) | MAGE-3 271-279 |
| L L C P A G H A V | (SEQ. ID NO.:502) | HCV NS3 163-171 |
| ILDSFDPLV | (SEQ. ID NO.:503) | HCV NSS 239-247 |
| LLLCLIFLL | (SEQ. ID NO.:504) | HBV env 250-258 |
| LIDYQGMLPV | (SEQ. ID NO.:505) | HBV env 260-269 |
| SIVSPFIPLL | (SEQ. ID NO.:506) | HBV env 370-379 |
| FLLTRILTI | (SEQ. ID NO.:507) | HBV env 183-191 |
| HLGNVKYLV | (SEQ. ID NO.:508) | *P. faciparum* TRAP 3-11 |
| GIAGGLALL | (SEQ. ID NO.:509) | *P. faciparum* TRAP 500-508 |
| IILAGYGAGV | (SEQ. ID NO.:510) | HCV NS S4A 236-244 |
| GLQDCTMLV | (SEQ. ID NO.:511) | HCV NS5 714-722 |
| TGAPVTYSTY | (SEQ. ID NO.:512) | HCV NS3 281-290 |
| VIYQYMDDLV | (SEQ. ID NO.:513) | HIV-1RT 179-187 |
| VLPDVFIRCV | (SEQ. ID NO.:514) | N-acetylglucosaminyltransferase V Gnt-V intron |
| VLPDVFIRC | (SEQ. ID NO.:515) | N-acetylglucosaminyltransferase V Gnt-V intron |
| AVGIGIAVV | (SEQ. ID NO.:516) | Human CD9 |
| LVVLGLLAV | (SEQ. ID NO.:517) | Human glutamyltransferase |
| ALGLGLLPV | (SEQ. ID NO.:518) | Human G protein coupled receptor 164-172 |
| GIGIGVLAA | (SEQ. ID NO.:519) | HSV-I gp C 480-488 |
| GAGIGVAVL | (SEQ. ID NO.:520) | HSV-2 gp C 446-454 |
| IAGIGILAI | (SEQ. ID NO.:521) | Pseudorabies gpGIN 455-463 |
| LIVIGILIL | (SEQ. ID NO.:522) | Adenovirus 3 E3 9 kD 30-38 |
| LAGIGLLIAA | (SEQ. ID NO.:523) | *S. Lincolnensis* ImrA |
| VDGIGTLTI | (SEQ. ID NO.:524) | Yeast ysa-1 77-85 |
| GAGIGVLTA | (SEQ. ID NO.:525) 157 | *B. polymyxa*, βcndoxylanase 149-157 |
| AAGIGIIQI | (SEQ. ID NO.:526) | *E. coli* methionine synthase 590-598 |
| QAGIGILLA | (SEQ. ID NO.:527) | *E. coli* hypothetical protein 4-12 |
| KARDPHSGHFV | (SEQ. ID NO.:528) | CDK4w1 22.32 |
| KACDPI-ISGIIFV | (SEQ. ID NO.:529) | CDK4-R24C 22-32 |

TABLE 5-continued

| HLA-A1 | Position (Antigen) | | Source |
|---|---|---|---|
| | ACDPFISGHFV | (SEQ. ID NO.:530) | CDK4-R24C 23-32 |
| | SLYNTVATL | (SEQ. ID NO.:531) | HIV-I gag p 17 77-85 |
| | ELVSEFSRV | (SEQ. ID NO.:532) | HER-2, m > V substituted 971-979 |
| | RGPGRAFVTI | (SEQ. ID NO.:533) | HIV-I gp 160 315-329 |
| | HMWNFISGI | (SEQ. ID NO.:534) | HCV NS4A 149-157 |
| | NLVPMVATVQ | (SEQ. ID NO.:535) | HCMV pp65 495-504 |
| | GLHCYEQLV | (SEQ. ID NO.:536) | HPV 6b E7 21-30 |
| | PLKQHFQIV | (SEQ. ID NO.:537) | HPV 6b E7 47-55 |
| | LLDFVRFMGV | (SEQ. ID NO.:538) | EBNA-6 284-293 |
| | AIMEKNIML | (SEQ. ID NO.:539) | Influenza Alaska NS 1 122-130 |
| | YLKTIQNSL | (SEQ. ID NO.:540) | *P. falciparum* cp36 CSP |
| | YLNKIQNSL | (SEQ. ID NO.:541) | *P. falciparum* cp39 CSP |
| | YMLDLQPETT | (SEQ. ID NO.:542) | HPV 16 E7 11-20* |
| | LLMGTLGIV | (SEQ. ID NO.:543) | HPV16 E7 82-90** |
| | TLGIVCPI | (SEQ. ID NO.:544) | HPV 16 E7 86-93 |
| | TLTSCNTSV | (SEQ. ID NO.:545) | HIV-1 gp120 197-205 |
| | KLPQLCTEL | (SEQ. ID NO.:546) | HPV 16 E6 18-26 |
| | TIHDIILEC | (SEQ. ID NO.:547) | HPV16 E6 29-37 |
| | LGIVCPICS | (SEQ. ID NO.:548) | HPV16 E7 87-95 |
| | VILGVLLLI | (SEQ. ID NO.:549) | Melan A/Mart-1 35-43 |
| | ALMDKSLHV | (SEQ. ID NO.:550) | Melan A/Mart-1 56-64 |
| | GILTVILGV | (SEQ. ID NO.:551) | Melan A/Mart-1 31-39 |
| T cell epitopes | MINAYLDKL | (SEQ. ID NO.:552) | *P. Falciparum* STARP 523-531 |
| | AAGIGILTV | (SEQ. ID NO.:553) | Melan A/Mart-127-35 |
| | FLPSDFFPSV | (SEQ. ID NO.:554) | HBV cAg 18-27 |
| Motif unknown T cell epitopes | SVRDRLARL | (SEQ. ID NO.:555) | EBNA-3 464-472 |
| T cell epitopes | AAGIGILTV | (SEQ. ID NO.:556) | Melan A/Mart-1 27-35 |
| | FAYDGKDYI | (SEQ. ID NO.:557) | Human MHC I-ot 140-148 |
| T cell epitopes | AAGIGILTV | (SEQ. ID NO.:558) | Melan A/Mart-1 27-35 |
| | FLPSDFFPSV | (SEQ. ID NO.:559) | HBV cAg 18-27 |
| Motif unknown T cell epitopes | AAGIGILTV | (SEQ. ID NO.:560) | Meland A/Mart-1 27-35 |
| | FLPSDFFPSV | (SEQ. ID NO.:561) | HBV cAg 18-27 |
| | AAGIGILTV | (SEQ. ID NO.:562) | Melan A/Mart-1 27-35 |
| | ALLAVGATK | (SEQ. ID NO.:563) | Pmel17 gp 100 17-25 |
| T cell epitopes | R L R D L L L I V T R | (SEQ. ID NO.:564) | HIV-1 gp41 768-778 |
| | QVPLRPMTYK | (SEQ. ID NO.:565) | HIV-1 nef 73-82 |
| | TVYYGVPVWK | (SEQ. ID NO.:566) | HIV-1 gp120-36-45 |
| | RLRPGGKKK | (SEQ. ID NO.:567) | HIV-1 gag p 17 20-29 |

TABLE 5-continued

| HLA-A1 | | Position (Antigen) | | Source |
|---|---|---|---|---|
| | ILRGSVAHK | (SEQ. ID NO.:568) | | Influenza NP 265-273 |
| | RLRAEAGVK | (SEQ. ID NO.:569) | | EBNA-3 603-611 |
| | RLRDLLLIVTR | (SEQ. ID NO.:570) | | HIV-1 gp41 770-780 |
| | VYYGVPVWK | (SEQ. ID NO.:571) | | HIV-I GP 120 38-46 |
| | RVCEKMALY | (SEQ. ID NO.:572) | | HCV NS5 575-583 |
| Motif unknown T cell epitope | KIFSEVTLK | (SEQ. ID NO.:573) | | Unknown; muta melanoma peptide ted (p I 83L) 175-183 |
| | YVNVNMGLK* | (SEQ. ID NO.:574) | | HBV cAg 88-96 |
| T cell epitopes | IVTDFSVIIK | (SEQ. ID NO.:575) | | EBNA-4 416-424 |
| | ELNEALELK | (SEQ. ID NO.:576) | | P53 343-351 |
| | VPLRPMTYK | (SEQ. ID NO.:577) | | HIV-1 NEF 74-82 |
| | AIFQSSMTK | (SEQ. ID NO.:578) | | HIV-I gag p24 325-333 |
| | QVPLRPMTYK | (SEQ. ID NO.:579) | | HIV-1 nef 73-82 |
| | TINYTIFK HCV | (SEQ. ID NO.:580) | | NSI 238-246 |
| | AAVDLSHFLKEK | (SEQ. ID NO.:581) | | HIV-1 nef 83-94 |
| | ACQ G V G G P G G H K | (SEQ. ID NO.:582) | | HIV-1 II 1B p24 349-359 |
| HLA-A24 | S Y L D S G I H F* | (SEQ. ID NO.:583) | | β-catenin, mutated (proto-onocogen) 29-37 |
| T cell epitopes | RYLKDQQLL | (SEQ. ID NO.:584) | | HIV GP 41 583-591 |
| | AYGLDFYIL | (SEQ. ID NO.:585) | | P15 melanoma Ag 10-18 |
| | AFLPWHRLFL | (SEQ. ID NO.:586) | | Tyrosinase 206-215 |
| | AFLPWHRLF | (SEQ. ID NO.:587) | | Tyrosinase 206-214 |
| | RYSIFFDY | (SEQ. ID NO.:588) | | Ebna-3 246-253 |
| T cell epitope | ETINEEAAEW | (SEQ. ID NO.:589) | | HIV-1 gag p24 203-212 |
| T cell epitopes | STLPETTVVRR | (SEQ. ID NO.:590) | | HBV cAg 141-151 |
| | MSLQRQFLR | (SEQ. ID NO.:591) | | ORF 3P-gp75 294-321 (bp) |
| | LLPGGRPYR | (SEQ. ID NO.:592) | | TRP (tyrosinase rel.) 197-205 |
| T cell epitope | IVGLNKIVR | (SEQ. ID NO.:593) | | HIV gag p24 267-267-275 |
| | AAGIGILTV | (SEQ. ID NO.:594) | | Melan A/Mart-127 35 |

Table 6 sets forth additional antigens useful in the invention that are available from the Ludwig Cancer Institute. The Table refers to patents in which the identified antigens can be found and as such are incorporated herein by reference. TRA refers to the tumor-related antigen and the LUD No. refers to the Ludwig Institute number.

TABLE 6

| TRA | LUD No. | Patent No. | Date Patent Issued | Peptide (Antigen) | HLA |
|---|---|---|---|---|---|
| MAGE-4 | 5293 | 5,405,940 | 11 Apr. 1995 | EVDPASNTY (SEQ. ID NO.: 979) | HLA-A1 |
| MAGE-41 | 5293 | 5,405,940 | 11 Apr. 1995 | EVDPTSNTY (SEQ ID NO: 595) | HLA-A I |
| MAGE-5 | 5293 | 5,405,940 | 11 Apr. 1995 | EADPTSNTY (SEQ ID NO: 596) | HLA-A I |

TABLE 6-continued

| TRA | LUD No. | Patent No. | Date Patent Issued | Peptide (Antigen) | HLA |
|---|---|---|---|---|---|
| MAGE-51 | 5293 | 5,405,940 | 11 Apr. 1995 | EADPTSNTY (SEQ ID NO: 597) | HLA-A1 |
| MAGE-6 | 5294 | 5,405,940 | 11 Apr. 1995 | EVDPIGHVY (SEQ ID NO: 598) | HLA-A1 |
| | 5299.2 | 5,487,974 | 30 Jan. 1996 | MLLAVLYCLL (SEQ ID NO: 599) | HLA-A2 |
| | 5360 | 5,530,096 | 25 Jun. 1996 | MLLAVLYGL (SEQ ID NO: 600) | HLA-B44 |
| Tyrosinase | 5360.1 | 5,519,117 | 21 May 1996 | SEIWRDIDFA (SEQ ID NO: 601) | HLA-B44 |
| | | | | SEIWRDIDF (SEQ ID NO: 602) | |
| Tyrosinase | 5431 | 5,774,316 | 28 Apr. 1998 | XEIWRDIDF (SEQ ID NO: 603) | HLA-B44 |
| MAGE-2 | 5340 | 5,554,724 | 10 Sep. 1996 | STLVEVTLGEV (SEQ ID NO: 604) | HLA-A2 |
| | | | | LVEVTLGEV (SEQ ID NO: 605) | |
| | | | | VIFSKASEYL (SEQ ID NO: 606) | |
| | | | | IIVLAIIA1 (SEQ ID NO: 607) | |
| | | | | KIWEELSMLEV (SEQ ID NO: 608) | |
| | | | | LIETSYVKV (SEQ ID NO: 609) | |
| | 5327 | 5,585,461 | 17 Dec. 1996 | FLWGPRALV (SEQ ID NO: 610) | HLA-A2 |
| | | | | TLVEVTLGEV (SEQ ID NO: 611) | |
| | | | | ALVETSYVKV (SEQ ID NO: 612) | |
| MAGE-3 | 5344 | 5,554,506 | 10 Sep. 1996 | KIWEELSVL (SEQ ID NO: 613) | HLA-A2 |
| MAGE-3 | 5393 | 5,405,940 | 11 Apr. 1995 | EVDPIGHLY (SEQ ID NO: 614) | HLA-A1 |
| MAGE | 5293 | 5,405,940 | 11 Apr. 1995 | EXDX5Y (SEQ. ID NO.: 615) (but not EADPTGHSY) (SEQ. ID NO.: 616) E (A/V) D X5 Y (SEQ. ID NO.: 617) E (A/V) D P X4 Y (SEQ. ID NO.: 618) E (A/V) D P (I/A/T) X3 Y (SEQ. ID NO.: 619) E (A/V) D P (I/A/T) (G/S) X2 Y (SEQ. ID NO.: 620) E (A/V) D P (I/A/T) (G/S) (H/N) X Y (SEQ. ID NO.: 621) E (A/V) DP (I/A/T) (G/S) (H/N) (L/T/V) Y (SEQ ID NO.: 622) | HLA-A1 |

TABLE 6-continued

| TRA | LUD No. | Patent No. | Date Patent Issued | Peptide (Antigen) | HLA |
|---|---|---|---|---|---|
| MAGE-1 | 5361 | 5,558.995 | 24 Sep. 1996 | ELHSAYGEPRKLLTQD (SEQ ID NO: 623) | HLA-C Clone 10 |
| | | | | EHSAYGEPRKLL (SEQ ID NO: 624) | |
| | | | | SAYGEPRKL (SEQ ID NO: 625) | |
| MAGE-1 | 5253.4 | TBA | TBA | EADPTGHSY (SEQ ID NO: 626) | HLA-A I |
| BAGE | 5310.1 | TBA | TBA | MAARAVFLALSAQLLQARLMKE (SEQ ID NO: 627) | HLA-C Clone 10 |
| | | | | MAARAVFLALSAQLLQ (SEQ ID NO: 628) | HLA-C Clone 10 |
| | | | | AARAVFLAL (SEQ ID NO: 629) | HLA-Clone 10 |
| GAGE | 5323.2 | 5,648,226 | 15 Jul. 1997 | YRPRPRRY (SEQ. ID NO.: 630) | HLA-CW6 |

TABLE 7

| Source | Protein | AA Position | MHC molecules | T cell epitope MHC ligand (Antigen) | SEQ. ID NO.: | Ref. |
|---|---|---|---|---|---|---|
| Synthetic peptides | synthetic peptides | synthetic peptides | HLA-A2 | ALFAAAAV | 631 | Parker, et al., "Scheme for ranking potential HLA-A2 binding peptides based on independent binding of individual peptide side-chains," J. Immunol. 152: 163-175 |
| | | | HLA-A2 | GIFGGVGGV | 632 | Parker, et al., "Scheme for ranking potential HLA-A2 binding peptides based on independent binding of individual peptide side-chains," J. Immunol. 152: 163-175 |
| | | | HLA-A2 | GLDKGGGV | 633 | Parker, et al., "Scheme for ranking potential HLA-A2 binding peptides based on independent binding of individual peptide side-chains," J. Immunol. 152: 163-175 |
| | | | HLA-A2 | GLFGGFGGV | 634 | Parker, et al., "Scheme for ranking potential HLA-A2 binding peptides based on independent binding of individual peptide side-chains," J. Immunol. 152: 163-175 |
| | | | HLA-A2 | GLFGGGAGV | 635 | Parker, et al., "Scheme for ranking potential HLA-A2 binding peptides based on independent binding of individual peptide side-chains," J. Immunol. 152: 163-175 |

TABLE 7-continued

| Source | Protein | AA Position | MHC molecules | T cell epitope MHC ligand (Antigen) | SEQ. ID NO.: | Ref. |
|---|---|---|---|---|---|---|
| | | | HLA-A2 | GLFGGGEGV | 636 | Parker, et al., "Scheme for ranking potential HLA-A2 binding peptides based on independent binding of individual peptide side-chains," J. Immunol. 152: 163-175 |
| | | | HLA-A2 | GLFGGGFGV | 637 | Parker, et al., "Scheme for ranking potential HLA-A2 binding peptides based on independent binding of individual peptide side-chains," J. Immunol. 152: 163-175 |
| | | | HLA-A2 | GLFGGGGGL | 638 | Parker, et al., "Scheme for ranking potential HLA-A2 binding peptides based on independent binding of individual peptide side-chains," J. Immunol. 152: 163-175 |
| | | | HLA-A2 | GLFGGGGGV | 639 | Parker, et al., "Scheme for ranking potential HLA-A2 binding peptides based on independent binding of individual peptide side-chains," J. Immunol. 152: 163-175 |
| | | | HLA-A2 | GLFGGGVGV | 640 | Parker, et al., "Scheme for ranking potential HLA-A2 binding peptides based on independent binding of individual peptide side-chains," J. Immunol. 152: 163-175 |
| | | | HLA-A2 | GLFGGVGGV | 641 | Parker, et al., "Scheme for ranking potential HLA-A2 binding peptides based on independent binding of individual peptide side-chains," J. Immunol. 152: 163-175 |
| | | | HLA-A2 | GLFGGVGKV | 642 | Parker, et al., "Scheme for ranking potential HLA-A2 binding peptides based on independent binding of individual peptide side-chains," J. Immunol. 152: 163-175 |
| | | | HLA-A2 | GLFKGVGGV | 643 | Parker, et al., "Scheme for ranking potential HLA-A2 binding peptides based on independent binding of individual peptide side-chains," J. Immunol. 152: 163-175 |
| | | | HLA-A2 | GLGGGGFGV | 644 | Parker, et al., "Scheme for ranking potential HLA-A2 binding peptides based on independent binding of individual peptide side-chains," J. Immunol. 152: 163-175 |
| | | | HLA-A2 | GLLGGGVGV | 645 | Parker, et al., "Scheme for ranking potential HLA-A2 binding peptides |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | based on independent binding of individual peptide side-chains," J. Immunol. 152: 163-175 |
| | | | HLA-A2 | GLYGGGGGV | 646 | Parker, et al., "Scheme for ranking potential HLA-A2 binding peptides based on independent binding of individual peptide side-chains," J. Immunol. 152: 163-175 |
| | | | HLA-A2 | GMFGGGGGV | 647 | Parker, et al., "Scheme for ranking potential HLA-A2 binding peptides based on independent binding of individual peptide side-chains," J. Immunol. 152: 163-175 |
| | | | HLA-A2 | GMFGGVGGV | 648 | Parker, et al., "Scheme for ranking potential HLA-A2 binding peptides based on independent binding of individual peptide side-chains," J. Immunol. 152: 163-175 |
| | | | HLA-A2 | GQFGGVGGV | 649 | Parker, et al., "Scheme for ranking potential HLA-A2 binding peptides based on independent binding of individual peptide side-chains," J. Immunol. 152: 163-175 |
| | | | HLA-A2 | GVFGGVGGV | 650 | Parker, et al., "Scheme for ranking potential HLA-A2 binding peptides based on independent binding of individual peptide side-chains," J. Immunol. 152: 163-175 |
| | | | HLA-A2 | KLFGGGGGV | 651 | Parker, et al., "Scheme for ranking potential HLA-A2 binding peptides based on independent binding of individual peptide side-chains," J. Immunol. 152: 163-175 |
| | | | HLA-A2 | KLFGGVGGV | 652 | Parker, et al., "Scheme for ranking potential HLA-A2 binding peptides based on independent binding of individual peptide side-chains," J. Immunol. 152: 163-175 |
| | | | HLA-A2 | AILGFVFTL | 653 | Parker, et al., "Scheme for ranking potential HLA-A2 binding peptides based on independent binding of individual peptide side-chains," J. Immunol. 152: 163-175 |
| | | | HLA-A2 | GAIGFVFTL | 654 | Parker, et al., "Scheme for ranking potential HLA-A2 binding peptides based on independent binding of individual peptide side-chains," J. Immunol. 152: 163-175 |

TABLE 7-continued

| Source | Protein | AA Position | MHC molecules | T cell epitope MHC ligand (Antigen) | SEQ. ID NO.: | Ref. |
|---|---|---|---|---|---|---|
| | | | HLA-A2 | GALGFVFTL | 655 | Parker, et al., "Scheme for ranking potential HLA-A2 binding peptides based on independent binding of individual peptide side-chains," J. Immunol. 152: 163-175 |
| | | | HLA-A2 | GELGFVFTL | 656 | Parker, et al., "Scheme for ranking potential HLA-A2 binding peptides based on independent binding of individual peptide side-chains," J. Immunol. 152: 163-175 |
| | | | HLA-A2 | GIAGFVFTL | 657 | Parker, et al., "Scheme for ranking potential HLA-A2 binding peptides based on independent binding of individual peptide side-chains," J. Immunol. 152: 163-175 |
| | | | HLA-A2 | GIEGFVFTL | 658 | Parker, et al., "Scheme for ranking potential HLA-A2 binding peptides based on independent binding of individual peptide side-chains," J. Immunol. 152: 163-175 |
| | | | HLA-A2 | GILAFVFTL | 659 | Parker, et al., "Scheme for ranking potential HLA-A2 binding peptides based on independent binding of individual peptide side-chains," J. Immunol. 152: 163-175 |
| | | | HLA-A2 | GILGAVFTL | 660 | Parker, et al., "Scheme for ranking potential HLA-A2 binding peptides based on independent binding of individual peptide side-chains," J. Immunol. 152: 163-175 |
| | | | HLA-A2 | GILGEVFTL | 661 | Parker, et al., "Scheme for ranking potential HLA-A2 binding peptides based on independent binding of individual peptide side-chains," J. Immunol. 152: 163-175 |
| | | | HLA-A2 | GILFGAFTL | 662 | Parker, et al., "Scheme for ranking potential HLA-A2 binding peptides based on independent binding of individual peptide side-chains," J. Immunol. 152: 163-175 |
| | | | HLA-A2 | GILGFEFTL | 663 | Parker, et al., "Scheme for ranking potential HLA-A2 binding peptides based on independent binding of individual peptide side-chains," J. Immunol. 152: 163-175 |
| | | | HLA-A2 | GILGFKFTL | 664 | Parker, et al., "Scheme for ranking potential HLA-A2 binding peptides |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | based on independent binding of individual peptide side-chains," J. Immunol. 152: 163-175 |
| | | | HLA-A2 | GILGFVATL | 665 | Parker, et al., "Scheme for ranking potential HLA-A2 binding peptides based on independent binding of individual peptide side-chains," J. Immunol. 152: 163-175 |
| | | | HLA-A2 | GILGFVETL | 666 | Parker, et al., "Scheme for ranking potential HLA-A2 binding peptides based on independent binding of individual peptide side-chains," J. Immunol. 152: 163-175 |
| | | | HLA-A2 | GILGFVFAL | 667 | Parker, et al., "Scheme for ranking potential HLA-A2 binding peptides based on independent binding of individual peptide side-chains," J. Immunol. 152: 163-175 |
| | | | HLA-A2 | GILGFVFEL | 668 | Parker, et al., "Scheme for ranking potential HLA-A2 binding peptides based on independent binding of individual peptide side-chains," J. Immunol. 152: 163-175 |
| | | | HLA-A2 | GILGFVFKL | 669 | Parker, et al., "Scheme for ranking potential HLA-A2 binding peptides based on independent binding of individual peptide side-chains," J. Immunol. 152: 163-175 |
| | | | HLA-A2 | GILGFVFTA | 670 | Parker, et al., "Scheme for ranking potential HLA-A2 binding peptides based on independent binding of individual peptide side-chains," J. Immunol. 152: 163-175 |
| | | | HLA-A2 | GILGFVFTL | 671 | Parker, et al., "Scheme for ranking potential HLA-A2 binding peptides based on independent binding of individual peptide side-chains," J. Immunol. 152: 163-175 |
| | | | HLA-A2 | GILGFVFVL | 672 | Parker, et al., "Scheme for ranking potential HLA-A2 binding peptides based on independent binding of individual peptide side-chains," J. Immunol. 152: 163-175 |
| | | | HLA-A2 | GILGFVKTL | 673 | Parker, et al., "Scheme for ranking potential HLA-A2 binding peptides based on independent binding of individual peptide side-chains," J. Immunol. 152: 163-175 |

TABLE 7-continued

| Source | Protein | AA Position | MHC molecules | T cell epitope MHC ligand (Antigen) | SEQ. ID NO.: | Ref. |
|---|---|---|---|---|---|---|
| | | | HLA-A2 | GILGKVFTL | 674 | Parker, et al., "Scheme for ranking potential HLA-A2 binding peptides based on independent binding of individual peptide side-chains," J. Immunol. 152: 163-175 |
| | | | HLA-A2 | GILKFVFTL | 675 | Parker, et al., "Scheme for ranking potential HLA-A2 binding peptides based on independent binding of individual peptide side-chains," J. Immunol. 152: 163-175 |
| | | | HLA-A2 | GILPFVFTL | 676 | Parker, et al., "Scheme for ranking potential HLA-A2 binding peptides based on independent binding of individual peptide side-chains," J. Immunol. 152: 163-175 |
| | | | HLA-A2 | GIVGFVFTL | 677 | Parker, et al., "Scheme for ranking potential HLA-A2 binding peptides based on independent binding of individual peptide side-chains," J. Immunol. 152: 163-175 |
| | | | HLA-A2 | GKLGFVFTL | 678 | Parker, et al., "Scheme for ranking potential HLA-A2 binding peptides based on independent binding of individual peptide side-chains," J. Immunol. 152: 163-175 |
| | | | HLA-A2 | GLLGFVFTL | 679 | Parker, et al., "Scheme for ranking potential HLA-A2 binding peptides based on independent binding of individual peptide side-chains," J. Immunol. 152: 163-175 |
| | | | HLA-A2 | GQLGFVFTL | 680 | Parker, et al., "Scheme for ranking potential HLA-A2 binding peptides based on independent binding of individual peptide side-chains," J. Immunol. 152: 163-175 |
| | | | HLA-A2 | KALGFVFTL | 681 | Parker, et al., "Scheme for ranking potential HLA-A2 binding peptides based on independent binding of individual peptide side-chains," J. Immunol. 152: 163-175 |
| | | | HLA-A2 | KILGFVFTL | 682 | Parker, et al., "Scheme for ranking potential HLA-A2 binding peptides based on independent binding of individual peptide side-chains," J. Immunol. 152: 163-175 |
| | | | HLA-A2 | KILGKVFTL | 683 | Parker, et al., "Scheme for ranking potential HLA-A2 binding peptides |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | based on independent binding of individual peptide side-chains," J. Immunol. 152: 163-175 |
| | | | HLA-A2 | AILLGVFML | 684 | Parker, et al., "Scheme for ranking potential HLA-A2 binding peptides based on independent binding of individual peptide side-chains," J. Immunol. 152: 163-175 |
| | | | HLA-A2 | AIYKRWIIL | 685 | Parker, et al., "Scheme for ranking potential HLA-A2 binding peptides based on independent binding of individual peptide side-chains," J. Immunol. 152: 163-175 |
| | | | HLA-A2 | ALFFFDIDL | 686 | Parker, et al., "Scheme for ranking potential HLA-A2 binding peptides based on independent binding of individual peptide side-chains," J. Immunol. 152: 163-175 |
| | | | HLA-A2 | ATVELLSEL | 687 | Parker, et al., "Scheme for ranking potential HLA-A2 binding peptides based on independent binding of individual peptide side-chains," J. Immunol. 152: 163-175 |
| | | | HLA-A2 | CLFGYPVYV | 688 | Parker, et al., "Scheme for ranking potential HLA-A2 binding peptides based on independent binding of individual peptide side-chains," J. Immunol. 152: 163-175 |
| | | | HLA-A2 | FIFPNYTIV | 689 | Parker, et al., "Scheme for ranking potential HLA-A2 binding peptides based on independent binding of individual peptide side-chains," J. Immunol. 152: 163-175 |
| | | | HLA-A2 | IISLWDSQL | 690 | Parker, et al., "Scheme for ranking potential HLA-A2 binding peptides based on independent binding of individual peptide side-chains," J. Immunol. 152: 163-175 |
| | | | HLA-A2 | ILASLFAAV | 691 | Parker, et al., "Scheme for ranking potential HLA-A2 binding peptides based on independent binding of individual peptide side-chains," J. Immunol. 152: 163-175 |
| | | | HLA-A2 | ILESLFAAV | 692 | Parker, et al., "Scheme for ranking potential HLA-A2 binding peptides based on independent binding of individual peptide side-chains," J. Immunol. 152: 163-175 |

TABLE 7-continued

| Source | Protein | AA Position | MHC molecules | T cell epitope MHC ligand (Antigen) | SEQ. ID NO.: | Ref. |
|---|---|---|---|---|---|---|
| | | | HLA-A2 | KLGEFFNQM | 693 | Parker, et al., "Scheme for ranking potential HLA-A2 binding peptides based on independent binding of individual peptide side-chains," J. Immunol. 152: 163-175 |
| | | | HLA-A2 | KLGEFYNQM | 694 | Parker, et al., "Scheme for ranking potential HLA-A2 binding peptides based on independent binding of individual peptide side-chains," J. Immunol. 152: 163-175 |
| | | | HLA-A2 | LLFGYPVYV | 695 | Parker, et al., "Scheme for ranking potential HLA-A2 binding peptides based on independent binding of individual peptide side-chains," J. Immunol. 152: 163-175 |
| | | | HLA-A2 | LLWKGEGAV | 696 | Parker, et al., "Scheme for ranking potential HLA-A2 binding peptides based on independent binding of individual peptide side-chains," J. Immunol. 152: 163-175 |
| | | | HLA-A2 | LMFGYPVYV | 697 | Parker, et al., "Scheme for ranking potential HLA-A2 binding peptides based on independent binding of individual peptide side-chains," J. Immunol. 152: 163-175 |
| | | | HLA-A2 | LNFGYPVYV | 698 | Parker, et al., "Scheme for ranking potential HLA-A2 binding peptides based on independent binding of individual peptide side-chains," J. Immunol. 152: 163-175 |
| | | | HLA-A2 | LQFGYPVYV | 699 | Parker, et al., "Scheme for ranking potential HLA-A2 binding peptides based on independent binding of individual peptide side-chains," J. Immunol. 152: 163-175 |
| | | | HLA-A2 | NIVAHTFKV | 700 | Parker, et al., "Scheme for ranking potential HLA-A2 binding peptides based on independent binding of individual peptide side-chains," J. Immunol. 152: 163-175 |
| | | | HLA-A2 | NLPMVATV | 701 | Parker, et al., "Scheme for ranking potential HLA-A2 binding peptides based on independent binding of individual peptide side-chains," J. Immunol. 152: 163-175 |
| | | | HLA-A2 | QMLLAIARL | 702 | Parker, et al., "Scheme for ranking potential HLA-A2 binding peptides based on independent binding of individual |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | peptide side-chains," J. Immunol. 152: 163-175 |
| | | | HLA-A2 | QMWQARLTV | 703 | Parker, et al., "Scheme for ranking potential HLA-A2 binding peptides based on independent binding of individual peptide side-chains," J. Immunol. 152: 163-175 |
| | | | HLA-A2 | RLLQTGIHV | 704 | Parker, et al., "Scheme for ranking potential HLA-A2 binding peptides based on independent binding of individual peptide side-chains," J. Immunol. 152: 163-175 |
| | | | HLA-A2 | RLVNGSLAL | 705 | Parker, et al., "Scheme for ranking potential HLA-A2 binding peptides based on independent binding of individual peptide side-chains," J. Immunol. 152: 163-175 |
| | | | HLA-A2 | SLYNTVATL | 706 | Parker, et al., "Scheme for ranking potential HLA-A2 binding peptides based on independent binding of individual peptide side-chains," J. Immunol. 152: 163-175 |
| | | | HLA-A2 | TLNAWVKVV | 707 | Parker, et al., "Scheme for ranking potential HLA-A2 binding peptides based on independent binding of individual peptide side-chains," J. Immunol. 152: 163-175 |
| | | | HLA-A2 | WLYRETCNL | 708 | Parker, et al., "Scheme for ranking potential HLA-A2 binding peptides based on independent binding of individual peptide side-chains," J. Immunol. 152: 163-175 |
| | | | HLA-A2 | YLFKRMIDL | 709 | Parker, et al., "Scheme for ranking potential HLA-A2 binding peptides based on independent binding of individual peptide side-chains," J. Immunol. 152: 163-175 |
| | | | HLA-A2 | GAFGGVGGV | 710 | Parker, et al., "Scheme for ranking potential HLA-A2 binding peptides based on independent binding of individual peptide side-chains," J. Immunol. 152: 163-175 |
| | | | HLA-A2 | GAFGGVGGY | 711 | Parker, et al., "Scheme for ranking potential HLA-A2 binding peptides based on independent binding of individual peptide side-chains," J. Immunol. 152: 163-175 |
| | | | HLA-A2 | GEFGGVGGV | 712 | Parker, et al., "Scheme for ranking potential |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | HLA-A2 binding peptides based on independent binding of individual peptide side-chains," J. Immunol. 152: 163-175 |
| | | | HLA-A2 | GGFGGVGGV | 713 | Parker, et al., "Scheme for ranking potential HLA-A2 binding peptides based on independent binding of individual peptide side-chains," J. Immunol. 152: 163-175 |
| | | | HLA-A2 | GIFGGGGGV | 714 | Parker, et al., "Scheme for ranking potential HLA-A2 binding peptides based on independent binding of individual peptide side-chains," J. Immunol. 152: 163-175 |
| | | | HLA-A2 | GIGGFGGGL | 715 | Parker, et al., "Scheme for ranking potential HLA-A2 binding peptides based on independent binding of individual peptide side-chains," J. Immunol. 152: 163-175 |
| | | | HLA-A2 | GIGGGGGGL | 716 | Parker, et al., "Scheme for ranking potential HLA-A2 binding peptides based on independent binding of individual peptide side-chains," J. Immunol. 152: 163-175 |
| | | | HLA-A2 | GLDGGGGV | 717 | Parker, et al., "Scheme for ranking potential HLA-A2 binding peptides based on independent binding of individual peptide side-chains," J. Immunol. 152: 163-175 |
| | | | HLA-A2 | GLDGKGGGV | 718 | Parker, et al., "Scheme for ranking potential HLA-A2 binding peptides based on independent binding of individual peptide side-chains," J. Immunol. 152: 163-175 |
| | | | HLA-A2 | GLDKKGGGV | 719 | Parker, et al., "Scheme for ranking potential HLA-A2 binding peptides based on independent binding of individual peptide side-chains," J. Immunol. 152: 163-175 |
| | | | HLA-A2 | GLFGGGFGF | 720 | Parker, et al., "Scheme for ranking potential HLA-A2 binding peptides based on independent binding of individual peptide side-chains," J. Immunol. 152: 163-175 |
| | | | HLA-A2 | GLFGGGFGG | 721 | Parker, et al., "Scheme for ranking potential HLA-A2 binding peptides based on independent binding of individual |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | peptide side-chains," J. Immunol. 152: 163-175 |
| | | | HLA-A2 | GLFGGGFGN | 722 | Parker, et al., "Scheme for ranking potential HLA-A2 binding peptides based on independent binding of individual peptide side-chains," J. Immunol. 152: 163-175 |
| | | | HLA-A2 | GLFGGGFGS | 723 | Parker, et al., "Scheme for ranking potential HLA-A2 binding peptides based on independent binding of individual peptide side-chains," J. Immunol. 152: 163-175 |
| | | | HLA-A2 | GLFGGGGI | 724 | Parker, et al., "Scheme for ranking potential HLA-A2 binding peptides based on independent binding of individual peptide side-chains," J. Immunol. 152: 163-175 |
| | | | HLA-A2 | GLFGGGGM | 725 | Parker, et al., "Scheme for ranking potential HLA-A2 binding peptides based on independent binding of individual peptide side-chains," J. Immunol. 152: 163-175 |
| | | | HLA-A2 | GLFGGGGT | 726 | Parker, et al., "Scheme for ranking potential HLA-A2 binding peptides based on independent binding of individual peptide side-chains," J. Immunol. 152: 163-175 |
| | | | HLA-A2 | GLFGGGGY | 727 | Parker, et al., "Scheme for ranking potential HLA-A2 binding peptides based on independent binding of individual peptide side-chains," J. Immunol. 152: 163-175 |
| | | | HLA-A2 | GLGFGGGGV | 728 | Parker, et al., "Scheme for ranking potential HLA-A2 binding peptides based on independent binding of individual peptide side-chains," J. Immunol. 152: 163-175 |
| | | | HLA-A2 | GLGGFGGGV | 729 | Parker, et al., "Scheme for ranking potential HLA-A2 binding peptides based on independent binding of individual peptide side-chains," J. Immunol. 152: 163-175 |
| | | | HLA-A2 | GLGGGFGGV | 730 | Parker, et al., "Scheme for ranking potential HLA-A2 binding peptides based on independent binding of individual peptide side-chains," J. Immunol. 152: 163-175 |
| | | | HLA-A2 | GLGGGGGFV | 731 | Parker, et al., "Scheme for ranking potential |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | HLA-A2 binding peptides based on independent binding of individual peptide side-chains," J. Immunol. 152: 163-175 |
| | | | HLA-A2 | GLGGGGGGY | 732 | Parker, et al., "Scheme for ranking potential HLA-A2 binding peptides based on independent binding of individual peptide side-chains," J. Immunol. 152: 163-175 |
| | | | HLA-A2 | GLGGGVGGV | 733 | Parker, et al., "Scheme for ranking potential HLA-A2 binding peptides based on independent binding of individual peptide side-chains," J. Immunol. 152: 163-175 |
| | | | HLA-A2 | GLLGGGGGV | 734 | Parker, et al., "Scheme for ranking potential HLA-A2 binding peptides based on independent binding of individual peptide side-chains," J. Immunol. 152: 163-175 |
| | | | HLA-A2 | GLPGGGGGV | 735 | Parker, et al., "Scheme for ranking potential HLA-A2 binding peptides based on independent binding of individual peptide side-chains," J. Immunol. 152: 163-175 |
| | | | HLA-A2 | GNFGGVGGV | 736 | Parker, et al., "Scheme for ranking potential HLA-A2 binding peptides based on independent binding of individual peptide side-chains," J. Immunol. 152: 163-175 |
| | | | HLA-A2 | GSFGGVGGV | 737 | Parker, et al., "Scheme for ranking potential HLA-A2 binding peptides based on independent binding of individual peptide side-chains," J. Immunol. 152: 163-175 |
| | | | HLA-A2 | GTFGGVGGV | 738 | Parker, et al., "Scheme for ranking potential HLA-A2 binding peptides based on independent binding of individual peptide side-chains," J. Immunol. 152: 163-175 |
| | | | HLA-A2 | AGNSAYEYV | 739 | Parker, et al., "Scheme for ranking potential HLA-A2 binding peptides based on independent binding of individual peptide side-chains," J. Immunol. 152: 163-175 |
| | | | HLA-A2 | GLFPGQFAY | 740 | Parker, et al., "Scheme for ranking potential HLA-A2 binding peptides based on independent binding of individual |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | peptide side-chains," J. Immunol. 152: 163-175 |
| | | | HLA-A2 | HILLGVFML | 741 | Parker, et al., "Scheme for ranking potential HLA-A2 binding peptides based on independent binding of individual peptide side-chains," J. Immunol. 152: 163-175 |
| | | | HLA-A2 | ILESLFRAV | 742 | Parker, et al., "Scheme for ranking potential HLA-A2 binding peptides based on independent binding of individual peptide side-chains," J. Immunol. 152: 163-175 |
| | | | HLA-A2 | KLKKYKLKHI | 743 | Parker, et al., "Scheme for ranking potential HLA-A2 binding peptides based on independent binding of individual peptide side-chains," J. Immunol. 152: 163-175 |
| | | | HLA-A2 | MLASTDLKY | 744 | Parker, et al., "Scheme for ranking potential HLA-A2 binding peptides based on independent binding of individual peptide side-chains," J. Immunol. 152: 163-175 |
| | | | HLA-A2 | MLERELVRK | 745 | Parker, et al., "Scheme for ranking potential HLA-A2 binding peptides based on independent binding of individual peptide side-chains," J. Immunol. 152: 163-175 |
| | | | HLA-A2 | KLFGFVFTV | 746 | Parker, et al., "Scheme for ranking potential HLA-A2 binding peptides based on independent binding of individual peptide side-chains," J. Immunol. 152: 163-175 |
| | | | HLA-A2 | ILDKKVEKV | 747 | Parker, et al., "Scheme for ranking potential HLA-A2 binding peptides based on independent binding of individual peptide side-chains," J. Immunol. 152: 163-175 |
| | | | HLA-A2 | ILKEPVHGV | 748 | Parker, et al., "Scheme for ranking potential HLA-A2 binding peptides based on independent binding of individual peptide side-chains," J. Immunol. 152: 163-175 |
| | | | HLA-A2 | ALFAAAAAY | 749 | Parker, et al., "Scheme for ranking potential HLA-A2 binding peptides based on independent binding of individual peptide side-chains," J. Immunol. 152: 163-175 |

TABLE 7-continued

| Source | Protein | AA Position | MHC molecules | T cell epitope MHC ligand (Antigen) | SEQ. ID NO.: | Ref. |
|---|---|---|---|---|---|---|
| | | | HLA-A2 | GIGFGGGGL | 750 | Parker, et al., "Scheme for ranking potential HLA-A2 binding peptides based on independent binding of individual peptide side-chains," J. Immunol. 152: 163-175 |
| | | | HLA-A2 | GKFGGVGGV | 751 | Parker, et al., "Scheme for ranking potential HLA-A2 binding peptides based on independent binding of individual peptide side-chains," J. Immunol. 152: 163-175 |
| | | | HLA-A2 | GLFGGGGGK | 752 | Parker, et al., "Scheme for ranking potential HLA-A2 binding peptides based on independent binding of individual peptide side-chains," J. Immunol. 152: 163-175 |
| | | | HLA-A2 | EILGFVFTL | 753 | Parker, et al., "Scheme for ranking potential HLA-A2 binding peptides based on independent binding of individual peptide side-chains," J. Immunol. 152: 163-175 |
| | | | HLA-A2 | GIKGFVFTL | 754 | Parker, et al., "Scheme for ranking potential HLA-A2 binding peptides based on independent binding of individual peptide side-chains," J. Immunol. 152: 163-175 |
| | | | HLA-A2 | GQLGFVFTK | 755 | Parker, et al., "Scheme for ranking potential HLA-A2 binding peptides based on independent binding of individual peptide side-chains," J. Immunol. 152: 163-175 |
| | | | HLA-A2 | ILGFVFTLT | 756 | Parker, et al., "Scheme for ranking potential HLA-A2 binding peptides based on independent binding of individual peptide side-chains," J. Immunol. 152: 163-175 |
| | | | HLA-A2 | KILGFVFTK | 757 | Parker, et al., "Scheme for ranking potential HLA-A2 binding peptides based on independent binding of individual peptide side-chains," J. Immunol. 152: 163-175 |
| | | | HLA-A2 | KKLGFVFTL | 758 | Parker, et al., "Scheme for ranking potential HLA-A2 binding peptides based on independent binding of individual peptide side-chains," J. Immunol. 152: 163-175 |
| | | | HLA-A2 | KLFEKVYNY | 759 | Parker, et al., "Scheme for ranking potential HLA-A2 binding peptides based on independent |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | binding of individual peptide side-chains," J. Immunol. 152: 163-175 |
| | | | HLA-A2 | LRFGYPVYV | 760 | Parker, et al., "Scheme for ranking potential HLA-A2 binding peptides based on independent binding of individual peptide side-chains," J. Immunol. 152: 163-175 |
| Human | HSP60 | 140-148 | HLA-B27 | IRRGVMLAV | 761 | Rammensee et al. 1997 160 |
| Human | HSP60 | 369-377 | HLA-B27 | KRIQEIIEQ | 762 | Rammensee et al. 1997 160 |
| Human | HSP60 | 469-477 | HLA-B27 | KRTLKIPAM | 763 | Rammensee et al. 1997 160 |
| Yersinia | HSP60 | 35-43 | HLA-B27 | GRNVVLDKS | 764 | Rammensee et al. 1997 160 |
| Yersinia | HSP60 | 117-125 | HLA-B27 | KRGIDKAVI | 765 | Rammensee et al. 1997 160 |
| Yersinia | HSP60 | 420-428 | HLA-B27 | IRAASAITA | 766 | Rammensee et al. 1997 160 |
| Yersinia | HSP 60 | 284-292 | HLA-B*2705 | RRKAMFEDI | 767 | 169 |
| P. falciparum | LSA-1 | 1850-1857 | HLA-B3501 | KPKDELDY | 768 | 170 |
| Influenza NP | | 379-387 | HLA-B*4402 | LELRSRYWA | 769 | 183 |
| | Tum-P35B | 4-13 | HLA-D$^d$ | GPPHSNNFGY | 770 | 230 |
| Rotavirus | VP7 | 33-40 | | IIYRFLLI | 771 | 262 |
| | OGDH (F108Y) | 104-112 | H2-L$^d$ | QLSPYPFDL | 772 | 253 |
| | TRP-2 | 181-188 | p287 | VYDFFVWL | 773 | 284 |
| | DEAD box p 68 | 547-554 | p287 | SNIFVFAGI | 774 | 283 |
| | Vector "artefact" | | p287 | SVVEFSSL | 775 | 260 |
| | Epitope mimic of tumor Ag | | p287 | AHYLFRNL | 776 | 278 |
| | | | p287 | THYLFRNL | 777 | 278 |
| | Epitope mimic of H-3 miHAg" | | p287 | LIVIYNTL | 778 | 279 |
| | | | p287 | LIYEFNTL | 779 | 279 |
| | | | p287 | IPYIYNTL | 780 | 279 |
| | | | p287 | IIYIYHRL | 781 | 279 |
| | | | p287 | LIYIFNTL | 782 | 279 |
| | HBV cAg | 93-100 | p287 | MGLKLFRQL | 783 | 280 |
| Human | autoantigen LA | 51-58 | p287 | IMIKFRNRL | 784 | 281 |
| Mouse | UTY protein | | H2D$^b$ | WMHHNMDLI | 785 | 303 |

TABLE 7-continued

| Source | Protein | AA Position | MHC molecules | T cell epitope MHC ligand (Antigen) | SEQ. ID NO.: | Ref. |
|---|---|---|---|---|---|---|
| Mouse | p53 | 232-240 | H2D$^b$ | KYMCNSSCM | 786 | 302 |
| MURINE | MDM2 | 441-449 | H2D$^b$ | GRPKNGCIV | 787 | 277 |
| | Epitope mimic of natural | | H2D$^b$ | AQHPNAELL | 788 | 278 |
| | MuLV gag75K | 75-83 | H2D$^b$ | CCLCLTVFL | 789 | 301 |
| P. Falciparum | CSP | 375-383 | p290 | YENDIEKK | 790 | 315 |
| P. Falciparum | CSP | 371-379 | p290 | DELDYENDI | 791 | 315 |
| HIV | -1RT | 206-214 | p290 | TEMEKEGKI | 792 | 316 |
| Rabies | NS | 197-205 | p290 | VEAEIAHQI | 793 | 309, 310 |
| Influenza A | NS | 1152-160 | p290 | EEGAIVGEI | 794 | 304 |
| Murine | SMCY | | p291 | TENSGKDI | 795 | 317 |
| | MHC class 1 leader | 3-11 | p293 | AMAPRTLLL | 796 | 318 |
| | ND1alpha | 1-12 | p293 | FFINILTLLVP | 797 | 323 |
| | ND Beta | 1-12 | p293 | FFINILTLLVP | 798 | 323 |
| | ND alpha | 1-17 | p293 | FFINILTLLVPI LIAM | 799 | 324 |
| | ND Beta | 1-17 | p293 | FFINALTLLVPI LIAM | 800 | 324 |
| | COI mitochondrial | 1-6 | p293 | FINRW | 801 | 325 |
| L. monocyto-genes | LemA | 1-6 | p293 | IGWII | 802 | 326 |
| | SW gag p11C | 179-190 | Mamu-A*01 | EGCTPYDINQ ML | 803 | 334 |
| | MAGE-3 | | HLA-A2 | ALSRKVAEL | 804 | 5,554,506 |
| | | | HLA-A2 | IMPKAGLLI | 805 | 5,554,506 |
| | | | HLA-A2 | KIWEELSVL | 806 | 5,554,506 |
| | | | HLA-A2 | ALVETSYVKV | 807 | 5,554,506 |
| | | | HLA-A2 | ThrLeuValGluVal ThrLeuGlyGluVal | 808 | 5,554,506 |
| | | | HLA-A2 | AlaLeuSerArgLys ValAlaGluLeu | 809 | 5,554,506 |
| | | | HLA-A2 | IleMetProLysAla GlyLeuLeuIle | 810 | 5,554,506 |
| | | | HLA-A2 | LysIleTrpGluGlu LeuSerValLeu | 811 | 5,554,506 |
| | | | HLA-A2 | AlaLeuValGluThr SerTyrValLys Val | 812 | 5,554,506 |
| | peptides which bind to MHCs | | HLA-A2 | Lys Gly Ile Leu Gly Phe Val Phe Thr Leu Thr Val | 813 | 5,989,565 |

TABLE 7-continued

| Source | Protein | AA Position | MHC molecules | T cell epitope MHC ligand (Antigen) | SEQ. ID NO.: | Ref. |
|---|---|---|---|---|---|---|
| | | | HLA-A2 | Gly Ile Ile Gly Phe Val Phe Thr Ile | 814 | 5,989,565 |
| | | | HLA-A2 | Gly Ile Ile Gly Phe Val Phe Thr Leu | 815 | 5,989,565 |
| | | | HLA-A2 | Gly Ile Leu Gly Phe Val Phe Thr Leu | 816 | 5,989,565 |
| | | | HLA-A2 | Gly Leu Leu Gly Phe Val Phe Thr Leu | 817 | 5,989,565 |
| | | | HLA-A2 | XXTVXXGVX, X=Leu or Ile (6-37) | 818 | 5,989,565 |
| | | | HLA-A2 | Ile Leu Thr Val Ile Leu Gly Val Leu | 819 | 5,989,565 |
| | | | HLA-A2 | Tyr Leu Glu Pro Gly Ala | 820 | 5,989,565 |
| | | | HLA-A2 | Gln Val Pro Leu Arg Tyr Lys | 821 | 5,989,565 |
| | | | HLA-A2 | Asp Gly Leu Ala Pro Pro Gln His Leu Ile Arg | 822 | 5,989,565 |
| | | | HLA-A2 | Leu Leu Gly Arg Asn Ser Phe Glu Val | 823 | 5,989,565 |
| | Peptides from MAGE-1 | | HLA-C clone 10 | GluHisSerAlaTyr GlyGluProArgLys LeuLeuThrGlnAsp Leu | 824 | 5,558,995 |
| | | | HLA-C clone 10 | GluHisSerAlaTyr GlyGluProArgLys LeuLeu | 825 | 5,558,995 |
| | | | HLA-C clone 10 | SerAlaTyrGlyGly ProArgLysLeu | 826 | 5,558,995 |
| | GAGE | | HLA-Cw6 | TyrArgProArgPro ArgArgTyr | 827 | 5,648,226 |
| | | | HLA-Cw6 | ThrTyrArgProArg ProArgArgTyr | 828 | 5,648,226 |
| | | | HLA-Cw6 | TyrArgProArgPro ArgArgTyrVal | 829 | 5,648,226 |
| | | | HLA-Cw6 | ThrTyrArgProArg ProArgArgTyrVal | 830 | 5,648,226 |
| | | | HLA-Cw6 | ArgProArgProArg ArgTyrValGlu | 831 | 5,648,226 |
| | | | HLA-Cw6 | MetSerTrpArgGly ArgSerThrTyrArg ProArgProArgArg | 832 | 5,648,226 |
| | | | HLA-Cw6 | ThrTyrArgProArg ProArgArgTyrVal GluProProGluMet Ile | 833 | 5,648,226 |

TABLE 7-continued

| Source | Protein | AA Position | MHC molecules | T cell epitope MHC ligand (Antigen) | SEQ. ID NO.: | Ref. |
|---|---|---|---|---|---|---|
| | MAGE | | HLA-A1, primarily | Isolated nonapeptide having Glu at its N terminal, Tyr at its C-terminal, and Asp at the third residue from its N terminal, with the proviso that said isolated nonapeptide is not Glu Ala Asp Pro Thr Gly His Ser Tyr (SEQ ID NO: 1), and wherein said isolated nonapeptide binds to a human leukocyte antigen molecule on a cell to form a complex, said complex provoking lysis of said cell by a cytolytic T cell specific to said complex | 834 | 5,405,940 |
| | | | HLA-A1, primarily | GluValValProIle SerHisLeuTyr | 835 | 5,405,940 |
| | | | HLA-A1, primarily | GluValValArgIle GlyHisLeuTyr | 836 | 5,405,940 |
| | | | HLA-A1, primarily | GluValAspProIle GlyHisLeuTyr | 837 | 5,405,940 |
| | | | HLA-A1, primarily | GluValAspProAla SerAsnThrTyr | 838 | 5,405,940 |
| | | | HLA-A1, primarily | GluValAspProThr SerAsnThrTyr | 839 | 5,405,940 |
| | | | HLA-A1, primarily | GluAlaAspProThr SerAsnThrTyr | 840 | 5,405,940 |
| | | | HLA-A1, primarily | GluValAspProIle GlyHisValTyr | 841 | 5,405,940 |
| | | | HLA-A1, primarily HLA-A1, | GAAGTGGTCC CCATCAGCCA CTTGTAC | 842 | 5,405,940 |
| | | | primarily HLA-A1, primarily | GAAGTGGTCC GCATCGGCCA CTTGTAC | 843 | 5,405,940 |
| | | | HLA-A1, primarily HLA-A1, | GAAGTGGAC CCCATCGGCC ACTTGTAC | 844 | 5,405,940 |
| | | | primarily HLA-A1, primarily | GAAGTGGAC CCCGCCAGCA ACACCTAC | 845 | 5,405,940 |
| | | | HLA-A1, primarily HLA-A1, | GAAGTGGAC CCCACCAGCA ACACCTAC | 846 | 5,405,940 |
| | | | primarily HLA-A1, primarily | GAAGCGGAC CCCACCAGCA ACACCTAC | 847 | 5,405,940 |

TABLE 7-continued

| Source | Protein | AA Position | MHC molecules | T cell epitope MHC ligand (Antigen) | SEQ. ID NO.: | Ref. |
|---|---|---|---|---|---|---|
| | | | HLA-A1, primarily | GAAGCGGACCCCACCAGCAACACCTAC | 848 | 5,405,940 |
| | | | HLA-A1, primarily | GAAGTGGACCCCATCGGCCACGTGTAC | 849 | 5,405,940 |
| | | | HLA-A1, primarily | GluAlaAspProThrGlyHisSer | 850 | 5,405,940 |
| | | | HLA-A1, primarily | AlaAspProTrpGlyHisSerTyr | 851 | 5,405,940 |
| | MAGE peptides | | HLA-A2 | SerThrLeuValGluValThrLeuGlyGluVal | 852 | 5,554,724 |
| | MAGE peptides | | HLA-A2 | LeuValGluValThrLeuGlyGluVal | 853 | 5,554,724 |
| | MAGE peptides | | HLA-A2 | LysMetValGluLeuValHisPheLeu | 854 | 5,554,724 |
| | MAGE peptides | | HLA-A2 | ValIlePheSerLysAlaSerGluTyrLeu | 855 | 5,554,724 |
| | MAGE peptides | | HLA-A2 | TyrLeuGlnLeuValPheGlyIleGluVal | 856 | 5,554,724 |
| | MAGE peptides | | HLA-A2 | GlnLeuValPheGlyIleGluValVal | 857 | 5,554,724 |
| | MAGE peptides | | HLA-A2 | GlnLeuValPheGlyIleGluValValGluVal | 858 | 5,554,724 |
| | MAGE peptides | | HLA-A2 | IleIleValLeuAlaIleIleAlaIle | 859 | 5,554,724 |
| | MAGE peptides | | HLA-A2 | LysIleTrpGluGluLeuSerMetLeuGluVal | 860 | 5,554,724 |
| | MAGE peptides | | HLA-A2 | AlaLeuIleGluThrSerTyrValLysVal | 861 | 5,554,724 |
| | MAGE peptides | | HLA-A2 | LeuIleGluThrSerTyrValLysVal | 862 | 5,554,724 |
| | MAGE peptides | | HLA-A2 | GlyLeuGluAlaArgGlyGluAlaLeuGlyLeu | 863 | 5,554,724 |
| | MAGE peptides | | HLA-A2 | GlyLeuGluAlaArgGlyGluAlaLeu | 864 | 5,554,724 |
| | MAGE peptides | | HLA-A2 | AlaLeuGlyLeuValGlyAlaGlnAla | 865 | 5,554,724 |
| | MAGE peptides | | HLA-A2 | GlyLeuValGlyAlaGlnAlaProAla | 866 | 5,554,724 |
| | MAGE peptides | | HLA-A2 | AspLeuGluSerGluPheGlnAlaAla | 867 | 5,554,724 |
| | MAGE peptides | | HLA-A2 | AspLeuGluSerGluPheGlnAlaAlaIle | 868 | 5,554,724 |
| | MAGE peptides | | HLA-A2 | AlaIleSerArgLysMetValGluLeuVal | 869 | 5,554,724 |
| | MAGE peptides | | HLA-A2 | AlaIleSerArgLysMetValGluLeu | 870 | 5,554,724 |

TABLE 7-continued

| Source | Protein | AA Position | MHC molecules | T cell epitope MHC ligand (Antigen) | SEQ. ID NO.: | Ref. |
|---|---|---|---|---|---|---|
| | MAGE peptides | | HLA-A2 | LysMetValGluLeu ValHisPheLeuLeu | 871 | 5,554,724 |
| | MAGE peptides | | HLA-A2 | LysMetValGluLeu ValHisPheLeuLeu Leu | 872 | 5,554,724 |
| | MAGE peptides | | HLA-A2 | LeuLeuLeuLysTyr ArgAlaArgGluPro Val | 873 | 5,554,724 |
| | MAGE peptides | | HLA-A2 | LeuLeuLysTyrArg AlaArgGluProVal | 874 | 5,554,724 |
| | MAGE peptides | | HLA-A2 | ValLeuArgAsnCys GlnAspPhePhePro Val | 875 | 5,554,724 |
| | MAGE peptides | | HLA-A2 | TyrLeuGlnLeuVal PheGlyIleGluVal Val | 876 | 5,554,724 |
| | MAGE peptides | | HLA-A2 | GlyIleGluValVal GluValValProIle | 877 | 5,554,724 |
| | MAGE peptides | | HLA-A2 | ProIleSerHisLeu TyrIleLeuVal | 878 | 5,554,724 |
| | MAGE peptides | | HLA-A2 | HisLeuTyrIleLeu ValThrCysLeu | 879 | 5,554,724 |
| | MAGE peptides | | HLA-A2 | HisLeuTyrIleLeu ValThrCysLeuGly Leu | 880 | 5,554,724 |
| | MAGE peptides | | HLA-A2 | TyrIleLeuValThr CysLeuGlyLeu | 881 | 5,554,724 |
| | MAGE peptides | | HLA-A2 | CysLeuGlyLeuSer TyrAspGlyLeu | 882 | 5,554,724 |
| | MAGE peptides | | HLA-A2 | CysLeuGlyLeuSer TyrAspGlyLeu Leu | 883 | 5,554,724 |
| | MAGE peptides | | HLA-A2 | ValMetProLysThr GlyLeuLeuIle | 884 | 5,554,724 |
| | MAGE peptides | | HLA-A2 | ValMetProLysThr GlyLeuLeuIleIle | 885 | 5,554,724 |
| | MAGE peptides | | HLA-A2 | ValMetProLysThr GlyLeuLeuIleIle Val | 886 | 5,554,724 |
| | MAGE peptides | | HLA-A2 | GlyLeuLeuIleIle ValLeuAlaIleIle | 887 | 5,554,724 |
| | MAGE peptides | | HLA-A2 | GlyLeuLeuIleIle ValLeuAlaIleIle | 888 | 5,554,724 |
| | MAGE peptides | | HLA-A2 | GlyLeuLeuIleIle ValLeuAlaIleIle Ala | 889 | 5,554,724 |
| | MAGE peptides | | HLA-A2 | LeuLeuIleIleVal LeuAlaIleIle | 890 | 5,554,724 |
| | MAGE peptides | | HLA-A2 | LeuLeuIleIleVal LeuAlaIleIleAla | 891 | 5,554,724 |
| | MAGE peptides | | HLA-A2 | LeuLeuIleIleVal LeuAlaIleIleAla Ile | 892 | 5,554,724 |

TABLE 7-continued

| Source | Protein | AA Position | MHC molecules | T cell epitope MHC ligand (Antigen) | SEQ. ID NO.: | Ref. |
|---|---|---|---|---|---|---|
| | MAGE peptides | | HLA-A2 | LeuIleIleValLeu AlaIleIleAla | 893 | 5,554,724 |
| | MAGE peptides | | HLA-A2 | LeuIleIleValLeu AlaIleIleAlaIle | 894 | 5,554,724 |
| | MAGE peptides | | HLA-A2 | IleIleAlaIleGlu GlyAspCysAla | 895 | 5,554,724 |
| | MAGE peptides | | HLA-A2 | LysIleTrpGluGlu LeuSerMetLeu | 896 | 5,554,724 |
| | MAGE peptides | | HLA-A2 | LeuMetGlnAspLeu ValGlnGluAsnTyr Leu | 897 | 5,554,724 |
| | MAGE peptides | | HLA-A2 | PheLeuTrpGlyPro ArgAlaLeuIle | 898 | 5,554,724 |
| | MAGE peptides | | HLA-A2 | LeuIleGluThrSer TyrValLysVal | 899 | 5,554,724 |
| | MAGE peptides | | HLA-A2 | AlaLeuIleGluThr SerTyrValLysVal Leu | 900 | 5,554,724 |
| | MAGE peptides | | HLA-A2 | ThrLeuLysIleGly GlyGluProHisIle | 901 | 5,554,724 |
| | MAGE peptides | | HLA-A2 | HisIleSerTyrPro ProLeuHisGluArg Ala | 902 | 5,554,724 |
| | MAGE peptides | | HLA-A2 | GlnThrAlaSerSer SerSerThrLeu | 903 | 5,554,724 |
| | MAGE peptides | | HLA-A2 | GlnThrAlaSerSer SerSerThrLeuVal | 904 | 5,554,724 |
| | MAGE peptides | | HLA-A2 | ValThrLeuGlyGlu ValProAlaAlaVal | 905 | 5,554,724 |
| | MAGE peptides | | HLA-A2 | ValThrLysAlaGlu MetLeuGluSerVal | 906 | 5,554,724 |
| | MAGE peptides | | HLA-A2 | ValThrLysAlaGlu MetLeuGluSerVal Leu | 907 | 5,554,724 |
| | MAGE peptides | | HLA-A2 | ValThrCysLeuGly LeuSerTyrAspGly Leu | 908 | 5,554,724 |
| | MAGE peptides | | HLA-A2 | LysThrGlyLeuLeu IleIleValLeu | 909 | 5,554,724 |
| | MAGE peptides | | HLA-A2 | LysThrGlyLeuLeu IleIleValLeuAla | 910 | 5,554,724 |
| | MAGE peptides | | HLA-A2 | LysThrGlyLeuLeu IleIleValLeuAla Ile | 911 | 5,554,724 |
| | MAGE peptides | | HLA-A2 | HisThrLeuLysIle GlyGlyGluProHis Ile | 912 | 5,554,724 |
| | MAGE peptides | | HLA-A2 | MetLeuAspLeuGln ProGluThrThr | 913 | 5,554,724 |
| | Mage-3 peptides | | HLA-A2 | GlyLeuGluAlaArg GlyGluAlaLeu | 914 | 5,585,461 |
| | Mage-3 peptides | | HLA-A2 | AlaLeuSerArgLys ValAlaGluLeu | 915 | 5,585,461 |

TABLE 7-continued

| Source | Protein | AA Position | MHC molecules | T cell epitope MHC ligand (Antigen) | SEQ. ID NO.: | Ref. |
|---|---|---|---|---|---|---|
| | Mage-3 peptides | | HLA-A2 | PheLeuTrpGlyPro ArgAlaLeuVal | 916 | 5,585,461 |
| | Mage-3 peptides | | HLA-A2 | ThrLeuValGluVal ThrLeuGlyGluVal | 917 | 5,585,461 |
| | Mage-3 peptides | | HLA-A2 | AlaLeuSerArgLys ValAlaGluLeuVal | 918 | 5,585,461 |
| | Mage-3 peptides | | HLA-A2 | AlaLeuValGluThr SerTyrValLysVal | 919 | 5,585,461 |
| | Tyrosinase | | HLA-A2 | TyrMetAsnGlyThr MetSerGlnVal | 920 | 5,487,974 |
| | Tyrosinase | | HLA-A2 | MetLeuLeuAlaVal LeuTyrCysLeuLeu | 921 | 5,487,974 |
| | Tyrosinase | | HLA-A2 | MetLeuLeuAlaVal LeuTyrCysLeu | 922 | 5,530,096 |
| | Tyrosinase | | HLA-A2 | LeuLeuAlaValLeu TyrCysLeuLeu | 923 | 5,530,096 |
| | Tyrosinase | | HLA-A2 and HLA-B44 | SerGluIleTrpArg AspIleAspPheAla HisGluAla | 924 | 5,519,117 |
| | Tyrosinase | | HLA-A2 and HLA-B44 | SerGluIleTrpArg AspIleAspPhe | 925 | 5,519,117 |
| | Tyrosinase | | HLA-A2 and HLA-B44 | GluGluAsnLeuLeu AspPheValArgPhe | 926 | 5,519,117 |
| | Melan A/MART-1 | | | EAAGIGILTV | 927 | Jäger, E. et al. Granulocyte-macrophage-colony-stimulating Factor Enhances Immune Responses To Melanoma-'associated Peptides in vivo Int. J Cancer 67, 54-62 (1996) |
| | Tyrosinase | | | MLLAVLYCL | 928 | Jäger, E. et al. Granulocyte-macrophage-colony-stimulating Factor Enhances Immune Responses To Melanoma-'associated Peptides in vivo Int. J Cancer 67, 54-62 (1996) |
| | Tyrosinase | | | YMDGTMSQV | 929 | Jäger, E. et al. Granulocyte-macrophage-colony-stimulating Factor Enhances Immune Responses To Melanoma-'associated Peptides in vivo Int. J Cancer 67, 54-62 (1996) |
| | gp100/Pme117 | | | YLEPGPVTA | 930 | Jäger, E. et al. Granulocyte-macrophage-colony-stimulating Factor Enhances Immune Responses To Melanoma-'associated Peptides in vivo Int. J Cancer 67, 54-62 (1996) |
| | gp100/Pme117 | | | LLDGTATLRL | 931 | Jäger, E. et al. Granulocyte-macrophage-colony-stimulating Factor Enhances Immune |

TABLE 7-continued

| Source | Protein | AA Position | MHC molecules | T cell epitope MHC ligand (Antigen) | SEQ. ID NO.: | Ref. |
|---|---|---|---|---|---|---|
| | | | | | | Responses To Melanoma-'associated Peptides in vivo Int. J Cancer 67, 54-62 (1996) |
| | Influenza matrix | | | GILGFVFTL | 932 | Jäger, E. et al. Granulocyte-macrophage-colony-stimulating Factor Enhances Immune Responses To Melanoma-'associated Peptides in vivo Int. J Cancer 67, 54-62 (1996) |
| | MAGE-1 | | | EADPTGHSY | 933 | Jäger, E. et al. Granulocyte-macrophage-colony-stimulating Factor Enhances Immune Responses To Melanoma-'associated Peptides in vivo Int. J Cancer 67, 54-62 (1996) |
| | MAGE-1 | | HLA-A1 | EADPTGHSY | 934 | |
| | BAGE | | HLA-C | MAARAVFLAL SAQLLQARLM KE | 935 | Jäger, E. et al. Granulocyte-macrophage-colony-stimulating Factor Enhances Immune Responses To Melanoma-'associated Peptides in vivo Int. J Cancer 67, 54-62 (1996) |
| | BAGE | | HLA-C | MAARAVFLAL SAQLLQ | 936 | Jäger, E. et al. Granulocyte-macrophage-colony-stimulating Factor Enhances Immune Responses To Melanoma-'associated Peptides in vivo Int. J Cancer 67, 54-62 (1996) |
| | BAGE | | HLA-C | AARAVFLAL | 937 | Jäger, E. et al. Granulocyte-macrophage-colony-stimulating Factor Enhances Immune Responses To Melanoma-'associated Peptides in vivo Int. J Cancer 67, 54-62 (1996) |
| Influenza | PR8 NP | 147-154 | $K^d$ | IYQRIRALV | 938 | Falk et al., Allele-specific motifs revealed by sequencing of self-peptides eluted from MHC molecules |
| SELF PEPTIDE | P815 | | $K^d$ | SYFPEITHI | 939 | Falk et al., Allele-specific motifs revealed by sequencing of self-peptides eluted from MHC molecules |
| Influenza | Jap HA 523-549 | | $K^d$ | IYATVAGSL | 940 | Falk et al., Allele-specific motifs revealed by sequencing of self-peptides eluted from MHC molecules |
| Influenza | Jap HA 523-549 | | $K^d$ | VYQILAIYA | 941 | Falk et al., Allele-specific motifs revealed by sequencing of self-peptides eluted from MHC molecules |

TABLE 7-continued

| Source | Protein | AA Position | MHC molecules | T cell epitope MHC ligand (Antigen) | SEQ. ID NO.: | Ref. |
|---|---|---|---|---|---|---|
| Influenza | Jap HA 523-549 | | $K^d$ | IYSTVASSL | 942 | Falk et al., Allele-specific motifs revealed by sequencing of self-peptides eluted from MHC molecules |
| Influenza | JAP HA 202-221 | | $K^d$ | LYQNVGTYV | 943 | Falk et al., Allele-specific motifs revealed by sequencing of self-peptides eluted from MHC molecules |
| | HLA-A24 | | $K^d$ | RYLENQKRT | 944 | Falk et al., Allele-specific motifs revealed by sequencing of self-peptides eluted from MHC molecules |
| | HLA-Cw3 | | $K^d$ | RYLKNGKET | 945 | Falk et al., Allele-specific motifs revealed by sequencing of self-peptides eluted from MHC molecules |
| | P815 | | $K^d$ | KYQAVTTTL | 946 | Falk et al., Allele-specific motifs revealed by sequencing of self-peptides eluted from MHC molecules |
| *Plasmodium berghei* | CSP | | $K^d$ | SYIPSAEKI | 947 | Falk et al., Allele-specific motifs revealed by sequencing of self-peptides eluted from MHC molecules |
| *Plasmodium yoelii* | CSP | | $K^d$ | SYVPSAFQI | 948 | Falk et al., Allele-specific motifs revealed by sequencing of self-peptides eluted from MHC molecules |
| *Vesicular stomatitis virus* | NP 52-59 | | $K^b$ | RGYVYQGL | 949 | Falk et al., Allele-specific motifs revealed by sequencing of self-by sequencing of self-peptides eluted from MHC molecules |
| Ovalbumin | | | $K^b$ | SIINFEKL | 950 | Falk et al., Allele-specific motifs revealed by sequencing of self-peptides eluted from MHC molecules |
| *Sendai virus* | NP 321-332 | | $K^b$ | APGNYPAL | 951 | Falk et al., Allele-specific motifs revealed by sequencing of self-peptides eluted from MHC molecules |
| | | | | VPYGSFKHV | 952 | Morel et al., Processing of some antigens by the standard proteasome but not by the immunoproteasome results in poor presentation by dendritic cells, Immunity, vol. 12: 107-117, 2000. |
| | | | MOTIFS | | | |
| Influenza | PR8 NP | | $K^d$ restricted | TYQRTRALV | 953 | 5,747,269 |

TABLE 7-continued

| Source | Protein | AA Position | MHC molecules | T cell epitope MHC ligand (Antigen) | SEQ. ID NO.: | Ref. |
|---|---|---|---|---|---|---|
| Self peptide | P815 | | $K^d$ restricted peptide motif | SYFPEITHI | 954 | 5,747,269 |
| Influenza | JAP HA | | $K^d$ restricted peptide motif | IYATVAGSL | 955 | 5,747,269 |
| Influenza | JAP HA | | $K^d$ restricted peptide motif | VYQILAIYA | 956 | 5,747,269 |
| Influenza | PR8 HA | | $K^d$ restricted peptide motif | IYSTVASSL | 957 | 5,747,269 |
| Influenza | JAP HA | | $K^d$ restricted peptide motif | LYQNVGTYV | 958 | 5,747,269 |
| | | | HLA-A24 | RYLENGKETL | 959 | 5,747,269 |
| | | | HLA-Cw3 | RYLKNGKETL | 960 | 5,747,269 |
| | P815 tumour antigen | | HLA-Cw3 | KYQAVTTTL | 961 | 5,747,269 |
| *Plasmodium berghei* | CSP | | HLA-Cw3 | SYIPSAEKI | 962 | 5,747,269 |
| *Plasmodium yoelii* | CSP | | HLA-Cw3 | SYVPSAEQI | 963 | 5,747,269 |
| Influenza | NP | | $D^b$-restricted peptide motif | ASNENMETM | 964 | 5,747,269 |
| *Adenovirus* | E1A | | $D^b$-restricted peptide motif | SGPSNTPPEI | 965 | 5,747,269 |
| Lymphocytic choriomeningitis | | | $D^b$-restricted peptide motif | SGVENPGGYCL | 966 | 5,747,269 |
| Simian virus | 40 T | | $D^b$-restricted peptide motif | SAINNY . . . | 967 | 5,747,269 |
| HIV | reverse transcriptase | | HLA-A2.1-restricted peptide motif | ILKEPVHGV | 968 | 5,747,269 |
| | influenza matrix protein | | HLA-A2.1-restricted peptide motif | GILGFVFTL | 969 | 5,747,269 |
| Influenza | influenza matrix | | HLA-A2.1- | ILGFVFTLTV | 970 | 5,747,269 |

TABLE 7-continued

| Source | Protein | AA Position | MHC molecules | T cell epitope MHC ligand (Antigen) | SEQ. ID NO.: | Ref. |
|---|---|---|---|---|---|---|
| | protein | | restricted peptide motif | | | |
| HIV | Gag protein | | | FLQSRPEPT | 971 | 5,747,269 |
| HIV | Gag protein | | | AMQMLKE . . . | 972 | 5,747,269 |
| HIV | Gag protein | | | PIAPGQMRE | 973 | 5,747,269 |
| HIV | Gag protein | | | QMKDCTERQ | 974 | 5,747,269 |
| | | | HLA-A*0205-restricted peptide motif | VYGVIQK | 975 | 5,747,269 |

TABLE 8

VSV-NP peptide (49-62)
LCMV-NP peptide (118-132)
LCMV glycoprotein peptide. 33-41

Still further embodiments are directed to methods, uses, therapies and compositions related to epitopes with specificity for MHC, including, for example, those listed in Tables 9-13. Other embodiments include one or more of the MHCs listed in Tables 9-13, including combinations of the same, while other embodiments specifically exclude any one or more of the MHCs or combinations thereof. Tables 11-13 include frequencies for the listed HLA antigens.

TABLE 9

| Class I MHC Molecules |
|---|
| Class I Human |
| HLA-A1 |
| HLA-A*0101 |
| HLA-A*0201 |
| HLA-A*0202 |
| HLA-A*0203 |
| HLA-A*0204 |
| HLA-A*0205 |
| HLA-A*0206 |
| HLA-A*0207 |
| HLA-A*0209 |
| HLA-A*0214 |
| HLA-A3 |
| HLA-A*0301 |
| HLA-A*1101 |
| HLA-A23 |
| HLA-A24 |
| HLA-A25 |
| HLA-A*2902 |
| HLA-A*3101 |
| HLA-A*3302 |
| HLA-A*6801 |
| HLA-A*6901 |
| HLA-B7 |
| HLA-B*0702 |
| HLA-B*0703 |
| HLA-B*0704 |
| HLA-B*0705 |
| HLA-B8 |

TABLE 9-continued

| Class I MHC Molecules |
|---|
| HLA-B13 |
| HLA-B14 |
| HLA-B*1501 (B62) |
| HLA-B17 |
| HLA-B18 |
| HLA-B22 |
| HLA-B27 |
| HLA-B*2702 |
| HLA-B*2704 |
| HLA-B*2705 |
| HLA-B*2709 |
| HLA-B35 |
| HLA-B*3501 |
| HLA-B*3502 |
| HLA-B*3701 |
| HLA-B*3801 |
| HLA-B*39011 |
| HLA-B*3902 |
| HLA-B40 |
| HLA-B*40012 (B60) |
| HLA-B*4006 (B61) |
| HLA-B44 |
| HLA-B*4402 |
| HLA-B*4403 |
| HLA-B*4501 |
| HLA-B*4601 |
| HLA-B51 |
| HLA-B*5101 |
| HLA-B*5102 |
| HLA-B*5103 |
| HLA-B*5201 |
| HLA-B*5301 |
| HLA-B*5401 |
| HLA-B*5501 |
| HLA-B*5502 |
| HLA-B*5601 |
| HLA-B*5801 |
| HLA-B*6701 |
| HLA-B*7301 |
| HLA-B*7801 |
| HLA-Cw*0102 |
| HLA-Cw*0301 |
| HLA-Cw*0304 |
| HLA-Cw*0401 |
| HLA-Cw*0601 |
| HLA-Cw*0602 |
| HLA-Cw*0702 |
| HLA-Cw8 |
| HLA-Cw*1601 M |
| HLA-G |

TABLE 9-continued

Class I MHC Molecules

Murine

H2-K$^d$
H2-D$^d$
H2-L$^d$
H2-K$^b$
H2-D$^b$
H2-K$^k$
H2-K$^{kml}$
Qa-1$^a$
Qa-2
H2-M3
Rat RT1.A$^a$
RT1.A$^1$
Bovine Bota-A11
Bota-A20
Chicken B-F4
B-F12
B-F15
B-F19
Chimpanzee Patr-A*04
Patr-A*11
Patr-B*01
Patr-B*13
Patr-B*16
Baboon Papa-A*06
Macaque Mamu-A*01
Swine SLA (haplotype d/d)
Virus homolog hCMV class I homolog UL18

TABLE 10

Class I MHC Molecules

Class I
Human

HLA-A1
HLA-A*0101
HLA-A*0201
HLA-A*0202
HLA-A*0204
HLA-A*0205
HLA-A*0206
HLA-A*0207
HLA-A*0214
HLA-A3
HLA-A*1101
HLA-A24
HLA-A*2902
HLA-A*3101
HLA-A*3302
HLA-A*6801
HLA-A*6901
HLA-B7
HLA-B*0702
HLA-B*0703

TABLE 10-continued

Class I MHC Molecules

HLA-B*0704
HLA-B*0705
HLA-B8
HLA-B14
HLA-B*1501 (B62)
HLA-B27
HLA-B*2702
HLA-B*2705
HLA-B35
HLA-B*3501
HLA-B*3502
HLA-B*3701
HLA-B*3801
HLA-B*39011
HLA-B*3902
HLA-B40
HLA-B*40012 (B60)
HLA-B*4006 (B61)
HLA-B44
HLA-B*4402
HLA-B*4403
HLA-B*4601
HLA-B51
HLA-B*5101
HLA-B*5102
HLA-B*5103
HLA-B*5201
HLA-B*5301
HLA-B*5401
HLA-B*5501
HLA-B*5502
HLA-B*5601
HLA-B*5801
HLA-B*6701
HLA-B*7301
HLA-B*7801
HLA-Cw*0102
HLA-Cw*0301
HLA-Cw*0304
HLA-Cw*0401
HLA-Cw*0601
HLA-Cw*0602
HLA-Cw*0702
HLA-G
Murine H2-K$^d$
H2-D$^d$
H2-L$^d$
H2-K$^b$
H2-D$^b$
H2-K$^k$
H2-K$^{kml}$
Qa-2
Rat RT1.A$^a$
RT1.A$^1$
Bovine Bota-A11
Bota-A20
Chicken B-F4
B-F12
B-F15
B-F19
Virus homolog hCMV class I homolog UL18

TABLE 11

Estimated gene frequencies of HLA-A antigens

| Antigen | CAU Gf[a] | SE[b] | AFR Gf | SE | ASI Gf | SE | LAT Gf | SE | NAT Gf | SE |
|---|---|---|---|---|---|---|---|---|---|---|
| A1 | 15.1843 | 0.0489 | 5.7256 | 0.0771 | 4.4818 | 0.0846 | 7.4007 | 0.0978 | 12.0316 | 0.2533 |
| A2 | 28.6535 | 0.0619 | 18.8849 | 0.1317 | 24.6352 | 0.1794 | 28.1198 | 0.1700 | 29.3408 | 0.3585 |
| A3 | 13.3890 | 0.0463 | 8.4406 | 0.0925 | 2.6454 | 0.0655 | 8.0789 | 0.1019 | 11.0293 | 0.2437 |
| A28 | 4.4652 | 0.0280 | 9.9269 | 0.0997 | 1.7657 | 0.0537 | 8.9446 | 0.1067 | 5.3856 | 0.1750 |
| A36 | 0.0221 | 0.0020 | 1.8836 | 0.0448 | 0.0148 | 0.0049 | 0.1584 | 0.0148 | 0.1545 | 0.0303 |
| A23 | 1.8287 | 0.0181 | 10.2086 | 0.1010 | 0.3256 | 0.0231 | 2.9269 | 0.0628 | 1.9903 | 0.1080 |
| A24 | 9.3251 | 0.0395 | 2.9668 | 0.0560 | 22.0391 | 0.1722 | 13.2610 | 0.1271 | 12.6613 | 0.2590 |
| A9 unsplit | 0.0809 | 0.0038 | 0.0367 | 0.0063 | 0.0858 | 0.0119 | 0.0537 | 0.0086 | 0.0356 | 0.0145 |
| A9 total | 11.2347 | 0.0429 | 13.2121 | 0.1128 | 22.4505 | 0.1733 | 16.2416 | 0.1382 | 14.6872 | 0.2756 |
| A25 | 2.1157 | 0.0195 | 0.4329 | 0.0216 | 0.0990 | 0.0128 | 1.1937 | 0.0404 | 1.4520 | 0.0924 |
| A26 | 3.8795 | 0.0262 | 2.8284 | 0.0547 | 4.6628 | 0.0862 | 3.2612 | 0.0662 | 2.4292 | 0.1191 |
| A34 | 0.1508 | 0.0052 | 3.5228 | 0.0610 | 1.3529 | 0.0470 | 0.4928 | 0.0260 | 0.3150 | 0.0432 |
| A43 | 0.0018 | 0.0006 | 0.0334 | 0.0060 | 0.0231 | 0.0062 | 0.0055 | 0.0028 | 0.0059 | 0.0059 |
| A66 | 0.0173 | 0.0018 | 0.2233 | 0.0155 | 0.0478 | 0.0089 | 0.0399 | 0.0074 | 0.0534 | 0.0178 |
| A10 unsplit | 0.0790 | 0.0038 | 0.0939 | 0.0101 | 0.1255 | 0.0144 | 0.0647 | 0.0094 | 0.0298 | 0.0133 |
| A10 total | 6.2441 | 0.0328 | 7.1348 | 0.0850 | 6.3111 | 0.0993 | 5.0578 | 0.0816 | 4.2853 | 0.1565 |
| A29 | 3.5796 | 0.0252 | 3.2071 | 0.0582 | 1.1233 | 0.0429 | 4.5156 | 0.0774 | 3.4345 | 0.1410 |
| A30 | 2.5067 | 0.0212 | 13.0969 | 0.1129 | 2.2025 | 0.0598 | 4.4873 | 0.0772 | 2.5314 | 0.1215 |
| A31 | 2.7386 | 0.0221 | 1.6556 | 0.0420 | 3.6005 | 0.0761 | 4.8328 | 0.0800 | 6.0881 | 0.1855 |
| A32 | 3.6956 | 0.0256 | 1.5384 | 0.0405 | 1.0331 | 0.0411 | 2.7064 | 0.0604 | 2.5521 | 0.1220 |
| A33 | 1.2080 | 0.0148 | 6.5607 | 0.0822 | 9.2701 | 0.1191 | 2.6593 | 0.0599 | 1.0754 | 0.0796 |
| A74 | 0.0277 | 0.0022 | 1.9949 | 0.0461 | 0.0561 | 0.0096 | 0.2027 | 0.0167 | 0.1068 | 0.0252 |
| A19 unsplit | 0.0567 | 0.0032 | 0.2057 | 0.0149 | 0.0990 | 0.0128 | 0.1211 | 0.0129 | 0.0475 | 0.0168 |
| A19 total | 13.8129 | 0.0468 | 28.2593 | 0.1504 | 17.3846 | 0.1555 | 19.5252 | 0.1481 | 15.8358 | 0.2832 |
| AX | 0.8204 | 0.0297 | 4.9506 | 0.0963 | 2.9916 | 0.1177 | 1.6332 | 0.0878 | 1.8454 | 0.1925 |

[a]Gene frequency.
[b]Standard error.

TABLE 12

Estimated gene frequencies for HLA-B antigens

| Antigen | CAU Gf[a] | SE[b] | AFR Gf | SE | ASI Gf | SE | LAT Gf | SE | NAT Gf | SE |
|---|---|---|---|---|---|---|---|---|---|---|
| B7 | 12.1782 | 0.0445 | 10.5960 | 0.1024 | 4.2691 | 0.0827 | 6.4477 | 0.0918 | 10.9845 | 0.2432 |
| B8 | 9.4077 | 0.0397 | 3.8315 | 0.0634 | 1.3322 | 0.0467 | 3.8225 | 0.0715 | 8.5789 | 0.2176 |
| B13 | 2.3061 | 0.0203 | 0.8103 | 0.0295 | 4.9222 | 0.0886 | 1.2699 | 0.0416 | 1.7495 | 0.1013 |
| B14 | 4.3481 | 0.0277 | 3.0331 | 0.0566 | 0.5004 | 0.0287 | 5.4166 | 0.0846 | 2.9823 | 0.1316 |
| B18 | 4.7980 | 0.0290 | 3.2057 | 0.0582 | 1.1246 | 0.0429 | 4.2349 | 0.0752 | 3.3422 | 0.1391 |
| B27 | 4.3831 | 0.0278 | 1.2918 | 0.0372 | 2.2355 | 0.0603 | 2.3724 | 0.0567 | 5.1970 | 0.1721 |
| B35 | 9.6614 | 0.0402 | 8.5172 | 0.0927 | 8.1203 | 0.1122 | 14.6516 | 0.1329 | 10.1198 | 0.2345 |
| B37 | 1.4032 | 0.0159 | 0.5916 | 0.0252 | 1.2327 | 0.0449 | 0.7807 | 0.0327 | 0.9755 | 0.0759 |
| B41 | 0.9211 | 0.0129 | 0.8183 | 0.0296 | 0.1303 | 0.0147 | 1.2818 | 0.0418 | 0.4766 | 0.0531 |
| B42 | 0.0608 | 0.0033 | 5.6991 | 0.0768 | 0.0841 | 0.0118 | 0.5866 | 0.0284 | 0.2856 | 0.0411 |
| B46 | 0.0099 | 0.0013 | 0.0151 | 0.0040 | 4.9292 | 0.0886 | 0.0234 | 0.0057 | 0.0238 | 0.0119 |
| B47 | 0.2069 | 0.0061 | 0.1305 | 0.0119 | 0.0956 | 0.0126 | 0.1832 | 0.0159 | 0.2139 | 0.0356 |
| B48 | 0.0865 | 0.0040 | 0.1316 | 0.0119 | 2.0276 | 0.0575 | 1.5915 | 0.0466 | 1.0267 | 0.0778 |
| B53 | 0.4620 | 0.0092 | 10.9529 | 0.1039 | 0.4315 | 0.0266 | 1.6982 | 0.0481 | 1.0804 | 0.0798 |
| B59 | 0.0020 | 0.0006 | 0.0032 | 0.0019 | 0.4277 | 0.0265 | 0.0055 | 0.0028 | 0[c] | — |
| B67 | 0.0040 | 0.0009 | 0.0086 | 0.0030 | 0.2276 | 0.0194 | 0.0055 | 0.0028 | 0.0059 | 0.0059 |
| B70 | 0.3270 | 0.0077 | 7.3571 | 0.0866 | 0.8901 | 0.0382 | 1.9266 | 0.0512 | 0.6901 | 0.0639 |
| B73 | 0.0108 | 0.0014 | 0.0032 | 0.0019 | 0.0047 |  | 0.0261 | 0.0060 | 0[c] | — |
| B51 | 5.4215 | 0.0307 | 2.5980 | 0.0525 | 7.4751 | 0.1080 | 6.8147 | 0.0943 | 6.9077 | 0.1968 |
| B52 | 0.9658 | 0.0132 | 1.3712 | 0.0383 | 3.5121 | 0.0752 | 2.2447 | 0.0552 | 0.6960 | 0.0641 |
| B5 unsplit | 0.1565 | 0.0053 | 0.1522 | 0.0128 | 0.1288 | 0.0146 | 0.1546 | 0.0146 | 0.1307 | 0.0278 |
| B5 total | 6.5438 | 0.0435 | 4.1214 | 0.0747 | 11.1160 | 0.1504 | 9.2141 | 0.1324 | 7.7344 | 0.2784 |
| B44 | 13.4838 | 0.0465 | 7.0137 | 0.0847 | 5.6807 | 0.0948 | 9.9253 | 0.1121 | 11.8024 | 0.2511 |
| B45 | 0.5771 | 0.0102 | 4.8069 | 0.0708 | 0.1816 | 0.0173 | 1.8812 | 0.0506 | 0.7603 | 0.0670 |
| B12 unsplit | 0.0788 | 0.0038 | 0.0280 | 0.0055 | 0.0049 | 0.0029 | 0.0193 | 0.0051 | 0.0654 | 0.0197 |
| B12 total | 14.1440 | 0.0474 | 11.8486 | 0.1072 | 5.8673 | 0.0963 | 11.8258 | 0.1210 | 12.6281 | 0.2584 |
| B62 | 5.9117 | 0.0320 | 1.5267 | 0.0404 | 9.2249 | 0.1190 | 4.1825 | 0.0747 | 6.9421 | 0.1973 |
| B63 | 0.4302 | 0.0088 | 1.8865 | 0.0448 | 0.4438 | 0.0270 | 0.8083 | 0.0333 | 0.3738 | 0.0471 |
| B75 | 0.0104 | 0.0014 | 0.0226 | 0.0049 | 1.9673 | 0.0566 | 0.1101 | 0.0123 | 0.0356 | 0.0145 |
| B76 | 0.0026 | 0.0007 | 0.0065 | 0.0026 | 0.0874 | 0.0120 | 0.0055 | 0.0028 | 0 | — |
| B77 | 0.0057 | 0.0010 | 0.0119 | 0.0036 | 0.0577 | 0.0098 | 0.0083 | 0.0034 | 0[c] | 0.0059 |
| B15 unsplit | 0.1305 | 0.0049 | 0.0691 | 0.0086 | 0.4301 | 0.0266 | 0.1820 | 0.0158 | 0.0059 | 0.0206 |
| B15 total | 6.4910 | 0.0334 | 3.5232 | 0.0608 | 12.2112 | 0.1344 | 5.2967 | 0.0835 | 0.0715 7.4290 | 0.2035 |
| B38 | 2.4413 | 0.0209 | 0.3323 | 0.0189 | 3.2818 | 0.0728 | 1.9652 | 0.0517 | 1.1017 | 0.0806 |

TABLE 12-continued

Estimated gene frequencies for HLA-B antigens

| Antigen | CAU Gf[a] | SE[b] | AFR Gf | SE | ASI Gf | SE | LAT Gf | SE | NAT Gf | SE |
|---|---|---|---|---|---|---|---|---|---|---|
| B39 | 1.9614 | 0.0188 | 1.2893 | 0.0371 | 2.0352 | 0.0576 | 6.3040 | 0.0909 | 4.5527 | 0.1615 |
| B16 unsplit | 0.0638 | 0.0034 | 0.0237 | 0.0051 | 0.0644 | 0.0103 | 0.1226 | 0.0130 | 0.0593 | 0.0188 |
| B16 total | 4.4667 | 0.0280 | 1.6453 | 0.0419 | 5.3814 | 0.0921 | 8.3917 | 0.1036 | 5.7137 | 0.1797 |
| B57 | 3.5955 | 0.0252 | 5.6746 | 0.0766 | 2.5782 | 0.0647 | 2.1800 | 0.0544 | 2.7265 | 0.1260 |
| B58 | 0.7152 | 0.0114 | 5.9546 | 0.0784 | 4.0189 | 0.0803 | 1.2481 | 0.0413 | 0.9398 | 0.0745 |
| B17 unsplit | 0.2845 | 0.0072 | 0.3248 | 0.0187 | 0.3751 | 0.0248 | 0.1446 | 0.0141 | 0.2674 | 0.0398 |
| B17 total | 4.5952 | 0.0284 | 11.9540 | 0.1076 | 6.9722 | 0.1041 | 3.5727 | 0.0691 | 3.9338 | 0.1503 |
| B49 | 1.6452 | 0.0172 | 2.6286 | 0.0528 | 0.2440 | 0.0200 | 2.3353 | 0.0562 | 1.5462 | 0.0953 |
| B50 | 1.0580 | 0.0138 | 0.8636 | 0.0304 | 0.4421 | 0.0270 | 1.8883 | 0.0507 | 0.7862 | 0.0681 |
| B21 unsplit | 0.0702 | 0.0036 | 0.0270 | 0.0054 | 0.0132 | 0.0047 | 0.0771 | 0.0103 | 0.0356 | 0.0145 |
| B21 total | 2.7733 | 0.0222 | 3.5192 | 0.0608 | 0.6993 | 0.0339 | 4.3007 | 0.0755 | 2.3680 | 0.1174 |
| B54 | 0.0124 | 0.0015 | 0.0183 | 0.0044 | 2.6873 | 0.0660 | 0.0289 | 0.0063 | 0.0534 | 0.0178 |
| B55 | 1.9046 | 0.0185 | 0.4895 | 0.0229 | 2.2444 | 0.0604 | 0.9515 | 0.0361 | 1.4054 | 0.0909 |
| B56 | 0.5527 | 0.0100 | 0.2686 | 0.0170 | 0.8260 | 0.0368 | 0.3596 | 0.0222 | 0.3387 | 0.0448 |
| B22 unsplit | 0.1682 | 0.0055 | 0.0496 | 0.0073 | 0.2730 | 0.0212 | 0.0372 | 0.0071 | 0.1246 | 0.0272 |
| B22 total | 2.0852 | 0.0217 | 0.8261 | 0.0297 | 6.0307 | 0.0971 | 1.3771 | 0.0433 | 1.9221 | 0.1060 |
| B60 | 5.2222 | 0.0302 | 1.5299 | 0.0404 | 8.3254 | 0.1135 | 2.2538 | 0.0553 | 5.7218 | 0.1801 |
| B61 | 1.1916 | 0.0147 | 0.4709 | 0.0225 | 6.2072 | 0.0989 | 4.6691 | 0.0788 | 2.6023 | 0.1231 |
| B40 unsplit | 0.2696 | 0.0070 | 0.0388 | 0.0065 | 0.3205 | 0.0230 | 0.2473 | 0.0184 | 0.2271 | 0.0367 |
| B40 total | 6.6834 | 0.0338 | 2.0396 | 0.0465 | 14.8531 | 0.1462 | 7.1702 | 0.0963 | 8.5512 | 0.2168 |
| BX | 1.0922 | 0.0252 | 3.5258 | 0.0802 | 3.8749 | 0.0988 | 2.5266 | 0.0807 | 1.9867 | 0.1634 |

[a]Gene frequency.
[b]Standard error.
[c]The observed gene count was zero.

TABLE 13

Estimated gene frequencies of HLA-DR antigens

| Antigen | CAU Gf[a] | SE[b] | AFR Gf | SE | ASI Gf | SE | LAT Gf | SE | NAT Gf | SE |
|---|---|---|---|---|---|---|---|---|---|---|
| DR1 | 10.2279 | 0.0413 | 6.8200 | 0.0832 | 3.4628 | 0.0747 | 7.9859 | 0.1013 | 8.2512 | 0.2139 |
| DR2 | 15.2408 | 0.0491 | 16.2373 | 0.1222 | 18.6162 | 0.1608 | 11.2389 | 0.1182 | 15.3932 | 0.2818 |
| DR3 | 10.8708 | 0.0424 | 13.3080 | 0.1124 | 4.7223 | 0.0867 | 7.8998 | 0.1008 | 10.2549 | 0.2361 |
| DR4 | 16.7589 | 0.0511 | 5.7084 | 0.0765 | 15.4623 | 0.1490 | 20.5373 | 0.1520 | 19.8264 | 0.3123 |
| DR6 | 14.3937 | 0.0479 | 18.6117 | 0.1291 | 13.4471 | 0.1404 | 17.0265 | 0.1411 | 14.8021 | 0.2772 |
| DR7 | 13.2807 | 0.0463 | 10.1317 | 0.0997 | 6.9270 | 0.1040 | 10.6726 | 0.1155 | 10.4219 | 0.2378 |
| DR8 | 2.8820 | 0.0227 | 6.2673 | 0.0800 | 6.5413 | 0.1013 | 9.7731 | 0.1110 | 6.0059 | 0.1844 |
| DR9 | 1.0616 | 0.0139 | 2.9646 | 0.0559 | 9.7527 | 0.1218 | 1.0712 | 0.0383 | 2.8662 | 0.1291 |
| DR10 | 1.4790 | 0.0163 | 2.0397 | 0.0465 | 2.2304 | 0.0602 | 1.8044 | 0.0495 | 1.0896 | 0.0801 |
| DR11 | 9.3180 | 0.0396 | 10.6151 | 0.1018 | 4.7375 | 0.0869 | 7.0411 | 0.0955 | 5.3152 | 0.1740 |
| DR12 | 1.9070 | 0.0185 | 4.1152 | 0.0655 | 10.1365 | 0.1239 | 1.7244 | 0.0484 | 2.0132 | 0.1086 |
| DR5 unsplit | 1.2199 | 0.0149 | 2.2957 | 0.0493 | 1.4118 | 0.0480 | 1.8225 | 0.0498 | 1.6769 | 0.0992 |
| DR5 total | 12.4449 | 0.0045 | 17.0260 | 0.1243 | 16.2858 | 0.1516 | 10.5880 | 0.1148 | 9.0052 | 0.2218 |
| DRX | 1.3598 | 0.0342 | 0.8853 | 0.0760 | 2.5521 | 0.1089 | 1.4023 | 0.0930 | 2.0834 | 0.2037 |

[a]Gene frequency.
[b]Standard error.

It can be desirable to express housekeeping peptides in the context of a larger protein. Processing can be detected even when a small number of amino acids are present beyond the terminus of an epitope. Small peptide hormones are usually proteolytically processed from longer translation products, often in the size range of approximately 60-120 amino acids. This fact has led some to assume that this is the minimum size that can be efficiently translated. In some embodiments, the housekeeping peptide can be embedded in a translation product of at least about 60 amino acids, in others 70, 80, 90 amino acids, and in still others 100, 110 or 120 amino acids, for example. In other embodiments the housekeeping peptide can be embedded in a translation product of at least about 50, 30, or 15 amino acids.

Due to differential proteasomal processing, the immunoproteasome of the pAPC produces peptides that are different from those produced by the housekeeping proteasome in peripheral body cells. Thus, in expressing a housekeeping peptide in the context of a larger protein, it is preferably expressed in the pAPC in a context other than its full-length native sequence, because, as a housekeeping epitope, it is generally only efficiently processed from the native protein by the housekeeping proteasome, which is not active in the pAPC. In order to encode the housekeeping epitope in a DNA sequence encoding a larger polypeptide, it is useful to find flanking areas on either side of the sequence encoding the epitope that permit appropriate cleavage by the immunoproteasome in order to liberate that housekeeping epitope. Such a sequence promoting appropriate processing is referred to hereinafter as having substrate or liberation sequence function. Altering flanking amino acid residues at the N-terminus and C-terminus of the desired housekeeping epitope can facilitate appropriate cleavage and generation of the housekeeping epitope in the pAPC. Sequences embedding housekeeping epitopes can be designed de novo and screened to determine which can be successfully processed by immunoproteasomes to liberate housekeeping epitopes.

Alternatively, another strategy is very effective for identifying sequences allowing production of housekeeping epitopes in APC. A contiguous sequence of amino acids can be generated from head to tail arrangement of one or more housekeeping epitopes. A construct expressing this sequence is used to immunize an animal, and the resulting T cell response is evaluated to determine its specificity to one or more of the epitopes in the array. These immune responses indicate housekeeping epitopes that are processed in the pAPC effectively. The necessary flanking areas around this epitope are thereby defined. The use of flanking regions of about 4-6 amino acids on either side of the desired peptide can provide the necessary information to facilitate proteasome processing of the housekeeping epitope by the immunoproteasome. Therefore, a substrate or liberation sequence of approximately 16-22 amino acids can be inserted into, or fused to, any protein sequence effectively to result in that housekeeping epitope being produced in an APC. In some embodiments, a broader context of a substrate sequence can also influence processing. In such embodiments, comparisons of a liberaton sequence in a variety of contexts can be useful in further optimizing a particular substrate sequence. In alternate embodiments the whole head-to-tail array of epitopes, or just the epitopes immediately adjacent to the correctly processed housekeeping epitope can be similarly transferred from a test construct to a vaccine vector.

In a preferred embodiment, the housekeeping epitopes can be embedded between known immune epitopes, or segments of such, thereby providing an appropriate context for processing. The abutment of housekeeping and immune epitopes can generate the necessary context to enable the immunoproteasome to liberate the housekeeping epitope, or a larger fragment, preferably including a correct C-terminus. It can be useful to screen constructs to verify that the desired epitope is produced. The abutment of housekeeping epitopes can generate a site cleavable by the immunoproteasome. Some embodiments of the invention employ known epitopes to flank housekeeping epitopes in test substrates; in others, screening as described below is used, whether the flanking regions are arbitrary sequences or mutants of the natural flanking sequence, and whether or not knowledge of proteasomal cleavage preferences are used in designing the substrates.

Cleavage at the mature N-terminus of the epitope, while advantageous, is not required, since a variety of N-terminal trimming activities exist in the cell that can generate the mature N-terminus of the epitope subsequent to proteasomal processing. It is preferred that such N-terminal extension be less than about 25 amino acids in length and it is further preferred that the extension have few or no proline residues. Preferably, in screening, consideration is given not only to cleavage at the ends of the epitope (or at least at its C-terminus), but consideration also can be given to ensure limited cleavage within the epitope.

Shotgun approaches can be used in designing test substrates and can increase the efficiency of screening. In one embodiment multiple epitopes can be assembled one after the other, with individual epitopes possibly appearing more than once. The substrate can be screened to determine which epitopes can be produced. In the case where a particular epitope is of concern, a substrate can be designed in which it appears in multiple different contexts. When a single epitope appearing in more than one context is liberated from the substrate additional secondary test substrates, in which individual instances of the epitope are removed, disabled, or are unique, can be used to determine which are being liberated and truly confer substrate or liberation sequence function.

Several readily practicable screens exist. A preferred in vitro screen utilizes proteasomal digestion analysis, using purified immunoproteasomes, to determine if the desired housekeeping epitope can be liberated from a synthetic peptide embodying the sequence in question. The position of the cleavages obtained can be determined by techniques such as mass spectrometry, HPLC, and N-terminal pool sequencing; as described in greater detail in U.S. patent application Ser. Nos. 09/561,074, 09/560,465 and 10/117,937, and Provisional U.S. Patent Application Nos. 60/282,211, 60/337,017, and 60/363, 210, which were all cited and incorporated by reference above.

Alternatively, in vivo and cell-based screens such as immunization or target sensitization can be employed. For immunization a nucleic acid construct capable of expressing the sequence in question is used. Harvested CTL can be tested for their ability to recognize target cells presenting the housekeeping epitope in question. Such targets cells are most readily obtained by pulsing cells expressing the appropriate MHC molecule with synthetic peptide embodying the mature housekeeping epitope. Alternatively, immunization can be carried out using cells known to express housekeeping proteasome and the antigen from which the housekeeping epitope is derived, either endogenously or through genetic engineering. To use target sensitization as a screen, CTL, or preferably a CTL clone, that recognizes the housekeeping epitope can be used. In this case it is the target cell that expresses the embedded housekeeping epitope (instead of the pAPC during immunization) and it must express immunoproteasome. Generally, the cell or target cell can be transformed with an appropriate nucleic acid construct to confer expression of the embedded housekeeping epitope. Loading with a synthetic peptide embodying the embedded epitope using peptide loaded liposomes, or complexed with cationic lipid protein transfer reagents such as BIOPORTER™ (Gene Therapy Systems, San Diego, Calif.), represents an alternative.

Once sequences with substrate or liberation sequence function are identified they can be encoded in nucleic acid vectors, chemically synthesized, or produced recombinantly. In any of these forms they can be incorporated into immunogenic compositions. Such compositions can be used in vitro in vaccine development or in the generation or expansion of CTL to be used in adoptive immunotherapy. In vivo they can be used to induce, amplify or sustain and active immune response. The uptake of polypeptides for processing and presentation can be greatly enhanced by packaging with cationic lipid, the addition of a tract of cationic amino acids such as poly-L-lysine (Ryser, H. J. et al., *J. Cell Physiol.* 113:167-178, 1982; Shen, W. C. & Ryser, H. J., *Proc. Natl. Aced. Sci. USA* 75:1872-1876, 1978), the incorporation into branched structures with importation signals (Sheldon, K. et al., *Proc. Natl. Aced. Sci. USA* 92:2056-2060, 1995), or mixture with or fusion to polypeptides with protein transfer function including peptide carriers such as pep-1 (Morris, M. C., et al., *Nat. Biotech.* 19:1173-1176, 2001), the PreS2 translocation motif of hepatitis B virus surface antigen, VP22 of herpes viruses, and HIV-TAT protein (Oess, S. & Hildt, E., *Gene Ther.* 7:750-758, 2000; Ford, K. G., et al., *Gene Ther.* 8:1-4, 2001; Hung, C. F. et al., *J. Virol.* 76:2676-2682, 2002; Oliveira, S. C., et a; *Hum. Gene Ther.* 12:1353-1359, 2001; Normand, N. et al., *J. Biol.*

*Chem.* 276:15042-15050, 2001; Schwartz, J. J. & Zhang, S., *Curr. Opin. Mol. Ther.* 2:162-167, 2000; Elliot G., 7 Hare, P. Cell 88:223-233, 1997), among other methodologies. Particularly for fusion proteins the immunogen can be produced in culture and the purified protein administered or, in the alternative, the nucleic acid vector can be administered so that the immunogen is produced and secreted by cells transformed in vivo. In either scenario the transport function of the fusion protein facilitates uptake by pAPC.

The following examples are intended for illustration purposes only, and should not be construed as limiting the scope of the invention in any way.

EXAMPLES

Example 1

A recombinant DNA plasmid vaccine, pMA2M, which encodes one polypeptide with an HLA A2-specific CTL epitope ELAGIGILTV (SEQ ID NO. 1) from melan-A (26-35A27L), and a portion (amino acids 31-96) of melan-A (SEQ ID NO. 2) including the epitope clusters at amino acids 31-48 and 56-69, was constructed. These clusters were previously disclosed in U.S. patent application Ser. No. 09/561,571 entitled EPITOPE CLUSTERS incorporated by reference above. Flanking the defined melan-A CTL epitope are short amino acid sequences derived from human tyrosinase (SEQ ID NO. 3) to facilitate liberation of the melan-A housekeeping epitope by processing by the immunoproteasome. In addition, these amino acid sequences represent potential CTL epitopes themselves. The cDNA sequence for the polypeptide in the plasmid is under the control of promoter/enhancer sequence from cytomegalovirus (CMVp) (see FIG. 4), which allows efficient transcription of messenger for the polypeptide upon uptake by APCs. The bovine growth hormone polyadenylation signal (BGH polyA) at the 3' end of the encoding sequence provides a signal for polyadenylation of the messenger to increase its stability as well as for translocation out of nucleus into the cytoplasm for translation. To facilitate plasmid transport into the nucleus after uptake, a nuclear import sequence (NIS) from simian virus 40 (SV40) has been inserted in the plasmid backbone. The plasmid carries two copies of a CpG immunostimulatory motif, one in the NIS sequence and one in the plasmid backbone. Lastly, two prokaryotic genetic elements in the plasmid are responsible for amplification in *E. coli*, the kanamycin resistance gene (Kan R) and the pMB1 bacterial origin of replication.

Substrate or Liberation Sequence

The amino acid sequence of the encoded polypeptide (94 amino acid residues in length) (SEQ ID NO. 4) containing a 28 amino acid substrate or liberation sequence at its N-terminus (SEQ ID NO. 5) is given below:

MLLAVLYCL-ELAGIGILTV-YMDGTMSQV-GILTVILGVLLLIGCWYCR

RRNGYRALMDKSLHVGTQCALTRRCPQEGFDHRDSKVSLQEKNCEPV

The first 9 amino acid residues are derived from tyrosinase$_{1-9}$ (SEQ ID NO. 6), the next ten constitute melan-A (26-35A27L) (SEQ ID NO. 1), and amino acid residues 20 to 29 are derived from tyrosinase$_{369-377}$ (SEQ ID NO. 7). These two tyrosinase nonamer sequences both represent potential HLA A2-specific CTL epitopes. Amino acid residues 10-19 constitute melan-A (26-35A27L) an analog of an HLA A2-specific CTL epitope from melan-A, EAAGIGILTV (SEQ ID NO. 8), with an elevated potency in inducing CTL responses during in vitro immunization of human PBMC and in vivo immunization in mice. The segment of melan-A constituting the rest of the polypeptide (amino acid residues 30 to 94) contain a number of predicted HLA A2-specific epitopes, including the epitope clusters cited above, and thus can be useful in generating a response to immune epitopes as described at length in the patent applications 'Epitope Synchronization in Antigen Presenting Cells' and 'Epitope Clusters' cited and incorporated by reference above. This region was also included to overcome any difficulties that can be associated with the expression of shorter sequences. A drawing of pMA2M is shown in FIG. 4.

Plasmid Construction

A pair of long complementary oligonucleotides was synthesized which encoded the first 30 amino acid residues. In addition, upon annealing, these oligonucleotides generated the cohesive ends of Afl II at the 5' end and that of EcoR I at the 3' end. The melan A$_{31-96}$ region was amplified with PCR using oligonucleotides carrying restriction sites for EcoR I at the 5' end and Not I at the 3' end. The PCR product was digested with EcoR I and Not I and ligated into the vector backbone, described in Example 1, that had been digested with Afl II and Not I, along with the annealed oligonucleotides encoding the amino terminal region in a three-fragment ligation. The entire coding sequence was verified by DNA sequencing. The sequence of the entire insert, from the Afl II site at the 5' end to the Not I site at the 3' end is disclosed as SEQ ID NO. 9. Nucleotides 12-293 encode the polypeptide.

Example 2

Figure 6:
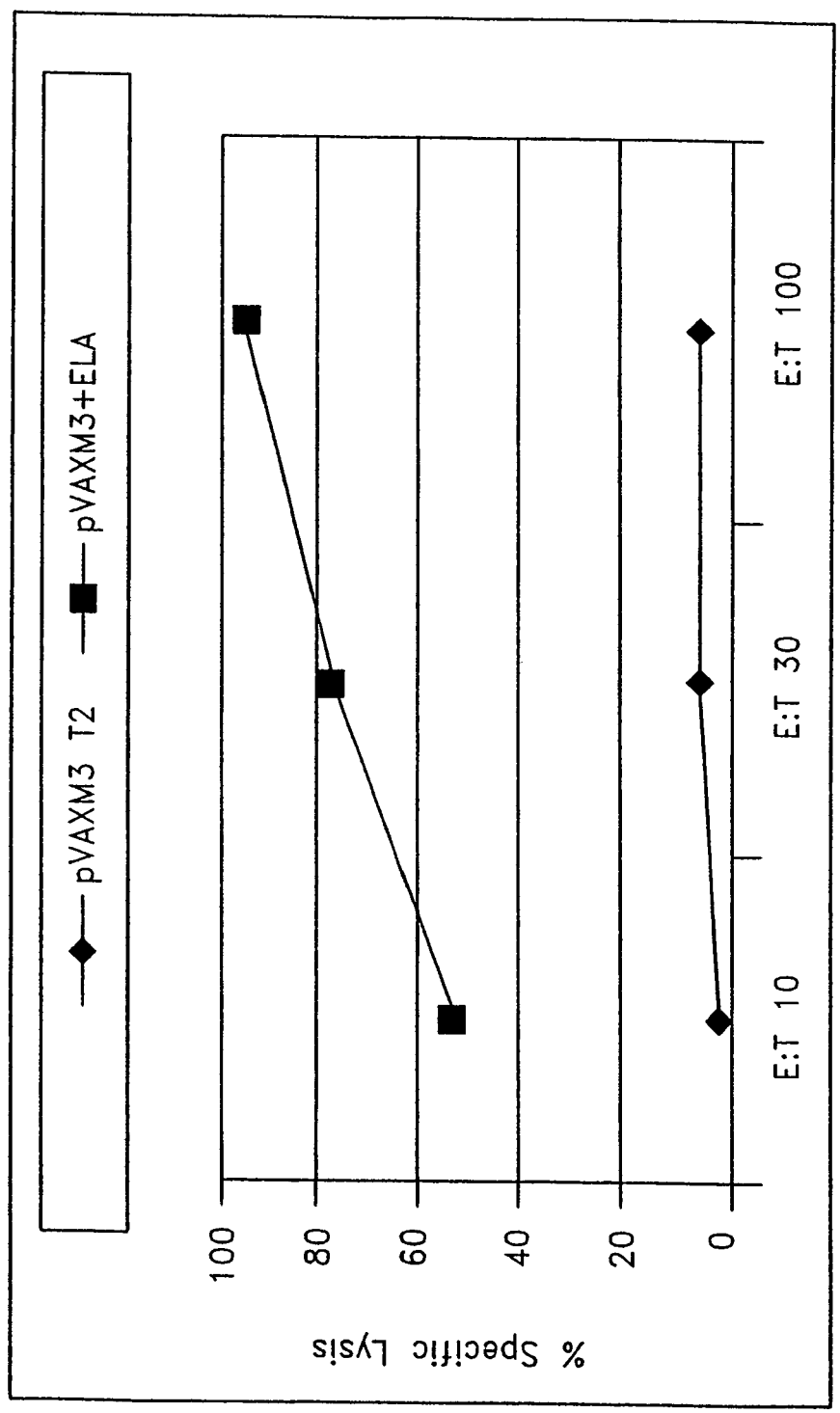
FIG. 6. Assay results showing the % of specific lysis of ELAGIGILTV (SEQ ID NO: 1) pulsed and unpulsed T2 target cells by pVXM3 immunized CTL.
Figure 7:
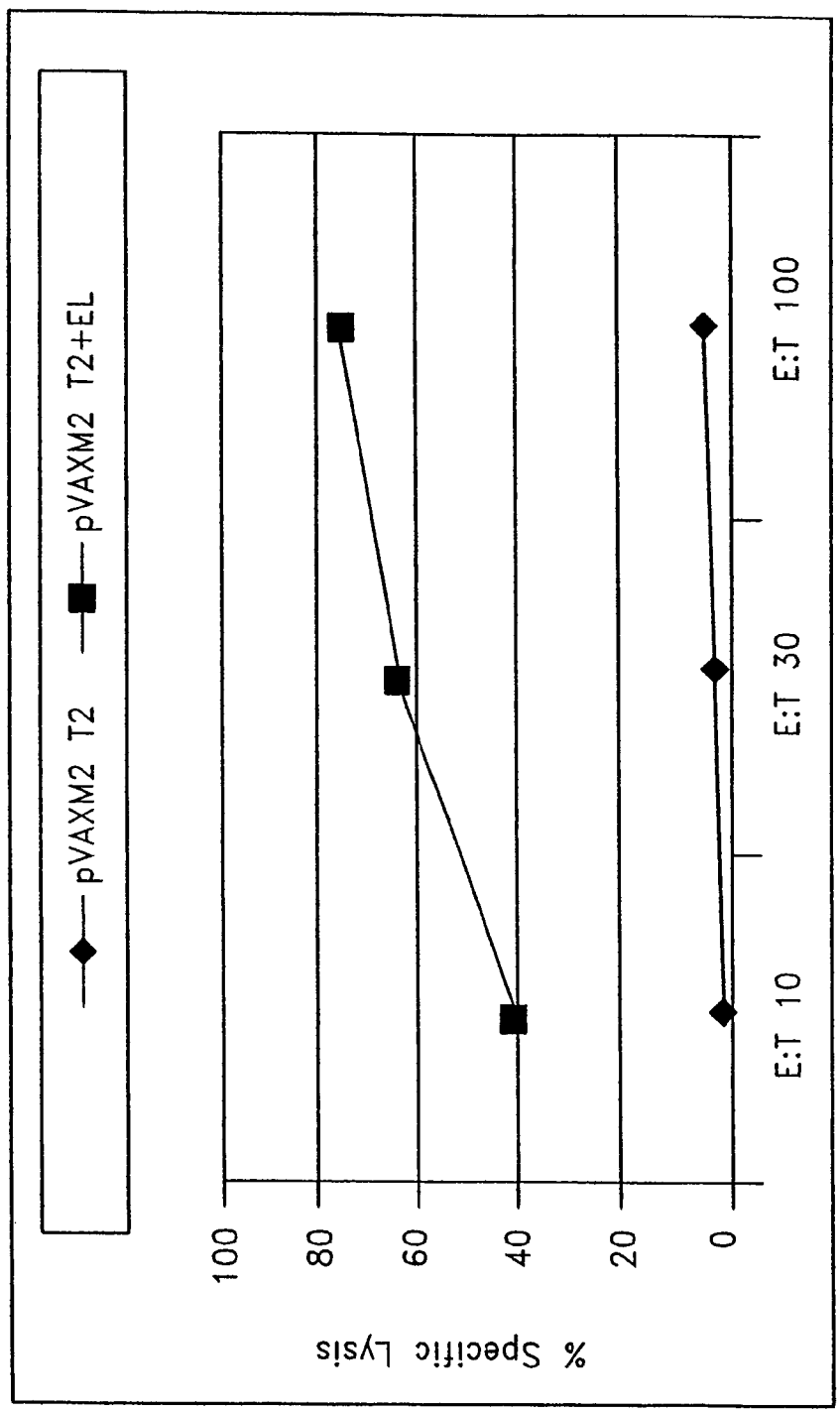
FIG. 7. Assay results showing the % of specific lysis of ELAGIGILTV (SEQ ID NO: 1) pulsed and unpulsed T2 target cells by pVXM2 immunized CTL.
Figure 8:
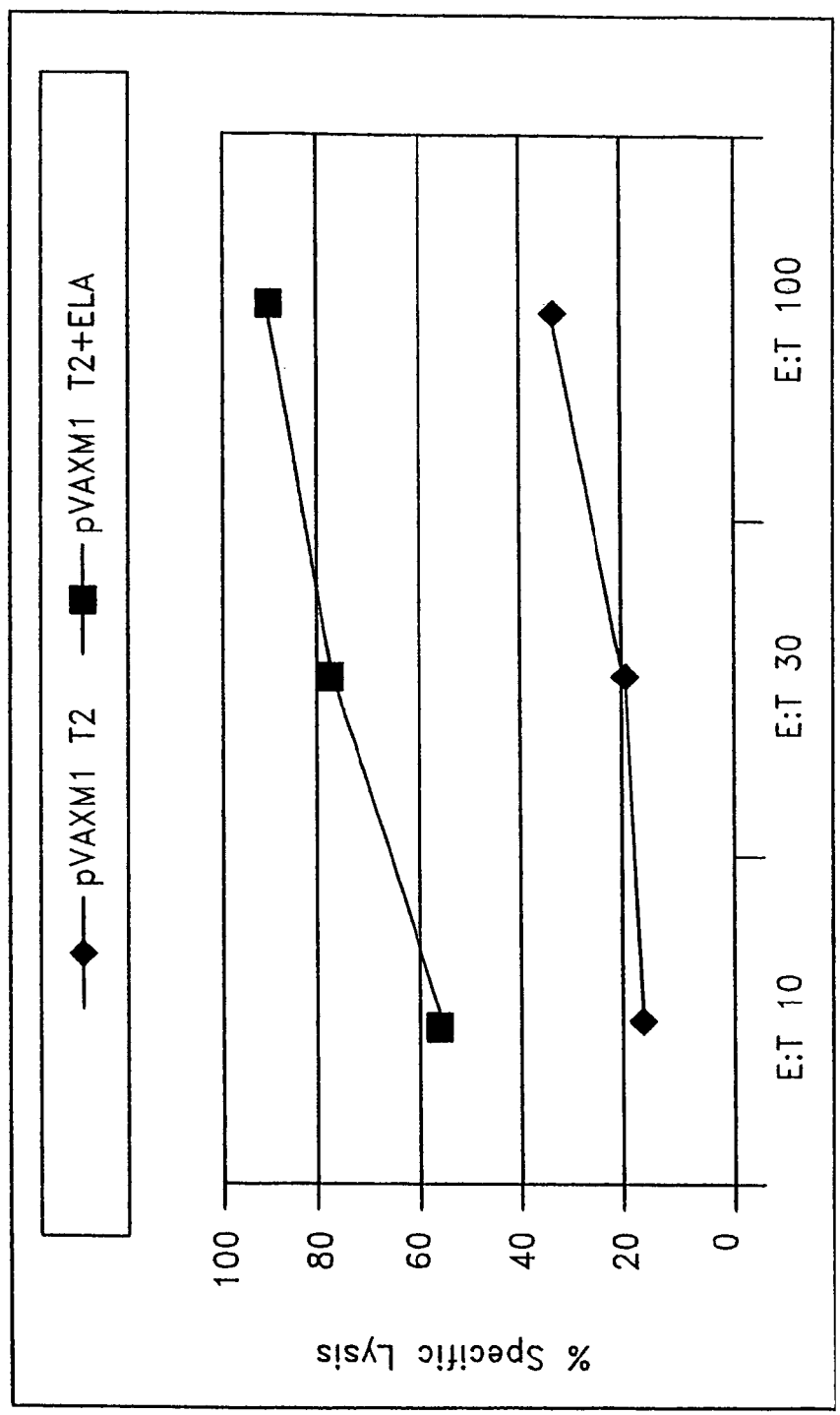
FIG. 8. Assay results showing the % of specific lysis of ELAGIGILTV (SEQ ID NO: 1) pulsed and unpulsed T2 target cells by pVXMI immunized CTL.

Three vectors containing melan-A (26-35A27L) (SEQ ID NO. 1) as an embedded housekeeping epitope were tested for their ability to induce a CTL response to this epitope in HLA-A2 transgenic HHD mice (Pascolo et al. *J. Exp. Med.* 185:2043-2051, 1997). One of the vectors was pMA2M described above (called pVAXM3 in FIG. 6). In pVAXM2 the same basic group of 3 epitopes was repeated several times with the flanking epitopes truncated by differing degrees in the various repeats of the array. Specifically the cassette consisted of:

```
                                         (SEQ ID NO. 10)
M-Tyr(5-9)-ELA-Tyr(369-373)-Tyr(4-9)-ELA-Tyr(369-

374)-Tyr(3-9)-ELA-Tyr(369-375)-Tyr(2-9)-ELA
``` where ELA represents melan-A (26-35A27L) (SEQ ID NO. 1). This cassette was inserted in the same plasmid backbone as used for pVAXM3. The third, pVAXM1 is identical to pVAXM2 except that the epitope array is followed by an IRES (internal ribosome entry site for encephalomyocarditis virus) linked to a reading frame encoding melan-A 31-70.

Four groups of three HHD A2.1 mice were injected intranodally in surgically exposed inguinal lymph nodes with 25 µl of 1 mg/ml plasmid DNA in PBS on days 0, 3, and 6, each group receiving one of the three vectors or PBS alone. On day 14 the spleens were harvested and restimulated in vitro one time with 3-day LPS blasts pulsed with peptide (melan-A (26-35A27L) (SEQ ID NO. 1)). The in vitro cultures were supplemented with Rat T-Stim (Collaborative Biomedical Products) on the 3$^{rd}$ day and assayed for cytolytic activity on the 7$^{th}$ day using a standard $^{51}$Cr-release assay. FIGS. 5 to 8 show % specific lysis obtained using the cells immunized with PBS, pVAXM1, pVAXM2, and pVAXM3, respectively on T2 target cells and T2 target cells pulsed with melan-A (26-35A27L) (ELA) (SEQ ID NO. 1). All three vectors generated strong CTL responses. These data indicated that the plasmids have been taken up by APCs, the encoded polypeptide has been synthesized and proteolytically processed to produce the decamer epitope in question (that is, it had substrate or liberation sequence function), and that the epitope became HLA-A2 bound for presentation. Also, an isolated variant of pVAXM2, that terminates after the 55$^{th}$ amino acid, worked similarly well as the full length version (data not shown). Whether other potential epitopes within the expression cassette can also be produced and be active in inducing CTL responses can be determined by testing for CTL activity against target cells pulsed with corresponding synthetic peptides.

Example 3

An NY-ESO-1 (SE ID NO. 11) Substrate/Liberation Sequence

Six other epitope arrays were tested leading to the identification of a substrate/liberation sequence for the housekeeping epitope NY-ESO-1$_{157-165}$ (SEQ ID NO. 12). The component epitopes of the arrays were:

```
SSX-2_{41-49}:
KASEKIFYV        (SEQ ID NO. 13)   Array element A

NY-ESO-1_{157-165}:
SLLMWITQC        (SEQ ID NO. 12)   Array element B

NY-ESO-1_{163-171}:
TQCFLPVFL        (SEQ ID NO. 14)   Array element C

PSMA_{288-297}:
GLPSIPVHPI       (SEQ ID NO. 15)   Array element D

TYR_{4-9}:
AVLYCL           (SEQ ID NO. 16)   Array element E
```

The six arrays had the following arrangements of elements after starting with an initiator methionine:

```
pVAX-PC-A:   B-A-D-D-A-B-A-A       (SEQ ID NO: 980)
pVAX-PC-B:   D-A-B-A-A-D-B-A       (SEQ ID NO: 981)
pVAX-PC-C:   E-A-D-B-A-B-E-A-A     (SEQ ID NO: 982)
pVAX-BC-A:   B-A-C-B-A-A-C-A       (SEQ ID NO: 983)
pVAX-BC-B:   C-A-B-C-A-A-B-A       (SEQ ID NO: 984)
pVAX-BC-C:   E-A-A-B-C-B-A-A       (SEQ ID NO: 985)
```

These arrays were inserted into the same vector backbone described in the examples above. The plasmid vectors were used to immunize mice essentially as described in Example 2 and the resulting CTL were tested for their ability to specifically lyse target cells pulsed with the peptide NY-ESO-1$_{157-165}$, corresponding to element B above. Both pVAX-PC-A and pVAX-BC-A were found to induce specific lytic activity. Comparing the contexts of the epitope (element B) in the various arrays, and particularly between pVAX-PC-A and pVAX-BC-A, between pVAX-PC-A and pVAX-PC-B, and between pVAX-BC-A and pVAX-BC-C, it was concluded that it was the first occurrence of the epitope in pVAX-PC-A and pVAX-BC-A that was being correctly processed and presented. In other words an initiator methionine followed by elements B-A constitute a substrate/liberation sequence for the presentation of element B. On this basis a new expression cassette for use as a vaccine was constructed encoding the following elements:
An initiator methionine,
NY-ESO-1$_{157-165}$ (bold)—a housekeeping epitope,
SSX2$_{41-49}$ (italic)—providing appropriate context for processing, and
NY-ESO-1$_{77-180}$—to avoid "short sequence" problems and provide immune epitopes.
Thus the construct encodes the amino acid sequence:

(SEQ ID NO. 17)
M-SLLMWITQC-*KASEKIFYV*-RCGARGPESRLLEFYLAMPFATPMEAE

LARRSLAQDAPPLPVPGVLLKEFTVSGNILTIRLTAADHRQLQLSISSC

LQQLSLLMWITQCFLPVFLAQPPSGQ

RR and MSLLMWITQCKASEKIFYV (SEQ ID NO. 18) constitutes the liberation or substrate sequence. A polynucleotide encoding SEQ ID NO. 17 (SEQ ID NO. 19: nucleotides 12-380) was inserted into the same plasmid backbone as used for pMA2M generating the plasmid pN157.

Example 4

A construct similar to pN157 containing the whole epitope array from pVAX-PC-A was also made and designated pBPL. Thus the encoded amino acid sequence in pBPL is:

(SEQ ID NO. 20)
M-SLLMWITQC-*KASEKIFYV*-GLPSIPVHPI-GLPSIPVHPI-

*KASEKIFYV*-SLLMWITQC-*KASEKIFYV*-*KASEKIFYV*-RCGA

RGPESRLLEFYLAMPFATPMEAELARRSLAQDAPPLPVPGVLLK

EFTVSGNILTIRLTAADHRQLQLSISSCLQQLSLLMWITQCFLP

VFLAQPPSGQRR.

SEQ ID NO. 21 is the polynucleotide encoding SEQ ID NO. 20 used in pBPL.

Figure 9:
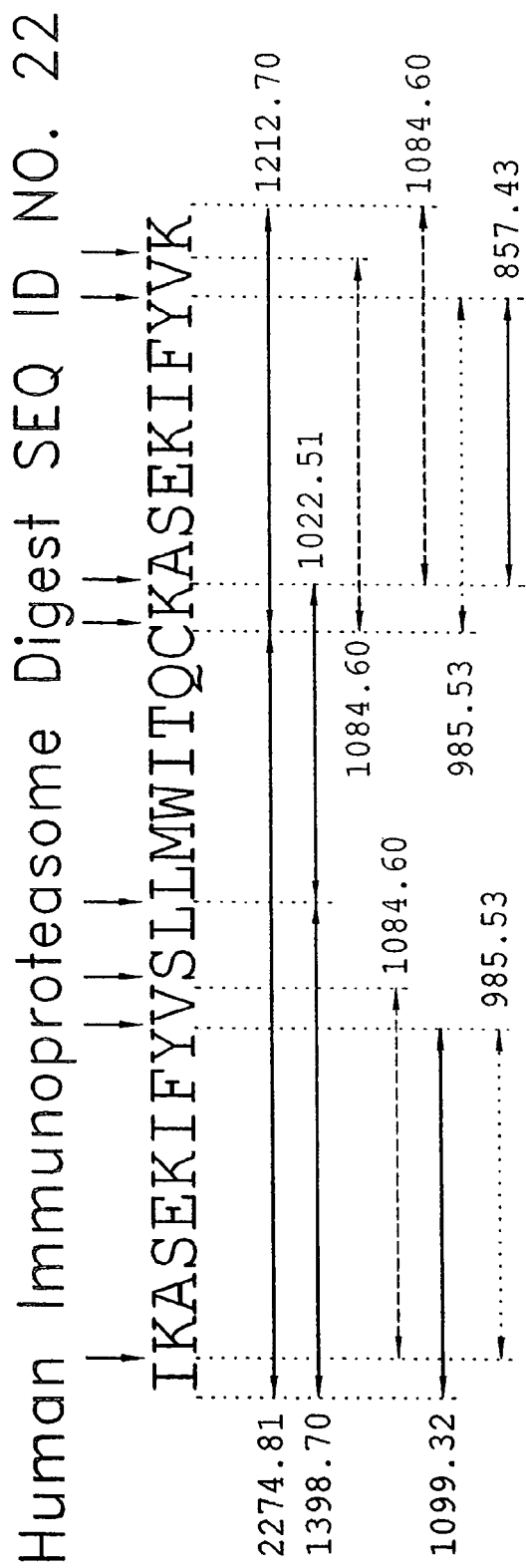
FIG. 9. Illustrates a sequence of SEQ ID NO. 22 from which the NY-ESO-$1_{157-165}$ epitope is liberated by immunoproteasomal processing.
Figure 10:
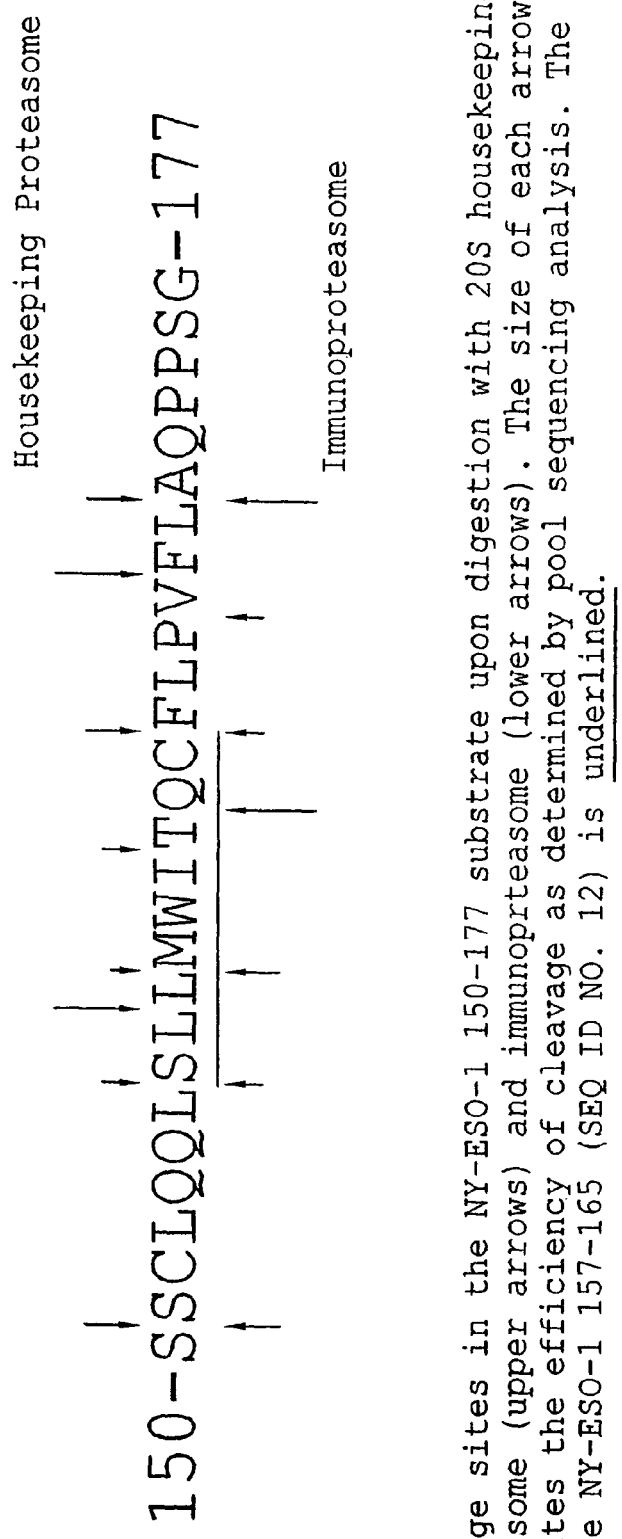
FIG. 10. Shows the differential processing by immunoproteasome and housekeeping proteasome of the SLLMWITQC (SEQ ID NO. 12) epitope in its native context where the cleavage following the C is more efficiently produced by housekeeping than immunoproteasome.

A portion of SEQ ID NO. 20, IKASEKIFYVSLLM-WITQCKASEKIFYVK (SEQ ID NO. 22) was made as a synthetic peptide and subjected to in vitro proteasomal digestion analysis with human immunoproteasome, utilizing both mass spectrometry and N-terminal pool sequencing. The identification of a cleavage after the C residue indicates that this segment of the construct can function as a substrate or liberation sequence for NY-ESO-1$_{157-165}$ (SEQ ID NO. 12) epitope (see FIG. 9). FIG. 10 shows the differential processing of the SLLMWITQC epitope (SEQ ID NO. 12) in its native context where the cleavage following the C is more efficiently produced by housekeeping than immunoproteasome. The immunoproteasome also produces a major cleavage internal to the epitope, between the T and the Q when the epitope is in its native context, but not in the context of SEQ ID NO. 22 (compare FIGS. 6 and 7).

Example 5

Screening of further epitope arrays led to the identification of constructs promoting the expression of the epitope SSX-2$_{41-49}$ (SEQ ID NO. 13). In addition to some of the array elements defined in Example 3, the following additional elements were also used:

SSX-4$_{57-65}$:
VMTKLGFKV        (SEQ ID NO. 23)    Array element F.

PSMA$_{730-739}$:
RQIYVAAFTV       (SEQ ID NO. 24)    Array element G.

A construct, denoted CTLA02, encoding an initiator methionine and the array F-A-G-D-C-F-G-A, was found to successfully immunize HLA-A2 transgenic mice to generate a CTL response recognizing the peptide SSX-2$_{41-49}$ (SEQ ID NO. 13).

As described above, it can be desirable to combine a sequence with substrate or liberation sequence function with one that can be processed into immune epitopes. Thus SSX-2$_{15-183}$ (SEQ ID NO. 25) was combined with all or part of the array as follows:

CTLS1: F-A-G-D-C-F-G-A-SSX-2$_{15-183}$    (SEQ ID NO. 26)

CTLS2: SSX-2$_{15-183}$-F-A-G-D-C-F-G-A    (SEQ ID NO. 27)

CTLS3: F-A-G-D-SSX-2$_{15-183}$            (SEQ ID NO. 28)

CTLS4: SSX-2$_{15-183}$-C-F-G-A.           (SEQ ID NO. 29)

All of the constructs except CTLS3 were able to induce CTL recognizing the peptide SSX-2$_{41-49}$ (SEQ ID NO. 13). CTLS3 was the only one of these four constructs which did not include the second element A from CTLA02 suggesting that it was this second occurrence of the element that provided substrate or liberation sequence function. In CTLS2 and CTLS4 the A element is at the C-terminal end of the array, as in CTLA02. In CTLS1 the A element is immediately followed by the SSX-2$_{15-183}$ segment which begins with an alanine, a residue often found after proteasomal cleavage sites (Toes, R. E. M., et al., *J. Exp. Med.* 194:1-12, 2001). SEQ ID NO. 30 is the polynucleotide sequence encoding SEQ ID NO. 26 used in CTLS1, also called pCBP.

A portion of CTLS1 (SEQ ID NO. 26), encompassing array elements F-A-SSX-2$_{15-23}$ with the sequence RQIY-VAAFTV-KASEKIFYV-AQIPEKIQK (SEQ ID NO. 31), was made as a synthetic peptide and subjected to in vitro proteasomal digestion analysis with human immunoproteasome, utilizing both mass spectrometry and N-terminal pool sequencing. The observation that the C-terminus of the SSX-2$_{41-49}$ epitope (SEQ ID NO. 13) was generated (see FIG. 11) provided further evidence in support of substrate or liberation sequence function. The data in FIG. 12 showed the differential processing of the SSX-2$_{41-49}$ epitope, KASEKIFYV (SEQ ID NO. 13), in its native context, where the cleavage following the V was the predominant cleavage produced by housekeeping proteasome, while the immunoproteasome had several major cleavage sites elsewhere in the sequence. By moving this epitope into the context provided by SEQ ID NO. 31 the desired cleavage became a major one and its relative frequency compared to other immunoproteasome cleavages was increased (compare FIGS. 11 and 12). The data in FIG. 11B also showed the similarity in specificity of mouse and human immunoproteasome lending support to the usefulness of the transgenic mouse model to predict human antigen processing.

Example 6

Screening also revealed substrate or liberation sequence function for a tyrosinase epitope, Tyr$_{207-215}$ (SEQ ID NO. 32), as part of an array consisting of the sequence [Tyr$_{1-17}$-Tyr$_{207-215}$]$_4$, [MLLAVLYCLLWSFQTSA-FLPWHRLFL]$_4$, (SEQ ID NO. 33). The same vector backbone described above was used to express this array. This array differs from those of the other examples in that the Tyr$_{1-17}$ segment, which was included as a source of immune epitopes, is used as a repeated element of the array. This is in contrast with the pattern shown in the other examples where sequence included as a source of immune epitopes and/or length occurred a single time at the beginning or end of the array, the remainder of which was made up of individual epitopes or shorter sequences.

Plasmid Construction

The polynucleotide encoding SEQ ID NO. 33 was generated by assembly of annealed synthetic oligonucleotides. Four pairs of complementary oligonucleotides were synthesized which span the entire coding sequence with cohesive ends of the restriction sites of Afl II and EcoR I at either terminus. Each complementary pair of oligonucleotides were first annealed, the resultant DNA fragments were ligated stepwise, and the assembled DNA fragment was inserted into the same vector backbone described above pre-digested with Afl II/EcoR I. The construct was called CTLT2/pMEL and SEQ ID NO. 34 is the polynucleotide sequence used to encode SEQ ID NO. 33.

Example 7

Administration of a DNA Plasmid Formulation of a Immunotherapeutic for Melanoma to Humans An MA2M melanoma vaccine with a sequence as described in Example 1 above, was formulated in 1% Benzyl alcohol, 1% ethyl alcohol, 0.5 mM EDTA, citrate-phosphate, pH 7.6. Aliquots of 200, 400, and 600 µg DNA/ml were prepared for loading into MINIMED 407C infusion pumps. The catheter of a SILHOUETTE infusion set was placed into an inguinal lymph node visualized by ultrasound imaging. The pump and infusion set assembly was originally designed for the delivery of insulin to diabetics. The usual 17 mm catheter was substituted with a 31 mm catheter for this application. The infusion set was kept patent for 4 days (approximately 96 hours) with an infusion rate of about 25 µl/hour resulting in a total infused volume of approximately 2.4 ml. Thus the total administered dose per infusion was approximately 500, and 1000 µg; and can be 1500 µg, respectively, for the three concentrations described above. Following an infusion, subjects were given a 10 day rest period before starting a subsequent infusion. Given the continued residency of plasmid DNA in the lymph node after administration and the usual kinetics of CTL response following disappearance of antigen, this schedule will be sufficient to maintain the immunologic CTL response.

Example 8

SEQ ID NO. 22 is made as a synthetic peptide and packaged with a cationic lipid protein transfer reagent. The composition is infused directly into the inguinal lymph node (see example 7) at a rate of 200 to 600 µg of peptide per day for seven days, followed by seven days rest. An initial treatment of 3-8 cycles are conducted.

Example 9

A fusion protein is made by adding SEQ ID NO. 34 to the 3' end of a nucleotide sequence encoding herpes simplex virus 1 VP22 (SEQ ID NO. 42) in an appropriate mammalian expression vector; the vector used above is suitable. The vector is used to transform HEK 293 cells and 48 to 72 hours later the cells are pelleted, lysed and a soluble extract prepared. The fusion protein is purified by affinity chromatography using an anti-VP22 monoclonal antibody. The purified fusion protein is administered intranodally at a rate of 10 to 100 μg per day for seven days, followed by seven days rest. An initial treatment of 3-8 cycles are conducted.

Examples 10-13

The following examples, Examples 10-13, all concern the prediction of 9-mer epitopes presented by HLA-A2.1, although the procedure is equally applicable to any HLA type, or epitope length, for which a predictive algorithm or MHC binding assay is available.

Example 10

Melan-A/MART-1 (SEQ ID NO: 2)

This melanoma tumor-associated antigen (TuAA) is 118 amino acids in length. Of the 110 possible 9-mers, 16 are given a score ≧16 by the SYFPEITHI/Rammensee algorithm. (See Table 14). These represent 14.5% of the possible peptides and an average epitope density on the protein of 0.136 per amino acid. Twelve of these overlap, covering amino acids 22-49 of SEQ ID NO: 2 resulting in an epitope density for the cluster of 0.428, giving a ratio, as described above, of 3.15. Another two predicted epitopes overlap amino acids 56-69 of SEQ ID NO: 2, giving an epitope density for the cluster of 0.143, which is not appreciably different than the average, with a ratio of just 1.05. See FIG. 1.

TABLE 14

SYFPEITHI (Rammensee algorithm) Results for Melan-A/MART-1 (SEQ ID NO: 2)

| Rank | Start | Score |
|---|---|---|
| 1 | 31 | 27 |
| 2 | 56 | 26 |
| 3 | 35 | 26 |
| 4 | 32 | 25 |
| 5 | 27 | 25 |
| 6 | 29 | 24 |
| 7 | 34 | 23 |
| 8 | 61 | 20 |
| 9 | 33 | 19 |
| 10 | 22 | 19 |
| 11 | 99 | 18 |
| 12 | 36 | 18 |
| 13 | 28 | 18 |
| 14 | 87 | 17 |
| 15 | 41 | 17 |
| 16 | 40 | 16 |

Restricting the analysis to the 9-mers predicted to have a half time of dissociation of ≧5 minutes by the BIMAS-NIH/Parker algorithm leaves only 5. (See Table 15). The average density of epitopes in the protein is now only 0.042 per amino acid. Three overlapping peptides cover amino acids 31-48 of SEQ ID NO: 2 and the other two cover 56-69 of SEQ ID: 2, as before, giving ratios of 3.93 and 3.40, respectively. (See Table 16).

TABLE 15

BIMAS-NIH/Parker algorithm Results for Melan-A/MART-1 (SEQ ID NO: 2)

| Rank | Start | Score | Log(Score) |
|---|---|---|---|
| 1 | 40 | 1289.01 | 3.11 |
| 2 | 56 | 1055.104 | 3.02 |
| 3 | 31 | 81.385 | 1.91 |
| 4 | 35 | 20.753 | 1.32 |
| 5 | 61 | 4.968 | 0.70 |

TABLE 16

Predicted Epitope Clusters for Melan-A/MART-1 (SEQ ID NO: 2)

| | | | Calculations (Epitopes/AAs) | | |
|---|---|---|---|---|---|
| Cluster | AA | Peptides | Cluster | Whole protein | Ratio |
| 1 | 31-48 | 3, 4, 1 | 0.17 | 0.042 | 3.93 |
| 2 | 56-69 | 2, 5 | 0.14 | 0.042 | 3.40 |

Example 11

SSX-2/HOM-MEL-40 (SEQ ID NO: 40)

This melanoma tumor-associated antigen (TuAA) is 188 amino acids in length. Of the 180 possible 9-mers, 11 are given a score ≧16 by the SYFPEITHI/Rammensee algorithm. These represent 6.1% of the possible peptides and an average epitope density on the protein of 0.059 amino acid. Three of these overlap, covering amino acids 99-114 of SEQ ID NO: 40 resulting in an epitope density for the cluster of 0.188, giving a ratio, as described above, of 3.18. There are also overlapping pairs of predicted epitopes at amino acids 16-28, 57-67, and 167-183 of SEQ ID NO: 40, giving ratios of 2.63, 3.11, and 2.01, respectively. There is an additional predicted epitope covering amino acids 5-28. Evaluating the region 5-28 SEQ ID NO: 40 containing three epitopes gives an epitope density of 0.125 and a ratio 2.14.

Restricting the analysis to the 9-mers predicted to have a half time of dissociation of ≧5 minutes by the BIMAS-NIH/Parker algorithm leaves only 6. The average density of epitopes in the protein is now only 0.032 per amino acid. Only a single pair overlap, at 167-180 of SEQ ID NO: 40, with a ratio of 4.48. However the top ranked peptide is close to another single predicted epitope if that region, amino acids 41-65 of SEQ ID NO: 40, is evaluated the ratio is 2.51, representing a substantial difference from the average. See FIG. 2.

TABLE 17

SYFPEITHI/Rammensee algorithm for SSX-2/HOM-MEL-40 (SEQ ID NO: 40)

| Rank | Start | Score |
|---|---|---|
| 1 | 103 | 23 |
| 2 | 167 | 22 |
| 3 | 41 | 22 |
| 4 | 16 | 21 |
| 5 | 99 | 20 |
| 6 | 59 | 19 |
| 7 | 20 | 17 |
| 8 | 5 | 17 |
| 9 | 175 | 16 |

TABLE 17-continued

SYFPEITHI/Rammensee algorithm for SSX-2/HOM-MEL-40 (SEQ ID NO: 40)

| Rank | Start | Score |
|---|---|---|
| 10 | 106 | 16 |
| 11 | 57 | 16 |

TABLE 18

Calculations(Epitopes/AAs) (SEQ ID NO: 40)

| | | | Calculations (Epitopes/AAs) | | |
|---|---|---|---|---|---|
| Cluster | AA | Peptides | Cluster | Whole protein | Ratio |
| 1 | 5 to 28 | 8, 4, 7 | 0.125 | 0.059 | 2.14 |
| 2 | 16-28 | 4, 7 | 0.15 | 0.059 | 2.63 |
| 3 | 57-67 | 11, 6 | 0.18 | 0.059 | 3.11 |
| 4 | 99-114 | 5, 1, 10 | 0.19 | 0.059 | 3.20 |
| 5 | 167-183 | 2, 9 | 0.12 | 0.059 | 2.01 |

TABLE 19

BIMAS-NIH/Parker algorithm (SEQ ID NO: 40)

| Rank | Start | Score | Log(Score) |
|---|---|---|---|
| 1 | 41 | 1017.062 | 3.01 |
| 2 | 167 | 21.672 | 1.34 |
| 3 | 57 | 20.81 | 1.32 |
| 4 | 103 | 10.433 | 1.02 |
| 5 | 172 | 10.068 | 1.00 |
| 6 | 16 | 6.442 | 0.81 |

TABLE 20

Calculations(Epitopes/AAs) (SEQ ID NO: 40)

| Cluster | AA | Peptides | Cluster | Whole protein | Ratio |
|---|---|---|---|---|---|
| 1 | 41-65 | 1, 3 | 0.08 | 0.032 | 2.51 |
| 2 | 167-180 | 2, 5 | 0.14 | 0.032 | 4.48 |

Example 12

NY-ESO (SEQ ID NO: 11)

This tumor-associated antigen (TuAA) is 180 amino acids in length. Of the 172 possible 9-mers, 25 are given a score $\geq 16$ by the SYFPEITHI/Rammensee algorithm. Like Melan-A above, these represent 14.5% of the possible peptides and an average epitope density on the protein of 0.136 per amino acid. However the distribution is quite different. Nearly half the protein is empty with just one predicted epitope in the first 78 amino acids. Unlike Melan-A where there was a very tight cluster of highly overlapping peptides, in NY-ESO the overlaps are smaller and extend over most of the rest of the protein. One set of 19 overlapping peptides covers amino acids 108-174 of SEQ ID NO: 11, resulting in a ratio of 2.04. Another 5 predicted epitopes cover 79-104 of SEQ ID NO: 11, for a ratio of just 1.38.

If instead one takes the approach of considering only the top 5% of predicted epitopes, in this case 9 peptides, one can examine whether good clusters are being obscured by peptides predicted to be less likely to bind to MHC. When just these predicted epitopes are considered we see that the region 108-140 of SEQ ID NO: 11 contains 6 overlapping peptides with a ratio of 3.64. There are also 2 nearby peptides in the region 148-167 of SEQ ID NO: 11 with a ratio of 2.00. Thus the large cluster 108-174 of SEQ ID NO: 11 can be broken into two smaller clusters covering much of the same sequence.

Restricting the analysis to the 9-mers predicted to have a half time of dissociation of $\geq 5$ minutes by the BIMAS-NIH/Parker algorithm brings 14 peptides into consideration. The average density of epitopes in the protein is now 0.078 per amino acid. A single set of 10 overlapping peptides is observed, covering amino acids 144-171 of SEQ ID NO: 11, with a ratio of 4.59. All 14 peptides fall in the region 86-171 of SEQ ID NO: 11 which is still 2.09 times the average density of epitopes in the protein. While such a large cluster is larger than we consider ideal it still offers a significant advantage over working with the whole protein. See FIG. 3.

TABLE 21

SYFPEITHI (Rammensee algorithm) Results for NY-ESO (SEQ ID NO: 11)

| Rank | Start | Score |
|---|---|---|
| 1 | 108 | 25 |
| 2 | 148 | 24 |
| 3 | 159 | 21 |
| 4 | 127 | 21 |
| 5 | 86 | 21 |
| 6 | 132 | 20 |
| 7 | 122 | 20 |
| 8 | 120 | 20 |
| 9 | 115 | 20 |
| 10 | 96 | 20 |
| 11 | 113 | 19 |
| 12 | 91 | 19 |
| 13 | 166 | 18 |
| 14 | 161 | 18 |
| 15 | 157 | 18 |
| 16 | 151 | 18 |
| 17 | 137 | 18 |
| 18 | 79 | 18 |
| 19 | 139 | 17 |
| 20 | 131 | 17 |
| 21 | 87 | 17 |
| 22 | 152 | 16 |
| 23 | 144 | 16 |
| 24 | 129 | 16 |
| 25 | 15 | 16 |

TABLE 22

Calculations(Epitopes/AAs) (SEQ ID NO: 11)

| Cluster | AA | Peptides | Cluster | Whole protein | Ratio |
|---|---|---|---|---|---|
| 1 | 108-140 | 1, 9, 8, 7, 4, 6 | 0.18 | 0.05 | 3.64 |
| 2 | 148-167 | 2, 3 | 0.10 | 0.05 | 2.00 |
| 3 | 79-104 | 5 12, 10, 18, 21 | 0.19 | 0.14 | 1.38 |
| 4 | 108-174 | 1, 11, 9, 8, 7, 4, 6, 17, 2, 16, 15, 3, 14, 13, 24, 20, 19, 23, 22 | 0.28 | 0.14 | 2.04 |

TABLE 23

BIMAS-NIH/Parker algorithm Results for NY-ESO (SEQ ID NO: 11)

| Rank | Start | Score | Log(Score) |
|---|---|---|---|
| 1 | 159 | 1197.321 | 3.08 |
| 2 | 86 | 429.578 | 2.63 |

TABLE 23-continued

BIMAS-NIH/Parker algorithm Results for NY-ESO (SEQ ID NO: 11)

| Rank | Start | Score | Log(Score) |
|---|---|---|---|
| 3 | 120 | 130.601 | 2.12 |
| 4 | 161 | 83.584 | 1.92 |
| 5 | 155 | 52.704 | 1.72 |
| 6 | 154 | 49.509 | 1.69 |
| 7 | 157 | 42.278 | 1.63 |
| 8 | 108 | 21.362 | 1.33 |
| 9 | 132 | 19.425 | 1.29 |
| 10 | 145 | 13.624 | 1.13 |
| 11 | 163 | 11.913 | 1.08 |
| 12 | 144 | 11.426 | 1.06 |
| 13 | 148 | 6.756 | 0.83 |
| 14 | 152 | 4.968 | 0.70 |

TABLE 24

Calculations(Epitopes/AAs) (SEQ ID NO: 11)

| Cluster | AA | Peptides | Cluster | Whole protein | Ratio |
|---|---|---|---|---|---|
| 1 | 86-171 | 2, 8, 3, 9, 10, 12, 13, 14, 6, 5, 7, 1, 4, 11 | 0.163 | 0.078 | 2.09 |
| 2 | 144-171 | 10, 12, 13, 14, 6, 5, 7, 1, 4, 11 | 0.36 | 0.078 | 4.59 |

Example 13

Tyrosinase (SEQ ID NO: 3)

This melanoma tumor-associated antigen (TuAA) is 529 amino acids in length. Of the 521 possible 9-mers, 52 are given a score $\geq 16$ by the SYFPEITHI/Rammensee algorithm. These represent 10% of the possible peptides and an average epitope density on the protein of 0.098 per amino acid. There are 5 groups of overlapping peptides containing 2 to 13 predicted epitopes each, with ratios ranging from 2.03 to 4.41, respectively. There are an additional 7 groups of overlapping peptides, containing 2 to 4 predicted epitopes each, with ratios ranging from 1.20 to 1.85, respectively. The 17 peptides in the region 444-506 of SEQ ID NO: 3, including the 13 overlapping peptides above, constitutes a cluster with a ratio of 2.20.

Restricting the analysis to the 9-mers predicted to have a half time of dissociation of $\geq 5$ minutes by the BIMAS-NIH/Parker algorithm brings 28 peptides into consideration. The average density of epitopes in the protein under this condition is 0.053 per amino acid. At this density any overlap represents more than twice the average density of epitopes. There are 5 groups of overlapping peptides containing 2 to 7 predicted epitopes each, with ratios ranging from 2.22 to 4.9, respectively. Only three of these clusters are common to the two algorithms. Several, but not all, of these clusters could be enlarged by evaluating a region containing them and nearby predicted epitopes.

TABLE 25

SYFPEITHI/Rammensee algorithm Results for Tyrosinase (SEQ ID NO: 3)

| Rank | Start | Score |
|---|---|---|
| 1 | 490 | 34 |
| 2 | 491 | 31 |
| 3 | 487 | 28 |
| 4 | 1 | 27 |
| 5 | 2 | 25 |
| 6 | 482 | 23 |
| 7 | 380 | 23 |
| 8 | 369 | 23 |
| 9 | 214 | 23 |
| 10 | 506 | 22 |
| 11 | 343 | 22 |
| 12 | 207 | 22 |
| 13 | 137 | 22 |
| 14 | 57 | 22 |
| 15 | 169 | 20 |
| 16 | 118 | 20 |
| 17 | 9 | 20 |
| 18 | 488 | 19 |
| 19 | 483 | 19 |
| 20 | 480 | 19 |
| 21 | 479 | 19 |
| 22 | 478 | 19 |
| 23 | 473 | 19 |
| 24 | 365 | 19 |
| 25 | 287 | 19 |
| 26 | 200 | 19 |
| 27 | 5 | 19 |
| 28 | 484 | 18 |
| 29 | 476 | 18 |
| 30 | 463 | 18 |
| 31 | 444 | 18 |
| 32 | 425 | 18 |
| 33 | 316 | 18 |
| 34 | 187 | 18 |
| 35 | 402 | 17 |
| 36 | 388 | 17 |
| 37 | 346 | 17 |
| 38 | 336 | 17 |
| 39 | 225 | 17 |
| 40 | 224 | 17 |
| 41 | 208 | 17 |
| 42 | 186 | 17 |
| 43 | 171 | 17 |
| 44 | 514 | 16 |
| 45 | 494 | 16 |
| 46 | 406 | 16 |
| 47 | 385 | 16 |
| 48 | 349 | 16 |
| 49 | 184 | 16 |
| 50 | 167 | 16 |
| 51 | 145 | 16 |
| 52 | 139 | 16 |

TABLE 26

Calculations(Epitopes/AAs) (SEQ ID NO: 3)

| Cluster | AA | Peptides | Cluster | Whole protein | Ratio |
|---|---|---|---|---|---|
| 1 | 1 to 17 | 4, 5, 27, 17 | 0.24 | 0.098 | 2.39 |
| 2 | 137-153 | 13, 52, 51 | 0.18 | 0.098 | 1.80 |
| 3 | 167-179 | 15, 43, 50 | 0.23 | 0.098 | 2.35 |
| 4 | 184-195 | 34, 42, 49 | 0.25 | 0.098 | 2.54 |
| 5 | 200-222 | 26, 41, 9, 12 | 0.17 | 0.098 | 1.77 |
| 6 | 224-233 | 39, 40 | 0.20 | 0.098 | 2.03 |
| 7 | 336-357 | 38, 11, 37, 48 | 0.18 | 0.098 | 1.85 |
| 8 | 365-377 | 24, 8 | 0.15 | 0.098 | 1.57 |
| 9 | 380-396 | 7, 47, 36 | 0.18 | 0.098 | 1.80 |
| 10 | 402-414 | 35, 46 | 0.15 | 0.098 | 1.57 |

TABLE 26-continued

Calculations(Epitopes/AAs) (SEQ ID NO: 3)

| Cluster | AA | Peptides | Cluster | Whole protein | Ratio |
|---|---|---|---|---|---|
| 11 | 473-502 | 29, 28, 23, 22, 21, 20, 6, 19, 3, 18, 1, 2, 45 | 0.43 | 0.098 | 4.41 |
| 12 | 506-522 | 10, 44 | 0.12 | 0.098 | 1.20 |
|  | 444-522 | 31, 30, 23, 29, 22, 21, 20, 6, 19, 28, 3, 18, 1, 2, 45, 10, 44 | 0.22 | 0.098 | 2.20 |

TABLE 27

BIMAS-NIH/Parker algorithm Results (SEQ ID NO: 3)

| Rank | Start | Score | Log(Score) |
|---|---|---|---|
| 1 | 207 | 540.469 | 2.73 |
| 2 | 369 | 531.455 | 2.73 |
| 3 | 1 | 309.05 | 2.49 |
| 4 | 9 | 266.374 | 2.43 |
| 5 | 490 | 181.794 | 2.26 |
| 6 | 214 | 177.566 | 2.25 |
| 7 | 224 | 143.451 | 2.16 |
| 8 | 171 | 93.656 | 1.97 |
| 9 | 506 | 87.586 | 1.94 |
| 10 | 487 | 83.527 | 1.92 |
| 11 | 491 | 83.527 | 1.92 |
| 12 | 2 | 54.474 | 1.74 |
| 13 | 137 | 47.991 | 1.68 |
| 14 | 200 | 30.777 | 1.49 |
| 15 | 208 | 26.248 | 1.42 |
| 16 | 460 | 21.919 | 1.34 |
| 17 | 478 | 19.425 | 1.29 |
| 18 | 365 | 17.14 | 1.23 |
| 19 | 380 | 16.228 | 1.21 |
| 20 | 444 | 13.218 | 1.12 |
| 21 | 473 | 13.04 | 1.12 |
| 22 | 57 | 10.868 | 1.04 |
| 23 | 482 | 8.252 | 0.92 |
| 24 | 483 | 7.309 | 0.86 |
| 25 | 5 | 6.993 | 0.84 |
| 26 | 225 | 5.858 | 0.77 |
| 27 | 343 | 5.195 | 0.72 |
| 28 | 514 | 5.179 | 0.71 |

TABLE 28

Calculations(Epitopes/AAs) (SEQ ID NO: 3)

| Cluster | AA | Peptides | Cluster | Whole protein | Ratio |
|---|---|---|---|---|---|
| 1 | 1 to 17 | 3, 12, 25, 4 | 0.24 | 0.053 | 4.45 |
| 2 | 200-222 | 14, 1, 15, 6 | 0.17 | 0.053 | 3.29 |
| 3 | 224-233 | 7, 26 | 0.20 | 0.053 | 3.78 |
| 4 | 365-377 | 18, 2 | 0.15 | 0.053 | 2.91 |
| 5 | 473-499 | 21, 17, 23, 24, 10, 5, 11 | 0.26 | 0.053 | 4.90 |
| 6 | 506-522 | 9, 28 | 0.12 | 0.053 | 2.22 |
| 7 | 365-388 | 18, 2, 19 | 0.13 | 0.053 | 2.36 |
| 8 | 444-499 | 20, 16, 21, 17, 23, 24, 10, 5, 11 | 0.16 | 0.053 | 3.03 |
| 9 | 444-522 | 20, 16, 21, 17, 23, 24, 10, 5, 11, 9, 28 | 0.14 | 0.053 | 2.63 |
| 10 | 200-233 | 14, 1, 15, 6, 7, 26 | 0.18 | 0.053 | 3.33 |

All references mentioned herein are hereby incorporated by reference in their entirety. Further, the present invention can utilize various aspects of the following, which are all incorporated by reference in their entirety: U.S. patent application Ser. No. 09/380,534, filed on Sep. 1, 1999, entitled A METHOD OF INDUCING A CTL RESPONSE; Ser. No. 09/776,232, filed on Feb. 2, 2001, entitled METHOD OF INDUCING A CTL RESPONSE; Ser. No. 09/715,835, filed on Nov. 16, 2000, entitled AVOIDANCE OF UNDESIRABLE REPLICATION INTERMEDIATES IN PLASMID PROPAGATION; Ser. No. 09/999,186, filed on Nov. 7, 2001, entitled METHODS OF COMMERCIALIZING AN ANTIGEN; and Provisional U.S. Patent Application No. 60/274,063, filed on Mar. 7, 2001, entitled ANTI-NEOVASCULAR VACCINES FOR CANCER.

TABLE 29

Partial listing of SEQ ID NOS.

| | | |
|---|---|---|
| SEQ ID NO: 1 | ELAGIGILTV | MELAN-A 26-35 (A27L) |
| SEQ ID NO: 2 | MELAN-A PROTEIN | ACCESSION NUMBER: NP_005502 |
| SEQ ID NO: 3 | TYROSINASE PROTEIN | ACCESSION NUMBER: P14679 |
| SEQ ID NO: 4 | MLLAVLYCLELAGIGILTVYMDGT MSQVGILTVILGVLLLIGCWYCRRR NGYRALMDKSLHVGTQCALTRRCP QEGFDIARDSKVSLQEKNCEPV | PMA2M EXPRESSION PRODUCT |
| SEQ ID NO: 5 | MLLAVLYCLELAGIGILTVYMDGT MSQV | LIBERATION OR SUBSTRATE SEQUENCE FOR SEQ ID NO. 1 FROM PMA2M |
| SEQ ID NO: 6 | MLLAVLYCL | TYROSINASE 1-9 |
| SEQ ID NO: 7 | YMDGTMSQV | TYROSINASE 369-377 |
| SEQ ID NO: 8 | EAAGIGILTV | MELAN-A 26-35 |
| SEQ ID NO: 9 | CTTAAGCCACCATGTTACTAGCTGTTTTGTACTGCC TGGAACTAGCAGGGATCGGCATATTGACAGTGTATA | PMA2M INSERT |

TABLE 29-continued

| Partial listing of SEQ ID NOS. | | |
|---|---|---|
| | TGGATGGAACAATGTCCCAGGTAGGAATTCTGACAG TGATCCTGGGAGTCTTACTGCTCATCGGCTGTTGGT ATTGTAGAAGACGAAATGGATACAGAGCCTTGATGG ATAAAAGTCTTCATGTTGGCACTCAATGTGCCTTAA CAAGAAGATGCCCACAAGAAGGGTTTGATCATCGGG ACAGCAAAGTGTCTCTTCAAGAGAAAAACTGTGAAC CTGTGTAGTGAGCGGCCGC | |
| SEQ ID NO: 10 | MVLYCLELAGIGILTVYMDGIAVL YCLELAGIGILTVYMDGTMLAVLY CLELAGIGILTVYMDGTMSLLAVLY CLELAGICHLTV | EPITOPE ARRAY FROM PVAXM2 AND PVAXM1 |
| SEQ ID NO: 11 | NY-ESO-1 PROTEIN | ACCESSION NUMBER: P78358 |
| SEQ ID NO: 12 | SLLMWITQC | NY-ESO-1 157-165 |
| SEQ ID NO: 13 | KASEKIFYV | SSX-2 41-49 |
| SEQ ID NO: 14 | TQCFLPVFL | NY-ESO-1 163-171 |
| SEQ ID NO: 15 | GLPSIPVHPI | PSMA 288-297 |
| SEQ ID NO: 16 | AVLYCL | TYROSINASE 4-9 |
| SEQ ID NO: 17 | MSLLMWIQCKASEKIFYVRCGAR GPESRLLEFYLAMPFATPMEAELAR RSLAQDAPPLPVPGVLLKEFFVSGN ILTIRLTAADHRQLQLSISSCLQQLSL LMWITQCFLPVFLAQPPSGQRR | PN157 EXPRESSION PRODUCT |
| SEQ ID NO: 18 | MSLLMWITQCKASEKIFYV | LIBERATION OR SUBSTRATE SEQUENCE FOR SEQ ID NO. 12 FROM PN157 |
| SEQ ID NO: 19 | CTTAAGCCACCATGTCCCTGTTGATGTGGATCACGC AGTGCAAAGCTTCGGAGAAAATCTTCTACGTACGGT GCGGTGCCAGGGGGCCGGAGAGCCGCCTGCTTGAGT TCTACCTCGCCATGCCTTTCGCGACACCCATGGAAG CAGAGCTGGCCCGCAGGAGCCTGGCCCAGGATGCCC CACCGCTTCCCGTGCCAGGGGTGCTTCTGAAGGAGT TCACTGTGTCCGGCAACATACTGACTATCCGACTGA CTGCTGCAGACCACCGCCAACTGCAGCTCTCCATCA GCTCCTGTCTCCAGCAGCTTTCCCTGTTGATGTGGA TCACGCAGTGCTTTCTGCCCGTGTTTTTGGCTCAGC CTCCCTCAGGGCAGAGGCGCTAGTGAGAATTC | INSERT FOR PN157 |
| SEQ ID NO: 20 | MSLLMWITQCKASEKIFYVGLPSIP VHPIGLPSIPVHPIKASEKIFYVSLLM WITQCKASEKIFYVKASEKIFYVRC GARGPESRLLEFYLAMPFATPMEAE LARRSLAQDAPPLPVPGVIAKEFTV SGNILTIRLTAADHRQLQLSISSCLQ QLSLLMWITQCFLPVFLAQPPSGQR R | PBPL EXPRESSION PRODUCT |
| SEQ ID NO: 21 | ATGTCCCTGTTGATGTGGATCACGCAGTGCAAAGCT TCGGAGAAAATCTTCTATGTGGGTCTTCCAAGTATT CCTGTTCATCCAATTGGTCTTCCAAGTATTCCTGTT CATCCAATTAAAGCTTCGGAGAAAATCTTCTATGTG TCCCTGTTGATGTGGATCACGCAGTGCAAAGCTTCG GAGAAAATCTTCTATGTGAAAGCTTCGGAGAAAATC TTCTACGTACGGTGCGGTGCCAGGGGGCCGGAGAGC CGCCTGCTTGAGTTCTACCTCGCCATGCCTTTCGCG ACACCCATGGAAGCAGAGCTGGCCCGCAGGAGCCTG GCCCAGGATGCCCCACCGCTTCCCGTGCCAGGGGTG CTTCTGAAGGAGTTCACTGTGTCCGGCAACATACTG ACTATCCGACTGACTGCTGCAGACCACCGCCAACTG CAGCTCTCCATCAGCTCCTGTCTCCAGCAGCTTTCC CTGTTGATGTGGATCACGCAGTGCTTTCTGCCCGTG TTTTTGGCTCAGCCTCCCTCAGGGCAGAGGCGCTAG TGA | PBPL INSERT CODING REGION |
| SEQ ID NO: 22 | IKASEKIFYVSLLMWITQCKASEKI FYVK | SUBSTRATE IN FIG. 9 |

TABLE 29-continued

Partial listing of SEQ ID NOS.

| | | |
|---|---|---|
| SEQ ID NO: 23 | VMTKLGFKV | SSX-4$_{57-65}$ |
| SEQ ID NO: 24 | RQIYVAAFTV | PSMA$_{730-739}$ |
| SEQ ID NO: 25 | AQIPEKIQKAIDDIAKYFSKEENVEK<br>MKASEKIFYVYMKRKYEAMTKLG<br>FKATLPPFMCNKRAEDFQGNDLDN<br>DPNRGNQVERPQMTFGRLQGISPKI<br>MPKKPAEEGNDSEEVPEASGPQND<br>GKELCPPGKPTTSEKIHERSGPKRG<br>EHAWTHRLRERKQLVIYEEISDP | SSX-2$_{15-183}$ |
| SEQ ID NO: 26 | MVMTKLGFKVKASEKIFYVRQIYV<br>AAFTVGLPSIPVHPITQCFLPVFLVM<br>TKLGFKVRQIYVAAFTVKASEKIFY<br>VAQIPEKIQKAFDDIAKYFSKEEWE<br>KMKASEKIFYVYMKRKYEAMTKL<br>GFKATLPPFMCNKRAEDFQGNDLD<br>NDPNRGNQVERPQMTFGRLQGISP<br>KIMPKKPAEEGNDSEEVPEASGPQN<br>DGKELCPPGKPTISEKIHERSGPKR<br>GEHAWTHRLRERKQLVIYEEISDP | CTLS1/PCBP EXPRESSION<br>PRODUCT |
| SEQ ID NO: 27 | TMAQIPEKIQKAFDDIAKYFSKEEWE<br>KMKASEKIFYVYMKRKYEAMTKL<br>GFKATLPPFMCNKRAEDFQGNDLD<br>NDPNRGNQVERPQMTFGRLQGISP<br>KIMPKKPAEEGNDSEEVPEASGPQN<br>DGKELCPPGKPITSEKIHERSGPKR<br>GEHAWTHRLRERKQLVIYEEISDPV<br>MTKLGFKVKASEKWYVRQIYVAAF<br>TVGLPSIPVHPITQCFLPVFLVMTKL<br>GFKVRQIYVAAFTVKASEKIFYV | CTLS2 EXPRESSION<br>PRODUCT |
| SEQ ID NO: 28 | MVMTKLGFKVKASEKIFYVRQIYV<br>AAFTVGLPSIPVHPIAQIPEKIQKAFD<br>DIAKYFSKEEWEKMKASEKIFYVY<br>MKRKYEAMTKLGFKATLPPFMCN<br>KRAEDFQGNDLDNDPNRGNQVERP<br>QMITGRLQGISPKIMPKKPAEEGND<br>SEEVPEASGPQNDGKELCPPGKPTT<br>SEKIHERSGPKRGEHAWTHRLRER<br>KQLVIYEEISDP | CTLS3 EXPRESSION<br>PRODUCT |
| SEQ ID NO: 29 | MAQIPEKIQKAFDDIAKYFSKEEWE<br>KMKASEKIFYVYMKRKYEAMTKL<br>GFKATLPPFMCNKRAEDFQGNDLD<br>NDPNRGNQVERPQMTFGRLQGISP<br>K1MPKKPAEEGNDSEEVPEASGPQN<br>DGKELCPPGKPTTSEKIHERSGPKR<br>GEHAWTHRLRERKQLVIYEEISDPT<br>QCFLPVFLVMTKLGFKVRQIYVAAF<br>TVKASEKIFYV | CTLS4 EXPRESSION<br>PRODUCT |
| SEQ ID NO: 30 | ATGGTCATGACTAAACTAGGTTTCAAGGTCAAAGCT<br>TCGGAGAAAATCTTCTATGTGAGACAGATTTATGTT<br>GCAGCCTTCACAGTGGGTCTTCCAAGTATTCCTGTT<br>CATCCAATTACGCAGTGCTTTCTGCCCGTGTTTTTG<br>GTCATGACTAAACTAGGTTTCAAGGTCAGACAGAIT<br>TATGTTGCAGCCTTCACAGTGAAAGCTTCGGAGAAA<br>ATCTTCTACGTAGCTCAAATACCAGAAGATCCAA<br>AAGGCCTTCGATGATATTGCCAAATACTTCTCTAAG<br>GAAGAGTGGGAAAAGATGAAAGCCTCGGAGAAAATC<br>TTCTATGTGTATATGAAGAGAAAGTATGAGGCTATG<br>ACTAAACTAGGTTTCAAGGCCACCCTCCCACCTTTC<br>ATGTGTAATAAACGGGCCGAAGACTTCCAGGGGAAT<br>GATTTGGATAATGACCCTAACCGTGGGAATCAGGTT<br>GAACGTCCTCAGATGACTTTCGGCAGGCTCCAGGGA<br>ATCTCCCCGAAGATCATGCCCAAGAAGCCAGCAGAG<br>GAAGGAAATGATTCGGAGGAAGTGCCAGAAGCATCT<br>GGCCCACAAAATGATGGGAAAGAGCTGTGCCCCCCG<br>GGGAAAACCAACTACCTCTGAGAAGATTCACGAGAGA<br>TCTGGACCCAAAAGGGGGGAACATGCCTGGACCCAC<br>AGACTGCGTGAGAGAAAACAGCTGGTGATTTATGAA<br>GAGATCAGCGACCCCTTAGTGA | PCBP INSERT CODING<br>REGION |

TABLE 29-continued

Partial listing of SEQ ID NOS.

Figure 11A:
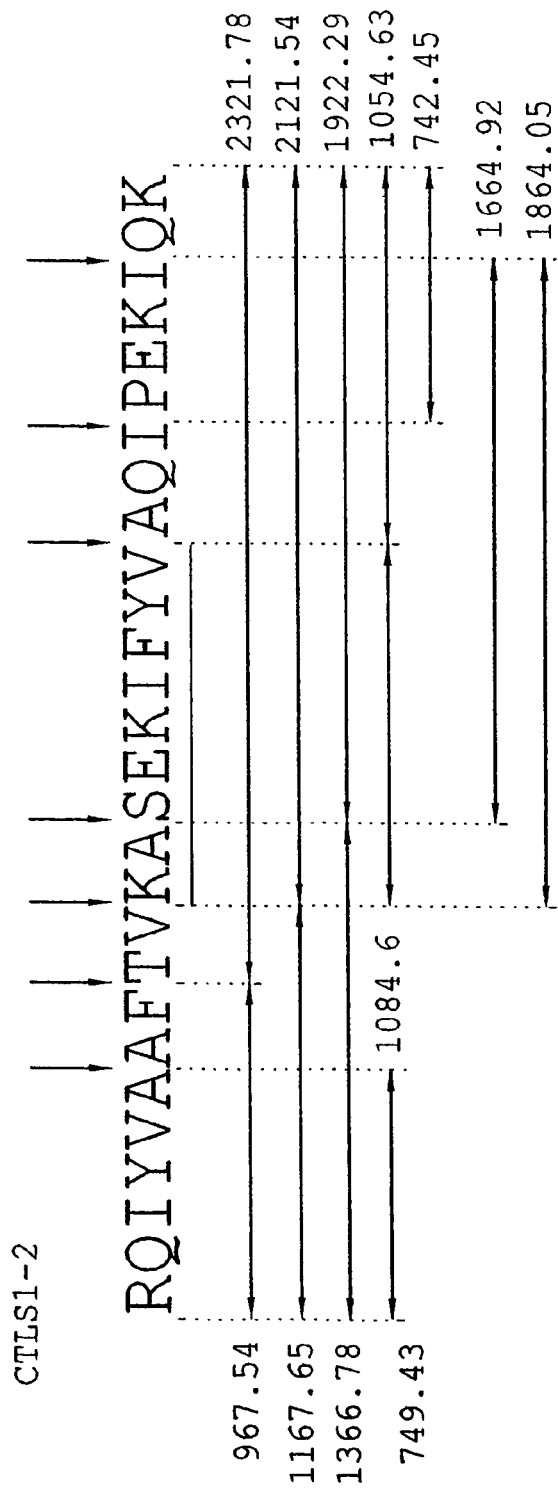
FIG. 11. 11A: Shows the results of the human immunoproteasome digest of SEQ ID NO. 31. 11B: Shows the comparative results of mouse versus human immunoproteasome digestion of SEQ ID NO. 31.
Figure 11B:
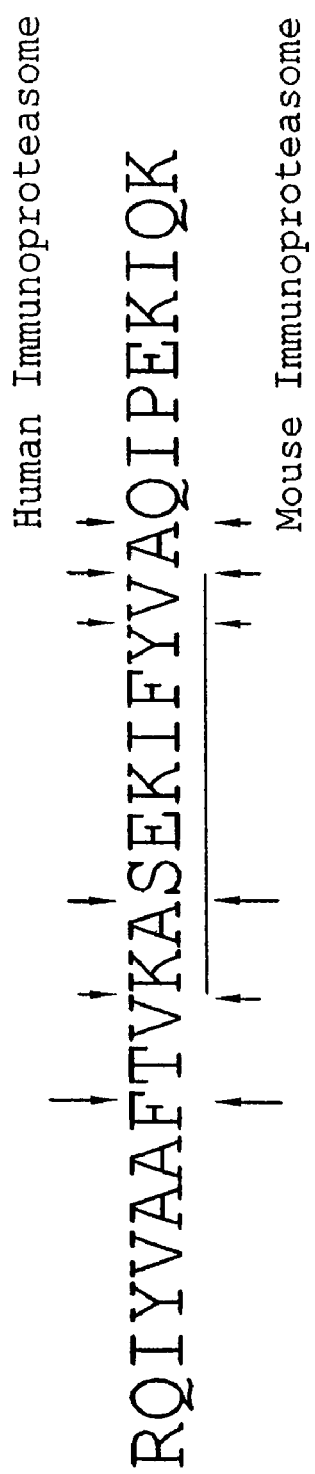
Figure 12:
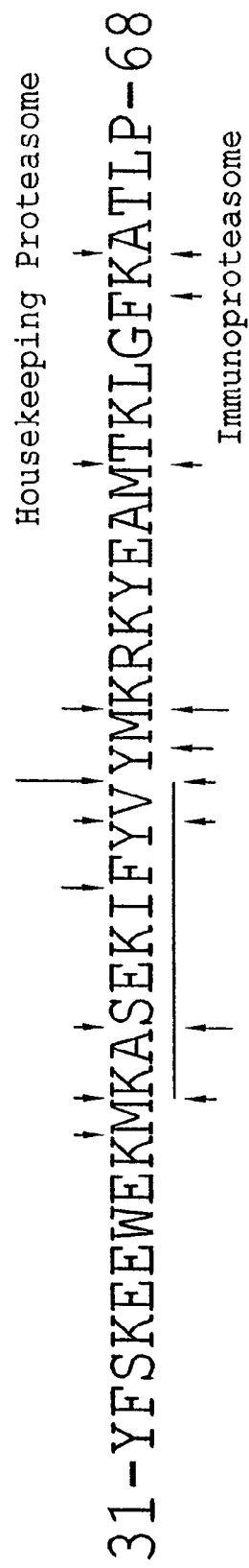
FIG. 12. Shows the differing processing of SSX-$2_{31-68}$ (SEQ ID NO: 986) by housekeeping and immunoproteasome.

| SEQ ID NO: 31 | RQIYVAAFTVKASEKIFYVAQIPEKI QK | FIG. 11 SUBSTRATE/ CTLS1-2 |
|---|---|---|
| SEQ ID NO: 32 | FLPWHRLFL | Tyr$_{207-215}$ |
| SEQ ID NO: 33 | MLLAVLYCLIMSFQTSAFLPWHRL FLMLLAVLYCLLWSFQTSAFLPWH RLFLMLLAVLYCLLWSFQTSAFLP WHRLFLMLLAVLYCLLWSFQTSAF LPWFIRLFL | CTLT2/PMEL EXPRESSION PRODUCT |
| SEQ ID NO: 34 | ATGCTCCTGGCTGTTTTGTACTGCCTGCTGTGGAGT TTCCAGACCTCCGCTTTTCTGCCTTGGCATAGACTC TTCTTGATGCTCCTGGCTGTlTTGTACTGCCTGCTG TGGAGTTTCCAGACCTCCGCTTTTCTGCCTTGGCAT AGACTCTTCTrGATGCTCCTGGCTGTTTTGTACTGC CTGCTGTGGAGTTTCCAGACCTCCGCTTTTCTGCCT TGGCATAGACTCTTCTTGATGCTCCTGGCTGTTTTG TACTGCCTGCTGTGGAGTTTCCAGACCTCCGCTTTT CTGCCTTGGCATAGACTCTTCTTGTAGTGA | CTLT2/PMEL INSERT CODING REGION |
| SEQ ID NO: 35 | MELAN-A CDNA | ACCESSION NUMBER: NM_005511 |
| SEQ ID NO: 36 | TYROSINASE CDNA | ACCESSION NUMBER: NM_000372 |
| SEQ ID NO: 37 | NY-ESO-1 CDNA | ACCESSION NUMBER: U87459 |
| SEQ ID NO: 38 | PSMA PROTEIN | ACCESSION NUMBER: NP_004467 |
| SEQ ID NO: 39 | PSMA CDNA | ACCESSION NUMBER: NM_004476 |
| SEQ ID NO: 40 | SSX-2 PROTEIN | ACCESSION NUMBER: NP_003138 |
| SEQ ID NO: 41 | SSX-2 CDNA | ACCESSION NUMBER: NM_003147 |
| SEQ ID NO: 42 | ATGACCTCTCGCCGCTCCGTGAAG TCGGGTCCGCGGGAGGTTCCGCG CGATGAGTACGAGGATCTGTACT ACACCCCGTCTTCAGGTATGGCGA GTCCCGATAGTCCGCCTGACACCT CCCGCCGTGGCGCCCTACAGACA CGCTCGCGCCAGAGGGGCGAGGT CCGTTTCGTCCAGTACGACGAGTC GGATTATGCCCTCTACGGGGGCTC GTCATCCGAAGACGACGAACACC CGGAGGTCCCCCGGACGCGGCGT CCCGTTTCCGGGGCGGTTTTGTCC GGCCCGGGGCCTGCGCGGGCGCC TCCGCCACCCGCTGGGTCCGGAG GGGCCGGACGCACACCCACCACC GCCCCCGGGCCCCCCGAACCCA GCGGGTGGCGACTAAGGCCCCQG CGGCCCCGGCGGCGGAGACCACC CGCGGCAGGAAATCGGCCCAGCC AGAATCCGCCGCACTCCCAGACG CCCCCGCGTCGACGGCGCCAACC CGATCCAAGACACCCGCGCAGGG GCTGGCCAGAAAGCTGCACTTTA GCACCGCCCCCCAAACCCCGAC GCGCCATGGACCCCCCGGGTGGC CGGCTTTAACAAGCGCGTCTTCTG CGCCGCGGTCGGGCGCCTGGCGG CCATGCATGCCCGGATGGCGGCG GTCCAGCTCTGGGACATGTCGCGT CCGCGCACAGACGAAGACCTCAA CGAACTCCTTGGCATCACCACCAT CCGCGTGACGGTCTGCGAGGGCA AAAACCTGCTTCAGCGCGCCAAC GAGTTGGTGAATCCAGACGTGGT GCAGGACGTCGACGCGGCCACGG | FROM ACCESSION: NUMBER: DI0879 HERPES SIMPLEX VIRUS 1 UL49 CODING SEQUENCE (V-P22) |

TABLE 29-continued

Partial listing of SEQ ID NOS.

| | | |
|---|---|---|
| | CGACTCGAGGGCGTTCTGCGGCG<br>TCGCGCCCCACCGAGCGACCTCG<br>AGCCCCAGCCCGCTCCGCTTCTCG<br>CCCCAGACGGCCCGTCGAG | |
| SEQ ID NO: 43 | MTSRRSVKSGPREVPRDEYEDLYY<br>TPSSGMASPDSPPDTSRRGALFTQT<br>RSRQRGEVRFVQYDESDYALYGGS<br>SSEDDEHPEVPRTIUOVSGAVLSGP<br>GPARAPPPFTPAGSGGAGRTPTTAP<br>RAPRTQRVATKAPAAPAAETTRGR<br>KSAQPESAALPDAPASTAPTFTRSK<br>TPAQGLARKLHFSTAPPNPDAPWTP<br>RVAGFNKRVFCAAVGRLAAMHAR<br>MAAVQLWDFTMSRPRTDEDLNELL<br>GITTIRVTVCEGKNLLQRANELVNP<br>DVVQDVDAATATRGRSAASRFTPT<br>ERPRAPARSASRPRRPVE | ACCESSION NUMBER:<br>P10233<br>HERPES SIMPLEX VIRUS 1<br>UL49/VP22 PROTEIN<br>SEQUENCE |

20

Melan-A mRNA Sequence
LOCUS NM_005511 1524 bp mRNA PRI 14 Oct. 2001
DEFINITION *Homo sapiens* melan-A (MLANA), mRNA.
ACCESSION NM_005511
VERSION NM_005511.1 GI:5031912

```
    /translation = "MPREDAHFIYGYPKKGHGHSYTTAEEAAGIGILTVILGVLLLIGCWYCR       (SEQ ID NO. 2)

RRNGYRALMDKSLHVGTQCALTRRCPQEGFDHRDSKVSLQEKNCEPVVPNAPPAYE

KLSAEQSPPPYSP"

ORIGIN
        1 agcagacaga ggactctcat taaggaaggt gtcctgtgcc ctgaccctac aagatgccaa    (SEQ ID NO. 35)

61 gagaagatgc tcacttcatc tatggttacc ccaagaaggg gcacggccac tcttacacca 121 cggctgaaga ggccgctggg atcggcatcc tgacagtgat cctgggagtc ttactgctca 181 tcggctgttg gtattgtaga agacgaaatg gatacagagc cttgatggat aaaagtcttc 241 atgttggcac tcaatgtgcc ttaacaagaa gatgccaca agaagggttt gatcatcggg 301 acagcaaagt gtctcttcaa gagaaaaact gtgaacctgt ggttcccaat gctccacctg 361 cttatgagaa actctctgca gaacagtcac caccacctta tcaccttaa gagccagcga 421 gacacctgag acatgctgaa attatttctc tcacactttt gcttgaattt aatacagaca 481 tctaatgttc tcctttggaa tggtgtagga aaaatgcaag ccatctctaa taataagtca 541 gtgttaaaat tttagtaggt ccgctagcag tactaatcat gtgaggaaat gatgagaaat 601 attaaattgg gaaaactcca tcaataaatg ttgcaatgca tgatactatc tgtgccagag 661 gtaatgttag taaatccatg gtgttatttt ctgagagaca gaattcaagt gggtattctg 721 gggccatcca atttctcttt acttgaaatt tggctaataa caaactagtc aggttttcga 781 accttgaccg acatgaactg tacacagaat tgttccagta ctatggagtg ctcacaaagg 841 atacttttac aggttaagac aaagggttga ctggcctatt tatctgatca agaacatgtc 901 agcaatgtct ctttgtgctc taaaattcta ttatactaca ataatatatt gtaaagatcc 961 tatagctctt ttttttgag atggagtttc gcttttgttg cccaggctgg agtgcaatgg 1021 cgcgatcttg gctcaccata acctccgcct cccaggttca agcaattctc ctgccttagc 1081 ctcctgagta gctgggatta caggcgtgcg ccactatgcc tgactaattt tgtagtttta 1141 gtagacacgg ggtttctcca tgttggtcag gctggtctca aactcctgac ctcaggtgat 1201 ctgcccgcct cagcctccca aagtgctgga attacaggcg tgagccacca cgcctggctg
```

-continued

```
1261 gatcctatat cttaggtaag acatataacg cagtctaatt acatttcact tcaaggctca 1321 atgctattct aactaatgac aagtattttc tactaaacca gaaattggta gaaggattta 1381 aataagtaaa agctactatg tactgcctta gtgctgatgc ctgtgtactg ccttaaatgt 1441 acctatggca atttagctct cttgggttcc caaatccctc tcacaagaat gtgcagaaga 1501 aatcataaag gatcagagat tctg
```

Tyrosinase mRNA Sequence
LOCUS NM_000372 1964 bp mRNA PRI 31 Oct. 2000
DEFINITION *Homo sapiens* tyrosinase (oculocutaneous
albinism IA) (TYR), mRNA.
ACCESSION NM_000372
VERSION NM_000372.1 GI:4507752

```
/translation = "MLLAVLYCLLWSFQTSAGHFPRACVSSKNLMEKECCPPWSGDRS       (SEQ ID NO. 3)

PCGQLSGRGSCQNILLSNAPLGPQFPFTGVDDRESWPSVFYNRTCQCSGNFMGFNCG

NCKFGFWGPNCTERRLLVRRNIFDLSAPEKDKFFAYLTLAKHTISSDYVIPIGTYGQM

KNGSTPMFNDINIYDLFVWMHYYVSMDALLGGSEIWRDIDFAHEAPAFLPWHRLFLL

RWEQEIQKLTGDENFTIPYWDWRDAEKCDICTDEYMGGQHPTNPNLLSPASFFSSW

QIVCSRLEEYNSHQSLCNGTPEGPLRRNPGNHDKSRTPRLPSSADVEFCLSLTQYESG

SMDKAANFSFRNTLEGFASPLTGIADASQSSMHNALHIYMNGTMSQVQGSANDPIFL

LHHAFVDSIFEQWLRRHRPLQEVYPEANAPIGHNRESYMVPFIPLYRNGDFFISSKDL

GYDYSYLQDSDPDSFQDYIKSYLEQASRIWSWLLGAAMVGAVLTALLAGLVSLLCR

HKRKQLP EEKQPLLMEKEDYHSLYQSHL"
ORIGIN 1 atcactgtag tagtagctgg aaagagaaat ctgtgactcc aattagccag ttcctgcaga       (SEQ ID NO. 36)

61 ccttgtgagg actagaggaa gaatgctcct ggctgttttg tactgcctgc tgtggagttt 121 ccagacctcc gctggccatt tccctagagc ctgtgtctcc tctaagaacc tgatggagaa 181 ggaatgctgt ccaccgtgga gcggggacag gagtccctgt ggccagcttt caggcagagg 241 ttcctgtcag aatatccttc tgtccaatgc accacttggg cctcaatttc ccttcacagg 301 ggtggatgac cgggagtcgt ggccttccgt cttttataat aggacctgcc agtgctctgg 361 caacttcatg ggattcaact gtggaaactg caagtttggc ttttggggac aaactgcac 421 agagagacga ctcttggtga agaaaacat cttcgatttg agtgccccag agaaggacaa 481 attttttgcc tacctcactt tagcaaagca taccatcagc tcagactatg tcatccccat 541 agggacctat ggccaaatga aaaatggatc aacacccatg tttaacgaca tcaatattta 601 tgacctcttt gtctggatgc attattatgt gtcaatggat gcactgcttg ggggatctga 661 aatctggaga gacattgatt ttgcccatga agcaccagct tttctgcctt ggcatagact 721 cttcttgttg cggtgggaac aagaaatcca gaagctgaca ggagatgaaa acttcactat 781 tccatattgg gactggcggg atgcagaaaa gtgtgacatt tgcacagatg agtacatggg 841 aggtcagcac cccacaaatc ctaacttact cagcccagca tcattcttct cctcttggca 901 gattgtctgt agccgattgg aggagtacaa cagccatcag tctttatgca atggaacgcc 961 cgagggacct ttacggcgta atcctggaaa ccatgacaaa tccagaaccc caaggctccc 1021 ctcttcagct gatgtagaat tttgcctgag tttgacccaa tatgaatctg gttccatgga 1081 taaagctgcc aatttcagct ttagaaatac actggaagga tttgctagtc cacttactgg
```

```
                                                -continued
1141  gatagcggat  gcctctcaaa  gcagcatgca  caatgccttg  cacatctata  tgaatggaac 1201  aatgtcccag  gtacagggat  ctgccaacga  tcctatcttc  cttcttcacc  atgcatttgt 1261  tgacagtatt  tttgagcagt  ggctccgaag  gcaccgtcct  cttcaagaag  tttatccaga 1321  agccaatgca  cccattggac  ataaccggga  atcctacatg  gttccttta  taccactgta 1381  cagaaatggt  gatttcttta  tttcatccaa  agatctgggc  tatgactata  gctatctaca 1441  agattcagac  ccagactctt  ttcaagacta  cattaagtcc  tatttggaac  aagcgagtcg 1501  gatctggtca  tggctccttg  gggcggcgat  ggtaggggcc  gtcctcactg  ccctgctggc 1561  agggcttgtg  agcttgctgt  gtcgtcacaa  gagaaagcag  cttcctgaag  aaaagcagcc 1621  actcctcatg  gagaaagagg  attaccacag  cttgtatcag  agccatttat  aaaaggctta 1681  ggcaatagag  tagggccaaa  aagcctgacc  tcactctaac  tcaaagtaat  gtccaggttc 1741  ccagagaata  tctgctggta  tttttctgta  aagaccattt  gcaaaattgt  aacctaatac 1801  aaagtgtagc  cttcttccaa  ctcaggtaga  acacacctgt  ctttgtcttg  ctgttttcac 1861  tcagccctt  taacattttc  ccctaagccc  atatgtctaa  ggaaaggatg  ctatttggta 1921  atgaggaact  gttatttgta  tgtgaattaa  agtgctctta  tttt
```

NY-ESO-1 mRNA Sequence
LOCUS HSU87459 752 bp mRNA PRI 22 Dec. 1999
DEFINITION Human autoimmunogenic cancer/testis antigen NY-ESO-1 mRNA, complete cds.
ACCESSION U87459
VERSION U87459.1 GI:1890098

```
    /translation = "MQAEGRGTGGSTGDADGPGGPGIPDGPGGNAGGPGEAGATGGRGPRG      (SEQ ID NO. 11)

AGAARASGPGGGAPRGPHGGAASGLNGCCRCGARGPESRLLEFYLAMPFATPMEAE

LARRSLAQDAPPLPVPGVLLKEFTVSGNILTIRLTAADHRQLQLSISSCLQQLSLLM

WITQCFLPVFLAQPPSGQRR"
ORIGIN
    1  atcctcgtgg  gccctgacct  tctctctgag  agccgggcag  aggctccgga  gccatgcagg   (SEQ ID NO. 37)

61  ccgaaggccg  gggcacaggg  ggttcgacgg  gcgatgctga  tgcccagga   ggccctggca 121  ttcctgatgg  cccagggggc  aatgctggcg  gcccaggaga  ggcgggtgcc  acgggcggca 181  gaggtccccg  gggcgcaggg  gcagcaaggg  cctcggggcc  gggaggaggc  gccccgcggg 241  gtccgcatgg  cggcgcggct  tcaggctga   atggatgctg  cagatgcggg  gccaggggc 301  cggagagccg  cctgcttgag  ttctacctcg  ccatgccttt  cgcgacaccc  atggaagcag 361  agctggcccg  caggagcctg  gccaggatg   ccccaccgct  tcccgtgcca  gggtgcttc 421  tgaaggagtt  cactgtgtcc  ggcaacatac  tgactatccg  actgactgct  gcagaccacc 481  gccaactgca  gctctccatc  agctcctgtc  tccagcagct  ttccctgttg  atgtggatca 541  cgcagtgctt  tctgcccgtg  tttttggctc  agcctccctc  agggcagagg  cgctaagccc 601  agcctggcgc  ccttcctag   gtcatgcctc  ctcccctagg  gaatggtccc  agcacgagtg 661  gccagttcat  tgtgggggc   tgattgtttg  tcgctggagg  aggacggctt  acatgtttgt 721  ttctgtagaa  aataaaactg  agctacgaaa  aa
```

PSMA cDNA Sequence
LOCUS NM_004476 2653 bp mRNA PRI 1 Nov. 2000
DEFINITION *Homo sapiens* folate hydrolase (prostate-specific membrane antigen) 1 (FOLH1), mRNA.
ACCESSION NM_004476
VERSION NM_004476.1 GI:4758397

/translation = "MWNLLHETDSAVATARRPRWLCAGALVLAGGFFLLGFLFGWFIKSSNE    (SEQ ID NO. 38)
ATNITPKHNMKAFLDELKAENIKKFLYNFTQIPHLAGTEQNFQLAKQIQSQWKEFGL
DSVELAHYDVLLSYPNKTHPNYISIINEDGNEIFNTSLFEPPPPGYENVSDIVPPFSAFSP
QGMPEGDLVYVNYARTEDFFKLERDMKINCSGKIVIARYGKVFRGNKVKNAQLAG
AKGVILYSDPADYFAPGVKSYPDGWNLPGGGVQRGNILNLNGAGDPLTPGYPANEY
AYRRGIAEAVGLPSIPVHPIGYYDAQKLLEKMGGSAPPDSSWRGSLKVPYNVGPGFT
GNFSTQKVKMHIHSTNEVTRIYNVIGTLRGAVEPDRYVILGGHRDSWVFGGIDPQSG
AAVVHEIVRSFGTLKKEGWRPRRTILFASWDAEEFGLLGSTEWAEENSRLLQERGVA
YINADSSIEGNYTLRVDCTPLMYSLVHNLTKELKSPDEGFEGKSLYESWTKKSPSPEF
SGMPRISKLGSGNDFEVFFQRLGIASGRARYTKNWETNKFSGYPLYHSVYETYELVE
KFYDPMFKYHLTVAQVRGGMVFELANSIVLPFDCRDYAVVLRKYADKIYSISMKHP
QEMKTYSVSFDSLFSAVKNFTEIASKFSERLQDFDKSNPIVLRMMNDQLMFLERAFID
PLGLPDRPFYRHVIYAPSSHNKYAGESFPGIYDALFDIESKVDPSKAWGEVKRQIYVA
AFTVQAAAETLSEVA"
ORIGIN
    1 ctcaaaaggg gccggatttc cttctcctgg aggcagatgt tgcctctctc tctcgctcgg    (SEQ ID NO. 39)
   61 attggttcag tgcactctag aaacactgct gtggtggaga aactggaccc caggtctgga
  121 gcgaattcca gcctgcaggg ctgataagcg aggcattagt gagattgaga gagactttac
  181 cccgccgtgg tggttggagg gcgcgcagta gagcagcagc acaggcgcgg gtcccgggag
  241 gccggctctg ctcgcgccga gatgtggaat ctccttcacg aaaccgactc ggctgtggcc
  301 accgcgcgcc gcccgcgctg gctgtgcgct ggggcgctgg tgctggcggg tggcttcttt
  361 ctcctcggct tcctcttcgg gtggtttata aaatcctcca atgaagctac aacattact
  421 ccaaagcata atatgaaagc atttttggat gaattgaaag ctgagaacat caagaagttc
  481 ttatataatt ttacacagat accacattta gcaggaacag aacaaaactt tcagcttgca
  541 aagcaaattc aatcccagtg gaaagaattt ggcctggatt ctgttgagct agcacattat
  601 gatgtcctgt tgtcctaccc aaataagact catcccaact acatctcaat aattaatgaa
  661 gatggaaatg agatttcaa cacatcatta tttgaaccac ctcctccagg atatgaaat
  721 gtttcggata ttgtaccacc tttcagtgct ttctctcctc aaggaatgcc agagggcgat
  781 ctagtgtatg ttaactatgc acgaactgaa gacttcttta aattggaacg ggacatgaaa
  841 atcaattgct ctgggaaaat tgtaattgcc agatatggga agttttcag aggaaataag
  901 gttaaaaatg cccagctggc aggggccaaa ggagtcattc tctactccga ccctgctgac
  961 tactttgctc ctggggtgaa gtcctatcca gatggttgga atcttcctgg aggtggtgtc
 1021 cagcgtggaa atatcctaaa tctgaatggt gcaggagacc ctctcacacc aggttaccca
 1081 gcaaatgaat atgcttatag gcgtggaatt gcagaggctg ttggtcttcc aagtattcct
 1141 gttcatccaa ttggatacta tgatgcacag aagctcctag aaaaaatggg tggctcagca
 1201 ccaccagata gcagctgag aggaagtctc aaagtgccct acaatgttgg acctggcttt
 1261 actggaaact ttctacaca aaaagtcaag atgcacatcc actctaccaa tgaagtgaca
 1321 agaatttaca atgtgatagg tactctcaga ggagcagtgg aaccagacag atatgtcatt
 1381 ctgggaggtc accgggactc atgggtgttt ggtggtattg accctcagag tggagcagct
 1441 gttgttcatg aaattgtgag gagctttgga acactgaaaa aggaagggtg gagacctaga
 1501 agaacaattt tgtttgcaag ctgggatgca gaagaatttg gtcttcttgg ttctactgag -continued

```
1561 tgggcagagg agaattcaag actccttcaa gagcgtggcg tggcttatat taatgctgac
1621 tcatctatag aaggaaacta cactctgaga gttgattgta caccgctgat gtacagcttg
1681 gtacacaacc taacaaaaga gctgaaaagc cctgatgaag ctttgaagg caaatctctt
1741 tatgaaagtt ggactaaaaa aagtccttcc ccagagttca gtggcatgcc caggataagc
1801 aaattgggat ctggaaatga ttttgaggtg ttcttccaac gacttggaat tgcttcaggc
1861 agagcacggt atactaaaaa ttgggaaaca aacaaattca gcggctatcc actgtatcac
1921 agtgtctatg aaacatatga gttggtggaa aagttttatg atccaatgtt taaatatcac
1981 ctcactgtgg cccaggttcg aggagggatg gtgtttgagc tagccaattc catagtgctc
2041 ccttttgatt gtcgagatta tgctgtagtt ttaagaaagt atgctgacaa aatctacagt
2101 atttctatga aacatccaca ggaaatgaag acatacagtg tatcatttga ttcactttt
2161 tctgcagtaa agaattttac agaaattgct tccaagttca gtgagagact ccaggacttt
2221 gacaaaagca acccaatagt attaagaatg atgaatgatc aactcatgtt tctggaaaga
2281 gcatttattg atccattagg gttaccagac aggcctttt ataggcatgt catctatgct
2341 ccaagcagcc acaacaagta tgcaggggag tcattcccag gaatttatga tgctctgttt
2401 gatattgaaa gcaaagtgga cccttccaag gcctggggag aagtgaagag acagatttat
2461 gttgcagcct tcacagtgca ggcagctgca gagactttga gtgaagtagc ctaagaggat
2521 tctttagaga atccgtattg aatttgtgtg gtatgtcact cagaaagaat cgtaatgggt
2581 atattgataa attttaaaat tggtatattt gaaataaagt tgaatattat atataaaaaa
2641 aaaaaaaaa aaa
```

NM 003147 *Homo sapiens* synovial sarcoma, X breakpoint 2 (SSX2), mRNA
LOCUS NM_003147 766 bp mRNA PRI 14 Mar. 2001
DEFINITION *Homo sapiens* synovial sarcoma, X breakpoint 2 (SSX2), mRNA.
ACCESSION NM_003147
VERSION NM_003147.1 GI:10337582

```
/translation = "MNGDDAFARRPTVGAQIPEKIQKAFDDIAKYFSKEEWEKMKASE    SEQ ID NO. 40

KIFYVYMKRKYEAMTKLGFKATLPPFMCNKRAEDFQGNDLDNDPNRGNQVERPQMTFG

RLQGISPKIMPKKPAEEGNDSEEVPEASGPQNDGKELCPPGKPTTSEKIHERSGPKRG

EHAWTHRLRERKQLVIYEEISDPEEDDE"

1 ctctctttcg attcttccat actcagagta cgcacggtct gattttctct ttggattctt    SEQ ID NO 41
  61 ccaaaatcag agtcagactg ctcccggtgc catgaacgga gacgacgcct ttgcaaggag
 121 acccacggtt ggtgctcaaa taccagaaga gatccaaaag gccttcgatg atattgccaa
 181 atacttctct aaggaagagt gggaaaagat gaaagcctcg agaaaatct tctatgtgta
 241 tatgaagaga aagtatgagg ctatgactaa actaggttc aaggccaccc tcccaccttt
 301 catgtgtaat aaacgggccg aagacttcca ggggaatgat ttggataatg accctaaccg
 361 tgggaatcag gttgaacgtc ctcagatgac tttcggcagg ctccagggaa tctccccgaa
 421 gatcatgccc aagaagccag cagaggaagg aaatgattcg gaggaagtgc cagaagcatc
 481 tggcccacaa aatgatggga aagagctgtg cccccgggaa aaccaacta cctctgagaa
 541 gattcacgag agatctggac ccaaaggggg gaacatgcc tggacccaca gactgcgtga
 601 gagaaaacag ctggtgattt atgaagagat cagcgaccct gaggaagatg acgagtaact
```

```
661 cccctcaggg atacgacaca tgcccatgat gagaagcaga acgtggtgac ctttcacgaa 721 catgggcatg gctgcggacc cctcgtcatc aggtgcatag caagtg
```

---

What is claimed is:

1. An isolated nucleic acid molecule comprising a reading frame comprising a first sequence, wherein said first sequence encodes one or more segments of a tumor-associated antigen, wherein the antigen is NY-ESO (SEQ ID NO: 11), wherein the first sequence comprises less than 30% of the length of the antigen, or greater than 55% and less than 60% of the length of the antigen, wherein the reading frame does not encode the complete NY-ESO antigen, and wherein each segment comprises an epitope cluster, said cluster comprising or encoding at least two amino acid sequences having a known or predicted affinity for a same MHC Class I receptor peptide binding cleft, wherein said first sequence encodes a fragment of NY-ESO, wherein said encoded fragment comprises an amino acid sequence beginning at one of amino acids selected from the group consisting of 77, 79, 86, and 108 of NY-ESO, and ending at one of the amino acids selected from the group consisting of 104, 140, 167, 171, 174, and 180 of NY-ESO.

2. The nucleic acid molecule of claim 1, wherein said reading frame is operably linked to a promoter.

3. An immunogenic composition comprising the nucleic acid molecule of claim 1.

4. The nucleic acid molecule of claim 1, wherein said encoded fragment consists essentially of amino acids 79-174 of NY-ESO.

5. The nucleic acid molecule of claim 4, wherein said first sequence encodes exactly amino acids 77-180 of NY-ESO.

6. The nucleic acid molecule of claim 1, wherein said one or more segments consist of said epitope cluster.

7. An isolated nucleic acid molecule comprising a reading frame comprising a first sequence, wherein said first sequence encodes one or more segments of tumor-associated antigen NY-ESO (SEQ ID NO: 11), wherein the first sequence comprises less than 60% of the length of the complete NY-ESO antigen, and wherein each segment comprises an epitope cluster, said cluster comprising or encoding at least two amino acid sequences having a known or predicted affinity for a same MHC Class I receptor peptide binding cleft, wherein the first sequence comprises an epitope cluster chosen from the group consisting of amino acids 79-104, 86-171, 108-140, and 108-174 of NY-ESO, and wherein said first sequence encodes a fragment of NY-ESO, and wherein said encoded fragment consists essentially of amino acids 79-174 of NY-ESO.

8. The nucleic acid molecule of claim 7, wherein said first sequence encodes exactly amino acids 77-180 of NY-ESO.

9. An isolated nucleic acid molecule comprising a reading frame comprising a first sequence, wherein said first sequence encodes one or more segments of tumor-associated antigen NY-ESO (SEQ ID NO: 11), wherein the first sequence comprises less than 90% of the length of the complete NY-ESO antigen, and wherein each segment comprises an epitope cluster, said cluster comprising or encoding at least two amino acid sequences having a known or predicted affinity for a same MHC Class I receptor peptide binding cleft, wherein the first sequence comprises an epitope cluster chosen from the group consisting of amino acids 86-171, 108-140, and 108-174 of NY-ESO.

10. The nucleic acid molecule of claim 9, wherein said first sequence encodes a fragment of NY-ESO.

11. The nucleic acid molecule of claim 10, wherein said encoded fragment consists of a polypeptide having a length, wherein the length of the polypeptide is less than about 80% of the length of NY-ESO.

12. The nucleic acid molecule of claim 10, wherein said encoded fragment consists of a polypeptide having a length, wherein the length of the polypeptide is less than about 50% of the length of NY-ESO.

13. The nucleic acid molecule of claim 10, wherein said encoded fragment consists of a polypeptide having a length, wherein the length of the polypeptide is less than about 25% of the length of NY-ESO.

14. The nucleic acid molecule of claim 10, wherein said encoded fragment consists of a polypeptide having a length, wherein the length of the polypeptide is less than about 10% of the length of NY-ESO.

15. The nucleic acid molecule of claim 10, wherein said encoded fragment comprises an amino acid sequence beginning at one of amino acids selected from the group consisting of 77, 79, 86, and 108 of NY-ESO, and ending at one of the amino acids selected from the group consisting of 104, 140, 167, 171, 174, and 180 of NY-ESO.

16. The nucleic acid molecule of claim 9, wherein said reading frame is operably linked to a promoter.

17. An immunogenic composition comprising the nucleic acid molecule of claim 16.

18. The nucleic acid molecule of claim 16, wherein said first sequence encodes exactly amino acids 77-180 of NY-ESO.

19. The nucleic acid molecule of claim 9, wherein said one or more segments consist of said epitope cluster.

20. The nucleic acid molecule of claim 9, wherein said wherein said one or more segments of a tumor-associated antigen comprise multiple segments of NY-ESO, each consisting of an epitope cluster.

21. An isolated nucleic acid molecule comprising a reading frame comprising a first sequence, wherein said first sequence encodes one or more segments of tumor-associated antigen NY-ESO (SEQ ID NO: 11), wherein the first sequence comprises less than 60% of the length of the complete NY-ESO antigen, and wherein each segment comprises an epitope cluster, said cluster comprising or encoding at least two amino acid sequences having a known or predicted affinity for a same MHC Class I receptor peptide binding cleft, wherein the first sequence comprises an epitope cluster chosen from the group consisting of amino acids 79-104, 86-171, 108-140, and 108-174 of NY-ESO, wherein said first sequence further comprises amino acids 148-167 of NY-ESO.

22. An isolated nucleic acid molecule comprising a reading frame comprising a first sequence, wherein said first sequence encodes one or more segments of a tumor-associated antigen, wherein the antigen is NY-ESO (SEQ ID NO: 11), wherein the first sequence comprises less than 30% of the length of the antigen, or greater than 55% and less than 60% of the length of the antigen, wherein the reading frame does not encode the complete NY-ESO antigen, and wherein each segment comprises an epitope cluster, said cluster comprising or encoding at least two amino acid sequences having a known or predicted affinity for a same MHC Class I receptor peptide binding cleft, wherein at least one cluster is at least 11% of the length of the antigen, wherein said encoded fragment comprises an amino acid sequence beginning at one of amino acids selected from the group consisting of 77, 79, 86, and 108 of NY-ESO, and ending at one of the amino acids selected from the group consisting of 104, 140, 167, 171, 174, and 180 of NY-ESO.

23. An isolated nucleic acid molecule comprising a reading frame comprising a first sequence, wherein said first sequence encodes one or more segments of a tumor-associated antigen, wherein the antigen is NY-ESO (SEQ ID NO: 11), wherein the first sequence comprises less than 30% of the length of the antigen, or greater than 55% and less than 60% of the length of the antigen, wherein the reading frame does not encode the complete NY-ESO antigen, and wherein each segment comprises an epitope cluster, said cluster comprising or encoding at least two amino acid sequences having a known or predicted affinity for a same MHC Class I receptor peptide binding cleft, wherein at least one cluster is at least 11% of the length of the antigen, wherein said encoded fragment consists essentially of amino acids 79-174 of NY-ESO.

24. The nucleic acid molecule of 23, wherein said first sequence encodes exactly amino acids 77-180 of NY-ESO.

25. An isolated nucleic acid molecule comprising a reading frame comprising a first sequence, wherein said first sequence encodes one or more segments of tumor-associated antigen NY-ESO (SEQ ID NO: 11), wherein the first sequence comprises less than 60% of the length of the complete NY-ESO antigen, and wherein each segment comprises an epitope cluster, said cluster comprising or encoding at least two amino acid sequences having a known or predicted affinity for a same MHC Class I receptor peptide binding cleft, wherein the first sequence comprises an epitope cluster chosen from the group consisting of amino acids 86-171, 108-140, and 108-174 of NY-ESO.

26. The nucleic acid molecule of 25, wherein said first sequence encodes a fragment of NY-ESO.

27. The nucleic acid molecule of claim 26, wherein said encoded fragment consists of a polypeptide having a length, wherein the length of the polypeptide is less than about 50% of the length of NY-ESO.

28. The nucleic acid molecule of claim 26, wherein said encoded fragment consists of a polypeptide having a length, wherein the length of the polypeptide is less than about 25% of the length of NY-ESO.

29. The nucleic acid molecule of claim 26, wherein said encoded fragment consists of a polypeptide having a length, wherein the length of the polypeptide is less than about 10% of the length of NY-ESO.

30. The nucleic acid molecule of claim 26, wherein said encoded fragment comprises an amino acid sequence beginning at one of amino acids selected from the group consisting of 77, 79, 86, and 108 of NY-ESO, and ending at one of the amino acids selected from the group consisting of 140, 167, 171, 174, and 180 of NY-ESO.

31. The nucleic acid molecule of claim 25, wherein said reading frame is operably linked to a promoter.

32. An immunogenic composition comprising the nucleic acid molecule of claim 31.

33. The nucleic acid molecule of claim 26, wherein said encoded fragment consists essentially of amino acids 79-174 of NY-ESO.

34. The nucleic acid molecule of claim 33, wherein said first sequence encodes exactly amino acids 77-180 of NY-ESO.

35. The nucleic acid molecule of claim 25, wherein said one or more segments consist of said epitope cluster.

36. The nucleic acid molecule of claim 25, wherein said one or more segments of a tumor-associated antigen comprise multiple segments of NY-ESO, each consisting of an epitope cluster.

37. The nucleic acid molecule of 1, wherein said encoded fragment consists of a polypeptide having a length, wherein the length of the polypeptide is less than about 25% of the length of NY-ESO.

38. The nucleic acid molecule of 1, wherein said encoded fragment consists of a polypeptide having a length, wherein the length of the polypeptide is less than about 10% of the length of NY-ESO.

39. An isolated nucleic acid molecule comprising a reading frame comprising a first sequence, wherein said first sequence encodes one or more segments of tumor-associated antigen NY-ESO (SEQ ID NO: 11), wherein the first sequence comprises less than 60% of the length of the complete NY-ESO antigen, and wherein each segment comprises an epitope cluster, said cluster comprising or encoding at least two amino acid sequences having a known or predicted affinity for a same MHC Class I receptor peptide binding cleft, wherein the first sequence comprises an epitope cluster chosen from the group consisting of amino acids 79-104, 108-140, and 108-174 of NY-ESO, wherein said first sequence further comprises amino acids 144-171 of NY-ESO.

* * * * *